US012678493B2

(12) United States Patent
Chen et al.

(10) Patent No.: US 12,678,493 B2
(45) Date of Patent: Jul. 14, 2026

(54) COMPOSITIONS AND METHODS FOR MULTIPLEXED TUMOR VACCINATION WITH ENDOGENOUS GENE ACTIVATION

(71) Applicant: YALE UNIVERSITY, New Haven, CT (US)

(72) Inventors: Sidi Chen, Milford, CT (US); Ryan D. Chow, San Jose, CA (US); Guangchuan Wang, New Haven, CT (US)

(73) Assignee: Yale University, New Haven, CT (US)

( * ) Notice: Subject to any disclaimer, the term of this patent is extended or adjusted under 35 U.S.C. 154(b) by 1214 days.

(21) Appl. No.: 17/048,021

(22) PCT Filed: Apr. 17, 2019

(86) PCT No.: PCT/US2019/027956
§ 371 (c)(1),
(2) Date: Oct. 15, 2020

(87) PCT Pub. No.: WO2019/204503
PCT Pub. Date: Oct. 24, 2019

(65) Prior Publication Data
US 2021/0113674 A1     Apr. 22, 2021

Related U.S. Application Data

(60) Provisional application No. 62/743,990, filed on Oct. 10, 2018, provisional application No. 62/659,543, filed on Apr. 18, 2018.

(51) Int. Cl.
| | |
|---|---|
| *A61K 39/00* | (2006.01) |
| *A61K 39/395* | (2006.01) |
| *A61P 35/00* | (2006.01) |
| *C07K 16/28* | (2006.01) |
| *C12N 9/22* | (2006.01) |
| *C12N 15/11* | (2006.01) |
| *C12N 15/86* | (2006.01) |

(52) U.S. Cl.
CPC ...... *A61K 39/0011* (2013.01); *A61K 39/3955* (2013.01); *A61P 35/00* (2018.01); *C07K 16/2818* (2013.01); *C12N 9/22* (2013.01); *C12N 15/11* (2013.01); *C12N 15/86* (2013.01); *A61K 2039/5152* (2013.01); *A61K 2039/53* (2013.01); *A61K 2039/545* (2013.01); *C12N 2310/20* (2017.05); *C12N 2750/14134* (2013.01); *C12N 2750/14143* (2013.01); *C12N 2800/80* (2013.01)

(58) Field of Classification Search
CPC . A61K 39/00; A61K 39/0011; C12N 2310/20
See application file for complete search history.

(56) References Cited

U.S. PATENT DOCUMENTS

2017/0204407 A1*     7/2017   Gilbert ............... C12N 15/1082

FOREIGN PATENT DOCUMENTS

| | | |
|---|---|---|
| WO | 2016/011080 A2 | 1/2016 |
| WO | WO-2016164356 A1 * | 10/2016   ......... A61K 31/7105 |
| WO | 2017/004153 A1 | 1/2017 |
| WO | 2017/07545 A1 | 5/2017 |
| WO | 2017/083722 A1 | 5/2017 |
| WO | 2017/152015 A1 | 9/2017 |
| WO | 2017/192924 A1 | 11/2017 |
| WO | 2018/161009 A1 | 9/2018 |

OTHER PUBLICATIONS

Gilbert et al. Genome-scale CRISPR-mediated control of gene repression and activation. Cell 2014, 159:647-661. (Year: 2014).*
Ravindranath et al. Immunogenicity of membrane-bound gangliosides in viable whole-cell vaccines. Cancer Investigation 1997, 15; 5:491-499. (Year: 1997).*
Lorenz et al. Anti-Tumor Immunity Elicited by a Recombinant Vaccinia Virus Expressing CD70 (CD27L). Human Gene Therapy 1999, 10:1095-1103. (Year: 1999).*
Fu et al. High-frequency off-target mutagenesis induced by CRISPR-Cas nucleases in human cells. Nature Biotechnology 2013, 31; 9:822-827. (Year: 2013).*
Wu et al. Target specificity of the CRISPR-Cas9 system. Quantitative Biology 2014, 2;2:59-70. (Year: 2014).*
Alejandro Chavez et al: "Comparison of Cas9 activators in multiple species", Nature Methods, vol. 13, No. 7, May 23, 2016 (May 23, 2016), pp. 563-567.
Supplementary information, May 23, 2016, for Alejandro Chavez et al.: "Comparison of Cas9 activators in multiple species", Nature Methods, May 23, 2016.
Chow, R.D. et al. "AAV-mediated direct in vivo CRISPR screen identifies functional suppressors in glioblastoma," Nature Neuroscience, Aug. 14, 2017 (Aug. 14, 2017), vol. 20, pp. 1329-1341.
De Charette, Marie et al: "Turning tumour cells into antigen presenting cells: The next step to improve cancer immunotherapy?", European Journal of Cancer, Elsevier, Amsterdam NL, vol. 68, Oct. 15, 2016 (Oct. 15, 2016), pp. 134-147.
Extended European Search Report issued Jan. 19, 2022 for European patent application No. 19788924.9.
Giovanni Germano et al: "Inactivation of DNA repair triggers neoantigen generation and impairs tumour growth", Nature, vol. 552, No. 7683, Nov. 9, 2017 (Nov. 9, 2017), pp. 116-120.

(Continued)

*Primary Examiner* — Christopher M Babic
*Assistant Examiner* — Jennifer S Spence
(74) *Attorney, Agent, or Firm* — Saul Ewing LLP; Kathryn Doyle; Peter Brunovskis

(57) ABSTRACT

The present invention includes compositions and methods for treating or preventing cancer. Embodiments include cell-based and viral vector-based vaccines that utilize gene expression activation systems to augment the product of endogenous genes to treat or prevent cancer.

7 Claims, 98 Drawing Sheets

Specification includes a Sequence Listing.

(56)                References Cited

OTHER PUBLICATIONS

Hisin-Kai Liao et al: "In Vivo Target Gene Activation via CRISPR/Cas9-Mediated Trans-epigenetic Modulation", Cell, vol. 171, No. 7, Dec. 14.

International Search Report and Written Opinion issued Aug. 29, 2019 for Intl. Appl. No. PCT/US2019/027956.

Luke A. Gilbert et al: "Genome-Scale CRISPR-Mediated Control of Gene Repression and Activation" , Cell, vol. 159, No. 3, Oct. 23, 2014 (Oct. 23, 2014), pp. 647-661.

Martin Kampmann: "CRISPRi and CRISPRa Screens in Mammalian Cells for Precision Biology and Medicine", ACS Chemical Biology, vol. 13, No. 2, Oct. 16, 2017, pp. 404-416.

Sau, S. et al., "Multifunctional Nanoparticles for Cancer Immunotherapy: A Groundbreaking Approach for Reprogramming Malfunctioned Tumor Environment," Journal of Controlled Release, Jan. 31, 2018 (Jan. 31, 2018), vol. 274, pp. 24-34.

Siebenkas Cornelia et al: "Inhibiting DNA methylation activates cancer testis antigens and expression of the antigen processing and presentation machinery in colon and ovarian cancer cells", PLOS One, vol. 12, No. 6, Jun. 16, 2017.

Wang Guangchuan et al: "Multiplexed activation of endogenous genes by CRISPRa elicits potent antitumor immunity", Nature Immulogy, Nature Publishing Group US, New York, vol. 20, No. 11, Oct. 14, 2019 (Oct. 14, 2019), pp. 1494-1505.

Zhuting Hu et al: "Towards personalized, tumour-specific, therapeutic vaccines for cancer", Nature Reviews Immunology, vol. 18, No. 3, Dec. 11, 2017 (Dec. 11, 2017), pp. 168-182.

Qi, Lei S. et al., "Repurposing CRISPR as an RNA-Guided Platform for SequenceSpecific Control of Gene Expression," Cell, 152(5): 1173-1183 (Feb. 2013).

Gilbert, Luke A. et al., "CRISPR-mediated modular RNA-guided regulation of transcription in eukaryotes," Cell, 154(2):442-51 (Jul. 2013).

Konermann, Silvana et al., "Genome-scale transcriptional activation by an engineered CRISPR-Cas9 complex," Nature, 517(7536):583-8 (Jan. 2015).

Chavez, Alejandro et al., "Highly efficient Cas9-mediated transcriptional programming," Nat Methods, 12(4):326-8 (Apr. 2015).

Tanenbaum, Marvin E. et al., "A protein-tagging system for signal amplification in gene expression and fluorescence imaging," Cell, 159(3):635-46 (Oct. 2014).

* cited by examiner

Day 0
Cancer cells
allograft

Day 4
CAVac
administration

Day 7
administration of
monoclonal antibodies (i.p.)

Day 10
CAVac
administration

Day 13 or 14
administration of
monoclonal antibodies (i.p.)

Day 18
CAVac
administration

Sample harvest for
molecular, cellular and
phenotypic profiling

E0771/B6 + PBS

E0771/B6 + AAV-PCAVac

E0771 on C57BL/6J

Spiders: E0771 on C57BL/6J

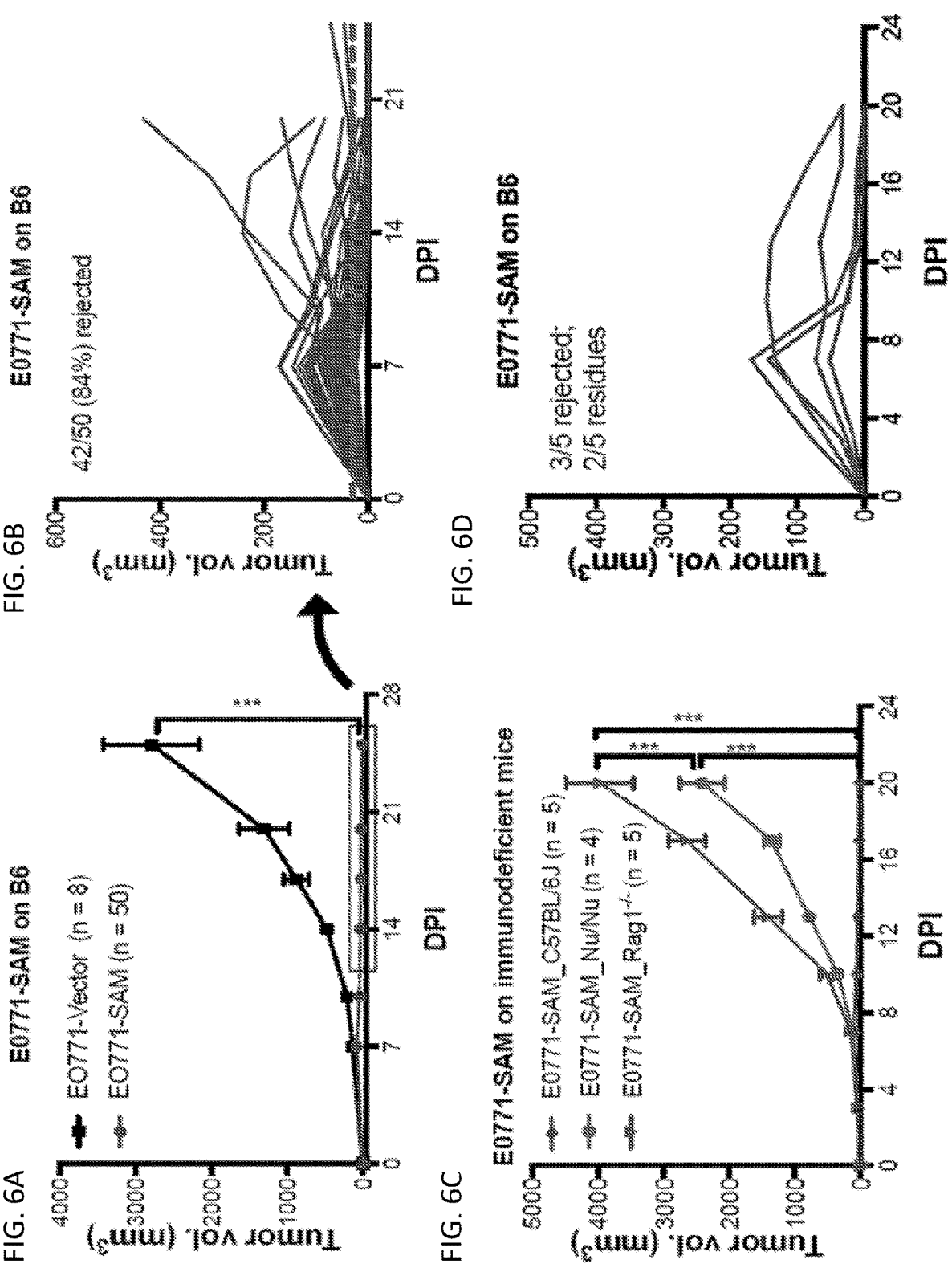

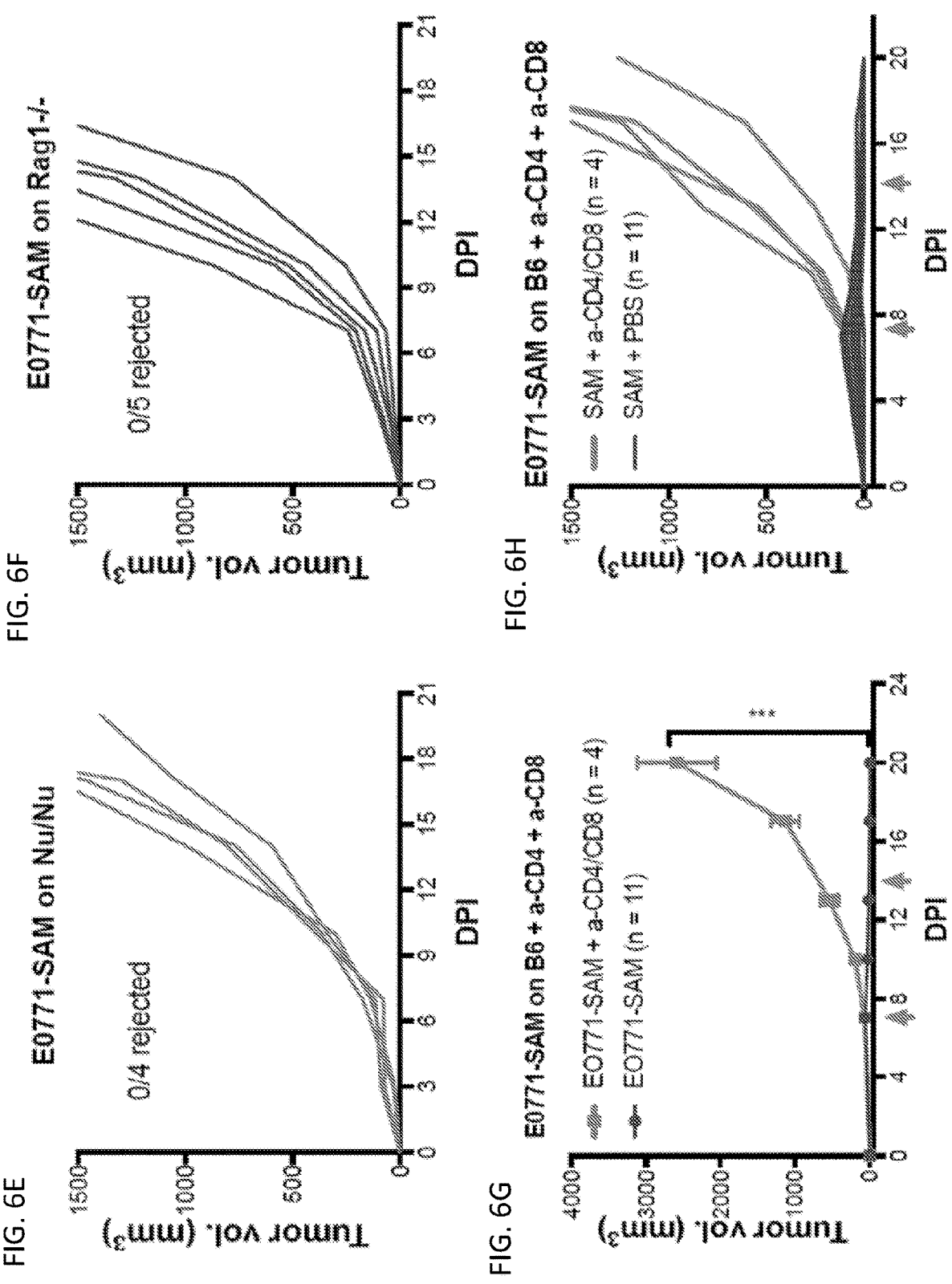

E0771 + Cell-based CAVac

E0771 + PBS

E0771 + CAVac in combinations

E0771 + PBS in combinations

FIG. 10A   Gene activation by AAV-CRISPRa

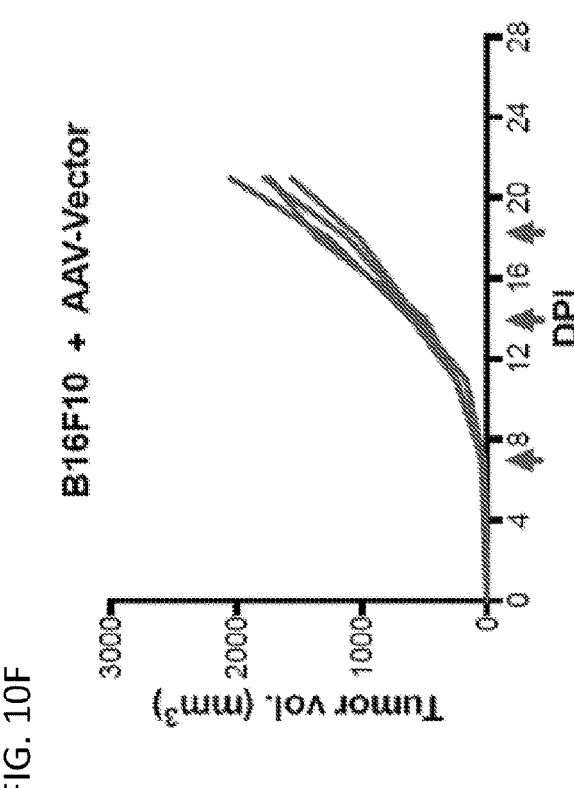
FIG. 10F
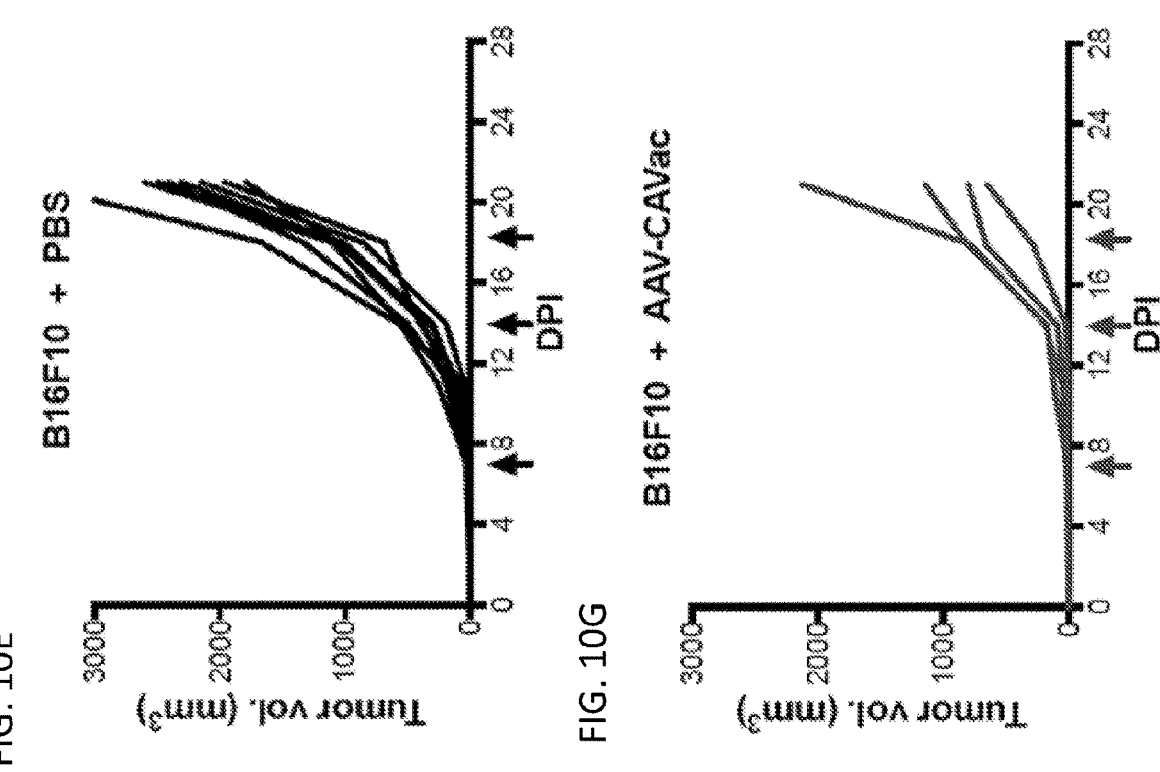
FIG. 10E
FIG. 10G

CAVac

| Sample | CDR3 | V | J | Frequency |
|---|---|---|---|---|
| TILs_15 | CASSSTGVQDTQYF | TRBV16 | TRBJ2-5 | 14.78% |
|  | CASSLGGLMTGQLYF | TRBV29 | TRBJ2-2 | 8.50% |
|  | CAWSQGASYNSPLYF | TRBV31 | TRBJ1-6 | 8.36% |
| TILs_16 | CASSPTGVQDTQYF | TRBV16 | TRBJ2-5 | 19.94% |
|  | CASSSEGVQNTLYF | TRBV16 | TRBJ2-4 | 3.18% |
|  | CASSFWGASSYEQYF | TRBV14 | TRBJ2-7 | 2.82% |
| TILs_17 | CASSTGGAQDTQYF | TRBV15 | TRBJ2-5 | 8.79% |
|  | CASSRTGVQDTQYF | TRBV16 | TRBJ2-5 | 8.78% |
|  | CASSDGGQ_NNSPLYF | TRBV13-3 | TRBJ1-6 | 3.79% |

AAV-CAVac

| Sample | CDR3 | V | J | Frequency |
|---|---|---|---|---|
| TILs_21 | CASSPDI_QDTQYF | TRBV24 | TRBJ2-5 | 20.69% |
|  | CAWSLQISNERLFF | TRBV31 | TRBJ1-4 | 13.44% |
|  | CASSIDDSGNTLYF | TRBV19 | TRBJ1-3 | 12.93% |
| TILs_20 | CAWSLVSNERLFF | TRBV31 | TRBJ1-4 | 10.78% |
|  | CASSLIDSGNTLYF | TRBV16 | TRBJ1-3 | 8.81% |
|  | CASGRNQDTQYF | TRBV13-2 | TRBJ2-5 | 4.91% |
| TILs_38 | CASGERTFNNQAPLF | TRBV13-2 | TRBJ1-5 | 1.42% |
|  | CASSFWGRGTEVFF | TRBV14 | TRBJ1-1 | 1.24% |
|  | CASSFWGRGAETLYF | TRBV14 | TRBJ2-3 | 0.97% |

FIG. 12E

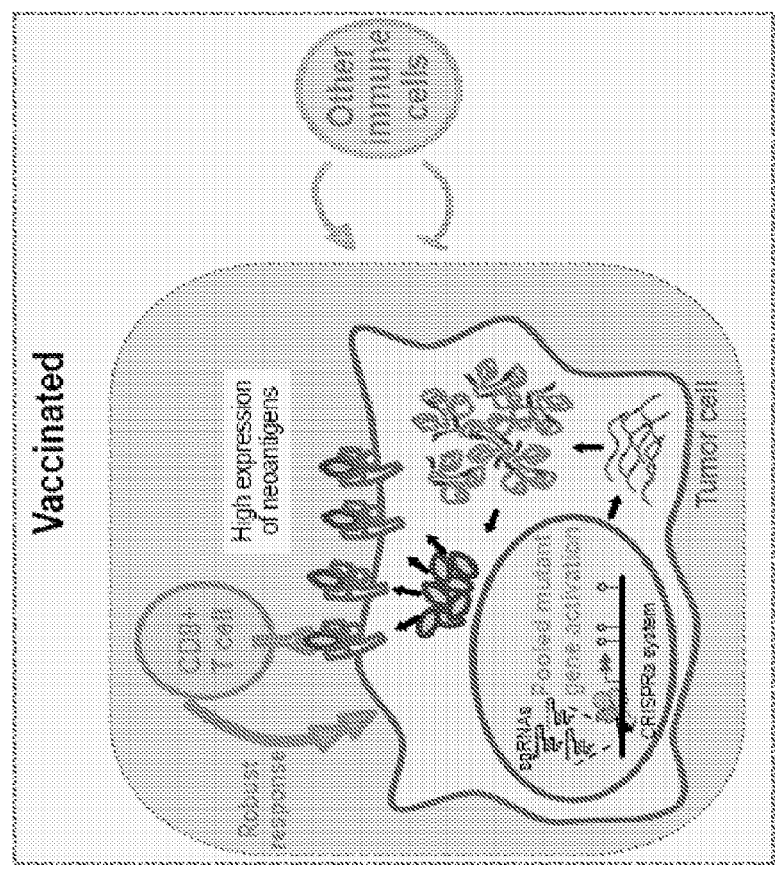
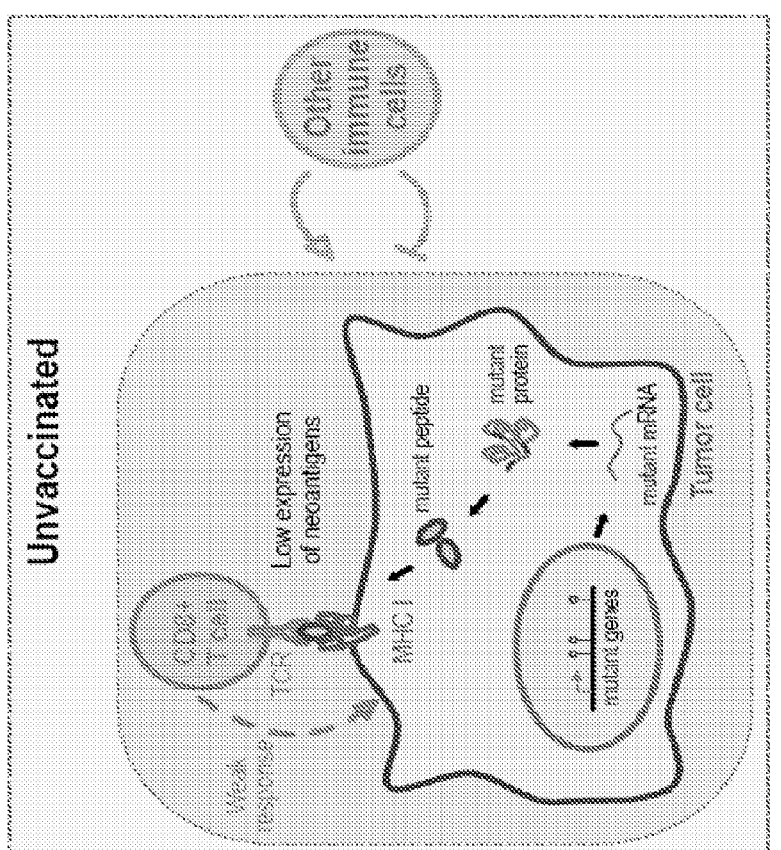
FIG. 14

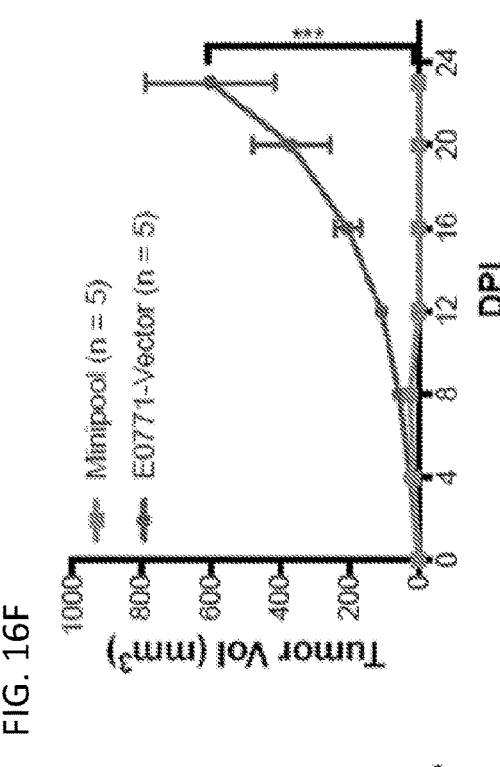
FIG. 16E
FIG. 16F
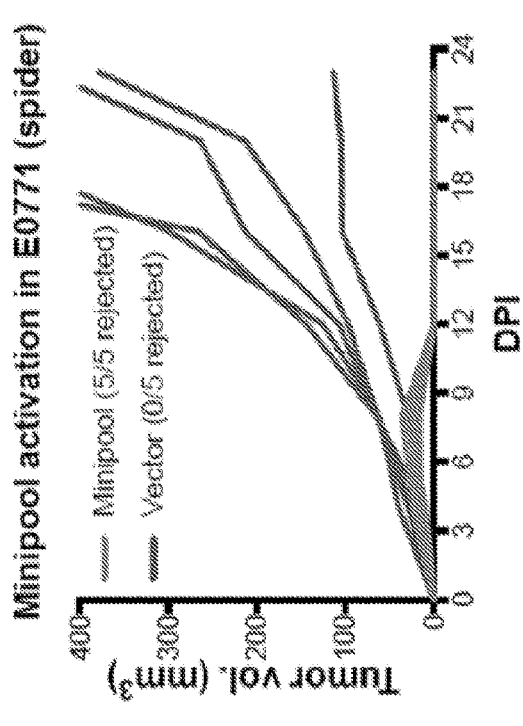
FIG. 16G

FIG. 17A
FIG. 17B
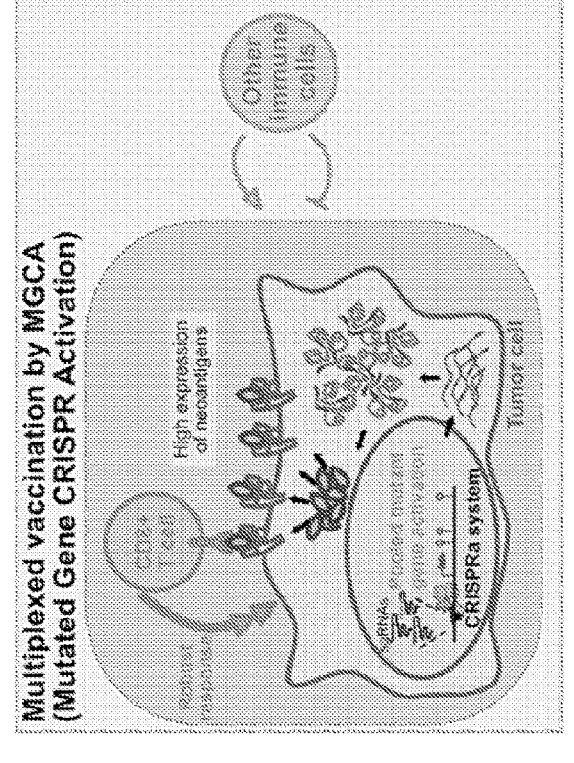
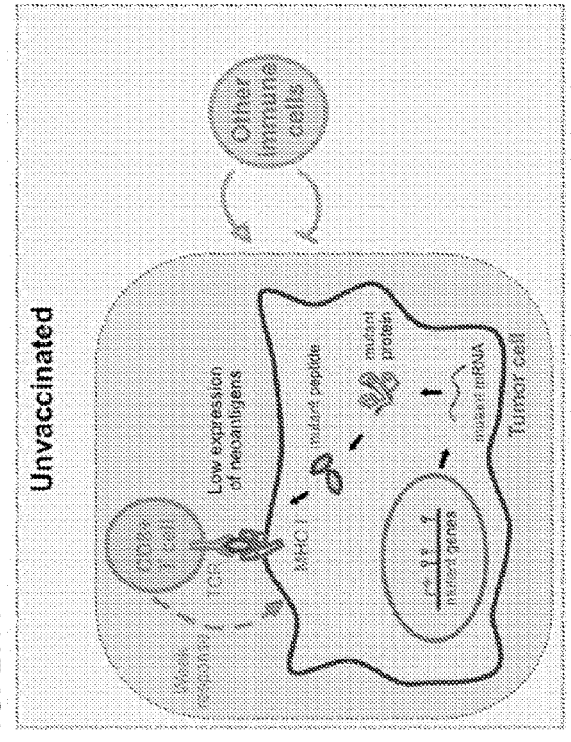
FIG. 17C

| Category | PBS | AAV-Vector | AAV-PCAVac |
|---|---|---|---|
| N | 21 | 11 | 15 |
| PD (>1.3) | 100% | 82% | 33% |
| SD (0.7~1.3) | 0% | 18% | 20% |
| PR (<0.7) | 0% | 0% | 20% |
| CR (=0) | 0% | 0% | 33% |
| CR+near-CR (residue) | 0% | 0% | 47% |
| Severe TRAE | 0% | 0% | 0% |

FIG. 19

| TNBC model, two-side tumor induction Treatment on one side ( n >=8) | PBS | AAV-Vector | AAV-PCAVac |
|---|---|---|---|
| Regression of primary tumor | 0% | 33% | 66.70% |
| Regression of distant tumor | 0% | 25% | 62.50% |

FIG. 20

| TNBC model, rechallenge after cure ( n = 5) | AAV-PCAVac |
|---|---|
| Growth of re-challenged tumor | 0% |

FIG. 21

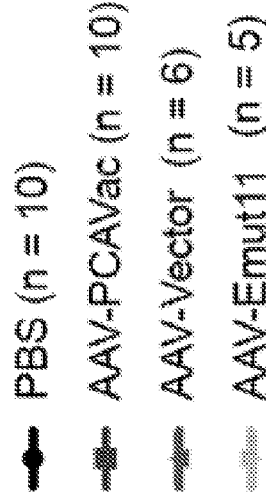
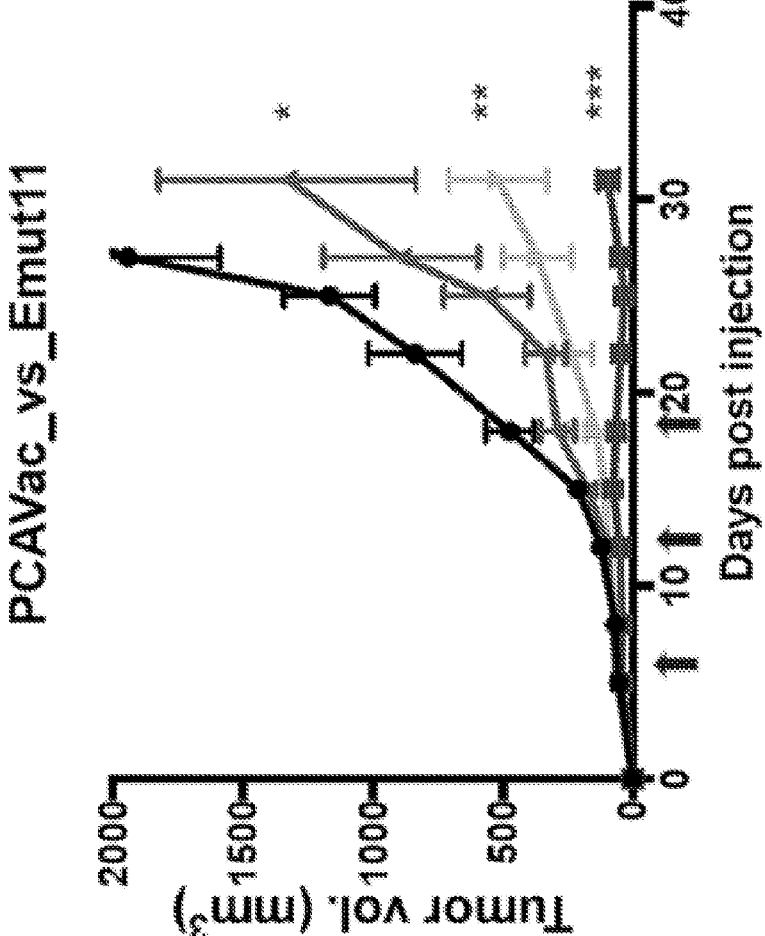
FIG. 22

| Gene | gRNA target sequence | SEQ ID NO: | Gene | gRNA target sequence | SEQ ID NO: |
|---|---|---|---|---|---|
| CD70 | GCTTCAGTTTGTCTGTGGGA | 23779 | TNFSF9 (4-1BBL) | CCCTCCCTCCCTTCCCTCCC | 23832 |
| | ATTCACTGAGCATCTATTAG | 23780 | | ACAGGGCCTGGACAGGGAAG | 23833 |
| | ATCAGGAAGCATCCGCATCC | 23781 | | AGAAAGTTCCGGGAGTCGAG | 23834 |
| CD80 | GAGAGTTCTGAATCAGGGTG | 23782 | TL1A (TNFSF15) | CAGAGGGCTGTCAGAGGGAG | 23835 |
| | TCCAGGCCTGTTCTGAGCAC | 23783 | | AACTTGGTTTCTGTTGTAGG | 23836 |
| | GGACCTTTGAGTTGCCCTCA | 23784 | | ATTCCCTAGCCGGGCAGGGC | 23837 |
| CD83 | CCAAGTCCGCGTTGCTGCTG | 23785 | CD30L(TNFSF8) | AATTGTAGCGAGATAGACGA | 23838 |
| | ATCTGCATGACCCACTCGAT | 23786 | | GTGGTTGGTGTACACTCACG | 23839 |
| | GTTTGAGGGTCATCTAGCTG | 23787 | | CGTTCTGTGGCTGAGCCTAA | 23840 |
| CD86 | GCAGGCAGGAGTGGGTGGGT | 23788 | TAP1 | TGCAGGCAACTTGCAGACTG | 23841 |
| | CTTTGTAGATTATTCGAGTT | 23789 | | TTCACGCAAGCAAGTTAAGG | 23842 |
| | GAGTTCGGTTTCAGTCTTGA | 23790 | | CGTGCCGTTCTACCAGCATT | 23843 |
| IFNa4 | AAAGAGAATTGGAAAGCAAG | 23791 | B2M | ACGACCTCCGGATCTGAGTC | 23844 |
| | TGTGTACATCTCTCTTAAAT | 23792 | | CCGTGATATTTCAAACAGCC | 23845 |
| | CAGGCTCTCAGAGAACCTGT | 23793 | | AGCATCAACAGCTAGGAGAC | 23846 |
| IFNb1 | GAAATTCCTCTGAGGCAGAA | 23794 | Tapasin | GCGGAGTCTAGGCTGATAAA | 23847 |
| | CCTGTGCTATTTATAAGGGA | 23795 | | GGTCTGGGAACGCGGGAGTG | 23848 |
| | GTGAGAATGATCTTCCTTCA | 23796 | | TATTTATTGGTCACTTCACT | 23849 |
| IFNg | AGAGTTTCCTTTCGACTCCT | 23797 | TAPBPR | CTCCAGCCCTCTCATAGTTG | 23850 |
| | TTAAGATGGTGACAGATAGG | 23798 | | AGGATTTAACATGGACTGAA | 23851 |
| | ATACCTGATCGAAGGCTCCT | 23799 | | CTGTGATCGAACAGACGAGA | 23852 |
| CXCL9 | AAACCCTACTCTCAGATCCC | 23800 | ERp57(PDIA3) | GCAGTGTGGCAGCCGCCGAT | 23853 |
| | TAGTTCTTCTACGGTCAGCTG | 23801 | | AACAGCTGGTAACTGCCGAT | 23854 |
| | TAACCACAAATTGATCGTCC | 23802 | | CTGCGTCACGCACGCGTCGGG | 23855 |
| CXCL10 | ACTTTGGAGATGACTCAGCA | 23803 | Calreticulin | GGTCGCACTATGGGCCAATG | 23856 |
| | TTTATTGTGACCCATGAACT | 23804 | | GTAGGTCTAAACCAGTCAAA | 23857 |
| | GCAATGCCCTCGGTTTACAG | 23805 | | GGGTCGACCACGCGTTGTGG | 23858 |
| IL-2 | TTTCAAAGAGTCTACCTGTG | 23806 | ERAP1 | TGATAGGGAATGCATTCTCC | 23859 |
| | GCAATTTATACTGTTAATGC | 23807 | | ACTTTGAGTTCCCGAAGCCC | 23860 |
| | TCCATTCAGTCAGTGTATGG | 23808 | | CAAGCCTAAGGGATCTAGCC | 23861 |
| CXCL3 | CACACTCATCAAGAGCCCGG | 23809 | NLRC5/CITA | AGCTGGCCGTGCAGAGAGGA | 23862 |
| | GTGGGCAAGAAGCGAAGGAA | 23810 | | TCATCTGGGAGATGAGCCTC | 23863 |
| | AGAGGACACACGTGTGCTAC | 23811 | | TTCGGTTGGCATTCGGCTAA | 23864 |
| CCL5 | AGGCAGAGTCATACTTCCAA | 23812 | TAP2 | GGGTCTGAGATGCTTTGAAA | 23865 |
| | CTACCCTGGCTCCCTATAAA | 23813 | | GGCGCCTGTCAATTTGCGGG | 23866 |
| | TTATGACAGCAACAAGTGTT | 23814 | | TTGCTAGTAGCGGCCTTGGA | 23867 |
| CD40L | TGGTGTCTTCTGACCAAGAA | 23815 | Cystatin C (x) | CTAGTCTGTTCTTGCCTTGT | 23868 |
| | TCGTCGCAACCCACACTTCC | 23816 | | GGGAGGGTGGCCGCCGGAAA | 23869 |
| | TTAACTAATCCTGAGTAAGG | 23817 | | GAATCTGGCAGCTCTTTAAG | 23870 |
| OX40L/TNFSF4 | AAGTCACTCAATTCATAACT | 23818 | Cystatin B | GGACGCTAAGAAGGGTTTGG | 23871 |
| | CAACTCCCTGTTAGCCCGGA | 23819 | | CTGTCACCACCCTCCGTTCC | 23872 |
| GITRL(TNFSF18) | AGTGCTTAGCAGTGTTCCAA | 23820 | | CTTCACGTCCTTTCCCTGAA | 23873 |
| | GCACCAGGCCAAACATACAA | 23821 | Calnexin | TGGGAAGGCGCTTCGAGCGA | 23874 |
| | CACTACAAGGGAAGTTCAGA | 23822 | | TTCTTAGATCTTGCGCAAAG | 23875 |
| Flt3L | CGCCACCTAGTGGTAACAAG | 23823 | | CCACGAAGAATAGCCCTAGG | 23876 |
| | GGGCCCTGAAAGGATAGCGA | 23824 | Sec61a1 | AGCGGCCGGTGGCCCATCCC | 23877 |
| | TTCTACATACACTTCGAAGC | 23825 | | GCTGTCGGGAAGACGACTGT | 23878 |
| LIGHT (TNFRSF14) | TGTGACTCAGGTGGGATGGA | 23826 | | GCACACGCCCAGTTCCGGTG | 23879 |
| | GAGGAGGTACGTGAGGGAAAG | 23827 | Sec61b | TCGCAGACTCTTGGATGACT | 23880 |
| | CAGTGAGAGTGATCGACCGG | 23828 | | AATCTTTACAGGCATATCTC | 23881 |
| B7-H2 (ICOSL) | GAGACTTGGGCATGAGTTAC | 23829 | | TCACACGGCCCAGTTGTTGT | 23882 |
| | AACCCAATCGGCTGCTGAGC | 23830 | Sec61g | GTACATCTAATTCCTCATTG | 23883 |
| | CCGCCTGTGCCCAATTAGCC | 23831 | | TTCAAACTATTCTCCATTCC | 23884 |
| | | | | GACTTTCTGCTTATTATTCA | 23885 |

FIG. 27

| Gene Name | Guide Sequence | SEQ ID NO: | Gene Name | Guide Sequence | SEQ ID NO: |
|---|---|---|---|---|---|
| TNFRSF14 | CCCACCTCACTCACACACTC | 23886 | CD86 | AGAGAAACAACACCACAGCC | 23995 |
| TNFRSF14 | GGGACCCTCGGCTGCTCCCC | 23887 | CD86 | CTTTGTCATGTTTGTGGATG | 23996 |
| TNFRSF14 | GAGAACTCGCCCCTCCCATC | 23888 | CD86 | CCAAGCAAGAGCACTGTCCC | 23997 |
| TNFRSF14 | TCCCCCTTCTACAGGAAACC | 23889 | CD86 | TCCAAATAACTTCTGCCGGC | 23998 |
| TNFRSF14 | GTGGACTGGAATGGTGCAGG | 23890 | CD86 | TTTGTAGTCATTCTCATCAG | 23999 |
| TNFRSF14 | ACCCACAGGGCCCCTTTATT | 23891 | CD86 | GCTTTACACTCATGCTCCGA | 24000 |
| TNFRSF14 | AAACACAGATGGACTTTGGG | 23892 | SEC61A1 | CCCGGCGGGCCCCGCGCGCC | 24001 |
| TNFRSF14 | AAAAATGTCAGTCAGCGCCC | 23893 | SEC61A1 | GCGCGGCGAAGCGCGGCGGC | 24002 |
| TNFSF18 | TTTATGTTCTGAGTTTGTGT | 23894 | SEC61A1 | GCCCCTTCCCGACAGGCCCC | 24003 |
| TNFSF18 | AAAGCACAAGGGAAGTTCAG | 23895 | SEC61A1 | CCGGCATGCAGCGGGGCTCC | 24004 |
| TNFSF18 | TTTTCTAACACAGTGACAGA | 23896 | SEC61A1 | GAGGTCTCGGCGAAGCGGCG | 24005 |
| TNFSF18 | CTTAAGTGCTGACTCTCATT | 23897 | SEC61A1 | GGTGTGCGGCTGCGCAGACT | 24006 |
| TNFSF18 | ACCAGATCAAATACAACAAA | 23898 | SEC61A1 | TAACGCGAGAGCGCGCGGGG | 24007 |
| TNFSF18 | AGCAATATGGTAATTAGTAG | 23899 | CXCL3 | GAAGGCGACGGCCCCGCCCC | 24008 |
| TNFSF4 | TTTTTTTCCTCTGGGCTAAC | 23900 | CXCL3 | CCCGTATCCGACTCCACCCC | 24009 |
| TNFSF4 | ACAGTCACTCAAATCAGAAC | 23901 | CXCL3 | GGTGGACTCACTGCCTCTCC | 24010 |
| TNFSF4 | TTTAACGCTGCAACTTTTGC | 23902 | CXCL3 | CATTTTCTGCCCCAAATTCC | 24011 |
| IFNG | AGAGTTTCCTTTAGACTCCT | 23903 | CXCL3 | TGCACGGGGGTTACTCTGGA | 24012 |
| IFNG | TAAATACCAGCAGCCAGAGG | 23904 | CXCL3 | GAGGCGTAGGCGTCACCAGT | 24013 |
| IFNG | ATCCTCAGGAGACTTCAATT | 23905 | CXCL3 | AGATCGATCCGGAGTCCCGA | 24014 |
| IFNG | AACTAAGGTTTTGTGGCATT | 23906 | CXCL9 | TGTTCTCTAAAGAATTTCTC | 24015 |
| IFNG | AAGATGAGATGGTGACAGAT | 23907 | CXCL9 | GACCACAAACTTGATTGTGC | 24016 |
| PDIA3 | CGGAGCGCGGGGCGGGGCCG | 23908 | CXCL9 | AAACCCTAGTCTCAGATCCA | 24017 |
| PDIA3 | GCTGTGTGGCAGCCGCTGAT | 23909 | CXCL9 | TTTCTCTCCTAAACTCTGAT | 24018 |
| PDIA3 | CAGGGGCTAGGGCCGGGTCC | 23910 | CXCL10 | TCCCTCTGCTCCTCTTTTTT | 24019 |
| PDIA3 | CCCAGGTTTCGGCTCACCCC | 23911 | CXCL10 | CTGCAACATGGGACTTCCCC | 24020 |
| PDIA3 | GGCTGCGCGTCGCCTTCGTC | 23912 | CXCL10 | TTATTGTAGCCTCCAAGTTA | 24021 |
| PDIA3 | GGCGAGTGTCTGGGCGAGCG | 23913 | CXCL10 | GTTGACTTAGCAAAACCTGC | 24022 |
| PDIA3 | GGCTGGGCCCGGTCCTGGGC | 23914 | ERAP1 | TCGGTCCCCAACTTGAGCAC | 24023 |
| PDIA3 | ACCAACTCGTTACCGCCGAG | 23915 | ERAP1 | GGGTTAGGGGCATGCAGGAA | 24024 |
| B2M | AAGAAAAGGAAACTGAAAAC | 23916 | ERAP1 | TGGACTTGTCAGCGCCTGCC | 24025 |
| B2M | AGACAGGTGACGGTCCCTGC | 23917 | ERAP1 | TTTCACTGTTTAGCGTTGCG | 24026 |
| B2M | GTGCCCAGCCAATCAGGACA | 23918 | ERAP1 | TTTCTCTCACACTAAAAGAA | 24027 |
| B2M | GAAAGTCCCTCTCTCTAACC | 23919 | ERAP1 | CTGGAACAATGATGTGAGCT | 24028 |
| B2M | CAAGCCAGCGACGCAGTGCC | 23920 | ERAP1 | TTCCGTTCCTCATTGACTAT | 24029 |
| B2M | GAGTCTCGTGATGTTTAAGA | 23921 | ERAP1 | TAGTTCCTTGCCATATCCTA | 24030 |
| B2M | TGAGTTTGCTGTCTGTACAT | 23922 | ERAP1 | AAACAGTCAGCAAAACACTG | 24031 |
| NLRC5 | CAGGGGCAAGGGCTGGTGCC | 23923 | ERAP1 | TCGGTCCCCAACTTGAGCAC | 24032 |
| NLRC5 | CCACTATTCCAGACTCCAAA | 23924 | ERAP1 | GGGTTAGGGGCATGCAGGAA | 24033 |
| NLRC5 | GGAGTTGGGGGGACTGTGTC | 23925 | ERAP1 | TGGACTTGTCAGCGCCTGCC | 24034 |
| NLRC5 | TTCTCAGATGTGTCTCCGGC | 23926 | ERAP1 | TTTCACTGTTTAGCGTTGCG | 24035 |
| NLRC5 | GAAGAACAAGGTCTAGCGGA | 23927 | CANX | GCCGGGAGTGAGGCAGGAAG | 24036 |
| NLRC5 | GACACAAGGAGCTGCAGTCG | 23928 | CANX | GCTACTCAGGGGCCAGGGGC | 24037 |
| CCL5 | TCTAGATGAGAGAGCAGTGA | 23929 | CANX | GCGGGACTTGGCGCCGGCTG | 24038 |
| CCL5 | GAGACAGAGACTCGAATTTC | 23930 | CANX | TGTTGGTTGGGCGGGAGGTG | 24039 |
| CCL5 | AAGAAAACTGAAATAGCCTC | 23931 | CANX | CGATGCCCACGCCGGCCAAC | 24040 |
| CCL5 | ATTTTGGAAACTCCCCTTAG | 23932 | CANX | TCTTCGTGGAGTGTGAAGAT | 24041 |
| CCL5 | GCCCTTTATAGGGCCAGTTG | 23933 | CANX | ACCGTCCCATACGCCCCCTA | 24042 |
| CCL5 | TTATGATACCGGCCAATGCT | 23934 | CANX | ATGTCGGGGCTTGCGCGGGA | 24043 |
| TNFSF9 | TGGCCGCGGGCGGAGGGGCG | 23935 | CD83 | ACTTGGCTCCCTGCCTTCCC | 24044 |
| TNFSF9 | GGGCGTGGCCGCGGGCGGAG | 23936 | CD83 | GTACTGACTGATAACCTCCC | 24045 |
| TNFSF9 | GAAAGGCTCTGGGCTGGGAA | 23937 | CD83 | ACACGCATACACAACATTTT | 24046 |
| TNFSF9 | CGCAGAGTCACGGGGACGAG | 23938 | CD83 | TACAGACTTGTATGTTTCCA | 24047 |
| TNFSF9 | AAAGCGGAGAGAGATCCGAG | 23939 | CD83 | TAATAGGAGACACTCTCCTT | 24048 |

FIG. 28A

| Gene Name | Guide Sequence | SEQ ID NO: | Gene Name | Guide Sequence | SEQ ID NO: |
|---|---|---|---|---|---|
| TNFSF9 | AGCTGCTTGGCTACAAAAGG | 23940 | CD83 | GACGGGGGCGGGGACGGGGG | 24049 |
| TNFSF9 | TTGGAAGGCCGGAAACGGAA | 23941 | CD83 | CCGCCCCCGCGCGCCCGGGC | 24050 |
| CD70 | GGCGGGGAGGGGTTGGGGGC | 23942 | CD83 | GCGCACGCGGCGAGGGCGGC | 24051 |
| CD70 | ATGTCTCCTGCCTGAAGGTC | 23943 | CD83 | CCCCGCGTGACGCCCAGCGC | 24052 |
| CD70 | CAGGATGCAGGCAGTGGCCC | 23944 | CD83 | CGACGCGAACTCGGGGCGCC | 24053 |
| CD70 | CAACTGCCTCCACCCACTTT | 23945 | TAP2 | GGGTCTCGCGCGCCCCCTCC | 24054 |
| CD70 | ATGTCCGGCCGGTCGAGGGG | 23946 | TAP2 | CGCTTTCGCTTCCCCAGCCA | 24055 |
| CD70 | TCAGACTGGCAGCGGTTGGA | 23947 | TAP2 | AGGCGAGTGAGACTCATTGC | 24056 |
| CD70 | GGCAACTCTGAGGCTCACCC | 23948 | TAP2 | GGCTCCAGTTCCGCTGTCTG | 24057 |
| CD70 | GGGACTTGAGCAATTGGCGA | 23949 | TAP2 | TTCATTCTGGGCTGGGCCGC | 24058 |
| CALR | CAGGGGCGGGCCCAAGGGCT | 23950 | TAP2 | TACAGTGCGAACCAGAGTTC | 24059 |
| CALR | GTCAGGTTGGTTTGAGAGGC | 23951 | TAP2 | TCTCGCGCGCCCCCTCCCGG | 24060 |
| CALR | CGGAACGCTGGGTTCCCAGA | 23952 | TAP2 | AGTAAAATACAGTTGTCTCA | 24061 |
| CALR | GTGGTGAGGCCAATAGAAAT | 23953 | TAP2 | AGGCGAGTGAGACTCATTGC | 24062 |
| CALR | GGCATAGACCAATGACAAAG | 23954 | TAP2 | GCTCCAGTTCCGCTGTCTGC | 24063 |
| CALR | CAATGGAAAAAGACGGCCAT | 23955 | TAP2 | TACAGTGCGAACCAGAGTTC | 24064 |
| CALR | TGGGTATAAAAGTGCAAGGC | 23956 | TAP1 | CGGCGCCGCCAGGAGGCGCC | 24065 |
| CALR | CTTCGTCGGTTCACTATGTT | 23957 | TAP1 | GGAGGCAGGGAGAGGCGAGA | 24066 |
| CST3 | GCGGGGAGAGGCAGGGGAGG | 23958 | TAP1 | TTCCCACCCCAGCCTCAGGG | 24067 |
| CST3 | GGGGAGAGGCAGGGGAGGCG | 23959 | TAP1 | AAAGCAGCCCCGCAGCACCC | 24068 |
| CST3 | GAGGGAGAAGGGAGGTGGGA | 23960 | TAP1 | GGCTGCCTCGTCACTTGTCT | 24069 |
| CST3 | GGGAGGGAAGGGGATGGATG | 23961 | TAP1 | ACTGGTGCAAGTGGAAAGGC | 24070 |
| CST3 | GCAGGGGAGGCTGGGATGGG | 23962 | TAP1 | GCGCGGCGCTAACGTGTGTA | 24071 |
| CST3 | GAGGCCGGGAGGGGCTGGGA | 23963 | SEC61G | AGCGCAGCGCGACGTGCGCC | 24072 |
| CST3 | AAGGACAGGGAAGCCTGGAG | 23964 | SEC61G | CTCTTCCAGGAAGCGTGGCC | 24073 |
| CST3 | ACTGATAGGGAGGGACCTGG | 23965 | SEC61G | CGCCCACTCCTCCGTCCTAT | 24074 |
| CSTB | GCGGGGCGCGGGGCGGGGCG | 23966 | SEC61G | TAGACTCACACTCCTAAGGA | 24075 |
| CSTB | GGGAGGAGGCACTTTGGCTT | 23967 | SEC61G | GCGCACTGAGGTTTCGCGTA | 24076 |
| CSTB | GGGAGGGAGCGCCCCCCTCC | 23968 | SEC61G | GCATTGCGGAGCTCGCTAGT | 24077 |
| CSTB | TGGGTCTCCGCGCCCAGCGC | 23969 | SEC61G | CGTTATCCCTTTTTTCCGGC | 24078 |
| CSTB | AGTCCCCTGCGGGGTCGCGG | 23970 | IFNB1 | TGAAAGGGAGAAGTGAAAGT | 24079 |
| CSTB | GCCCCGCAAGAAGGGACGCG | 23971 | IFNB1 | ATGGTCCTCTCTCTATTCAG | 24080 |
| CSTB | GGAAAGACGATACCAGCCCC | 23972 | IFNA4 | GAAGACTTTGCTCTGTGCAT | 24081 |
| CSTB | ACCTGGCCACCACTCGCCGC | 23973 | IFNA4 | TATTTTTCACCTGCACTCAA | 24082 |
| ICOSLG | GGGCGGGGCGGGGACGGGGC | 23974 | IFNA4 | CAACTAGGGAATTTAGAAAA | 24083 |
| ICOSLG | GGGGCGCTGCGCGGCGGCTC | 23975 | SEC61B | ACTGACTCAGGCCCCGCCCC | 24084 |
| ICOSLG | CGGCGCCCAGGTCCGCGTCC | 23976 | SEC61B | ATCCAAAGGAAGGAGGCCGG | 24085 |
| ICOSLG | CGAGACCGCCCCGGGACAGG | 23977 | SEC61B | AGACGACCCAGGCGTCCCTG | 24086 |
| ICOSLG | TCGCCAGAGGAGCCAGGCCG | 23978 | SEC61B | AGGACCTTGCCTGCAAGTCC | 24087 |
| ICOSLG | GTGTGCCCGTCGGCCGGAGG | 23979 | SEC61B | GTCTCTACTTCCCATACAGC | 24088 |
| ICOSLG | GGCAGGTCGGCCTGTCCGCC | 23980 | SEC61B | GTAGGGATTGGACTTTCTGA | 24089 |
| ICOSLG | CTGGGCAGAGCCGAACTTTC | 23981 | SEC61B | GTCTGTAGCAGACTGTCTAC | 24090 |
| CD80 | TTCTCCTCCCCTAGGCCGCC | 23982 | TNFSF15 | TTCCAATCCAAAATCCTGCA | 24091 |
| CD80 | GCCTCCCTCACCACCGTGCA | 23983 | TNFSF15 | ACCCGCAGCAAGCACCACCA | 24092 |
| CD80 | GCTTTTGTAGAGGCTGTGGC | 23984 | TNFSF15 | TAAACTTGCCCAAAGCCATG | 24093 |
| CD80 | CAAACACCCTGTCCAACTCC | 23985 | TNFSF15 | GTGGCACTGGACCAAGCTGG | 24094 |
| CD80 | TAGAAGAAGACGGCAGCAGA | 23986 | TNFSF15 | TCTTGAACACAAATGAATCT | 24095 |
| CD80 | AATGGTGCCCGAGAAGAGTG | 23987 | TNFSF15 | CAAGGTTTCTCTCCTATCAT | 24096 |
| CD80 | CATGAAACACCACGAGCACC | 23988 | TNFSF15 | TGTGCTCTTGAAGAGGGGAG | 24097 |
| CD86 | TTAAAGAAAGTTAGCTGGGT | 23989 | TNFSF15 | CTCCTTCCTTCGTTTACAGA | 24098 |
| CD86 | GAGTTTAAACTGCAAGGAAA | 23990 | TNFSF15 | GTGCATTCTCTAGCAGGGTA | 24099 |
| CD86 | TCAAAATCTGTAGAGAAAAG | 23991 | TNFSF15 | AACTTGGTTTCTGTTGTAGG | 24100 |
| CD86 | TTAAATTTCTTCCTCAAGTG | 23992 | TNFSF8 | GGGGAGGTCTTCTGAGCCAC | 24101 |
| CD86 | GCTCATCTTAACGTCATGTC | 23993 | TNFSF8 | AGCTGCACCTTCTTTCAGCG | 24102 |
| CD86 | CTCCCTTTGGGGGTTTCCCA | 23994 | TNFSF8 | CCCAGCAAGGACTCATTATC | 24103 |
| | | | TNFSF8 | TTGAACAGGAAGGCGTTTTG | 24104 |

FIG. 28B

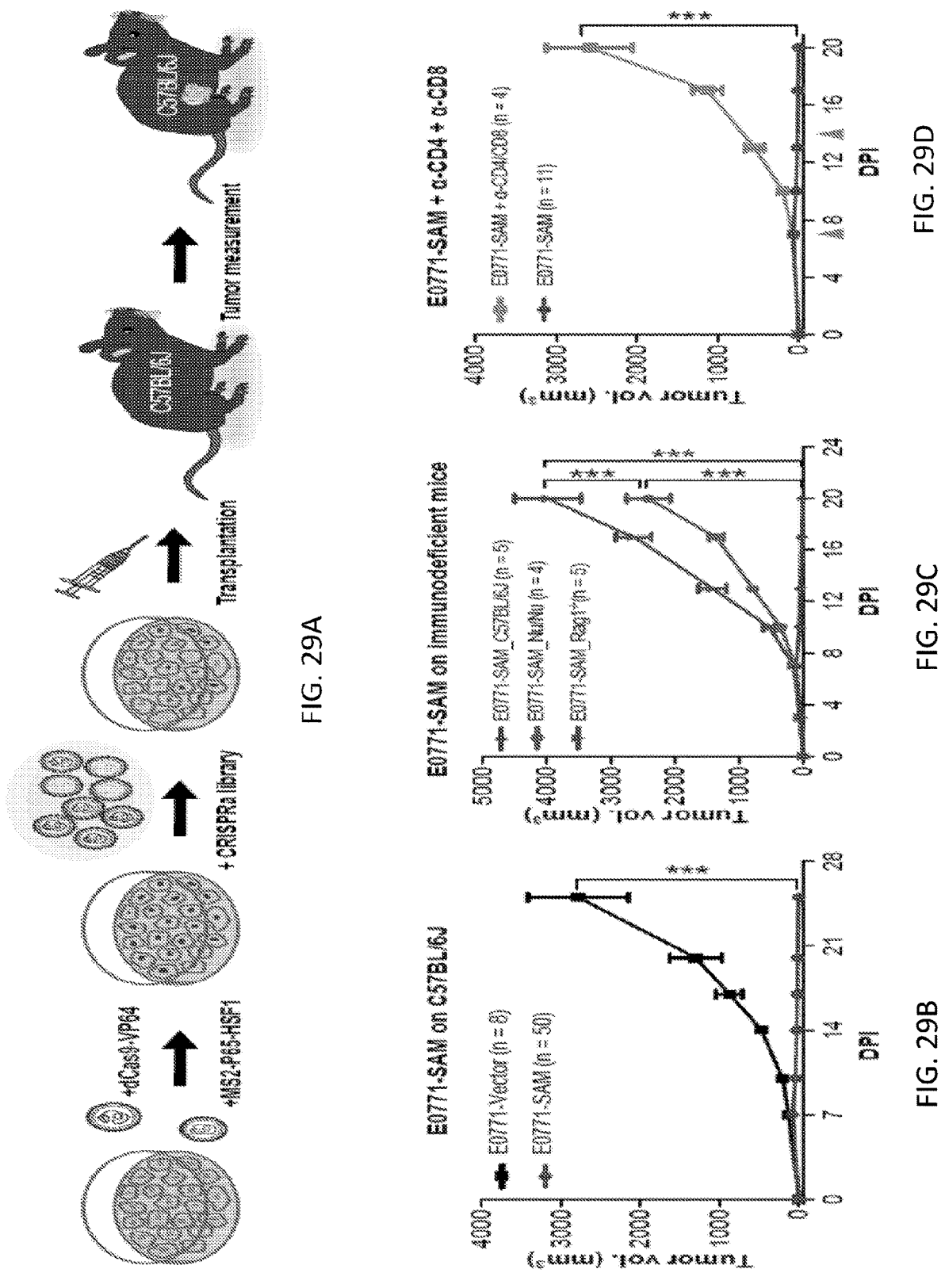

PBS

| Sample | CDR3 | V | J | Frequency |
|---|---|---|---|---|
| TILs_18 | CASRGHW_AETLYF | TRBV16 | TRBJ2-3 | 4.17% |
|  | CASSAGT_TYEQYF | TRBV12-2 | TRBJ2-7 | 3.90% |
|  | CASSSLGDNQDTQYF | TRBV19 | TRBJ2-5 | 3.80% |
| TILs_37 | CGAGLGGLDTQYF | TRBV20 | TRBJ2-5 | 4.84% |
|  | CASSPDWGEQYF | TRBV19 | TRBJ2-7 | 4.57% |
|  | CGARLGGRAEQFF | TRBV20 | TRBJ2-1 | 2.71% |
| TILs_42 | CAIGTGGYKVVF | TRAV8N-2 | TRAJ12 | 5.80% |
|  | CASSIANRGFSDYTF | TRBV19 | TRBJ1-2 | 4.53% |
|  | CASSLDGVYAEQFF | TRBV18 | TRBJ2-1 | 3.97% |

AAV-vector

| Sample | CDR3 | V | J | Frequency |
|---|---|---|---|---|
| TILs_31 | CASSFWGRYAEQFF | TRBV14 | TRBJ2-1 | 8.69% |
|  | CASSPRLGGAETLYF | TRBV16 | TRBJ2-3 | 2.37% |
|  | CASSIVTGGGEQFF | TRBV19 | TRBJ2-1 | 1.57% |
| TILs_28 | CASSLYGAGAEQFF | TRBV16 | TRBJ2-1 | 8.41% |
|  | CASSASSYEQYF | TRBV13-3 | TRBJ2-7 | 7.61% |
|  | CALINMGYKLTF | TRAV8D-6 | TRAJ9 | 4.59% |
| TILs_53 | CAMENNYAQGLIF | TRAV13N-1 | TRAJ26 | 2.11% |
|  | CAMGRSGSFNKLTF | TRAV13N-1 | TRAJ4 | 1.44% |
|  | CAVGPEPGYQNYYF | TRAV7-5 | TRAJ49 | 1.36% |

AAV-g-MAEGI

| Sample | CDR3 | V | J | Frequency |
|---|---|---|---|---|
| TILs_58 | CATGTGGYKVVF | TRAV8N-2 | TRAJ12 | 3.31% |
|  | CALRAPYGSSGNKLIF | TRAV12N-2 | TRAJ32 | 2.65% |
|  | CASSSDWNYAEQFF | TRBV4 | TRBJ2-1 | 2.38% |
| TILs_36 | CATSSGGSMQLIF | TRAV8D-2 | TRAJ22 | 3.36% |
|  | CGARDHRAQAPLF | TRBV20 | TRBJ1-5 | 1.99% |
|  | CASADWGNQDTQYF | TRBV19 | TRBJ2-5 | 1.47% |
| TILs_38 | CASGERTFMNQAPLF | TRBV13-2 | TRBJ1-5 | 1.42% |
|  | CASSFWGRGTEVFF | TRBV14 | TRBJ1-1 | 1.24% |
|  | CASSFWGRGAETLYF | TRBV14 | TRBJ2-3 | 0.97% |

AAV-p-MAEGI

| Sample | CDR3 | V | J | Frequency |
|---|---|---|---|---|
| TILs_45 | CASSIGTSGERLFF | TRBV19 | TRBJ1-4 | 0.91% |
|  | CAWSQIGGGAETLYF | TRBV31 | TRBJ2-3 | 0.79% |
|  | CILRGTGGNNKLTF | TRAV21 | TRAJ56 | 0.52% |
| TILs_46 | CALILNTGNYKYVF | TRAV6-5 | TRAJ40 | 1.89% |
|  | CGARLGGYEQYF | TRBV20 | TRBJ2-7 | 1.71% |
|  | CASSRRGGADTQYF | TRBV17 | TRBJ2-5 | 1.63% |
| TILs_48 | CASSLGGTMSDYTF | TRBV16 | TRBJ1-2 | 1.11% |
|  | CASRETGVISNERLFF | TRBV14 | TRBJ1-4 | 0.62% |
|  | CAANTEGADRLTF | TRAV14D-2 | TRAJ45 | 0.56% |

FIG. 35C

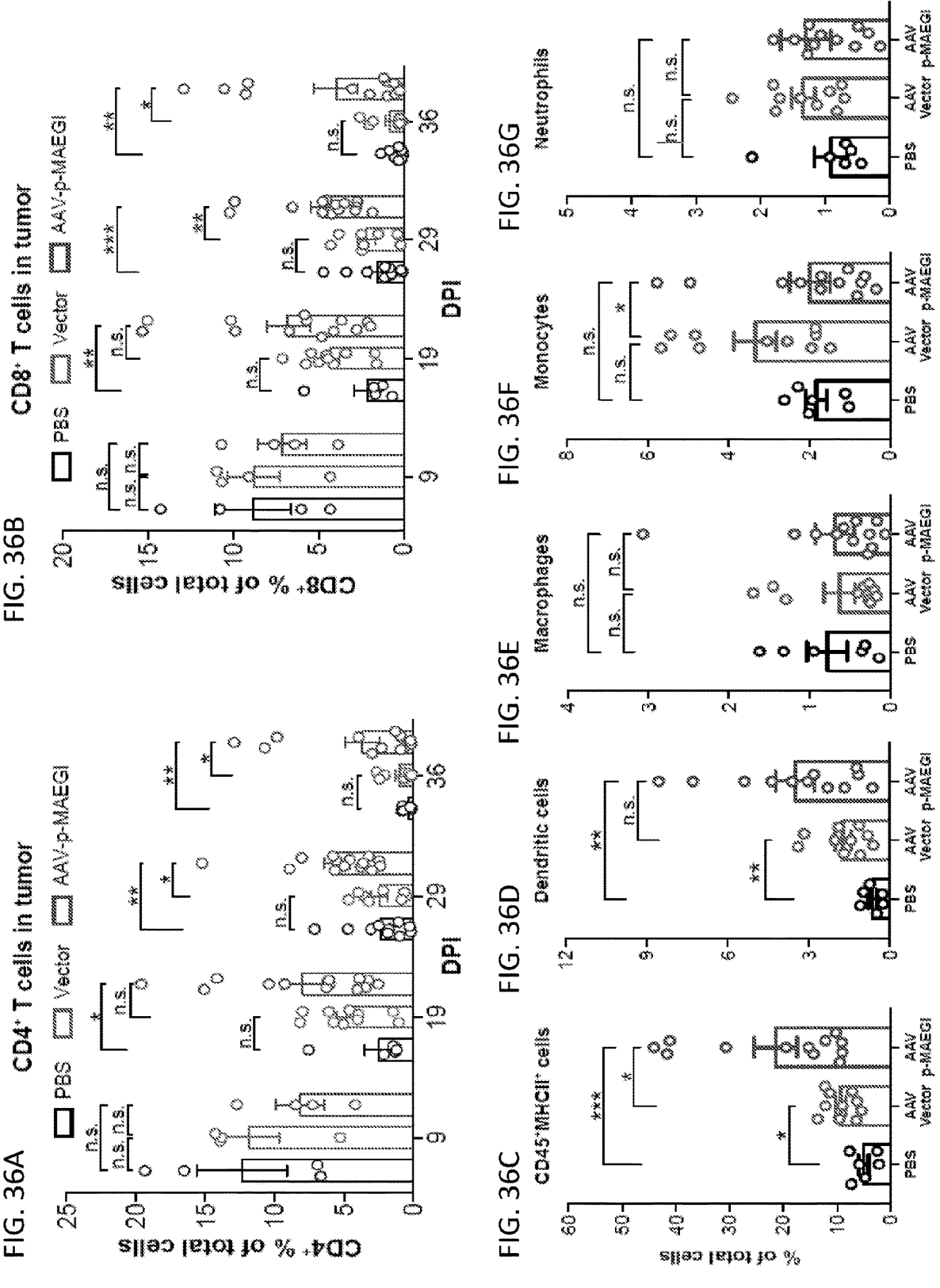

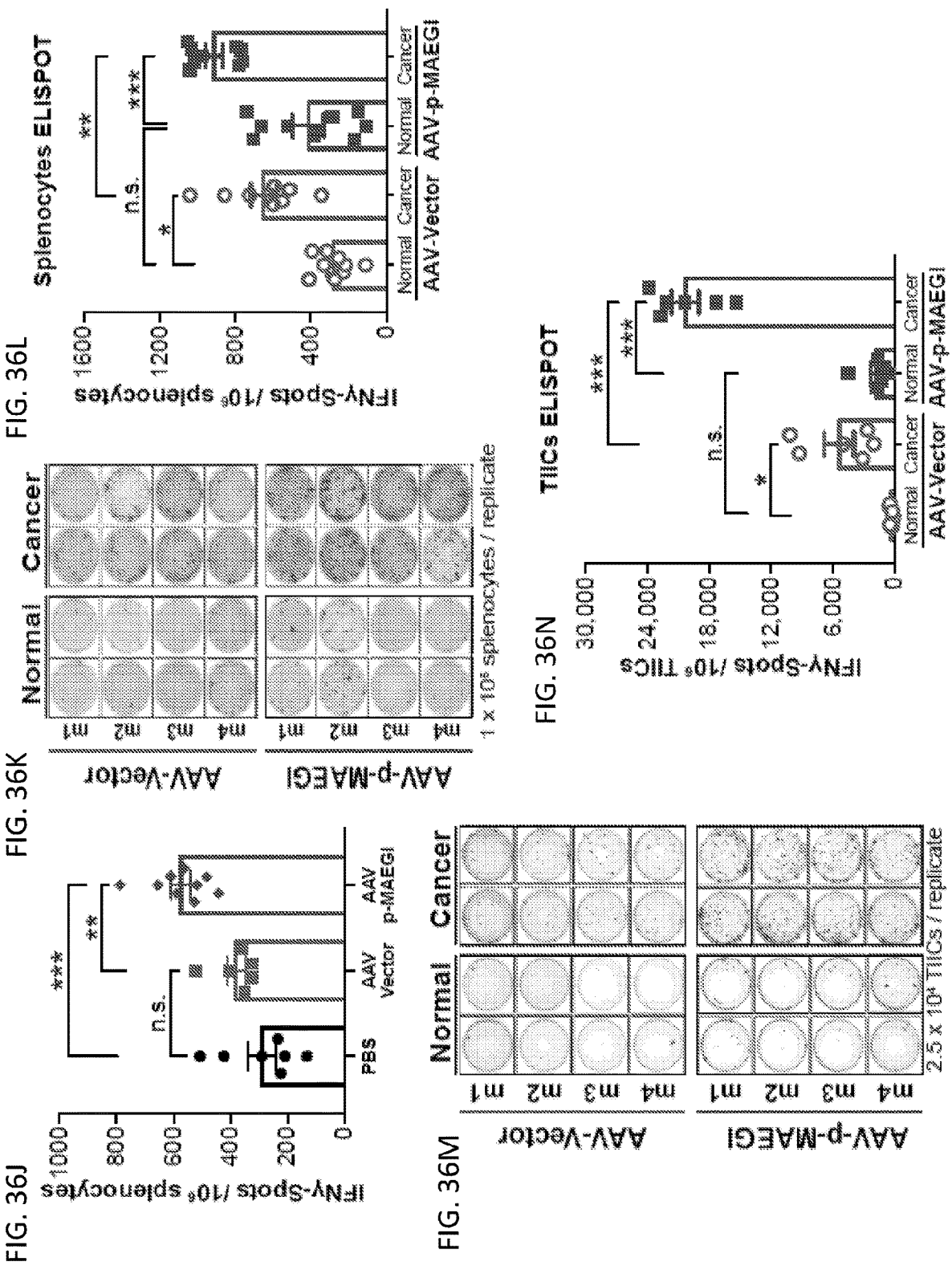

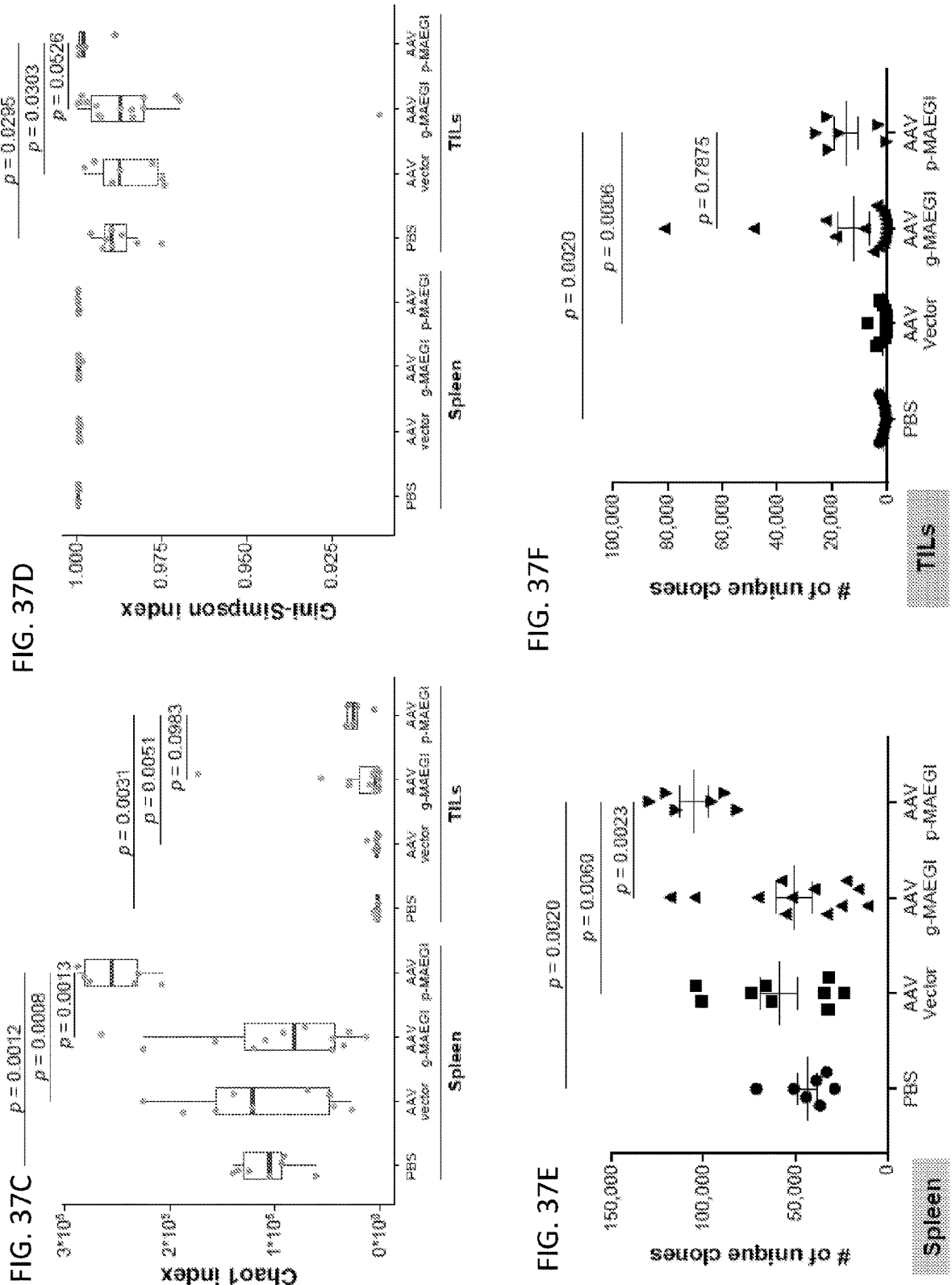

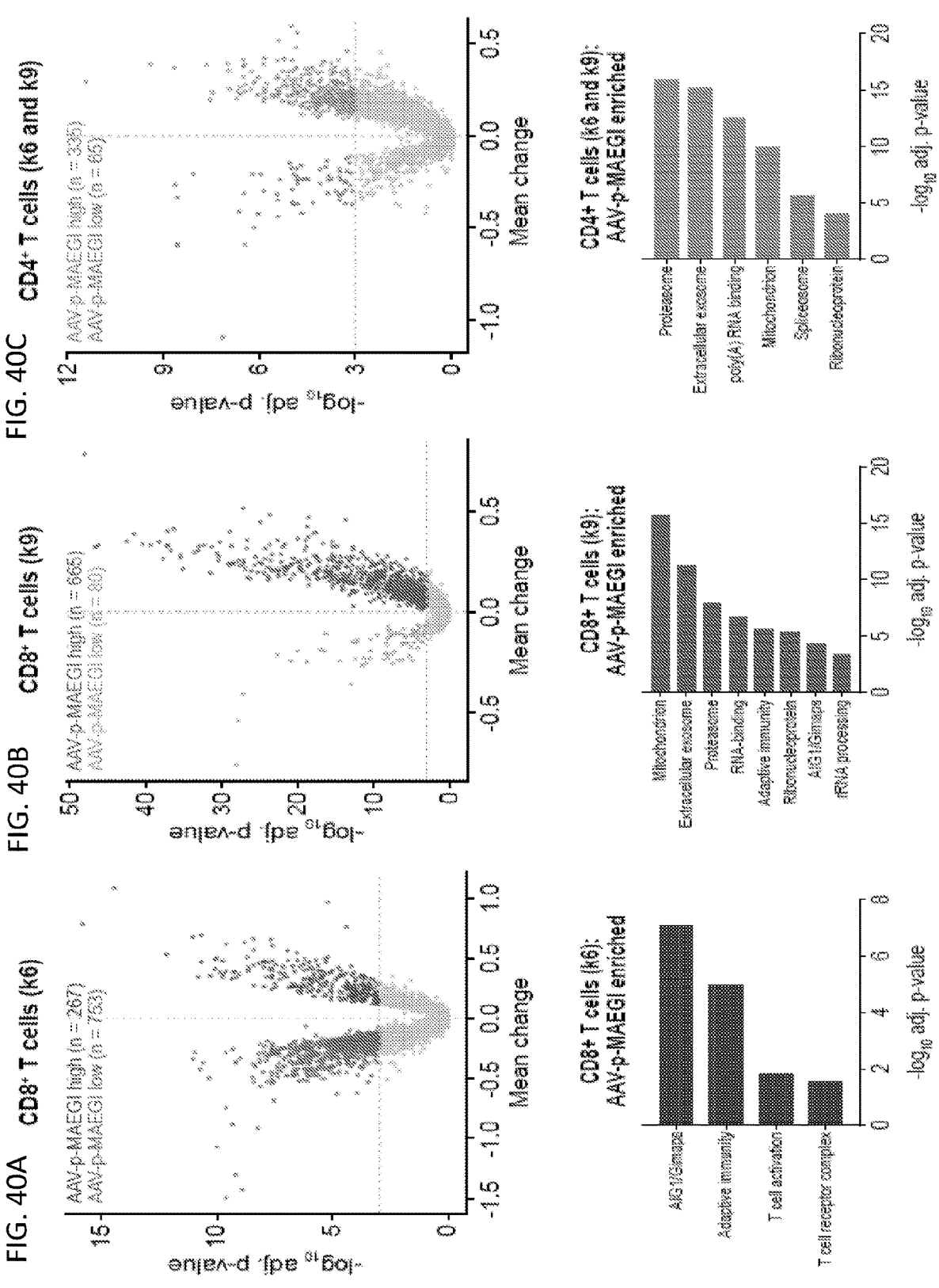

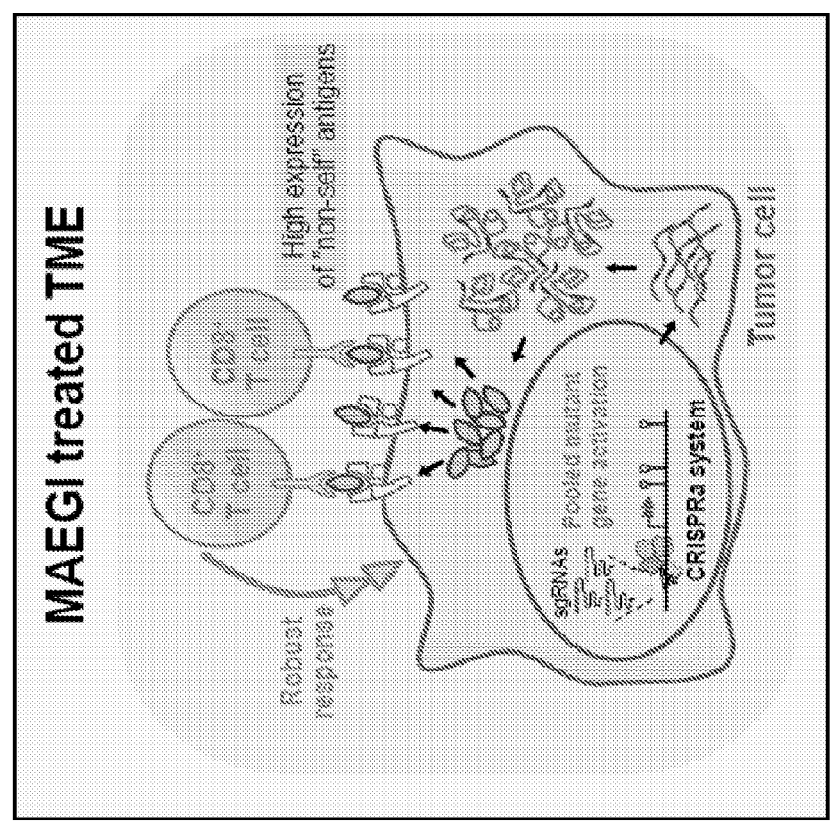
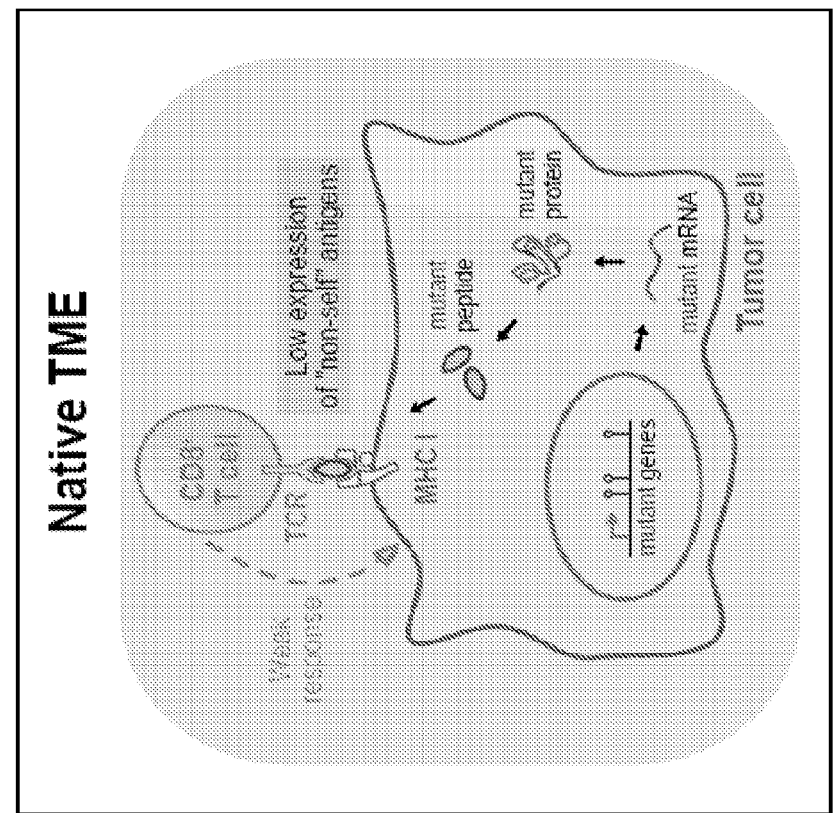
FIG. 40D

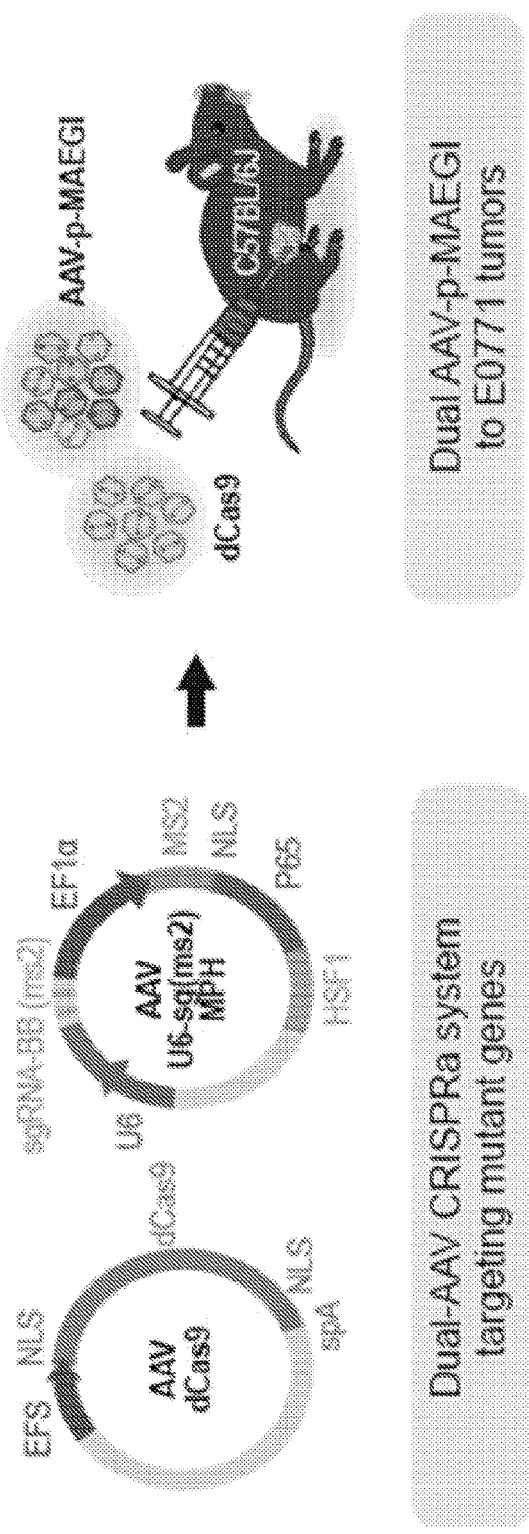
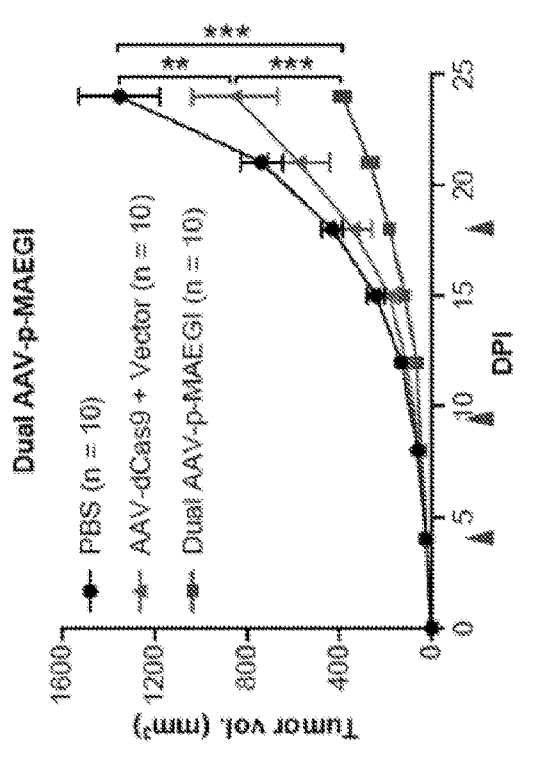
FIG. 46

COMPOSITIONS AND METHODS FOR MULTIPLEXED TUMOR VACCINATION WITH ENDOGENOUS GENE ACTIVATION

CROSS-REFERENCE TO RELATED APPLICATIONS

The present application is a 35 U.S.C. § 371 national phase application from, and claims priority to, International Application No. PCT/US2019/027956, filed Apr. 17, 2019, and published under PCT Article 21(2) in English, which is entitled to priority under 35 U.S.C. § 119(e) to U.S. Provisional Application No. 62/659,543, filed Apr. 18, 2018, and U.S. Provisional Patent Application No. 62/743,990, filed Oct. 10, 2018, which are hereby incorporated by reference in their entireties herein.

STATEMENT REGARDING FEDERALLY SPONSORED RESEARCH OR DEVELOPMENT

This invention was made with government support under CA238295, CA231112 and CA209992 awarded by the National Institutes of Health; and under W81XWH-17-1-0235 awarded by the United States Army Medical Research and Material Command. The government has certain rights in the invention.

BACKGROUND OF THE INVENTION

Immunotherapy has transformed cancer treatment by leveraging the patient's own immune system against the tumor, thereby turning several previously lethal cancers into manageable diseases for a subset of patients. Major types of immunotherapy include checkpoint blockade, adoptive cell transfer, human recombinant cytokines, and cancer vaccines. Although antigen recognition is a key process in the anti-tumor immune response, there has been limited success using cancer vaccines in the clinic over the past several decades. Traditional cancer vaccines are often dendritic cell-based vaccines such as sipuleucel-T. Recent advances of peptide- and RNA-based vaccines showed that targeted delivery of multiple mutated neoantigens can generate a strong anti-tumor effect, providing direct clinical evidence of effective cancer vaccines against late-stage melanoma. Tumor cells harbor a multitude of mutations that frequently encode mutated, partially truncated, or amplified genes that are immunogenic. However, many of these mutations might not be expressed at levels sufficient to elicit an effective T-cell-mediated response. Synthesis of these peptides or transcripts is possible with parallel protein- or RNA-synthesis, but the cost of this approach is proportional to the number of mutations identified.

A need exists for new types of cancer vaccines that can elicit strong, durable, and specific immune responses against cancer antigens, while maintaining efficacy, versatility, and cost-effectiveness. The present invention satisfies this need.

SUMMARY OF THE INVENTION

As described herein, the present invention relates to compositions and methods for or treating or vaccinating against cancer via multiplexed activation of endogenous genes by the CRISPRa system.

In one aspect, the invention includes a method of vaccinating against cancer in a subject. The method comprises contacting a cell with a composition comprising a CRISPR activation (CRISPRa) system, wherein the CRISPRa system increases expression of at least one endogenous gene resulting in a modified cell. A therapeutically effective amount of a composition comprising the modified cell is administered to the subject, thereby vaccinating against cancer in the subject.

In another aspect, the invention includes a method of treating cancer in a subject in need thereof. The method comprises contacting a cell with a composition comprising a CRISPRa system, wherein the CRISPRa system increases expression of at least one endogenous gene resulting in a modified cell. A therapeutically effective amount of a composition comprising the modified cell is administered to the subject, thereby treating the cancer in the subject.

In yet another aspect, the invention includes a method of vaccinating against cancer in a subject in need thereof. The method comprises administering to the subject a therapeutically effective amount of a composition comprising a vector comprising a CRISPRa system. The CRISPRa system increases expression of at least one endogenous gene in the subject, thereby vaccinating against cancer in the subject.

In still another aspect, the invention includes a method of treating cancer in a subject in need thereof. The method comprises administering to the subject a therapeutically effective amount of a composition comprising a vector comprising a CRISPRa system. The CRISPRa system increases expression of at least one endogenous gene in the subject, thereby treating the cancer in the subject.

Another aspect of the invention includes a method of vaccinating against cancer in a subject in need thereof. The method comprises obtaining a cancer cell from the subject, determining at least one mutated endogenous gene, and designing a CRISPRa system comprising an sgRNA library specific for the at least one mutated endogenous gene. A therapeutically effective amount of a composition comprising the CRISPRa system is administered to the subject, thereby vaccinating against cancer in the subject.

Yet another aspect of the invention includes a method of vaccinating against cancer in a subject in need thereof. The method comprises obtaining a cancer cell from the subject, determining at least one mutated endogenous gene, and designing a CRISPRa system comprising an sgRNA library specific for the at least one mutated endogenous gene. A cell is contacted with a composition comprising the CRISPRa system, wherein the CRISPRa system increases expression of the at least one mutated endogenous gene resulting in a modified cell. A therapeutically effective amount of a composition comprising the modified cell is administered to the subject, thereby vaccinating against cancer in the subject.

Still another aspect of the invention includes a method of treating cancer in a subject in need thereof. The method comprises obtaining a cancer cell from the subject, determining at least one mutated endogenous gene, and designing a CRISPRa system comprising an sgRNA library specific for the at least one mutated endogenous gene. A therapeutically effective amount of a composition comprising the CRISPRa system is administered to the subject, thereby treating the cancer in the subject.

In another aspect, the invention includes a method of treating cancer in a subject in need thereof. The method comprises obtaining a cancer cell from the subject, determining at least one mutated endogenous gene, and designing a CRISPRa system comprising an sgRNA library specific for the at least one mutated endogenous gene. A cell is contacted with a composition comprising the CRISPRa system. The CRISPRa system increases expression of the at least one mutated endogenous gene resulting in a modified cell. A therapeutically effective amount of a composition comprising the modified cell is administered to the subject, thereby treating the cancer in the subject.

In another aspect, the invention includes a method of generating an anti-tumor response in a subject. The method comprises contacting a cell with a composition comprising a CRISPRa system. The CRISPRa system increases expression of a plurality of endogenous genes resulting in a modified cell. A therapeutically effective amount of a composition comprising the modified cell is administered to the subject, thereby generating an anti-tumor response.

In yet another aspect, the invention includes a composition comprising a cancer vaccine comprising a modified cell comprising a CRISPRa system capable of increasing expression of a plurality of endogenous genes.

In yet another aspect, the invention includes a composition comprising an AAV vector comprising a CRISPRa system capable of increasing expression of a plurality of endogenous genes.

Another aspect of the invention includes a vector comprising two sgRNA cassettes in a CRISPRa system, wherein the first sgRNA cassette is used for activation of antigen presentation machinery, and the second sgRNA cassette is used for activation of patient-specific mutated endogenous genes, either in single gene or pooled format.

Yet another aspect of the invention includes a method of treating cancer in a subject in need thereof. The method comprises administering to the subject a therapeutically effective amount of a composition comprising a vector comprising a CRISPRa system. The CRISPRa system increases expression of at least one antigen presentation gene in the subject, thereby treating the cancer in the subject.

Still another aspect of the invention includes a composition comprising an sgRNA library, wherein the sgRNA library comprises a plurality of sgRNAs that target a plurality genes in the cell.

In another aspect, the invention includes a vector comprising the nucleic acid sequence of SEQ ID NO: 24,105.

In yet another aspect, the invention includes a vector comprising the nucleic acid sequence of SEQ ID NO: 24,106.

In still another aspect, the invention includes a method treating cancer in a subject in need thereof. The method comprises contacting a cell with a first AAV vector comprising a CRISPRa system, and a second AAV vector comprising dCas9. The CRISPRa system increases expression of at least one endogenous gene resulting in a modified cell. A therapeutically effective amount of a composition comprising the modified cell is administered to the subject, thereby treating the cancer in the subject.

In various embodiments of the above aspects or any other aspect of the invention delineated herein, the CRISPRa system comprises an sgRNA library. In certain embodiments, the CRISPRa system comprises an sgRNA library comprising a plurality of sgRNAs. In certain embodiments, the sgRNA library comprises at least one sgRNA that targets at least one endogenous gene in the cell. In certain embodiments, the sgRNA library comprises a plurality of sgRNAs that target a plurality of endogenous genes in the cell. In certain embodiments, the sgRNA library comprises a plurality of sgRNAs that target a plurality of antigen presentation genes in the cell. In certain embodiments, the sgRNAs are customized.

In certain embodiments, the sgRNA library comprises at least one sequence selected from the group consisting of SEQ ID NOs. 1-37. In certain embodiments, at least one of the sgRNAs comprises a nucleotide sequence selected from the group consisting of SEQ ID NOs: 23,886-24,104. In certain embodiments, the plurality of sgRNAs comprise at least one sgRNA selected from the group consisting of SEQ ID NOs: 23,886-24,104. In certain embodiments, the plurality of sgRNAs comprise the nucleotide sequences consisting of SEQ ID NOs: 23,886-24,104. In certain embodiments, the plurality of sgRNAs comprise at least one sgRNA selected from the group consisting of SEQ ID NOs: 51-259. In certain embodiments, the plurality of sgRNAs comprise the nucleotide sequences consisting of SEQ ID NOs: 51-259. In certain embodiments, the plurality of sgRNAs comprise at least one sgRNA selected from the group consisting of SEQ ID NOs: 260-348. In certain embodiments, the plurality of sgRNAs comprise the nucleotide sequences consisting of SEQ ID NOs: 260-348. In certain embodiments, the plurality of sgRNAs comprise at least one sgRNA selected from the group consisting of SEQ ID NOs: 349-4,187. In certain embodiments, the plurality of sgRNAs comprise the nucleotide sequences consisting of SEQ ID NOs: 349-4,187. In certain embodiments, the plurality of sgRNAs comprise at least one sgRNA selected from the group consisting of SEQ ID NOs: 4,188-7,980. In certain embodiments, the plurality of sgRNAs comprise the nucleotide sequences consisting of SEQ ID NOs: 4,188-7,980. In certain embodiments, the plurality of sgRNAs comprise at least one sgRNA selected from the group consisting of SEQ ID NOs: 7,981-11,808. In certain embodiments, the plurality of sgRNAs comprise the nucleotide sequences consisting of SEQ ID NOs: 7,981-11,808. In certain embodiments, the plurality of sgRNAs comprise at least one sgRNA selected from the group consisting of SEQ ID NOs: 11,809-23,776. In certain embodiments, the plurality of sgRNAs comprise the nucleotide sequences consisting of SEQ ID NOs: 11,809-23,776. In certain embodiments, the plurality of sgRNAs comprise at least one sgRNA selected from the group consisting of SEQ ID NOs: 23,779-23,885. In certain embodiments, the plurality of sgRNAs comprise the nucleotide sequences consisting of SEQ ID NOs: 23,779-23,885.

In certain embodiments, the CRISPRa system comprises a nucleic acid encoding dCas9-VP64, and a nucleic acid encoding MS2-p65-HSF1 and a genome-scale lentiviral SAM CRISPRa sgRNA library. In certain embodiments, the CRISPRa system comprises a nucleic acid encoding dCas9-VP64, a nucleic acid encoding MS2-p65-HSF1, and a nucleic acid encoding a genome-scale lentiviral SAM CRISPRa sgRNA library.

In certain embodiments, the cell is from a cancer cell line. In certain embodiments, the cell is from the subject. In certain embodiments, the cell from the subject is a cancer cell.

In certain embodiments, the subject is a mammal. In certain embodiments, the subject is a human.

In certain embodiments, administering the therapeutically effective amount of the composition comprises a one dose, a two dose, a three dose, a four dose, or a multi-dose treatment.

In certain embodiments, the method further comprises contacting the cell with a substance that induces senescence in the cell prior to administering to the subject. In certain embodiments, the substance that induces senescence in the cell is mitomycin.

In certain embodiments, the cancer is selected from the group consisting of breast cancer, lung cancer, pancreatic cancer, melanoma, glioma, hepatoma, colon cancer, pancreatic cancer and brain cancer.

In certain embodiments, the method further comprises administering an additional treatment. In certain embodiments, the additional treatment is selected from the group consisting of chemotherapy, radiation, surgery, an immune checkpoint inhibitor, and an immune checkpoint blockade (ICB) antibody. In certain embodiments, the immune checkpoint inhibitor blocks CTLA-4 or PD1 or other immune checkpoint targets. In certain embodiments, the immune checkpoint inhibitor is a monoclonal antibody selected from the group consisting of anti-CTLA4 and anti-PD1.

In certain embodiments, administering the composition alters the tumor microenvironment. In certain embodiments, administering the composition augments host immune responses against established tumors.

In certain embodiments, the composition is administered intratumorally.

In certain embodiments, the composition comprises a vector. In certain embodiments, the sgRNA library is cloned and packaged into an AAV vector.

In certain embodiments, the CRISPRa system is in an AAV vector, a lentiviral vector, or an adenoviral vector. In certain embodiments, the AAV vector is AAV2, AAV8, AAV9, AAV-DJ, or other AAV serotypes.

In certain embodiments, the cell comprises a plurality of mutated endogenous genes, and the activation system comprises an sgRNA library specific for the plurality of mutated endogenous genes and increases expression of the plurality of mutated endogenous genes.

In certain embodiments, determining the subject-specific mutated endogenous gene or genes comprises whole-exome sequencing of the cancer cell and whole-exome sequencing of a non-cancer cell from the subject. The sequencing data from the cancer cell is compared to sequencing data from the non-cancer cell and at least one mutation is determined. Thereby, the subject-specific mutated endogenous gene or genes is determined.

In certain embodiments, the mutation is selected from the group consisting of a single nucleotide polymorphism (SNP), an insertion, a deletion, a frameshift, and a rearrangement.

In certain embodiments, the endogenous genes contain detected somatic mutations.

In certain embodiments, the vector comprises the nucleic acid of SEQ ID NO: 38. In certain embodiments, the first AAV vector comprises the nucleic acid sequence of SEQ ID NO: 38 or SEQ ID NO: 49. In certain embodiments, the second AAV vector comprises the nucleic acid sequence of SEQ ID NO 24,105 or SEQ ID NO 24,106.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A is a schematic of the experimental design for cell-based endogenous gene tumor vaccination used in this study. The E0771 version of CRISPR activation based vaccine (E0771-CAVac, or CAVac for short) was generated by transducing E0771 cells with lentiviral vectors carrying CRISPRa machinery and a genome-scale CRISPR activation sgRNA library, then treating the cells with mitomycin. For prophylactic vaccination, C57BL/6J mice were pre-inoculated with cell-based CAVac, and then challenged by transplanting syngeneic tumors with identical cell of origin or tumors with different cell of origin. For therapeutic vaccination, syngeneic orthotopic breast tumors were established by intramammary transplantation of E0771 cells into C57BL/6J mice. After transplantation, tumor-bearing mice were treated with PBS, or E0771-CAVac at indicated times. Tumor sizes along time were measured to assess the therapeutic effects. FIG. 1B shows prophylactic efficacy of E0771-CAVac against syngeneic tumors with identical cell of origin. Growth curves of orthotopic transplanted tumors of E0771 in C57BL/6J mice pre-inoculated with PBS or E0771-CAVac. (PBS treated mice, n=7; E0771-CAVac treated mice at indicated dates prior to tumor induction. CAVac@-d14, CAVac treatment at dpi=−14 (n=5); CAVac@-d7, dpi=−7 (n=6); CAVac@-d3, dpi=−3 (n=6)). Two-way ANOVA using Sidak's multiple comparisons test for the following comparisons on study endpoint (dpi=23): CAVac@-d14 vs. PBS, p<0.0001; CAVac@-d7 vs. PBS, p<0.0001; CAVac@-d3 vs. PBS, p<0.0001. Two-sided Kolmogorov-Smirnov (KS) test of whole-curves for the following comparisons: CAVac@-d14 vs. PBS, p<2.2e-16; CAVac@-d7 vs. PBS, p<2.2e-16; CAVac@-d3 vs. PBS, p=9.62e-11. FIG. 1C shows therapeutic efficacy of E0771-CAVac against established orthotopic tumors. $2 \times 10^6$ E0771 cells were transplanted into the mammary fatpad of syngeneic C57BL/6J mice. Tumor-bearing mice were treated with PBS or E0771-CAVac at indicated times (arrows), and tumor sizes were measured after these treatments. (PBS treated mice, n=11; E0771-CAVac, n=8). Two-way ANOVA using Sidak's multiple comparisons test for the following comparisons on the last two time points (dpi=24 and 28): CAVac vs. PBS, p=0.0009 & 0.0488 respectively. Two-sided KS test of late-stage curves (13 dpi onward) of CAVac vs. PBS, p=0.016. FIG. 1D shows Haemotoxylin and Eosin (H&E) staining of representative end-point tumor sections from PBS and E0771-CAVac treated mice. Arrows point to inflamed tumor regions with lymphocyte infiltration. FIG. 1E shows CD8 immunohistochemistry (IHC) staining of representative end-point tumor sections from PBS and E0771-CAVac treated mice. Arrows point to inflamed tumor regions with CD8$^+$ cells. FIGS. 1F-1G show results from ELISPOT experiments for CAVac. Tumor-specific immune responses in tumor-bearing C57BL/6J mice in different treatment groups were assessed by measuring the ratios of tumor-stimulated IFNγ-producing splenocytes with ELISPOT assay, using mitomycin-treated tumor cells as the stimulants. Spots were counted using CTL Immunospot Analyzer. FIG. 1F shows representative pictures of spots obtained from triplicates per mouse with three mice for each treatment group. FIG. 1G shows quantification of ELISPOT experiment of PBS (n=4), cell lysate (n=4) or CAVac (n=5). Two sided unpaired t-test for the following comparisons: PBS vs. cell lysate not significant; CAVac vs. PBS, p=0.0159; CAVac vs. cell lysates, p=0.0317. Results were shown from an average of 2 independent experiments. FIG. 1H is a schematic of an experiment to test the combinatory therapeutic effects of CAVac plus immune checkpoint blockade or CD4$^+$ T cells depletion. FIG. 1I shows combinatorial therapeutic efficacy of CAVac plus anti-CTLA4 or anti-CD4 against established breast tumors of E0771. Experiment in (FIG. 1I) is also plotted separately for anti-CTLA4 (FIG. 1J) and anti-CD4 (FIG. 1IK) respectively for better visualization and statistics of data. (PBS treated mice, n=8; E0771-CAVac treated mice, n=8; anti-CTLA4 treated mice; n=6; CAVac+anti-CTLA4 combination treated mice, n=4; anti-CD4 treated mice; n=3; CAVac+anti-CD4 combination treated mice, n=6). FIG. 1J shows combinatorial therapeutic efficacy of CAVac plus anti-CTLA4 against established breast tumors of E0771. Tumor growth curves in syngeneic C57BL6J mice that were treated by PBS, E0771-CAVac, anti-CLTA4, or the combination with scheme indicated in FIG. 1H. Two-sided KS test of whole-curves for the following comparisons: CAVac vs. PBS, p=0.5899; anti-CTLA4 vs. PBS, p=0.00537; Combination vs. PBS p=1.068e-08; Combination vs. anti-CTLA4, =3.437e-05; Combination vs. CAVac, =1.375e-08. Two-way ANOVA using Turkey's multiple comparisons test at last time point (dpi=27) for the following comparisons: E0771-CAVac vs. PBS, p<0.0001; anti-CTLA4 vs. PBS, p<0.0001; Combination vs. PBS, p<0.0001; Combination vs. anti-CTLA4, p=0.016; Combination vs. CAVac, p<0.0001. FIG. 1K shows combinatorial therapy efficacy of CAVac plus anti-CD4 against established syngeneic tumors. Tumor growth curves in C57BL/6J mice treated by PBS, E0771-CAVac, anti-CD4, or the combination administrated as indicated. Two-sided KS test of whole-curves for the following comparisons: anti-CD4 vs. PBS, p=2.02e-5; Combination vs. PBS p=6.89e-6; Combination vs. anti-CD4, =0.81; Combination vs. CAVac, =1.49e-05. Two-way ANOVA using Turkey's multiple comparisons test at last time point (dpi=27) for the following comparisons: E0771-CAVac vs. PBS, p<0.0001; anti-CD4 vs. PBS, p<0.0001; Combination vs. PBS p<0.0001; Combination vs. anti-CD4, p=0.05; Combination vs. CAVac, p<0.0001. Error bars: All data points in this figure were presented as mean±s.e.m. Asterisks: * p<0.05,  p<0.01, * p<0.001.

FIG. 2A shows schematics of an experimental design used in the study. AAV-CAVac was generated by cloning of a genome-scale activation sgRNA library mSAM into AAV-CRISPRa vector, followed by pooled viral packaging into AAV9. C57BL/6J mice with established tumor(s) were treated with AAV-CAVac. FIG. 2B shows therapeutic efficacy of AAV-CAVac against established orthotopic syngeneic E0771 tumors by intratumoral administration. Growth curves of orthotopic transplanted E0771 tumors in C57BL/6J mice treated with PBS, AAV-Vector, and AAV-CAVac at indicated times (arrows). (PBS treated mice, n=8; AAV-Vector treated mice, n=6; AAV-CAVac treated mice, n=6). Two-way ANOVA using Turkey's multiple comparisons test at last time point (dpi=31) for the following comparisons: AAV-CAVac vs. PBS, p<0.0001; AAV-CAVac vs. AAV-Vector, p=0.0224. Two-sided KS test of whole-curves for the following comparisons: PBS vs. AAV-Vector, p=0.26; AAV-CAVac vs. PBS, p=0.00014; AAV-CAVac vs. AAV-Vector, p=0.0048. FIG. 2C shows therapeutic efficacy of AAV-CAVac against established orthotopic syngeneic B16F10 tumors by intratumoral administration. Growth curves of orthotopic transplanted B16F10 tumors in C57BL/6J mice treated with PBS and AAV-CAVac at indicated times (arrows). (PBS treated mice, n=8; AAV-vector treated mice, n=4; AAV-CAVac treated mice, n=4). Two-way ANOVA using Turkey's multiple comparisons test at last two time points (dpi=21 and 25) for the following comparisons: AAV-CAVac vs. PBS, p<0.0001 for both time points; AAV-CAVac vs. AAV-Vector, p=0.0008 at dpi=21. FIG. 2D shows H&E staining of representative end-point E0771 syngeneic tumor sections from PBS, AAV-Vector, and AAV-CAVac treated mice. Arrows point to inflamed tumor regions with lymphocyte infiltration. FIG. 2E shows CD8 IHC staining of representative end-point E0771 syngeneic tumor sections from PBS, AAV-Vector, and AAV-CAVac treated mice. Arrows point to inflamed tumor regions with CD8+ cells. FIGS. 2F-2G show results from ELISPOT experiments for AAV-CAVac. Tumor-specific immune responses in tumor-bearing C57BL/6J mice in different treatment groups were assessed by measuring the ratios of tumor-stimulated IFNγ-producing splenocytes with ELISpot assay, using mitomycin-treated tumor cells as the stimulants. Spots were counted using CTL Immunospot Analyzer. FIG. 2F shows representative pictures of spots obtained from triplicates per mouse with four mice for each treatment group (PBS, AAV-Vector and AAV-CAVac). FIG. 2G shows quantification of ELISPOT experiment of PBS (n=4), AAV-Vector (n=7) and AAV-CAVac (n=9). Datapoints from all mice from FIG. 2F were shown. Two sided Mann-Whitney test for AAV-CAVac vs. PBS, p=0.0028; AAV-CAVac vs. AAV-Vector, p=0.005. Results were shown from the combination of 2 independent experiments. Error bars: All data points in this figure were presented as mean±s.e.m. Asterisks: * p<0.0,  p<0.01, * p<0.001.

FIG. 3A is a schematic of the experimental design. Syngeneic orthotopic E0771 tumor bearing mice were treated with PBS or AAV-CAVac. Whole immune population within the tumor microenvironment was purified by anti-CD45 enrichments by FACS (CD45+ tumor infiltrating immune cells, TIIs), and subjected to single cell RNA-seq. FIG. 3B shows a t-SNE based dimensional reduction plot showing the clustering patterns of immune cell populations from all TIIs sequenced. Clusters 0 to 10 have 1,256, 1,215, 1213, 964, 901, 870, 302, 266, 181, 180, and 101 cells, respectively. FIG. 3C shows a t-SNE based dimensional reduction plot showing the clustering patterns of immune cell populations based on TIIs scRNAseq data from mice treated with PBS (n=5,383 cells) or AAV-CAVac (n=2,075 cells). FIG. 3D is a bar plot showing proportions of cells in each of the 11 clusters of the whole CD45 immune cells from mice treated with PBS and AAV-CAVac, respectively. Differences in cluster-specific proportions were assessed by two-sided Fischer's exact test (***, p<0.0001). FIG. 3E is a heat map of cluster-specific markers identified from scRNA-seq. Of note, cluster 0 is marked by MHC-II molecules, cluster 1 is marked by Ifit family genes, and cluster 9 is marked by T cell specific markers including Cd3d, Cd3g and Gzmb.

FIGS. 4A-4Q illustrate exome-guided AAV-CRISPRa based mutated gene set activation as precision multiplexed tumor vaccination (AAV-PCAVac or p-MAEGI, which are used interchangeably herein) against established tumors. FIG. 4A is a schematic of the experimental design. Genomic DNA of cancer cells and normal tissues were extracted, purified, and subjected to whole-exome sequencing. Somatic SNPs and indels in cancer cells were identified by comparison to matched normal tissues, and the CRISPRa sgRNAs targeting these mutants were designed. The mutated gene set customized sgRNA library was synthesized and pool-cloned into the AAV-CRISPRa vector, which was packaged into AAV9 to generate AAV-PCAVac. FIGS. 4P-4Q are growth curves of E0771 local (FIG. 4P) and distant (FIG. 4Q) tumors in mice treated by AAV-Vector (n=18), or AAV-PCAVac (AAV-p-MAEGI) (n=18). Inset, pie charts detailing the response rates for each treatment. (FIG. 4P) Two-way ANOVA: AAV-p-MAEGI vs. AAV-Vector, p<0.0001. (FIG. 4Q) Two-way ANOVA: AAV-p-MAEGI vs. AAV-Vector, p=0.0003. Error bars: All data points in this figure are presented as mean±s.e.m. Asterisks: * p<0.05,  p<0.01, * p<0.001.

FIG. 5A shows library representation of genome-scale CRISPRa library (mouse SAM) transduced E0771 cells from 6 infection replicates from two independent experiments. Out of the 66,749 sgRNAs in the library, the six replicates cover from 99.44% to 99.69% of the total sgRNAs. FIG. 5B is a heat map of pairwise Spearman correlations of library representation of mSAM transduced E0771 cells between the 6 infection replicates from two independent experiments. Pairwise correlation coefficients range from 0.88 to 0.93 between infection replicates, indicating high reproducibility. FIG. 5C shows the expression of dCas9 protein in dCas9-VP64 transduced cell lines E0771-dCas9 and E0771-dCas9-MPH confirmed by western blot using monoclonal antibody against Cas9. Anti-GAPDH was used as an internal control. FIG. 5D shows quantification of gene activation by CRISPRa at mRNA level based on qPCR assay for genes including Cd70, Cd80, Cd86, $Ifn\alpha4$, $Ifn\beta1$, and $Ifn\gamma$. Two-sided unpaired t test for the following comparisons, each gene vs. vector: Cd70, p<0.0001; Cd80, p<0.001; Cd86, p<0.05; $Ifn\alpha4$, p<0.001; $Ifn\beta1$, p<0.001; $Ifn\gamma$, p<0.0001.

FIGS. 6A-6H illustrate the finding that genome-scale activation of endogenous genes leads to robust immune rejection of syngeneic tumors. FIG. 6A shows growth curves of SAM activated E0771 cell induced syngeneic orthotopic tumor. As compared to vector transduced cells (n=8), SAM transduced E0771 cells (n=50) generated tumors were often quickly rejected by the C57BL/6J host. As compared to vector transduced cells (n=8), SAM transduced E0771 cells (n=50) generated tumors were often quickly rejected by the C57BL/6J host. Two-sided KS test, p<2.2e-16. FIG. 6B shows spider plot growth curves of SAM activated (n=50) E0771 cell induced syngeneic orthotopic tumor. Most (42/50, 84%) of SAM E0771 tumors were rejected by C57BL/6J mice; None (0/8) of vector E0771 tumors were rejected. FIG. 6C shows growth curves of SAM activated E0771 cell induced orthotopic tumor in syngeneic immunocompetent mice (C57BL/6J, n=5) and two strains of immunodeficient mice (Nu/Nu, n=4; $Rag1^{-/-}$, n=5). Two-sided KS test for the following comparisons of full-curve: C57BL6/J vs. Nu/Nu, p=3.2e-06; C57BL/6J vs. $Rag1^{-/-}$, p=1.97e-07; Nu/Nu vs. $Rag1^{-/-}$, p=0.22; Two-sided KS test for the following comparisons of late-stage curve (14 dpi onward): C57BL/6J vs. Nu/Nu, p=3.2e-06; C57BL/6J vs. $Rag1^{-/-}$, p=6.1e-07; Nu/Nu vs. $Rag1^{-/-}$, p=0.022; Two-way ANOVA using Tukey's multiple comparisons test for the last timepoint (20 dpi) of the following comparisons: C57BL6/J vs. Nu/Nu, p<0.0001; C57BL6/J vs. Rag1$^{-/-}$, p<0.0001; Nu/Nu vs. Rag1$^{-/-}$, p<0.0001. FIGS. 6D-6F show spider plot growth curves of SAM activated (n=50) E0771 cell induced syngeneic orthotopic tumor. Most (4/5, 80%) of SAM E0771 tumors were rejected by (FIG. 6D) C57BL/6J mice; None (0/9) of SAM E0771 tumors were rejected by (FIG. 6E) Nu/Nu (0/4) or (FIG. 6F) Rag1$^{-/-}$ (0/5) mice. FIG. 6G shows growth curves of SAM activated E0771 cell induced syngeneic orthotopic tumor under T cell depletion. SAM transduced E0771 cells (n=11) generated tumors were quickly rejected by the C57BL/6J host if the mice were not treated. Depleting T cells by treating mice with both anti-CD4 and anti-CD8 (n=4) rendered the tumors capable to grow rapidly C57BL/6J host. Two-sided KS test, untreated vs anti-CD4+ anti-CD8 treated p<7.9e-10. FIG. 6H shows spider plot growth curves of SAM activated E0771 cell induced syngeneic orthotopic tumor under T cell depletion. All (11/11, 100%) of SAM E0771 tumors were rejected by C57BL/6J mice untreated; None (0/4) of vector E0771 tumors were rejected by C57BL/6J mice treated with both anti-CD4 and anti-CD8. Error bars: All data points in this figure were presented as mean±s.e.m. Asterisks: * p<0.05,  p<0.01, * p<0.001.

FIG. 7A shows growth curves of E0771-SAM escaper tumors in C57BL/6J mice, either untreated (n=13), or treated by checkpoint blockade antibodies anti-PD1 (n=11) or anti-CTLA4 (n=11). When treated with either anti-PD1 (n=11) or anti-CTLA4 (n=11), all E0771-SAM transplanted C57BL/6J mice rejected the tumors. Two-sided KS test for these comparisons: anti-PD1 vs untreated, p=6.008e-06; anti-CTLA4 vs untreated, p=2.853e-06. FIGS. 7B-7D show spider plot growth curves of E0771-SAM tumors in C57BL/6J mice, either (FIG. 7B) untreated (n=13), or treated by checkpoint blockade antibodies (FIG. 7C) anti-PD1 (n=11) or (FIG. 7D) anti-CTLA4 (n=11). In the duration of study (28 dpi), of the 13 E0771-SAM transplanted mice in untreated group, 5/13 completely rejected tumor, and 8/13 either grew larger or remained sizable tumor; All anti-PD1 (11/11) and anti-CTLA4 (11/11) treated mice completely rejected E0771-SAM tumors. Error bars: All data points in this figure were presented as mean±s.e.m. Asterisks: * p<0.05,  p<0.01, * p<0.001.

FIGS. 8A-8F are spider plots of tumor growth curves of the experiment shown in FIGS. 1A-1F. FIGS. 8A-8B illustrate the therapeutic effect of CAVac on syngeneic orthotopic E0771 tumors in C57BL/6J mice. FIG. 8A shows growth curves of PBS treated E0771 tumors. FIG. 8B shows growth curves of CAVac treated E0771 tumors. FIGS. 8C-8F show growth curves of synergistic effect testing of CAVac and CTLA4 blockade or CD4$^+$ T cell depletion on syngeneic orthotopic E0771 tumors in C57BL/6J mice. FIG. 8C is a spider plot of tumor growth curves of PBS treated E0771 tumors. FIG. 8D is a spider plot of tumor growth curves of CAVac treated E0771 tumors. FIG. 8E is a spider plot of tumor growth curves of anti-CTLA4 and anti-CTLA4+ CAVac treated E0771 tumors. FIG. 8F is a spider plot of tumor growth curves of anti-CD4 and anti-CD4+CAVac treated E0771 tumors. FIG. 8G is a spider plot of anti-CTLA4+CAVac treated E0771 tumors with data of long-time points after tumor rejection. Data from PBS-treated tumors in FIG. 8C was used as a control. Arrowhead points out that no tumor relapse was observed in these mice after 90 days, indicating the anti-tumor responses induced by combining CAVac and anti-CTLA4 were long-lasting.

FIG. 9A shows results from testing the effect of untransduced E0771 lysate against established syngeneic orthotopic E0771 tumors. Tumor-bearing mice were treated with PBS or E0771 lysate at indicated times (arrows). (PBS treated mice, n=6; E0771 lysate, n=10). Two-sided KS test for E0771 lysate vs. PBS, p=0.77. FIG. 9B shows results from testing the effect of active CAVac and inactivated CAVac against established syngeneic orthotopic E0771 tumors. (PBS treated mice, n=4; CAVac, n=3; CAVac lysate, n=3). Tumor-bearing mice were treated with PBS, CAVac, or CAVac lysate at indicated times (arrows). Two-sided KS test of late-stage curves (17 dpi onward) of the following comparisons: CAVac vs. PBS, p=0.004; CAVac lysate vs. PBS, p=0.97. Two-way ANOVA using Tukey's multiple comparisons test for the last timepoint after tumor induction (24 dpi) of the following comparisons: CAVac vs. PBS, p=0.0004; CAVac lysate vs. PBS, p=0.2115. FIG. 9C shows the single dose effect of CAVac against established syngeneic orthotopic E0771 tumors. Tumor-bearing mice were treated with PBS or CAVac at +3 dpi (arrows). (PBS treated mice, n=6; CAVac@d3 (CAVac at +3 dpi), n=5). Two-way ANOVA using Sidak's multiple comparisons test for the last two timepoint after tumor induction (dpi=24 or 28) of the following comparisons: CAVac@d3 vs. PBS, p=0.013 and p=0.003 respectively. Two-sided KS test of late-stage curves (17 dpi onward) of CAVac vs. PBS, p=0.0078. FIG. 9D shows CD8$^+$ T cell depletion abolished the effect of CAVac against established syngeneic orthotopic E0771 tumors. Tumor-bearing mice were treated with PBS (n=5) or CAVac+anti-CD8 (n=3) at indicated days (upward arrows for CAVac, downward arrows for anti-CD8). Of note, the data of the PBS-treated mice here were same as the five PBS-treated mice (experiment 2) used in FIG. 1I-K, as these treatments were done together. Two-sided KS test of CAVac+anti-CD8 vs. PBS, p=0.78. Error bars: All data points in this figure were presented as mean±s.e.m. Asterisks: * p<0.05,  p<0.01, * p<0.001.

FIGS. 10A-10G illustrate additional spider plot growth curves of AAV-CAVac and combinatorial treatments. FIG. 10A shows quantification of AAV-CRISPRa mediated gene activation at mRNA level based on qPCR assay for genes in minipool, including Cd70, Cd80, Cd86. Two-sided unpaired t test for the following comparisons, each gene vs. vector: Cd70, p<0.0001; Cd80, p<0.001; Cd86, p=0.0054. FIG. 10B is a spider plot of tumor growth curves of PBS treated E0771 tumors. FIG. 10C is a spider plot of tumor growth curves of AAV-Vector treated E0771 tumors. FIG. 10D is a spider plot of tumor growth curves of AAV-CAVac treated E0771 tumors. FIG. 10E is a spider plot of tumor growth curves of PBS treated B16F10 tumors. FIG. 10F is a spider plot of tumor growth curves of AAV-Vector treated B16F10 tumors. FIG. 10G is a spider plot of tumor growth curves of AAV-CAVac treated B16F10 tumors.

FIG. 11A are a series of Violin plots of representative cluster #0 specific differentially expressed genes between AAV-CAVac and PBS treated mice. Cc18 and Cc17 were more highly expressed in AAV-CAVac treated mice (adjusted p=1.6e-33 and p=2.73e-10), whereas Pkm and Aldoa were more highly expressed in PBS treated mice (adjusted p=8.57e-22 and p=4.85e-19). FIG. 11B are a set of Violin plots of representative cluster #1 specific differentially expressed genes between AAV-CAVac and PBS treated mice. Cc18 was more highly expressed in AAV-CAVac treated mice (adjusted p=6.65e-20), whereas Pkm was more highly expressed in PBS treated mice (adjusted p=3.03e-14. FIG. 11C are a series of Violin plots of representative cluster #9 specific differentially expressed genes between AAV-CAVac and PBS treated mice. Cc18 and Gm26917 were more highly expressed in AAV-CAVac treated mice (adjusted p=1.73e-12 and p=1.46e-6), whereas mt-Nd2 and Hmox1 were more highly expressed in PBS treated mice (adjusted p=5.97e-6 and p=9.79e-5).

FIGS. 12A-12E illustrate interrogation of the T cell repertoire in CAVac or AAV-CAVac treated mice using TCR sequencing. FIG. 12A is a schematics of the TCR-seq experimental design. Mice were treated with PBS, CAVac, or AAV-CAVac. Samples including spleens and tumors were harvested from mice for genomic DNA extraction, and subjected to RT-based TCRa/TCRb capture followed by Illumina sequencing. FIG. 12B is a global occupied clonal homeostasis plot showing clone size patterns of TCRseq data from T cell populations in tumors or in spleens. Hyperexpanded clones are shown in black. FIG. 12C is a global clonal proportion plot showing the relative frequency of the top N clones. FIG. 12D is a scatterplot demonstrating positive correlation between endpoint tumor size and Gini-Simpson index of clonal distribution of the TCR repertoire of all TIL samples from CAVac and AAV-CAVac treated mice. Spearman correlation coefficient R=0.5433, p=0.03632. FIG. 12E shows CDR3 amino acid sequences from major (top 3) clones from three example TIL samples from CAVac and AAV-CAVac treated mice.

FIG. 14 illustrates a simplified model of action for vaccination by multiplexed endogenous gene activation. Left, the unvaccinated tumor microenvironment. In a setting of low neoantigen expression, CD8+ T cells detect rare mutant peptides presented on MHC-I by tumor cells and initiate weak tumor killing. Right, the vaccinated tumor microenvironment. Using CRISPRa, mutated genes in tumor cells are overexpressed, leading to amplified production and presentation of neoantigens to CD8+ T cells. With enhanced engagement of the TCR, CD8+ T cells initiate more robust killing in the vaccinated microenvironment.

FIG. 15A shows representative flow cytometry pictures and gating of CD45$^+$, CD3$^+$, CD4$^+$, and CD8$^+$ T cell populations in the spleens (splenocytes) from tumor-bearing mice treated with PBS or AAV-PCAVac. FIG. 15B shows quantification of CD4$^+$ and CD8$^+$ T cell populations from splenocytes of tumor-bearing mice treated with PBS, AAV-Vector, or AAV-PCAVac. From left to right, bar-dot plots with Mann Whitney test for the following comparisons: Fraction of CD4$^+$ T cells in all cells in spleen (absolute fraction); AAV-PCAVac vs. PBS, p=0.0003; AAV-PCAVac vs. AAV-Vector, p=0.0028. Fraction of CD4$^+$ T cells in all CD45$^+$ immune cells in spleen (relative fraction); AAV-PCAVac vs. PBS, p=0.0007; AAV-PCAVac vs. AAV-Vector, p=0.0048. Fraction of CD8$^+$ T cells in all cells in spleen (absolute fraction); AAV-PCAVac vs. PBS, p=0.0032; AAV-PCAVac vs. AAV-Vector, p=0.0016. Fraction of CD8$^+$ T cells in all CD45$^+$ immune cells in spleen (relative fraction);

AAV-PCAVac vs. PBS, p=0.0012; AAV-PCAVac vs. AAV-Vector, p=0.0016. FIG. 15C shows representative flow cytometry pictures and gating of CD45$^+$, CD3$^+$, CD4$^+$, and CD8$^+$ T cell populations in the tumor from tumor-bearing mice treated with PBS or AAV-PCAVac. FIG. 15D shows quantification of CD4$^+$ and CD8$^+$ T cell populations of the tumors from mice treated with PBS or AAV-PCAVac. From left to right, bar-dot plots with Mann Whitney test for the following comparisons: Fraction of CD4$^+$ T cells in all cells in tumor (absolute fraction); AAV-PCAVac vs. PBS, p=0.0007; AAV-PCAVac vs. AAV-Vector, p=0.0256. Fraction of CD4$^+$ T cells in all CD45$^+$ immune cells in tumor (relative fraction); AAV-PCAVac vs. PBS, p=0.0115; AAV-PCAVac vs. AAV-Vector, p=0.0256. Fraction of CD8$^+$ T cells in all cells in tumor (absolute fraction); AAV-PCAVac vs. PBS, p=0.0047; AAV-PCAVac vs. AAV-Vector, p=0.0332. Fraction of CD8$^+$ T cells in all CD45*immune cells in tumor (relative fraction); AAV-PCAVac vs. PBS, p=0.0161, AAV-PCAVac vs. AAV-Vector, p=0.0248. Error bars: All data points in this figure were presented as mean±s.e.m. Asterisks: * p<0.05,  p<0.01, * p<0.001.

FIGS. 16A-16G illustrate boosting the expression levels of single genes or a small set of genes in tumor cells with CRISPRa resulted in tumor rejection in mice. FIG. 16A shows growth curves of Arhgap30 or Nolc1 activated E0771 cell induced syngeneic orthotopic tumor. As compared to vector transduced cells, sg-Arhgap30 or sg-Nolc1 transduced E0771 cells generated tumors that grew slower and often got rejected by the C57Bl/6J host. Two-way ANOVA using Tukey's multiple comparisons test for the following comparisons: sg-Arhgap30 vs. vector, p=0.0003 and p<0.0001 for dpi 20 and 23, respectively; sg-Nolc1 vs. vector, p=0.0123 and p=0.0002 for dpi 20 and 23, respectively. Two-sided Kolmogorov-Smirnov (KS) test for the following comparisons: sg-Arhgap30 vs. vector, p=0.003; sg-Nolc1 vs. vector, p=0.02. FIGS. 16B-16D show spider plot growth curves of Arhgap30 or Nolc1 activated E0771 cell induced syngeneic orthotopic tumor in vector (n=7) (FIG. 16B), sg-Arhgap30 (n=3) (FIG. 16C), and sg-Nolc1 (n=3) (FIG. 16D). All (3/3) of sg-Arhgap30 E0771 tumors were rejected by C57BL/6J mice; 2/3 of sg-Nolc1 E0771 tumors were rejected; None (0/7) of vector E0771 tumors were rejected. FIG. 16E shows quantification of gene activation by CRISPRa at mRNA level based on qPCR assay for genes used in minipools experiment, including Cd70, Cd80, Cd86, Ifnα4, Ifnβ1, and Ifnγ. Two-sided unpaired t test for the following comparisons, each gene vs. vector: Cd70, p<0.0001; Cd80, p<0.001; Cd86, p<0.05; Ifnα4, p<0.001; Ifnβ1, p<0.001; Ifnγ, p<0.0001. FIG. 16F shows growth curves of minipool (sg-Cd70, sg-Cd80, sg-Cd86, sg-Ifnα4, sg-Inβ1, and sg-Ifnγ) activated E0771 cell induced syngeneic orthotopic tumor. As compared to vector transduced cells, minipool transduced E0771 cells generated tumors were all quickly rejected by the C57BL/6J host. Two-sided KS test, p=3.51e-8. FIG. 16G shows spider plot growth curves of minipool activated (n=5) and vector control (n=5) E0771 cell induced syngeneic orthotopic tumor. All (5/5) of minipool E0771 tumors were rejected by C57BL/6J mice; None (0/5) of vector E0771 tumors were rejected. Error bars: All data points in this figure were presented as mean+/- s.e.m. Asterisks: * p<0.05,  p<0.01, * p<0.001.

FIGS. 17A-17C illustrate concepts for two modes of multiplexed vaccination with endogenous gene activation using the CRISPRa system. FIG. 17A is a schematic illustrating mutated antigen presentation and T cell recognition in the unvaccinated tumor microenvironment. FIG. 17B is a schematic illustrating augmentation of the immune response by CRISPRa amplification of mutated endogenous genes in cancer cells. FIG. 17C is a schematic illustrating augmentation of the immune response by CRISPRa amplification of genes encoding antigen-presentation machinery in cancer cells.

Figure 18:
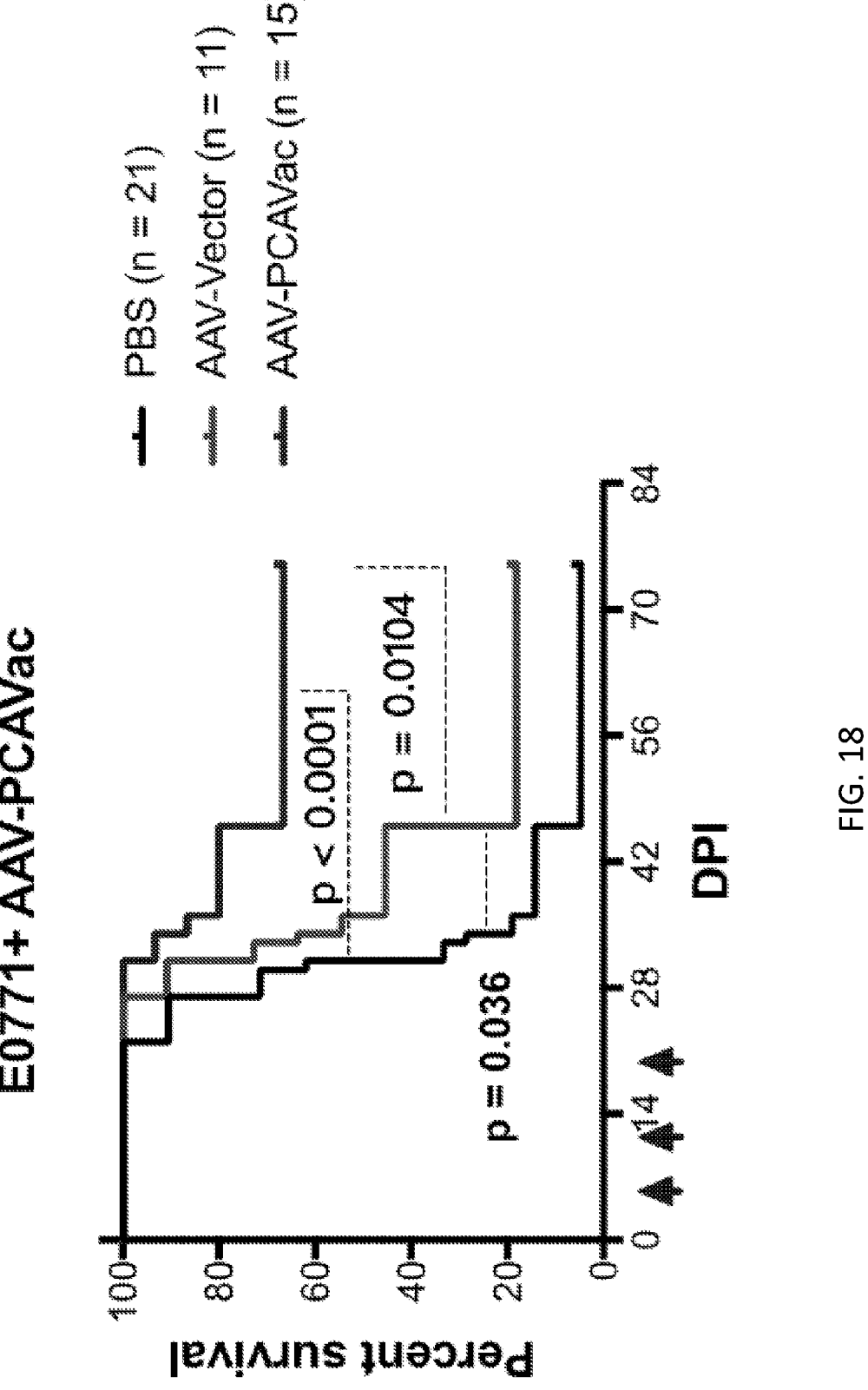

FIG. 18 illustrates the Precision ("Personalized") AAV-PCAVac system as a therapeutic vaccine against triple-negative breast cancer (TNBC). Efficacy of AAV-PCAVac multiplexed endogeneous gene activation is demonstrated in a syngeneic orthotopic model in C57BL/6J host. Shown is a survival curve of E0771 TNBC engrafted in the mammary fatpad of C57BL/6J female mice, treated with PBS, AAV-Vector, or AAV-PCAVac library, which targets a set of most highly mutated genes in E0771 cells as compared to normal mammary fatpad of C57BL/6J female mice. Efficacy is seen in both AAV-Vector and AAV-PCAVac, where AAV-PCAVac has stronger anti-tumor effect. Log-rank test p values were shown for comparison of survival curves.

FIG. 19 is a table showing a summary of treatment responses of PBS, AAV-Vector, and AAV-PCAVac in E0771 TNBC syngeneic orthotopic model in C57BL/6J host.

FIG. 20 is a table showing a summary of treatment responses of PBS, AAV-Vector, and AAV-PCAVac in a two-side tumor induction E0771 TNBC syngeneic orthotopic model in C57BL/6J host.

FIG. 21 is a table showing a summary of E0771 tumor re-challenge after complete regression of first E0771 tumor with AAV-treatment in a syngeneic orthotopic TNBC model in C57BL/6J host.

FIG. 22 illustrates the Precision ("Personalized") AAV-PCAVac system as a therapeutic vaccine against TNBC. Efficacy of AAV-PCAVac multiplexed endogenous gene activation was demonstrated in a syngeneic orthotopic model in C57BL/6J host. Survival curve of E0771 TNBC engrafted in the mammary fatpad of C57BL/6J female mice, treated with PBS, AAV-Vector, AAV-Emut11 library or AAV-PCAVac library. The Emut11 library targets a set of top 11 mutated genes in E0771 cells. Efficacy is seen in both AAV-Vector, AAV-Emut11 and AAV-PCAVac, where AAV-PCAVac has strongest anti-tumor effect. Log-rank test p values were shown for comparison of tumor growth curves to PBS group. * p<0.05;  p<0.01; * p<0.001.

Figures 23, 24:
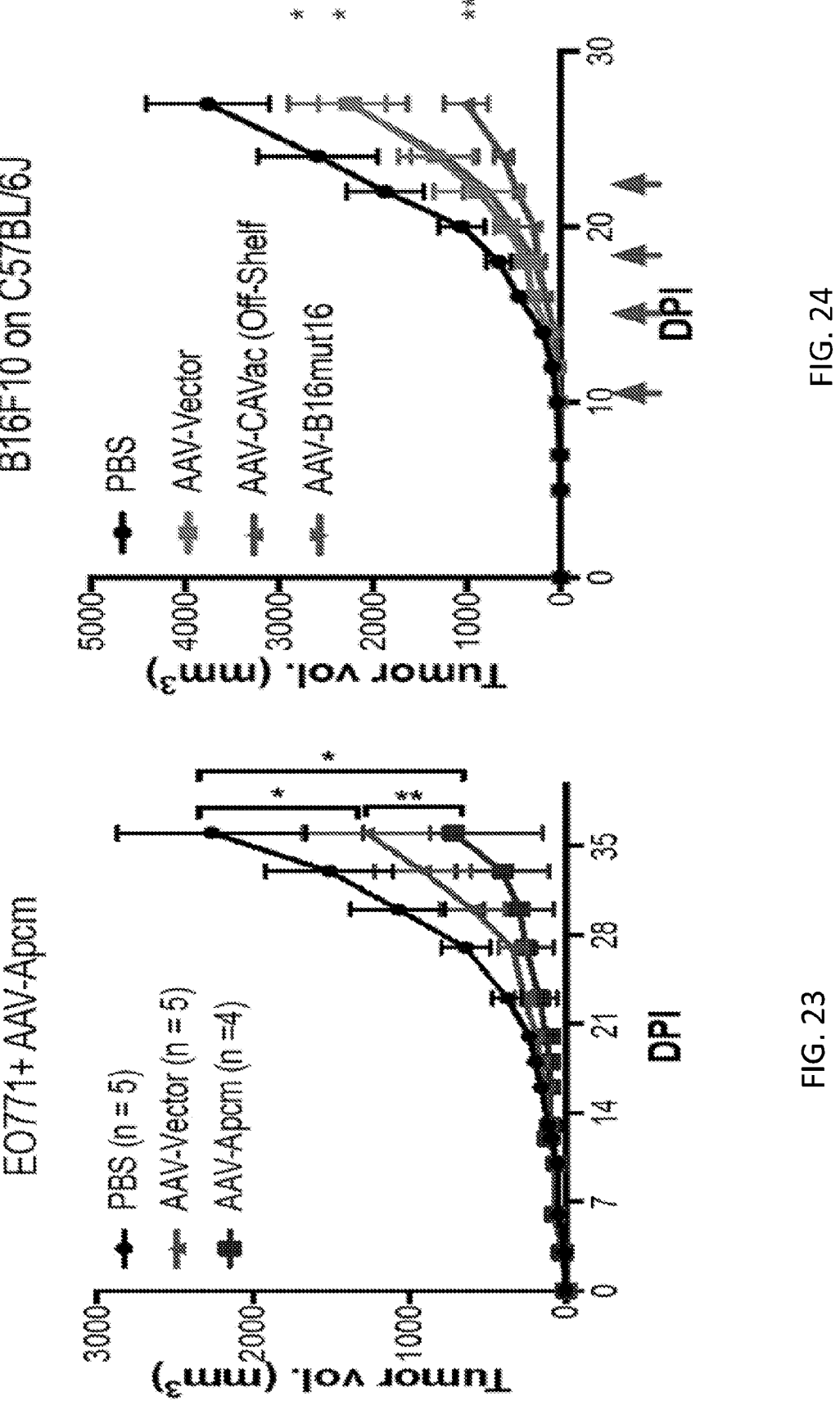

FIG. 23 illustrates an off-the-shelf AAV-APCM system as a therapeutic vaccine. Efficacy of AAV-APCM multiplexed endogenous gene activation is demonstrated in a syngeneic orthotopic model in C57BL/6J host. Shown is a tumor growth curve of E0771 TNBC engrafted in the mammary fatpad of C57BL/6J female mice, treated with PBS, AAV-Vector, or AAV-Apcm library, which targets a small set of genes chosen to elicit immune response (36 genes, 107 sgRNAs). Efficacy is seen in both AAV-Vector and AAV-Apcm, where AAV-Apcm has stronger anti-tumor effect Log-rank test, * p<0.05; ** p<0.01.

FIG. 24 illustrates an off-the-shelf whole-genome AAV-CAVac system as a therapeutic vaccine against melanoma. Therapeutic efficacy of whole-genome gene activation AAV-CAVac (i.e. AAV-SAM) against established orthotopic syngeneic B16F10 tumors by intratumoral administration is demonstrated. Growth curves of orthotopic transplanted B16F10 tumors in C57BL/6J mice treated with PBS and AAV-CAVac at indicated times (arrows) are shown. Log-rank test, * p<0.05; ** p<0.01.

Figures 25, 26:
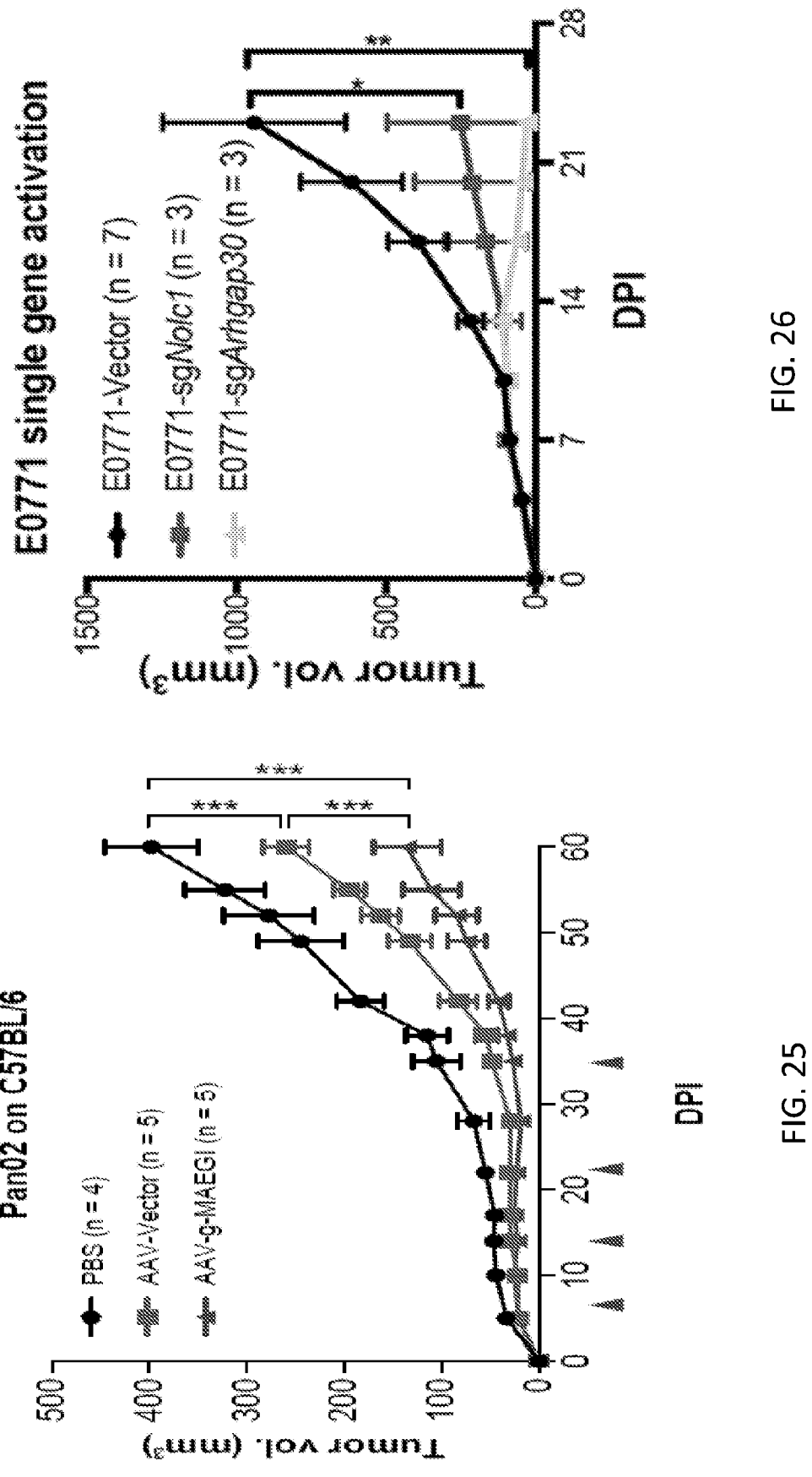

FIG. 25 illustrates an off-the-shelf whole-genome AAV-CAVac system as a therapeutic vaccine against pancreatic cancer. Therapeutic efficacy of whole-genome gene activation AAV-CAVac (also referred to as AAV-g-MAEGI) against established orthotopic syngeneic Pan02 tumors by intratumoral administration is demonstrated. Growth curves of subcutaneous transplanted Pan02 tumors in C57BL/6J mice treated with PBS, AAV-Vector and AAV-CAVac (AAV-g-MAEGI) at indicated times (arrows) are shown. (PBS treated mice, n=4; AAV-vector treated mice, n=5; AAV-g-MAEGI treated mice, n=5). Two-way ANOVA: AAV-Vector vs. PBS, p<0.0001; AAV-g-MAEGI vs. PBS, p<0.0001; AAV-g-MAEGI vs. AAV-Vector, p<0.0001. Asterisks:* p<0.05;  p<0.01, * p<0.001.

FIG. 26 illustrates an off-the-shelf AAV-SingleCAVac system as a prophylatic vaccine. Efficacy of AAV-Single-CAVac endogenous gene activation in a syngeneic orthotopic model in C57BL/6J host is demonstrated. Shown are growth curves of Arhgap30 or Nolc1 activated E0771 cell induced syngeneic orthotopic tumor. As compared to vector transduced cells, sg-Arhgap30 or sg-Nolc1 transduced E0771 cells generated tumors that grew slower and often got rejected by the C57Bl/6J host. Two-way ANOVA using Tukey's multiple comparisons test for the following comparisons: sg-Arhgap30 vs. vector, p=0.0003 and p<0.0001 for dpi 20 and 23, respectively; sg-Nolc1 vs. vector, p=0.0123 and p=0.0002 for dpi 20 and 23, respectively. Two-sided Kolmogorov-Smirnov (KS) test for the following comparisons: sg-Arhgap30 vs. vector, p=0.003; sg-Nolc1 vs. vector, p=0.02. * p<0.05; ** p<0.01.

FIG. 27 is a table illustrating the sgRNA sequences for an AAV-Apcm library (SEQ ID NOs: 23,779-23,885).

FIGS. 28A-28B are a set of tables illustrating the sgRNA sequences of an AAV-Apch library (SEQ ID NOs: 23,886-24,104).

FIGS. 29A-29D illustrate multiplexed activation of endogenous genes as an immunotherapy (MAEGI) in a cellular formulation. FIG. 29A shows schematics for generating genome-scale CRISPR activation (SAM) sgRNA library-transduced cells and analysis of tumorigenic capacity. FIG. 29B shows tumor growth curves of Vector or SAM transduced E0771-dCas9-VP64-MPH cells (E0771-Vector or E0771-SAM). As compared to vector transduced cells (n=8), orthotopic tumors from E0771-SAM cells (n=50) were robustly rejected by the C57BL/6J host. Two-way ANOVA: p<0.0001. FIG. 29C shows tumor growth curves of E0771-SAM cells in syngeneic immunocompetent mice (C57BL/6J, n=5) and two strains of immunodeficient mice (Nu/Nu, n=4; Rag1$^{-/-}$, n=5). Two-way ANOVA: C57BL/6J vs. Nu/Nu, p<0.0001; C57BL/6J vs. Rag1$^{-/-}$, p<0.0001; Nu/Nu vs. Rag1$^{-/-}$, p<0.0001. FIG. 29D shows tumor growth curves of E0771-SAM cells under T cell depletion. Whereas tumors from E0771-SAM cells (n=11) were quickly rejected in C57BL/6J mice, depletion of T cells by α-CD4 and α-CD8 (n=4) enabled rapid tumor growth. Two-way ANOVA test, untreated vs. α-CD4+α-CD8 treated, p<0.0001.

Figures 30A, 30B, 30C, 30D, 30E:
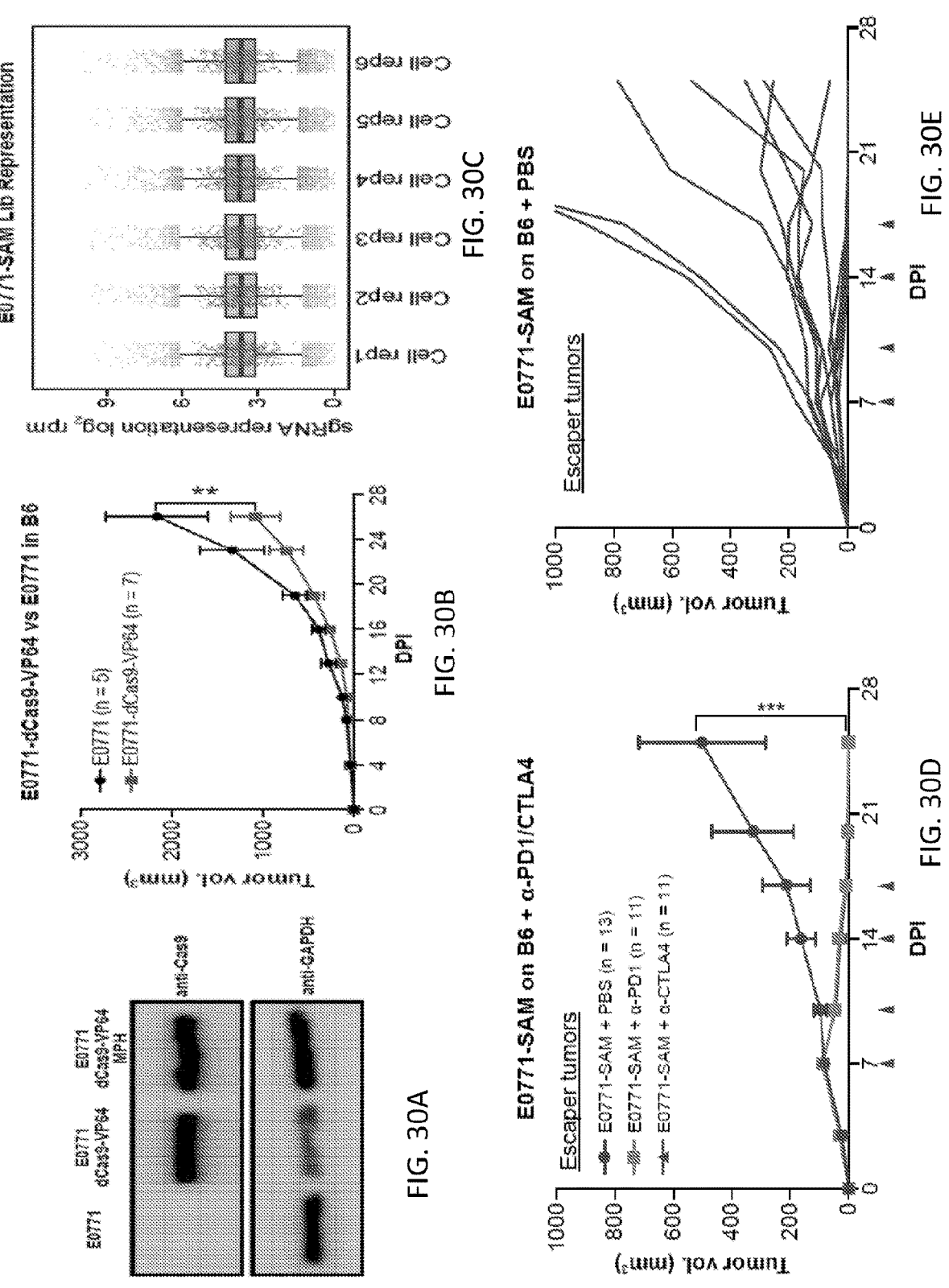
Figures 30F, 30G:
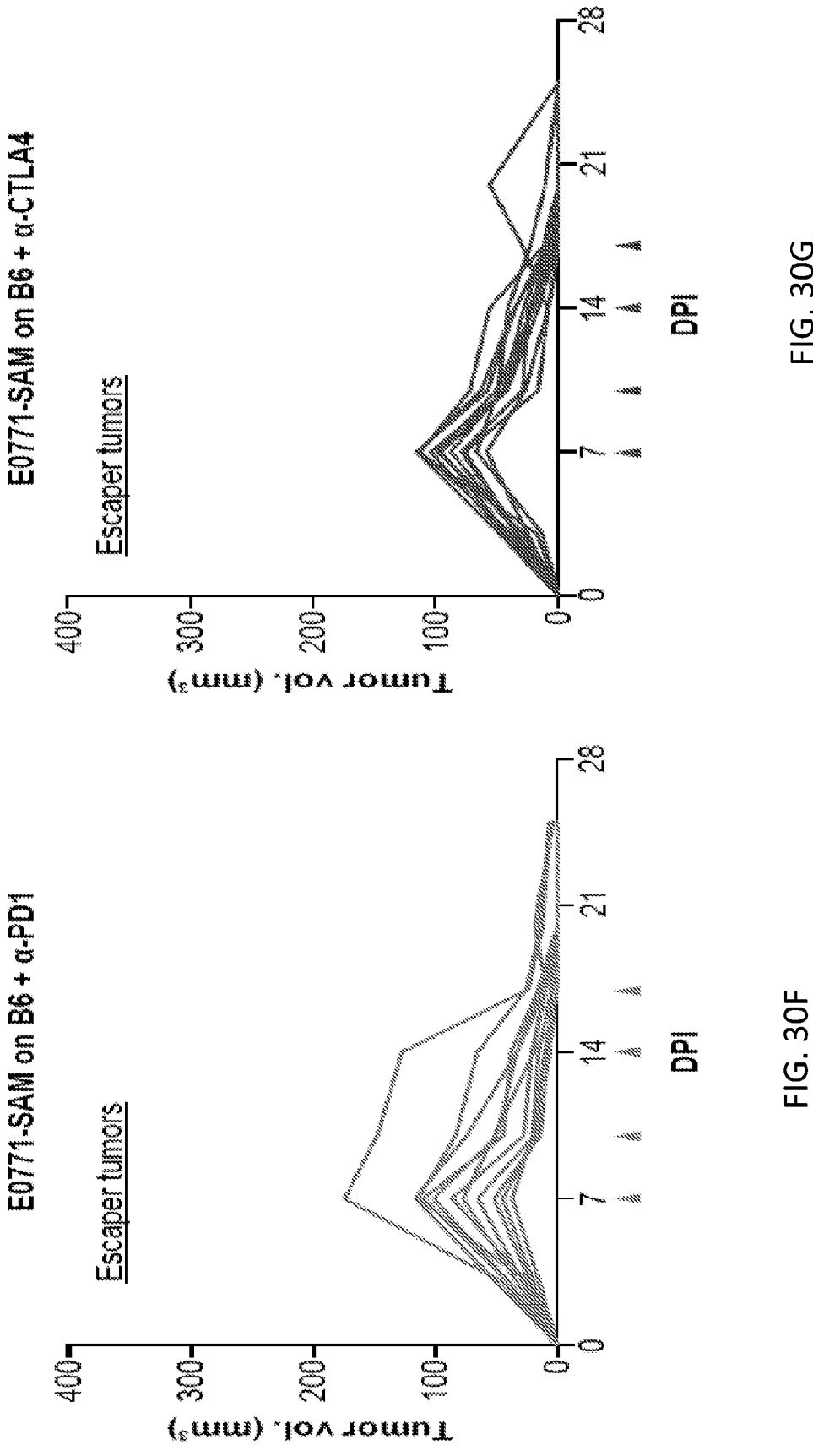

FIGS. 30A-30G illustrate characterization of cells transduced with the CRISPRa system, and escaper tumors formed by CRISPRa library-transduced cells are sensitive to checkpoint antibodies. FIG. 30A shows the expression of dCas9 protein in E0771-dCas9-VP64 and E0771-dCas9-VP64-MPH cell lines confirmed by western blot using a monoclonal antibody against Cas9. Anti-GAPDH was used as an internal control. FIG. 30B shows tumor growth curves of parental E0771 cells compared to E0771 cells transduced to express dCas9-VP64. Two-way ANOVA: p=0.0023. FIG. 30C shows library representation of genome-scale mouse CRISPRa (SAM) library-transduced E0771 cells from 6 infection replicates from two independent experiments. Out of the 66,749 sgRNAs in the library, the six replicates cover from 99.44% to 99.69% of the total sgRNAs. FIG. 30D shows growth curves of E0771-SAM escaper tumors in C57BL/6J mice, either PBS-treated (n=13), or treated by checkpoint blockade antibodies α-PD1 (n=11) or α-CTLA4 (n=11). Arrows indicate time points of treatment. When treated with either α-PD1 (n=11) or α-CTLA4 (n=11), all E0771-SAM transplanted C57BL/6J mice rejected the tumors. Two-way ANOVA: p=0.0003 for PBS vs. α-PD1 or α-CTLA4. (FIGS. 30E-30G) (Related to FIG. 30D) show spider plot growth curves of E0771-SAM escaper tumors in C57BL/6J mice, either (FIG. 30E) PBS-treated (n=13), or treated by checkpoint blockade antibodies (FIG. 30F) α-PD1 (n=11) or (FIG. 30G) α-CTLA4 (n=11). Arrows indicate time points of treatment. Over the duration of study (28 dpi), 5/13 E0771-SAM escaper tumors were eventually rejected by PBS-treated mice, while 8/13 either grew larger or remained sizable tumors. All α-PD1 (11/11) and α-CTLA4 (11/11) treated mice completely rejected E0771-SAM tumors. Error bars: All data points in this figure were presented as mean±s.e.m. Asterisks: * p<0.05,  p<0.01, * p<0.001.

Figures 31A, 31B, 31C:
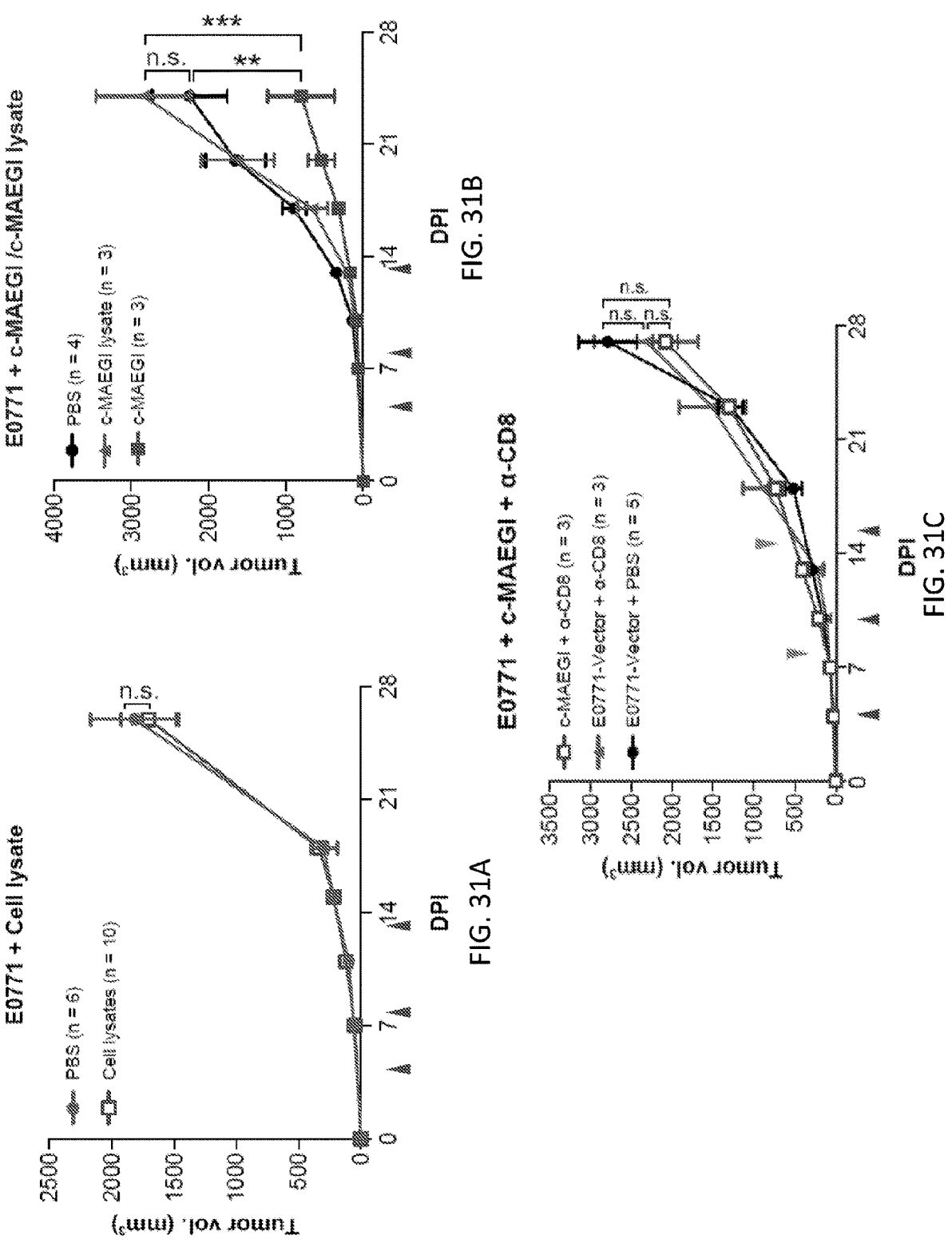
Figure 31D:
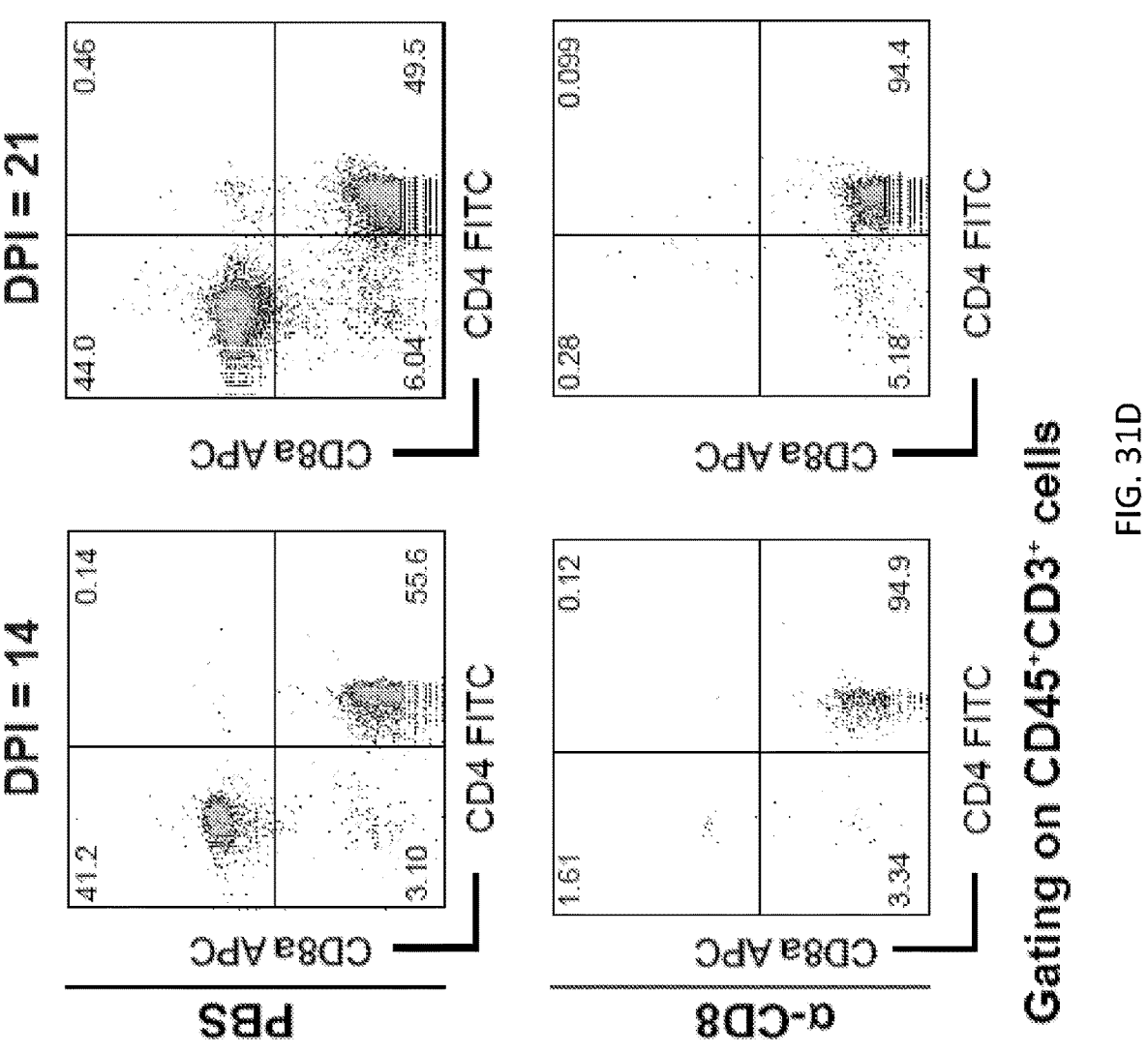
Figures 31E, 31F, 31G:
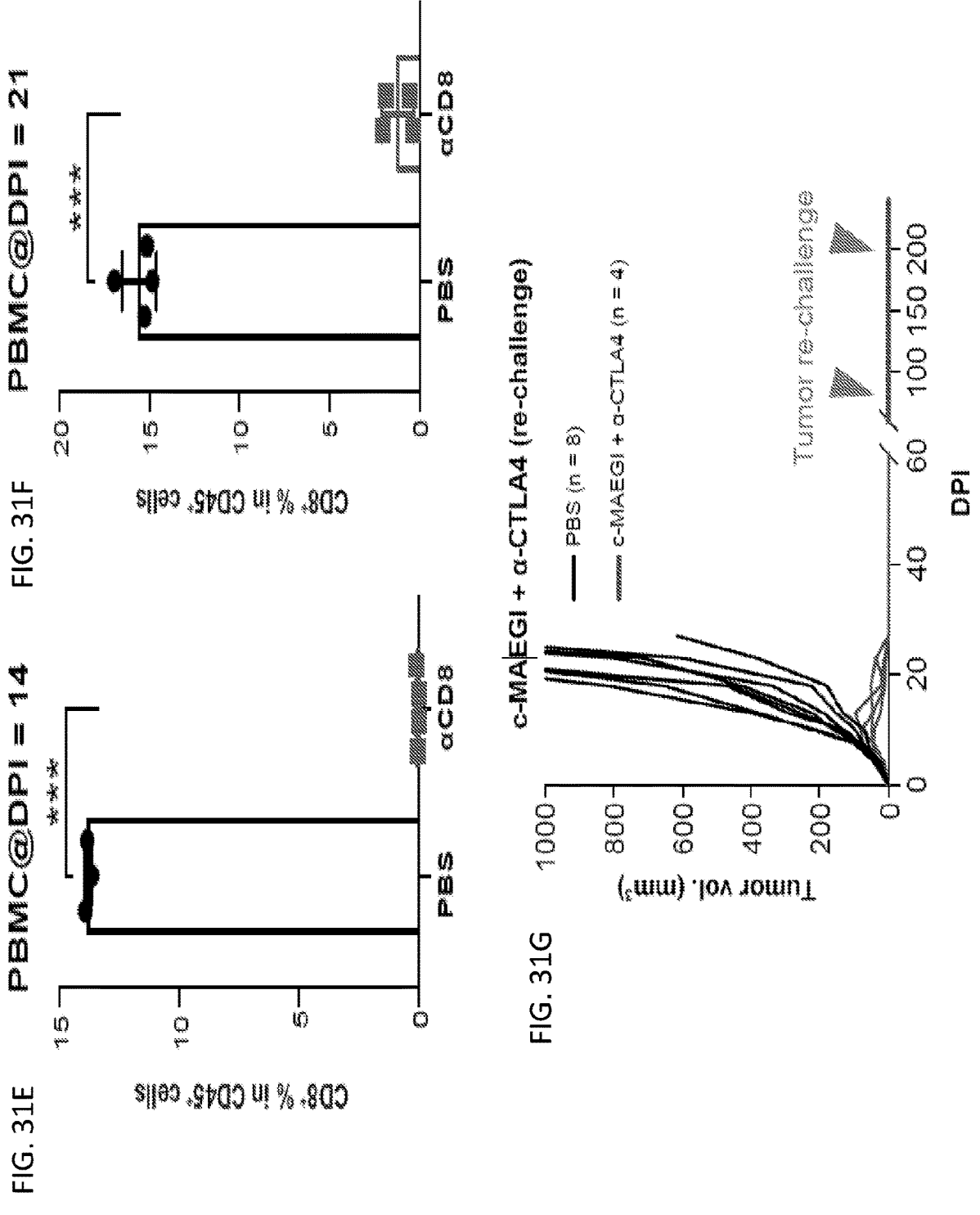

FIGS. 31A-31G illustrate thermally-induced cell lysis or CD8+ T cell depletion abolishes the therapeutic effect of c-MAEGI. FIG. 31A shows results from testing the therapeutic effect of heat-induced cell lysates from non-transduced E0771 against established syngeneic orthotopic E0771 tumors. Tumor-bearing mice were treated with PBS or E0771 lysate at indicated times (arrows). (PBS treated mice, n=6; E0771 lysate, n=10). Two-way ANOVA: p=0.8916. FIG. 31B shows a comparison of the therapeutic effects of c-MAEGI and heat-induced lysates of c-MAEGI against established syngeneic E0771 tumors. Tumor-bearing mice were treated with PBS, c-MAEGI, or c-MAEGI lysates at indicated times (arrows). (PBS treated mice, n=4; c-MAEGI, n=3; c-MAEGI lysates, n=3). Two-way ANOVA: PBS vs. c-MAEGI, p=0.0004; PBS vs. c-MAEGI lysates, p=0.8856; c-MAEGI lysates vs. c-MAEGI, p=0.0007. FIG. 31C shows tumor growth curves of E0771-Vector derived tumors that were treated with PBS, α-CD8, or c-MAEGI+ α-CD8. Dark grey arrows: c-MAEGI treatment; light grey arrows: α-CD8 treatment. CD8+ T cell depletion abolished the effect of c-MAEGI against established syngeneic E0771 tumors. Two-way ANOVA: PBS vs α-CD8, p=0.9744; PBS vs. c-MAEGI+α-CD8, p=0.6037; α-CD8 vs. c-MAEGI+α-CD8, p=0.705. FIG. 31D shows representative peripheral blood flow cytometry analysis of CD8+ T cells after PBS or α-CD8 treatment, gated on CD45+CD3+ cells. Top row, PBS treatment; bottom row, α-CD8 treatment. Left column, DPI=14; right column, DPI=21. X-axis of scatterplots, CD4; Y-axis of scatterplots, CD8a. Percentages are noted in each quadrant. Over 50,000 PBMCs were analyzed for each sample. FIG. 31E is a bar plot detailing the % of CD8+ T cells among CD45+ PBMCs, 14 days after PBS or α-CD8 treatment. Two-tailed unpaired t-test: PBS vs. α-CD8, p<0.0001. FIG. 31F is a bar plot detailing the % of CD8+ T cells among CD45+ PBMCs, 21 days after PBS or α-CD8 treatment. Two-tailed unpaired t-test: PBS vs. α-CD8, p<0.0001. FIG. 31G is a spider plot of tumor growth curves of syngeneic orthotopic E0771 tumors in C57BL/6J mice, evaluating the combination of c-MAEGI and CTLA4 blockade with extended follow-up and tumor re-challenges. Arrowheads indicate time points of tumor re-challenge, indicating that the anti-tumor responses induced by combining c-MAEGI and α-CTLA4 were long-lasting. Error bars: All data in this figure are presented as mean±s.e.m., with individual data points shown. Asterisks: * p<0.05,  p<0.01, * p<0.001.

Figures 32A, 32B, 32C:
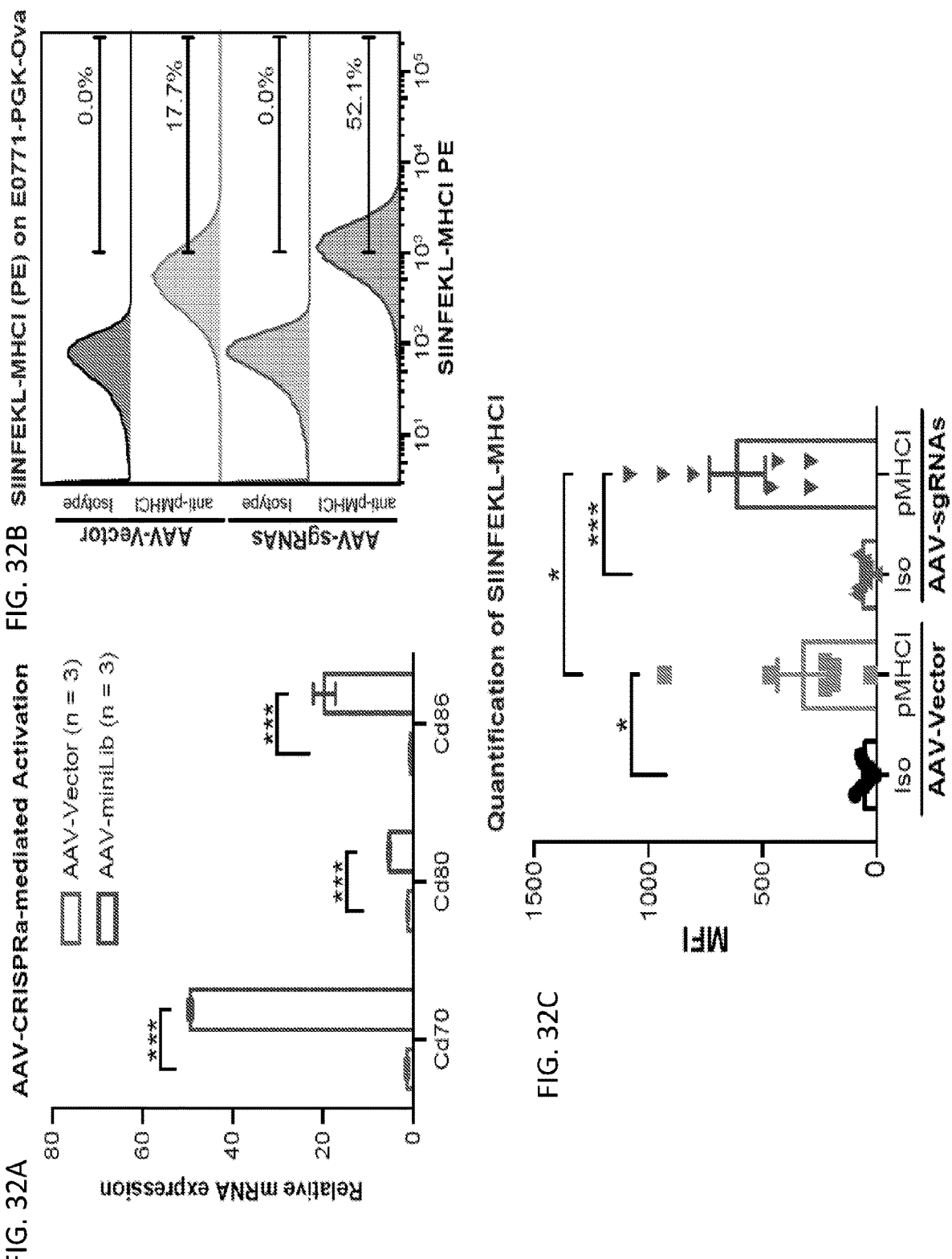

FIGS. 32A-32C illustrate the finding that AAV-CRISPRa system specifically enhances gene expression and cell surface presentation of antigens. FIG. 32A shows AAV-CRISPRa activation of multiple endogenous genes in a pooled manner. The transcript levels of Cd70, Cd80, Cd86 were quantified by qRT-PCR after transducing E0771-dCas9-VP64 cells with either AAV-Vector or AAV-sgRNA-mini-Lib. Two-sided unpaired t-test for sgRNAs vs. vector: Cd70, p<0.0001; Cd80, p=0.0005; Cd86, p<0.0001. FIGS. 32B-32C show AAV-CRISPRa specifically enhances the cell surface presentation of a model antigen in the form of peptide-MHC-I complexes. In cells transduced with lentivirus to express ovalbumin (Ova) under a PGK promoter, AAV-CRISPRa targeted to the PGK promoter augments the presentation of Ova-derived SIINFEKL-MHC-I complex on cell surface. FIG. 32B shows representative flow cytometry analysis of surface staining for SIINFEKL-H-2K$^b$ complex on cells treated with AAV-Vector or AAV-sgRNAs. FIG. 32C shows quantitative analysis of mean fluorescence intensity (MFI) of PE-SIINFEKL-H-2K$^b$ on cells treated with AAV-Vector or AAV-sgRNAs with data from 4 independent experiments. Two sided Mann-Whitney test: SIINFEKL-H-2K$^b$ staining vs. isotype in AAV-Vector, p=0.0146; SIINFEKL-H-2K$^b$ staining vs. isotype in AAV-sgRNAs, p=0.0006; SIINFEKL-H-2K$^b$ staining in AAV-sgRNAs vs. AAV-Vector, p=0.0484.

Figure 33A:
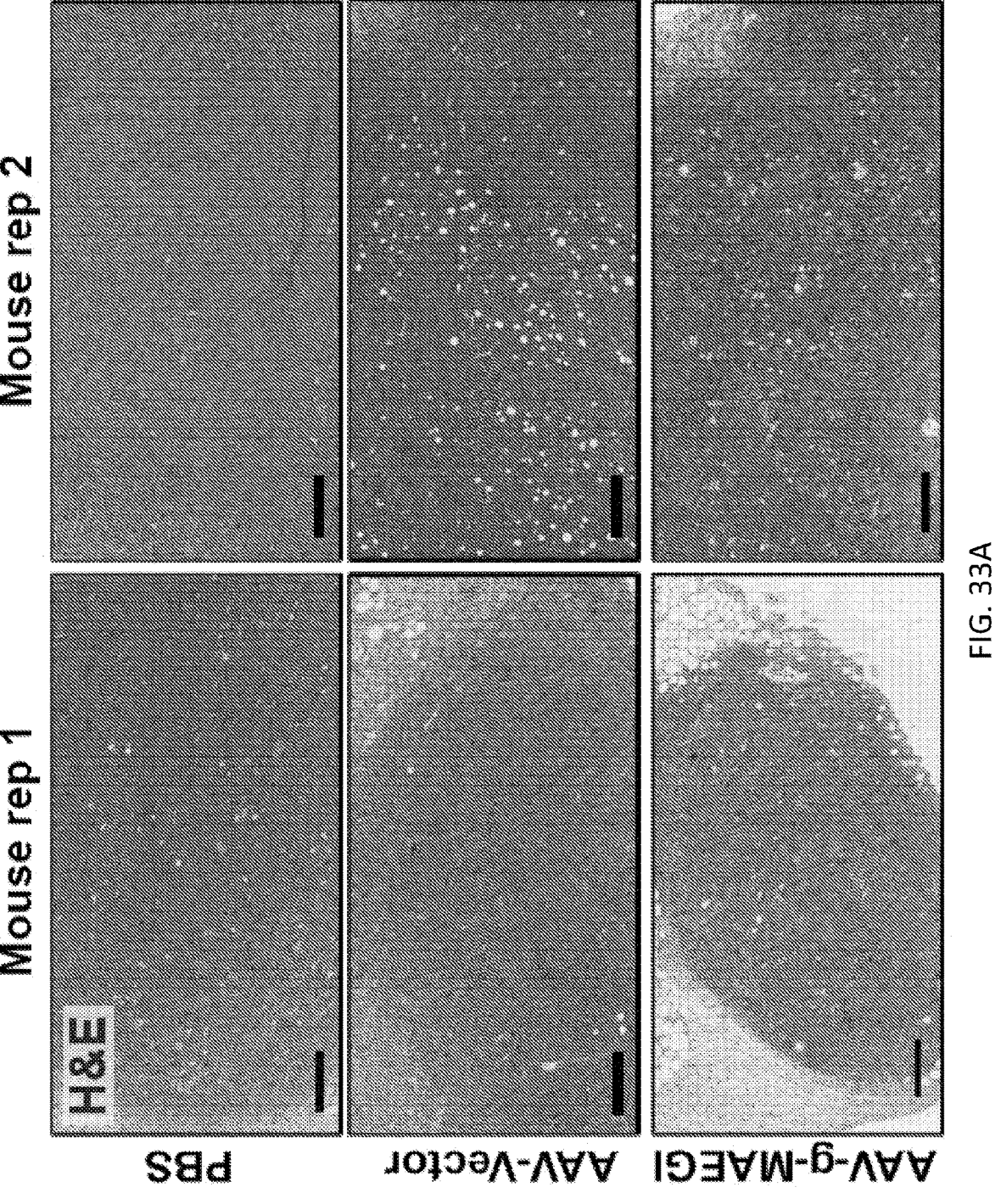
Figure 33B:
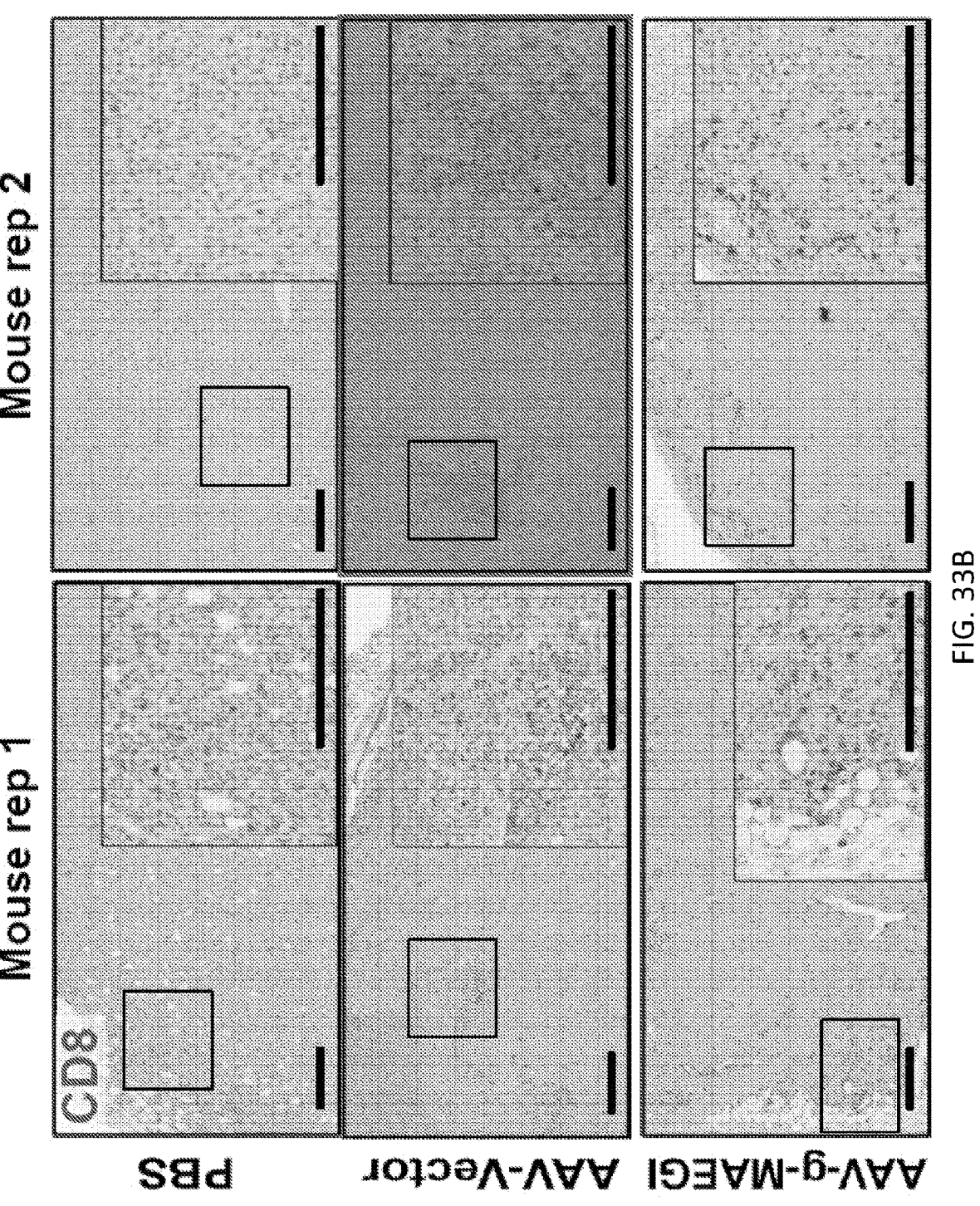
Figures 33C, 33D:
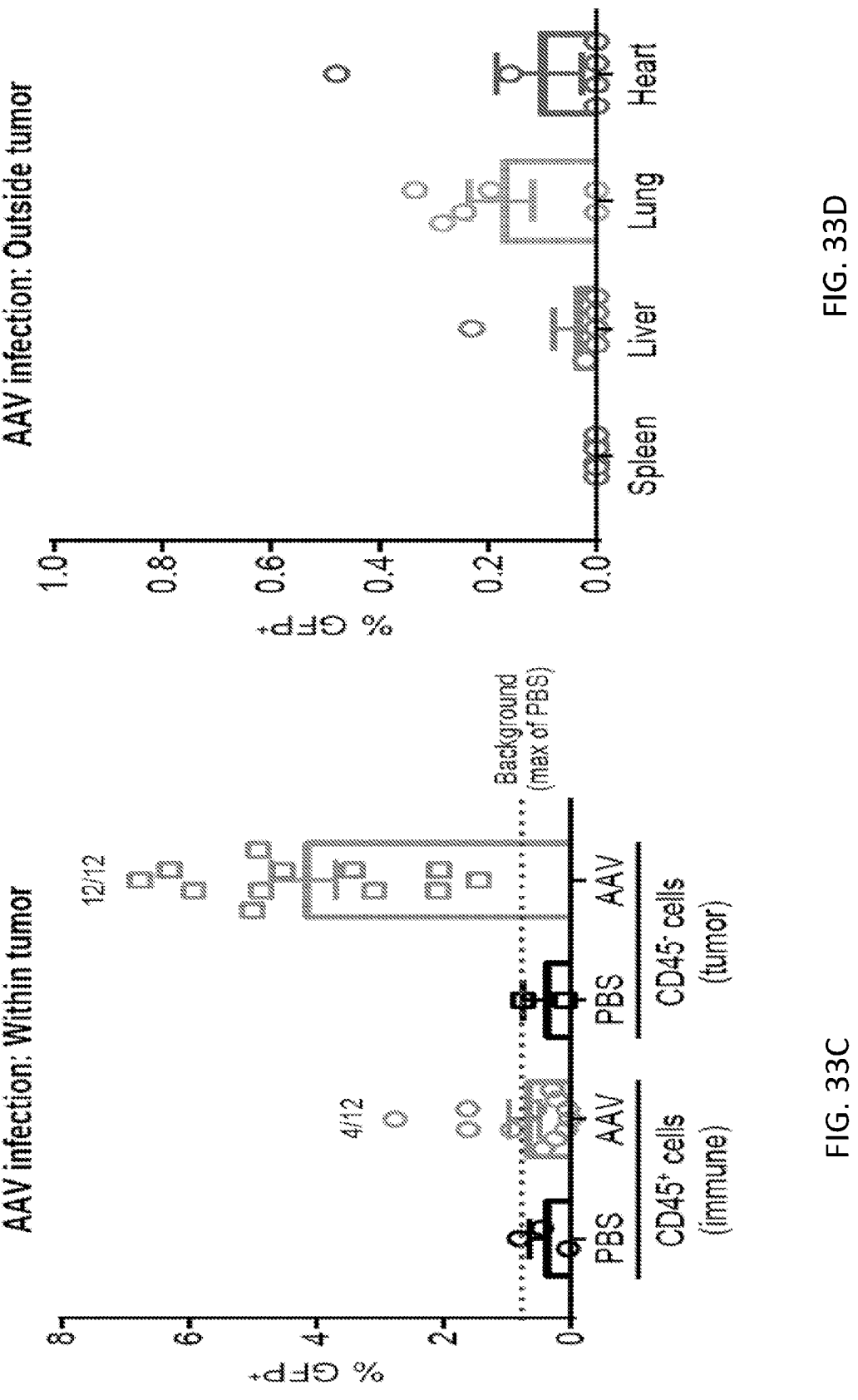

FIGS. 33A-33D illustrate additional characterization of AAV-MAEGI. FIGS. 33A-33B show H&E (FIG. 33A) or CD8 (FIG. 33B) staining of E0771 tumors in mice treated with PBS, AAV-Vector, or AAV-g-MAEGI. (Tumor harvest dpi=31). Scale bars of zoomed-out images and insets=200 μm. FIGS. 33C-33D show AAV infection efficiency assessed by intratumoral delivery of GFP-expressing AAVs and flow cytometry analysis. FIG. 33C shows percentages of GFP+ cells within tumors from mice 4 days after intratumoral injection of PBS (n=3) or AAV-GFP (n=12), grouped by CD45+ and CD45− cells. The background GFP fluorescence was set as the maximum % GFP positivity in PBS samples, denoted by a dashed line. Fractions above AAV conditions denote the number of samples with % GFP positivity above background in the indicated cell population. FIG. 33D shows percentages of GFP+ cells in various organs after intratumoral injection of AAV-GFP (n=6). Error bars: All data in this figure are presented as mean±s.e.m., with individual data points shown. Asterisks: * p<0.05,  p<0.01, * p<0.001.

Figure 34A:
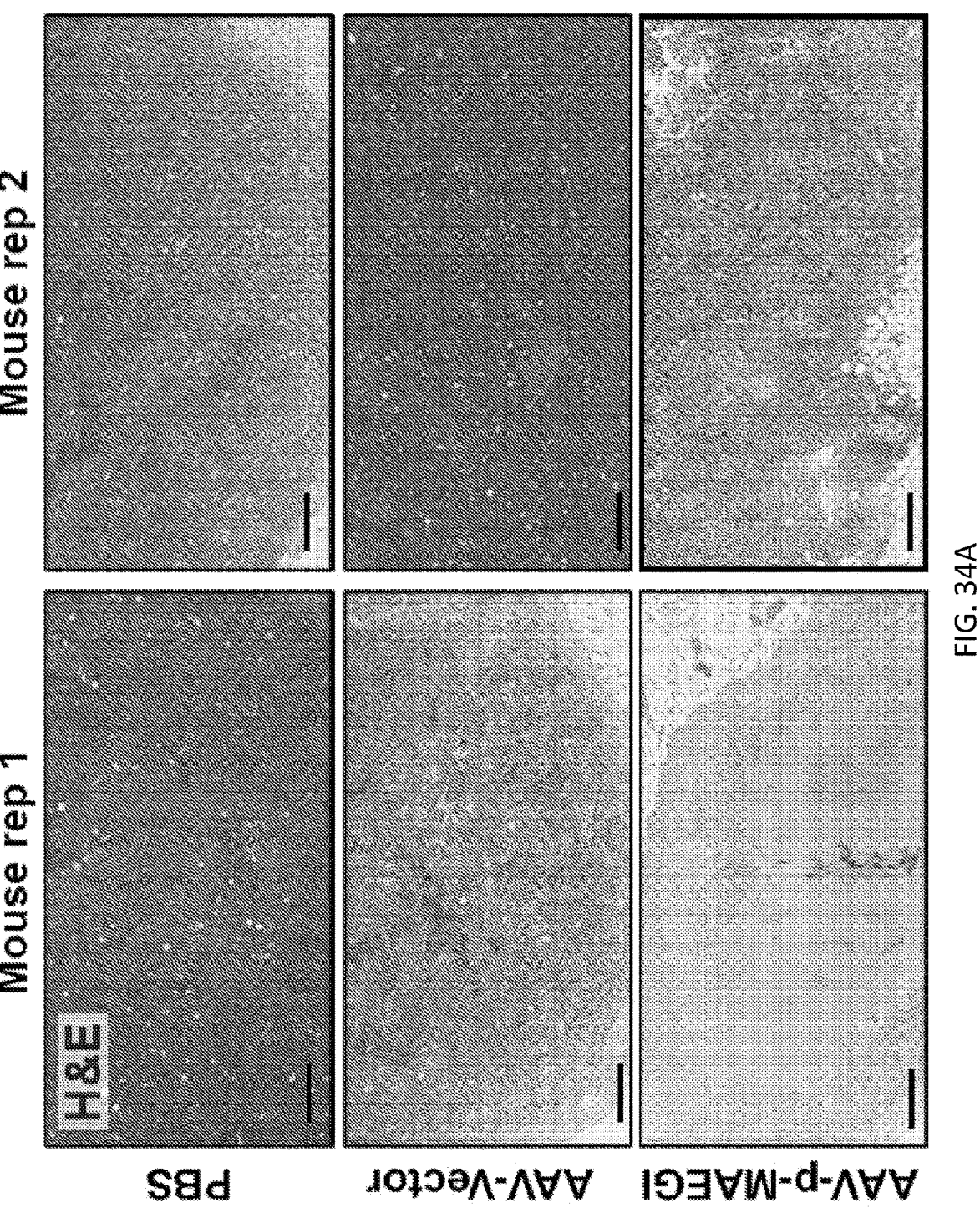
Figure 34B:
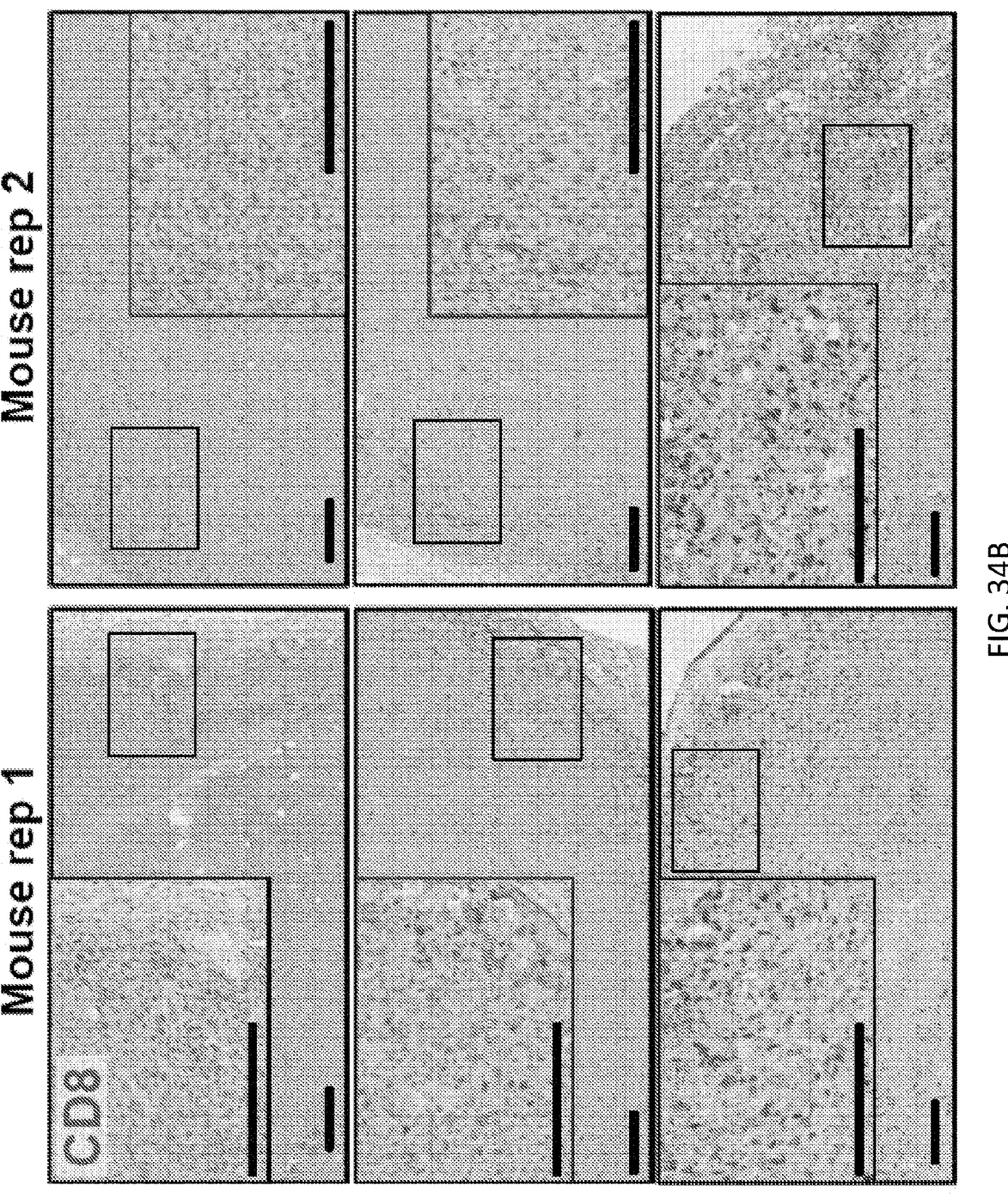
Figure 34C:
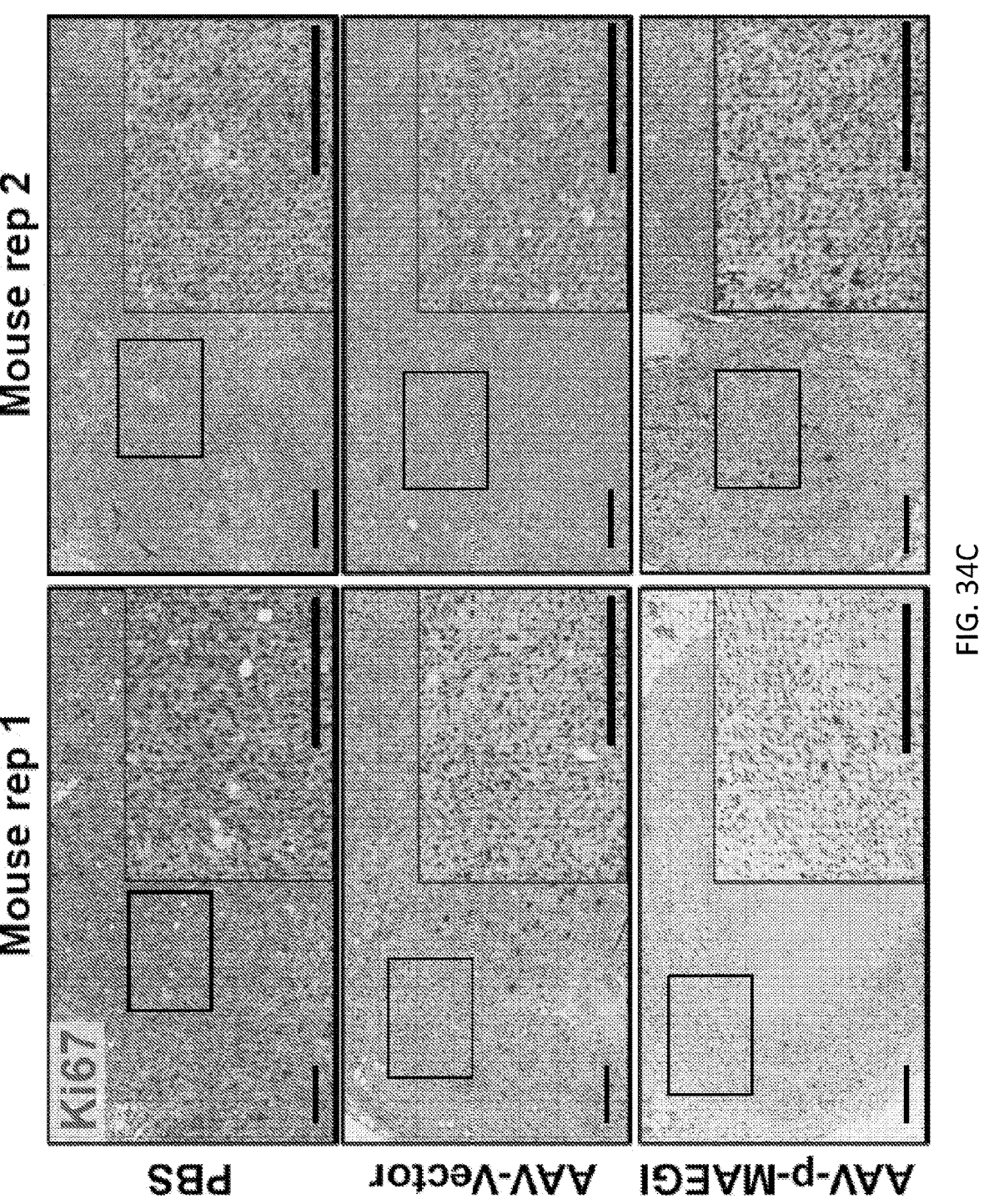
Figure 34D:
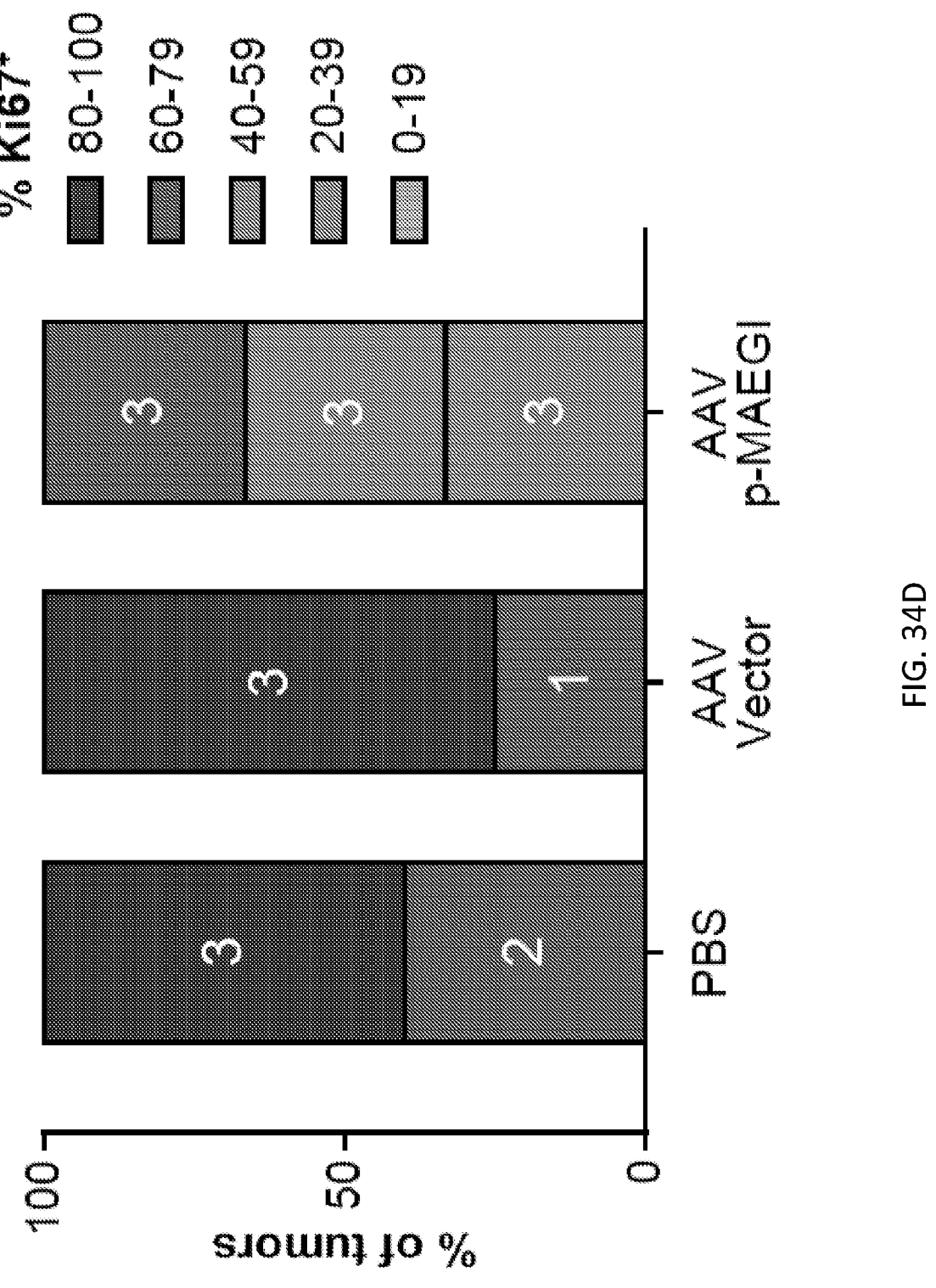

FIGS. 34A-34D illustrate histological characterization of E0771 tumors treated with AAV-p-MAEGI. FIGS. 34A-34C show H&E (FIG. 34A), CD8 (FIG. 34B), or Ki67 (FIG. 34C), staining of E0771 tumors collected from mice treated with PBS, AAV-Vector, or AAV-p-MAEGI. (Tumor harvest dpi=36). FIG. 34D illustrates quantification of % Ki67 positivity in E0771 tumors collected from mice treated with PBS, AAV-Vector, or AAV-p-MAEGI. Scale bars of zoomed-out images and insets=200 m.

Figures 35A, 35B:
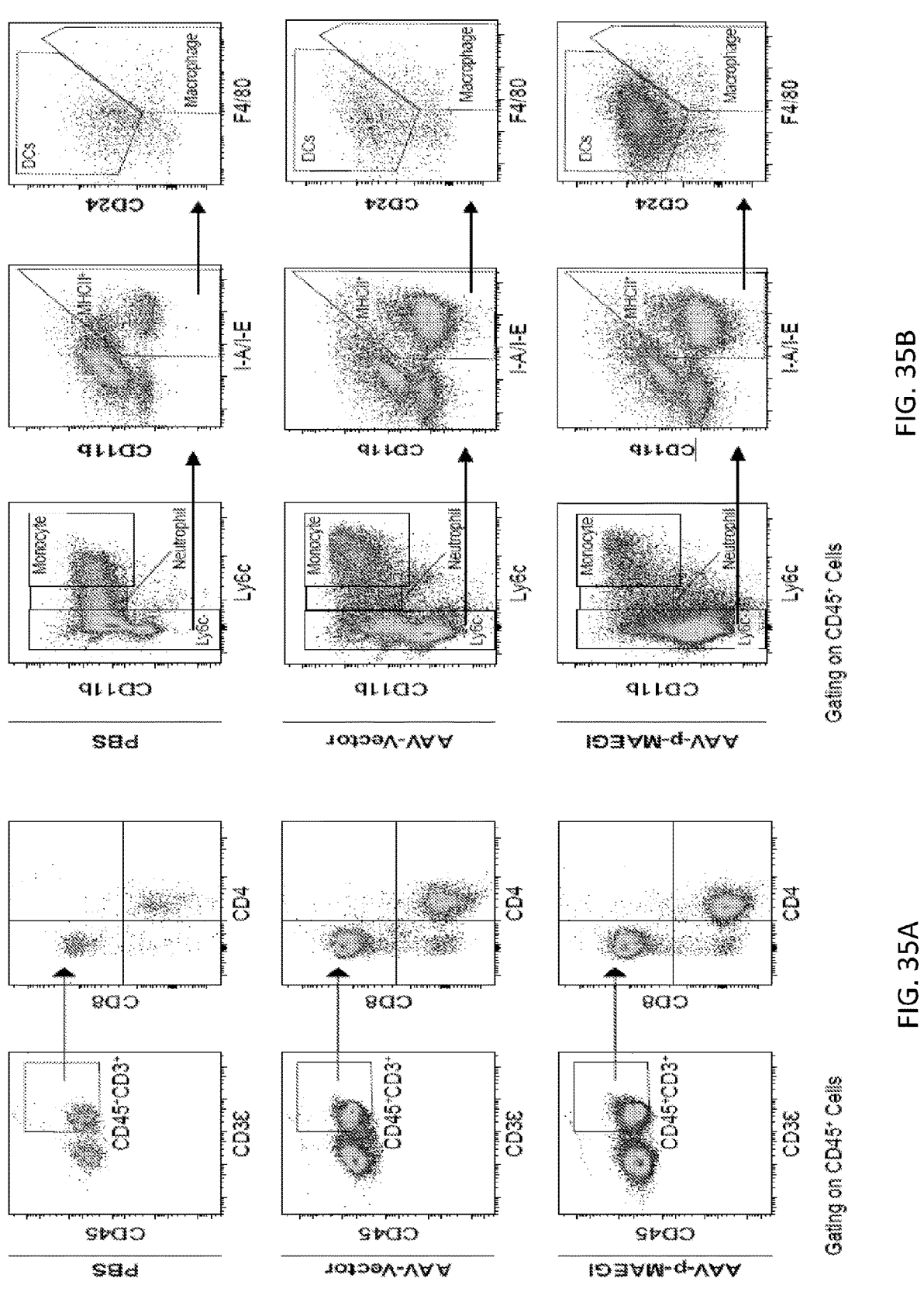

FIGS. 35A-35C illustrate representative flow cytometry gating and CDR3 amino acid sequences from major tumor-infiltrating T cell clones. FIG. 35A shows representative flow cytometry gating of CD45+, CD3+, CD4+, and CD8+ cell populations within tumors from mice treated with PBS, AAV-Vector or AAV-p-MAEGI. FIG. 35B shows representative flow cytometry gating of monocytes, neutrophils, MHCII+ cells, dendritic cells, and macrophages in tumors from mice treated with PBS, AAV-Vector, or AAV-p-MAEGI, 19 days after tumor induction. FIG. 35C shows CDR3 amino acid sequences from major (top 3) clones in three example TIL samples from PBS, AAV-Vector, AAV-g-MAEGI, and AAV-p-MAEGI treated mice.

Figures 36H, 36I:
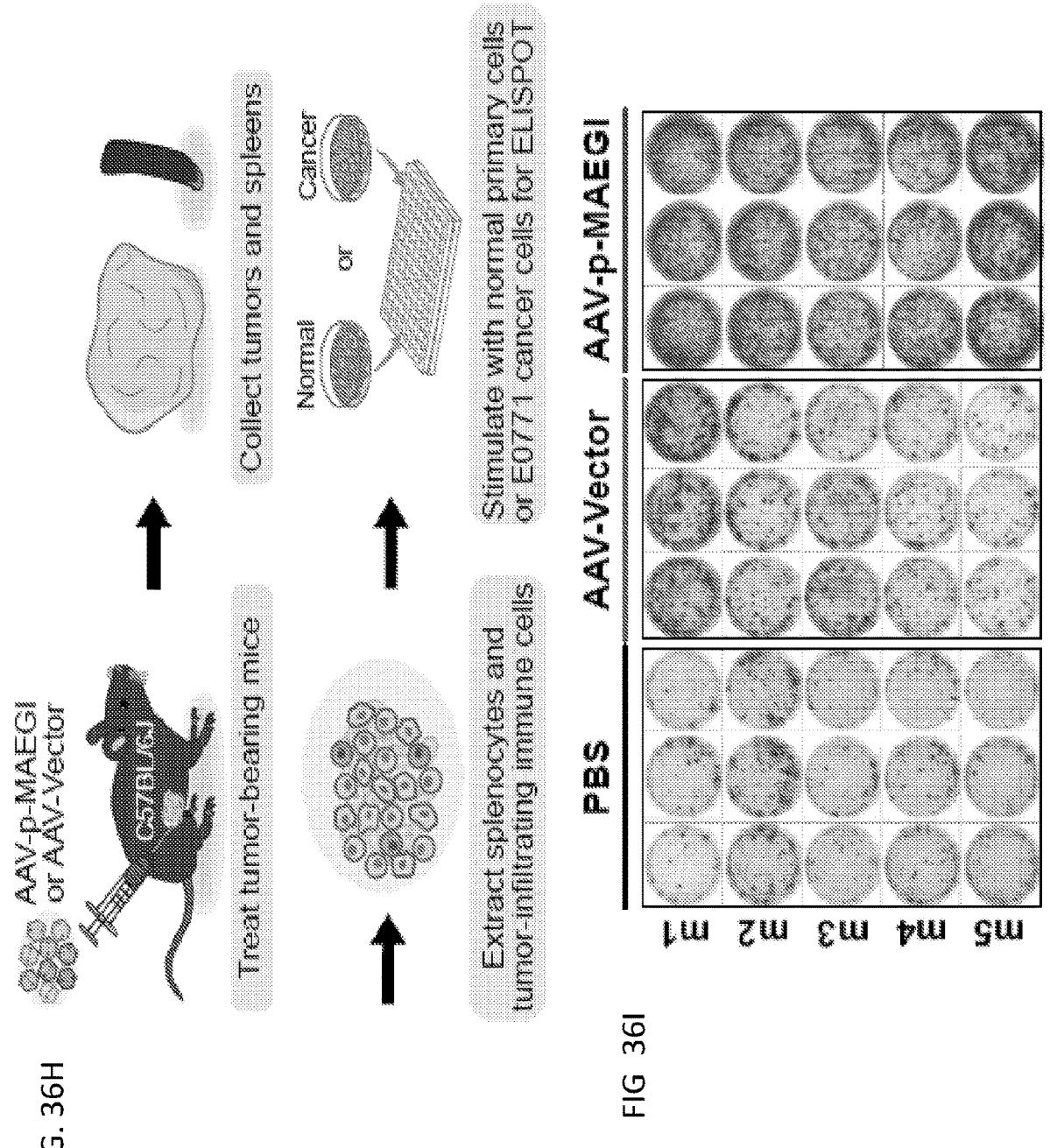

FIGS. 36A-36N illustrate the finding that AAV-p-MAEGI treatment promotes infiltration of tumor-reactive immune populations. FIG. 36A shows AAV-p-MAEGI treatment is associated with increased CD4$^+$ T cell abundance in the tumor microenvironment. Flow cytometry time-course quantification of CD4$^+$ T cells out of total tumor cells from mice treated with PBS, AAV-Vector, or AAV-p-MAEGI. Two-tailed Mann-Whitney test: AAV-p-MAEGI vs. PBS at dpi 9 (p=0.6857), dpi 19 (p=0.0047), dpi 29 (p=0.0048), and dpi 36 (p=0.0015); AAV-p-MAEGI vs. AAV-Vector at dpi 9 (p=0.2000), dpi 19 (p=0.2569), dpi 29 (p=0.0159), and dpi 36 (p=0.0422); FIG. 36B shows AAV-p-MAEGI treatment is associated with increased CD8$^+$ T cell abundance in the tumor microenvironment. Flow cytometry time-course quantification of CD8$^+$ T cells out of total tumor cells from mice treated with PBS, AAV-Vector, or AAV-p-MAEGI. Two-tailed Mann-Whitney test: AAV-p-MAEGI vs. PBS at dpi 9 (p=0.6857), dpi 19 (p=0.0047), dpi 29 (p=0.0005), and dpi 36 (p=0.0014); AAV-p-MAEGI vs. AAV-Vector at dpi 9 (p=0.4857), dpi 19 (p=0.2569), dpi 29 (p=0.0064), and dpi 36 (p=0.0200). FIG. 36C shows percentage of CD45$^+$MHC-II$^+$ antigen presenting cells in tumors from mice treated with PBS, AAV-Vector, or AAV-PCAVac. Two-tailed Mann-Whitney test: AAV-Vector vs. PBS, p=0.0225; AAV-PCAVac vs. PBS, p=0.0001; AAV-PCAVac vs. AAV-Vector, p=0.0147. FIG. 36D shows percentage of dendritic cells in tumors from mice treated with PBS, AAV-Vector, or AAV-PCAVac. Two-tailed Mann-Whitney test: AAV-Vector vs. PBS, p=0.0075; AAV-PCAVac vs. PBS, p=0.0008; AAV-PCAVac vs. AAV-Vector, p=0.0692. FIG. 36E shows percentage of macrophages in tumors from mice treated with PBS, AAV-Vector, or AAV-PCAVac. Two-tailed Mann-Whitney test: AAV-Vector vs. PBS, p=0.6353; AAV-PCAVac vs. PBS, p=0.5532; AAV-PCAVac vs. AAV-Vector, p=0.9229. FIG. 36F shows percentage of monocytes in tumors from mice treated with PBS, AAV-Vector, or AAV-PCAVac. Two-tailed Mann-Whitney test: AAV-Vector vs. PBS, p=0.1471; AAV-PCAVac vs. PBS, p=0.5533; AAV-PCAVac vs. AAV-Vector, p=0.0426. FIG. 36G shows percentage of neutrophils in tumor from mice treated with PBS, AAV-Vector, or AAV-PCAVac. Two-tailed Mann-Whitney test: AAV-Vector vs. PBS, p=0.0559; AAV-PCAVac vs. PBS, p=0.6165; AAV-PCAVac vs. AAV-Vector, p=0.4176. FIG. 36H is a schematic of an experimental design to assess anti-tumor specificity of the immune response elicited by AAV-p-MAEGI. FIG. 36I shows representative images of IRNγ ELISPOTs on splenocytes obtained from five E0771 tumor-bearing mice for each treatment group (PBS, AAV-Vector, and AAV-p-MAEGI). FIG. 36J shows quantification of IFN7 ELISPOTs on splenocytes from PBS (n=7), AAV-Vector (n=6) and AAV-g-MAEGI (n=9) treated mice bearing E0771 tumors. Two sided unpaired t-test: AAV-Vector vs. PBS, p=0.1499; AAV-g-MAEGI vs. PBS, p=0.0006; AAV-g-MAEGI vs. AAV-Vector, p=0.0011. Results shown are from the aggregation of 2 independent experiments. FIG. 36K shows representative images of IFNγ ELISPOTs on splenocytes from AAV-Vector or AAV-p-MAEGI treated mice bearing E0771 tumors, stimulated with either normal primary cells from wildtype C57BL/6J fat pad tissue (Normal) or E0771 cells (Cancer). FIG. 36L shows quantification of IFNγ ELISPOTs on splenocytes from AAV-Vector (n=9) or AAV-p-MAEGI (n=9) treated mice bearing E0771 tumors that were stimulated with primary C57BL/6J normal cells or cancer cells. Two sided unpaired t-test: AAV-p-MAEGI vs. AAV-Vector stimulated by normal cells, p=0.1667; AAV-p-MAEGI vs. AAV- Vector stimulated by E0771 cancer cells, p=0.0057; Cancer vs. Normal cells stimulation within AAV-Vector group, p=0.0004; Cancer vs. Normal cells stimulation within AAV-p-MAEGI group, p=0.0002. Results shown are aggregated from 2 independent experiments. FIG. 36M shows representative images of IFNγ ELISPOTs on tumor-infiltrating immune cells (TIICs) from AAV-Vector or AAV-p-MAEGI treated mice bearing E0771 tumors, stimulated with either primary cells from wildtype C57BL/6J fat pad tissue (Normal) or E0771 cells (Cancer). FIG. 36N shows quantification of IFNγ ELISPOTs for TIICs from AAV-Vector (n=6) or AAV-p-MAEGI (n=6) treated mice bearing E0771 tumors that were stimulated with primary C57BL/6J normal cells or cancer cells. Two-sided unpaired t-test: AAV-p-MAEGI vs. AAV-Vector stimulated by Normal cells, p=0.0577; AAV-p-MAEGI vs. AAV-Vector stimulated by cancer cells, p<0.0001; Cancer vs. Normal cells stimulation for AAV-Vector group, p=0.0175; Cancer vs. Normal cells stimulation for AAV-p-MAEGI group, p<0.0001. Error bars: All data points in this figure are presented as mean±s.e.m. Asterisks: * p<0.05,  p<0.01, * p<0.001.

Figure 37A:
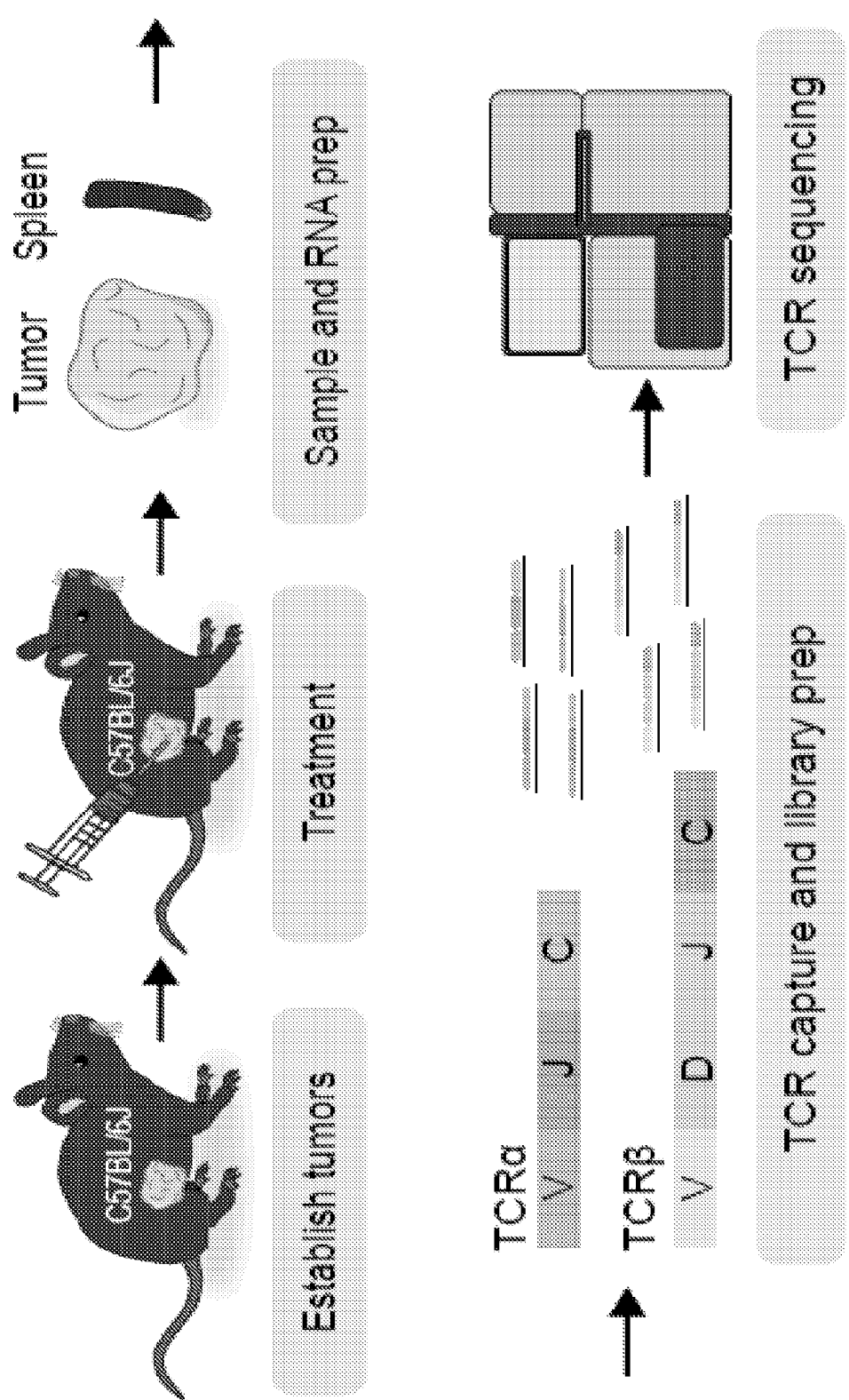
Figure 37B:
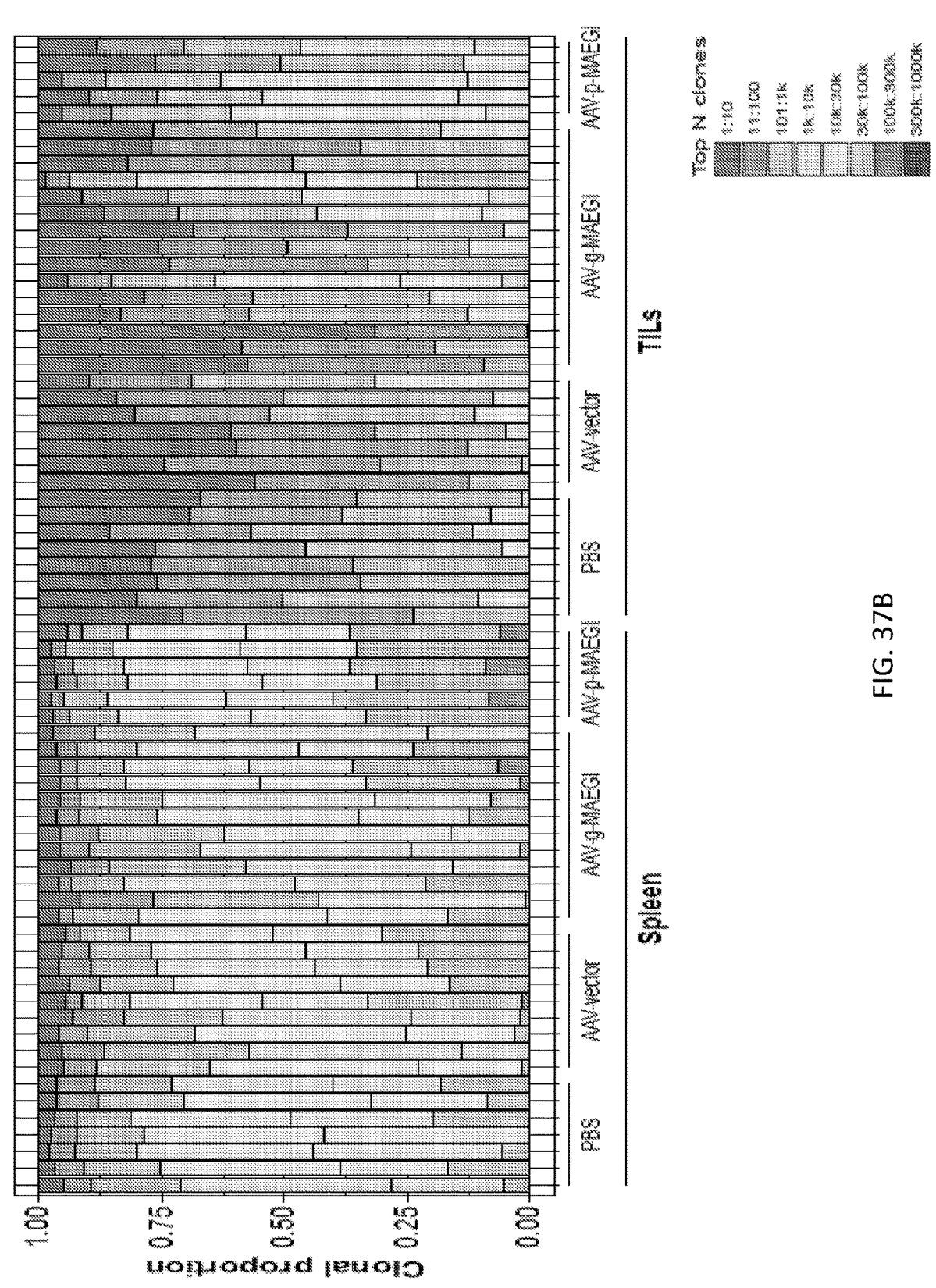

FIGS. 37A-37F illustrate interrogation of the T cell repertoire in MAEGI-treated mice by TCR sequencing. FIG. 37A is a schematic of a TCR-seq experiment design. Mice bearing E0771 tumors were treated with PBS, AAV-Vector, AAV-g-MAEGI (genome-wide), or AAV-p-MAEGI (exome-guided). Spleens and tumors were harvested from mice for genomic DNA extraction, and subjected to RT-based TCRα/TCRβ capture followed by Illumina sequencing. FIG. 37B is a global clonal proportion plot showing the relative frequencies of the top N clones. FIG. 37C is a boxplot of Chao1 indices (TCR diversity) for each sample. Statistical significance was assessed by unpaired two-tailed Mann-Whitney test. FIG. 37D is a boxplot of Gini-Simpson indices (TCR evenness) for each sample. Statistical significance was assessed by unpaired two-tailed Mann-Whitney test. FIGS. 37E-37F are dot plots of the number of unique clonotypes identified (TCR richness) in each spleen sample (FIG. 37E) or TIL sample (FIG. 37F), compared across treatment conditions. Statistical significance was assessed by unpaired two-tailed t-test.

Figures 38A, 38B, 38C:
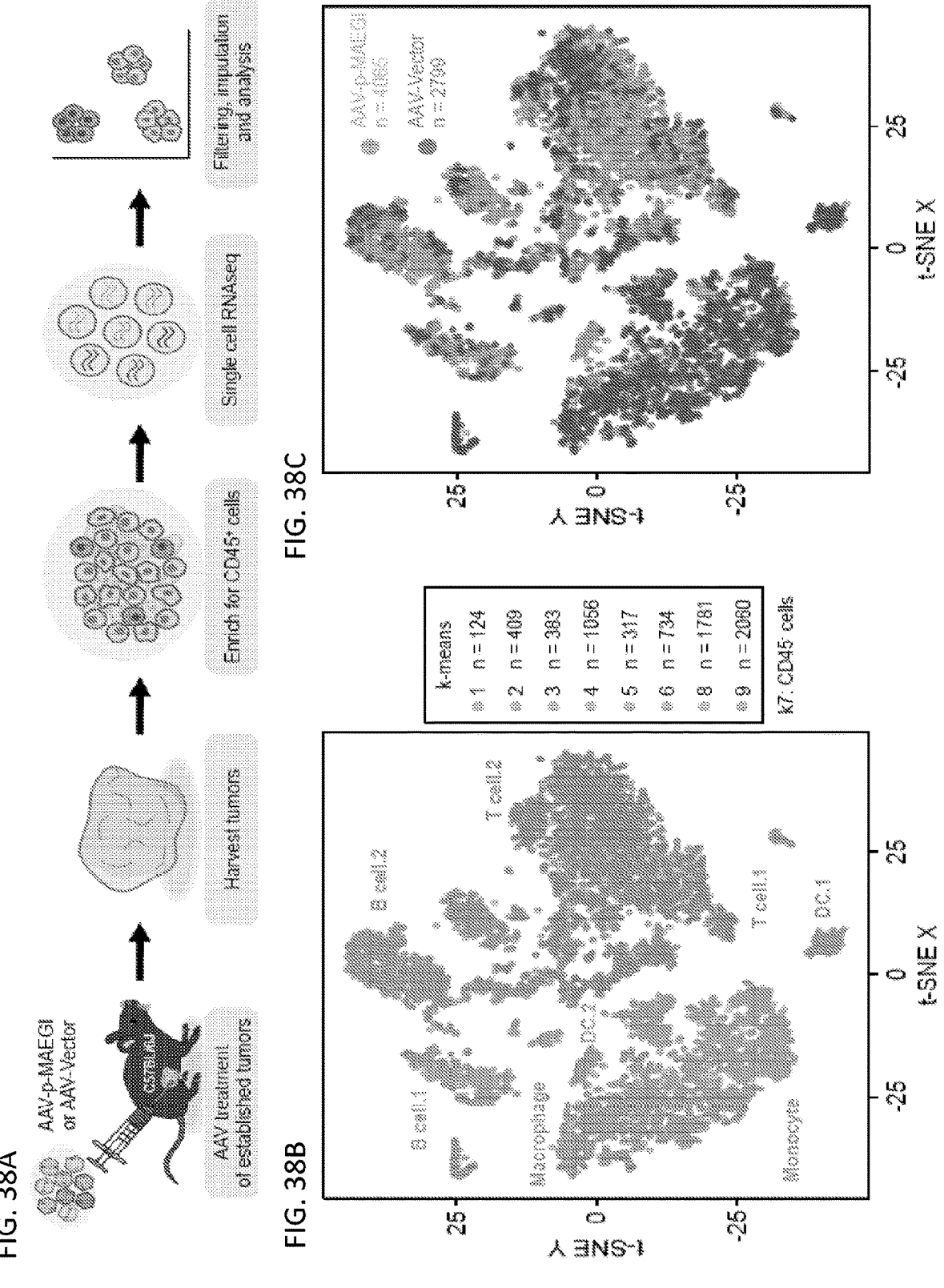
Figures 38D, 38E, 38F:
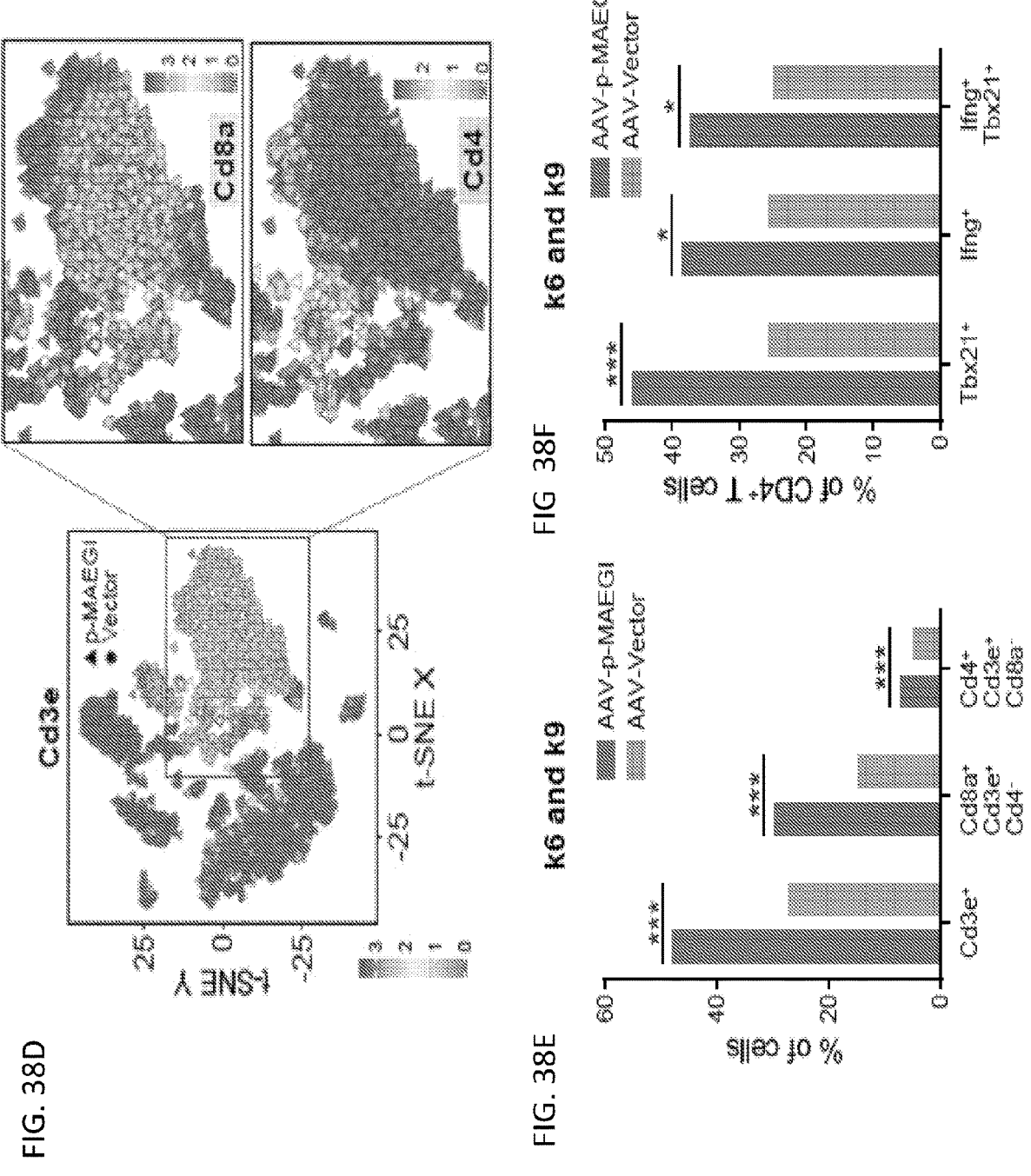

FIGS. 38A-38F illustrate single cell RNAseq profiling of immune populations in the tumor microenvironment. FIG. 38A is a schematic of an experimental design for single cell RNAseq (scRNAseq) analysis of immune populations in AAV-Vector (n=3) or AAV-p-MAEGI treated mice (n=3). Cells from replicate mice were pooled together for scRNAseq library preparation. FIG. 38B is a scatter plot of t-SNE dimensional reduction, with cells colored by k-means cluster. Putative cell types associated with each cluster are annotated on the plot. Cluster 7 (k7) is composed of CD45$^-$ cells and was excluded from further analyses (see FIGS. 39A-39F). The number of cells in each cluster is noted to the right. FIG. 38C is a scatter plot of t-SNE dimensional reduction as in (FIG. 38B) but colored by treatment group. scRNAseq cell numbers after preprocessing: AAV-p-MAEGI, n=4,065 cells; AAV-Vector, n=2,799 cells. FIG. 38D shows identification of T cell populations from scRNAseq. Left, t-SNE dimensional reduction, with cells colored by Cd3e expression. Right, zoomed-in view of clusters k6 and k9, colored by Cd8a expression (top) or Cd4 expression (bottom). Triangles correspond to cells from AAV-p-MAEGI, while circles correspond to cells from AAV-Vector. FIG. 38E shows quantification of T cell populations in k6 and k9. AAV-p-MAEGI mice have a higher proportion of CD3$^+$ T cells, CD8$^+$ T cells, and CD4$^+$ T cells out of total TIICs. Two-sided Fisher's exact test, AAV-p-MAEGI vs AAV-Vector: $p<0.0001$ for CD3e$^+$ T cells, CD8$^+$ T cells, and CD4$^+$ T cells. FIG. 38F shows quantification of CD4$^+$ T cell subpopulations in k6 and k9. AAV-p-MAEGI mice have a higher proportion of Tbx21$^+$ cells, Ifng$^+$ cells, and Thx21$^+$ Ifng$^+$ cells out of total CD4$^+$ T cells. Two-sided Fisher's exact test, AAV-p-MAEGI vs AAV-Vector: $p<0.0001$ for Tbx21$^+$ cells, $p=0.0111$ for Ifng$^+$ cells, and $p=0.0109$ for Thx21$^+$Ifng$^+$ cells. Error bars: All data points in this figure are presented as mean±s.e.m. Asterisks: * $p<0.05$,  $p<0.01$, * $p<0.001$.

Figures 39A, 39B:
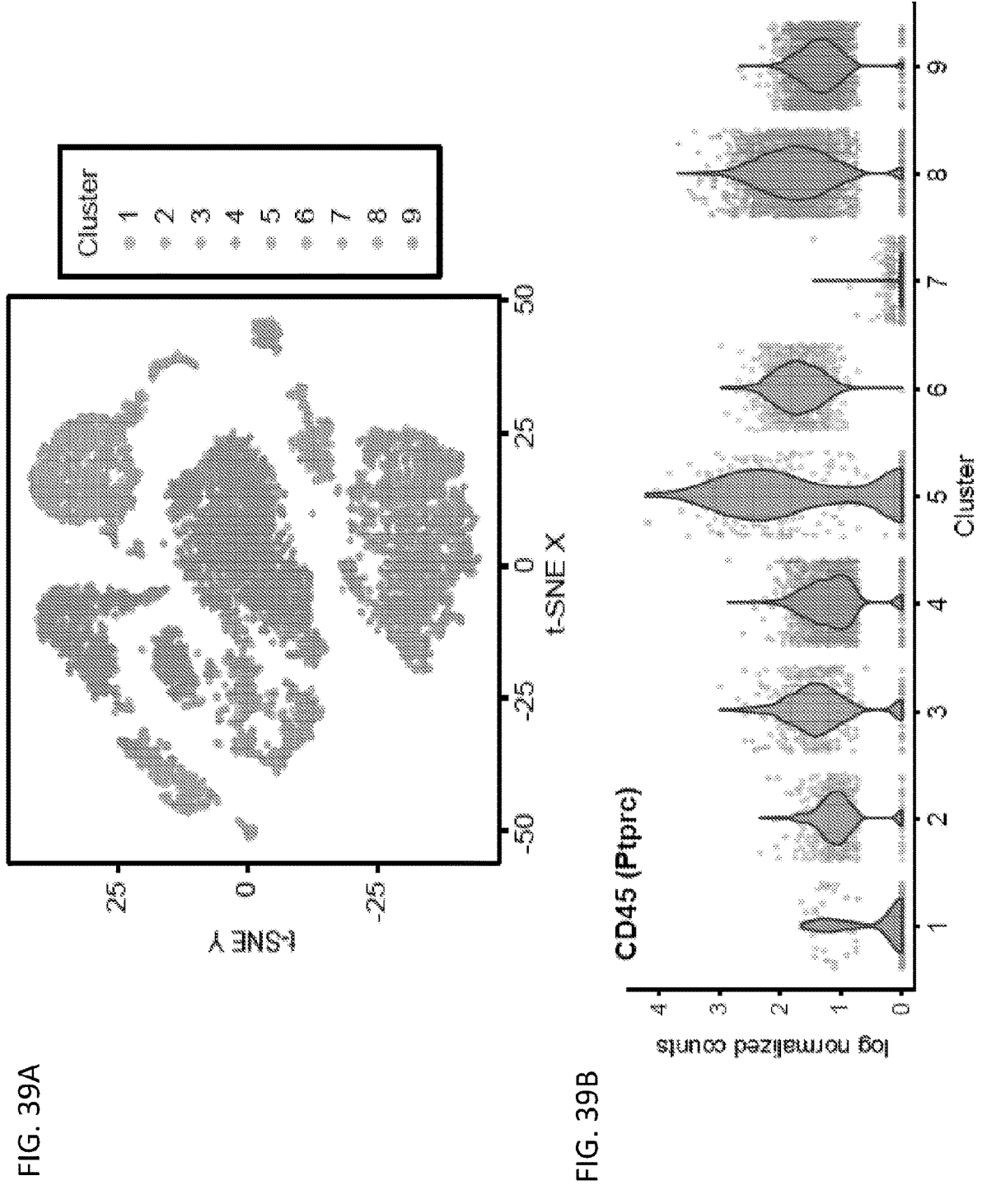
Figures 39C, 39D:
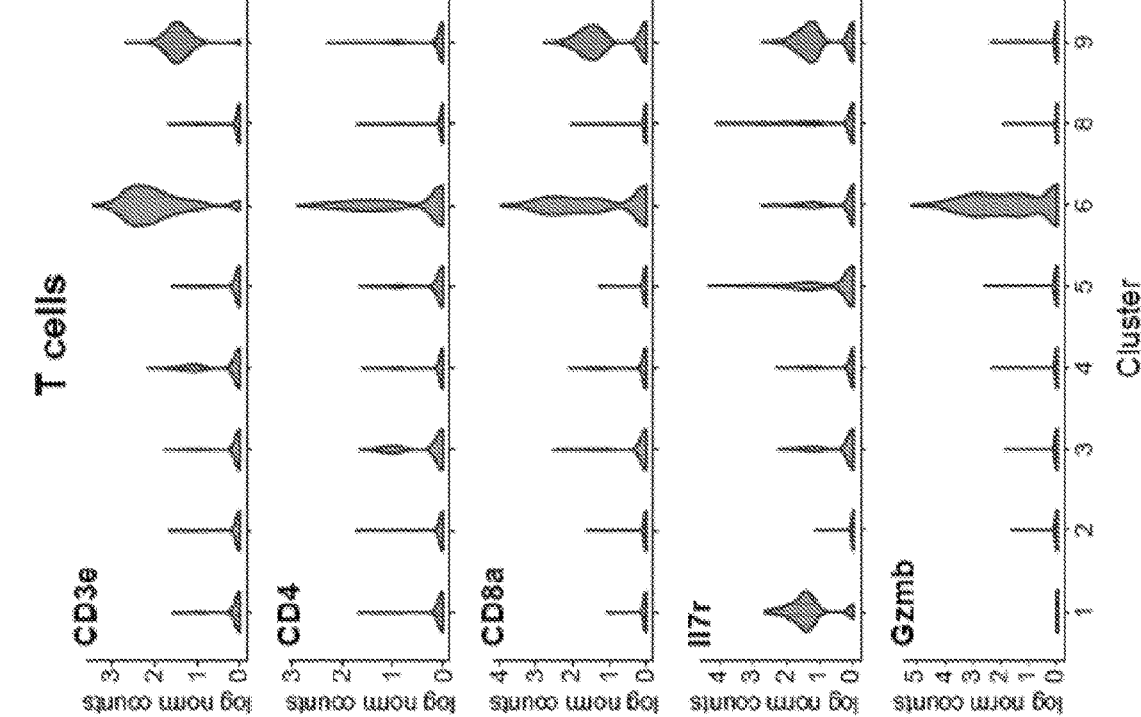
Figure 39E:
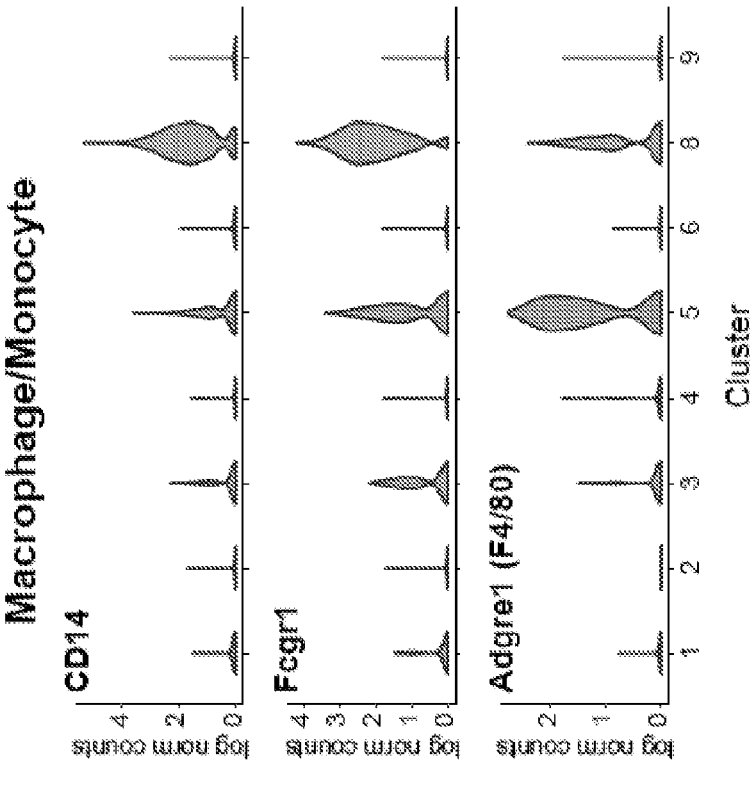
Figure 39F:
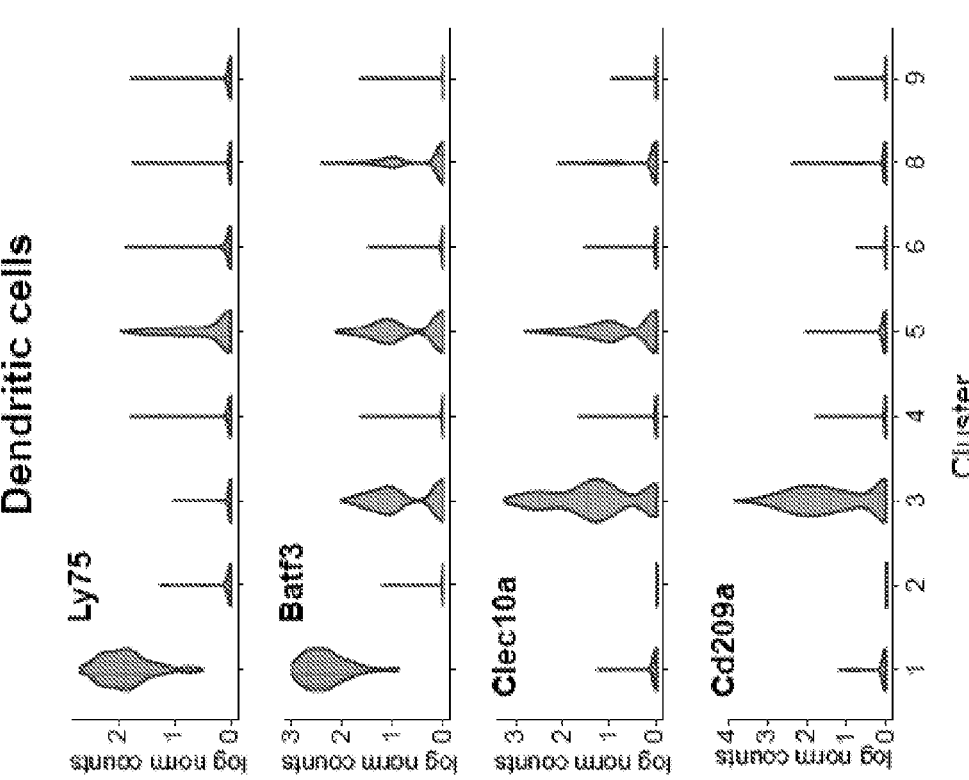

FIGS. 39A-39F illustrate processing of scRNAseq data to exclude CD45$^-$ cells and characteristic markers of each scRNAseq cluster. FIG. 39A shows t-SNE of all single cells passing the filtering criteria, colored by k-means clustering. FIG. 39B shows Violin plots of Ptprc (encoding CD45) expression, grouped k-means cluster. Cluster 7 is largely absent for Ptprc expression. FIG. 39C shows Violin plots of Cd3e, Cd4, CD8a, Il7r, and Gzmb expression, defining different T cells. FIG. 39D show Violin plots of Cd19, Cd20, Par5, Jchain, and Ly6d expression, defining different B cells. FIG. 39E shows Violin plots of Ly75, Batf3, Clec10a, and CD209a expression, defining different dendritic cells. FIG. 39F shows Violin plots of Cd14, Fcgr1, and Adgre1 (encoding F4/80) expression, defining macrophages and monocytes.

FIGS. 40A-40D illustrate the finding that AAV-p-MAEGI treatment is associated with transcriptional changes in tumor-infiltrating T cells. FIGS. 40A-40C show in the top panel, volcano plots of CD8$^+$ T cells in k6 (FIG. 40A), CD8$^+$ T cells in k9 (FIG. 40B), and CD4$^+$ T cells in k6 and k9 (FIG. 40C), comparing AAV-p-MAEGI to AAV-Vector. Bottom panel shows gene ontology enrichment analysis of upregulated genes in T cells from AAV-p-MAEGI mice. FIG. 40D shows a simplified model of action for multiplexed activation of endogenous genes as an immunotherapy (MAEGI). Left panel: the untreated tumor microenvironment. In a setting of low neoantigen expression, CD8$^+$ T cells detect rare mutant peptides presented on MHC-I by tumor cells and initiate weak tumor killing. Right panel: the MAEGI-treated tumor microenvironment. Using CRISPRa, mutated genes in tumor cells are overexpressed from endogenous loci, leading to amplified production and presentation of neoantigens to CD8$^+$ T cells, thereby resulting in a robust anti-tumor response.

Figure 4A:
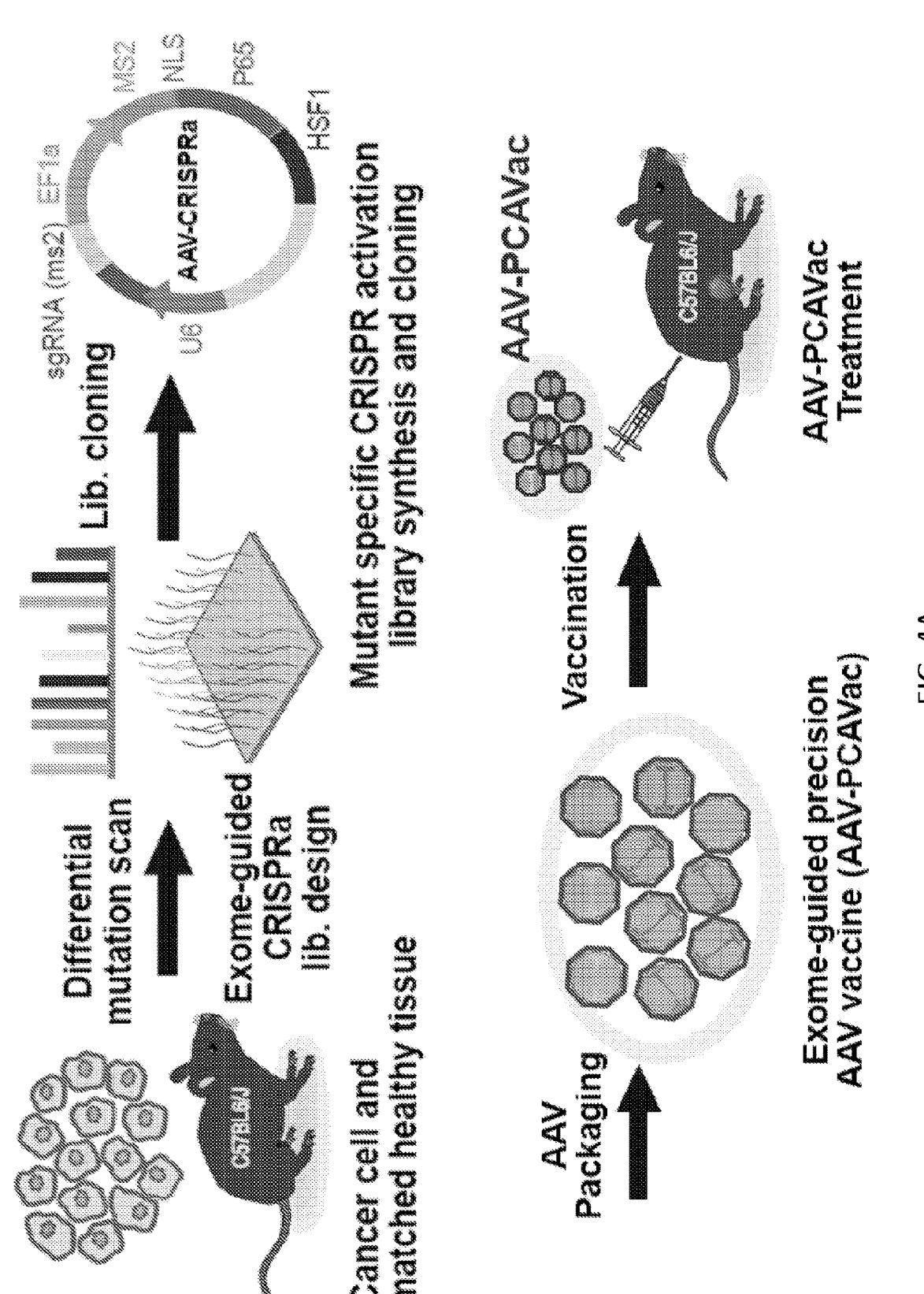
Figure 4B:
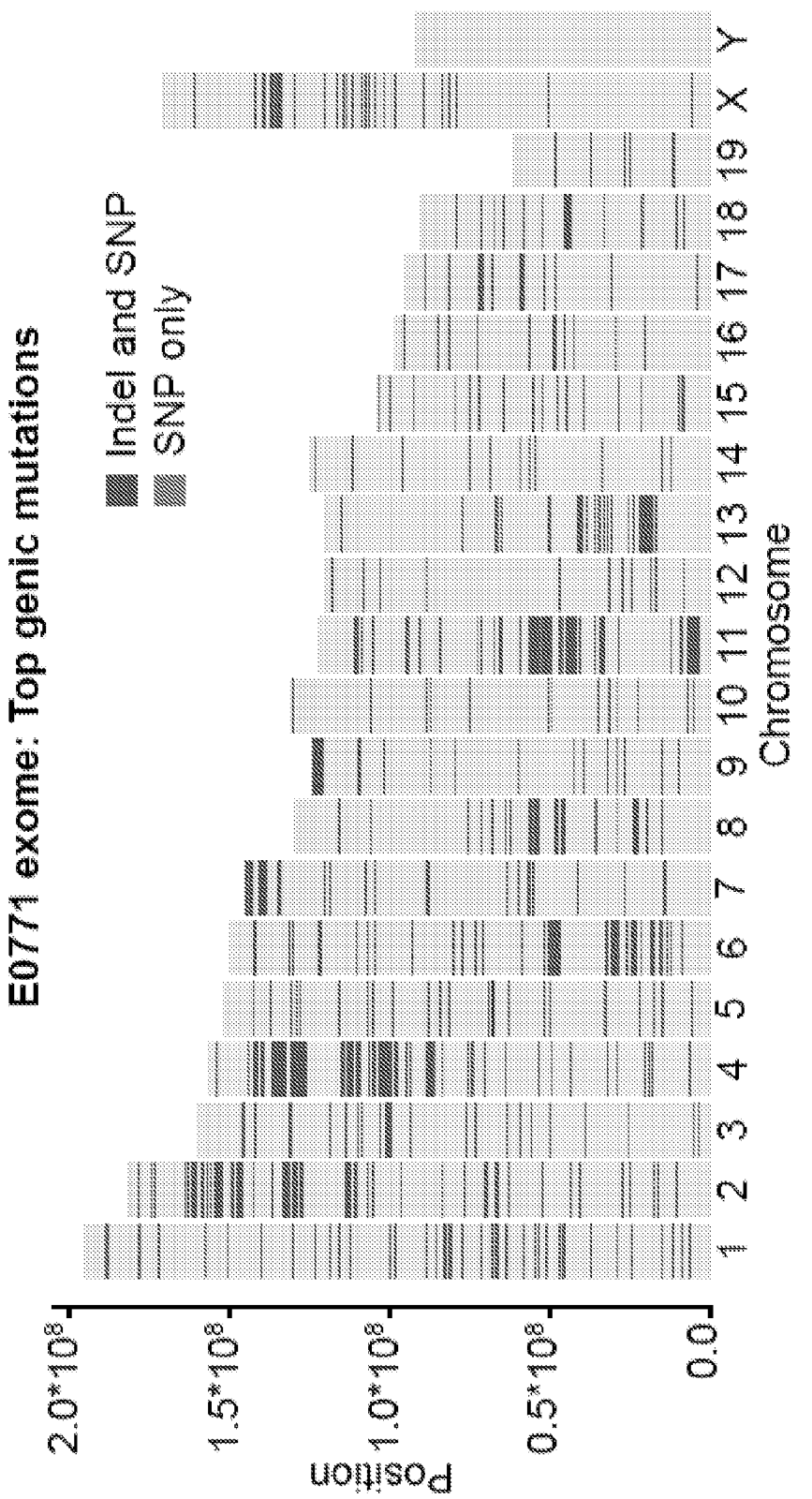
FIG. 4B shows whole-exome sequencing identified top genomic mutations in E0771 cells, as shown over their positions in the mouse genome. Genes were colored by the presence or absence of SNPs and/or indels.
Figure 4C:
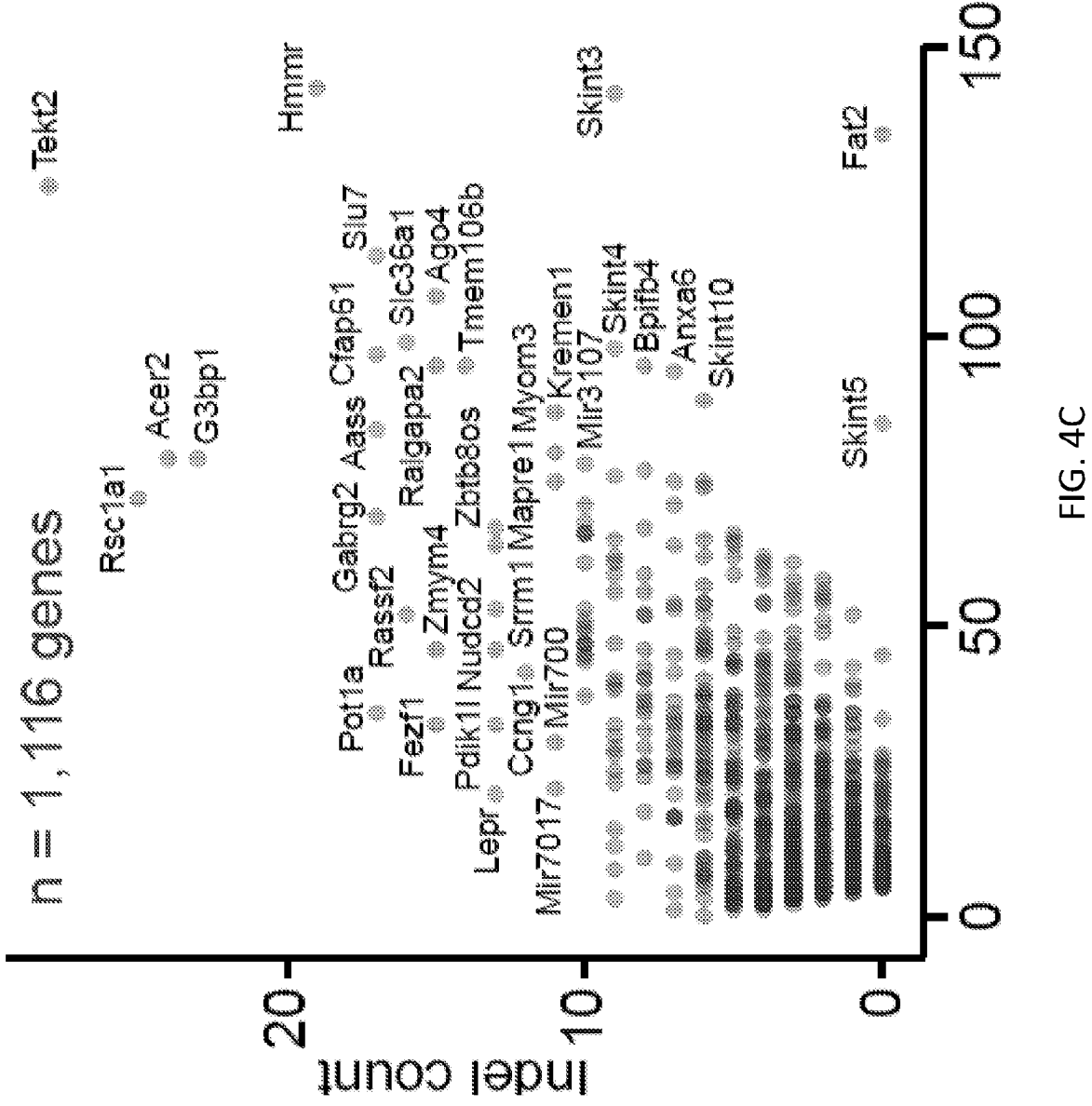
FIG. 4C is a scatter plot showing the number of mutations as SNPs or indels per gene. Genes were filtered by a minimum number of total mutations in E0771 cells compared to wildtype mammary fatpad. Examples of most highly mutated genes are Tekt2, Hmmr, Acer2, G3bp1, Rsc1a1, Slu7, and Skint3. A total of 1,116 genes were used in customized library design.
Figures 4D, 4E, 4F:
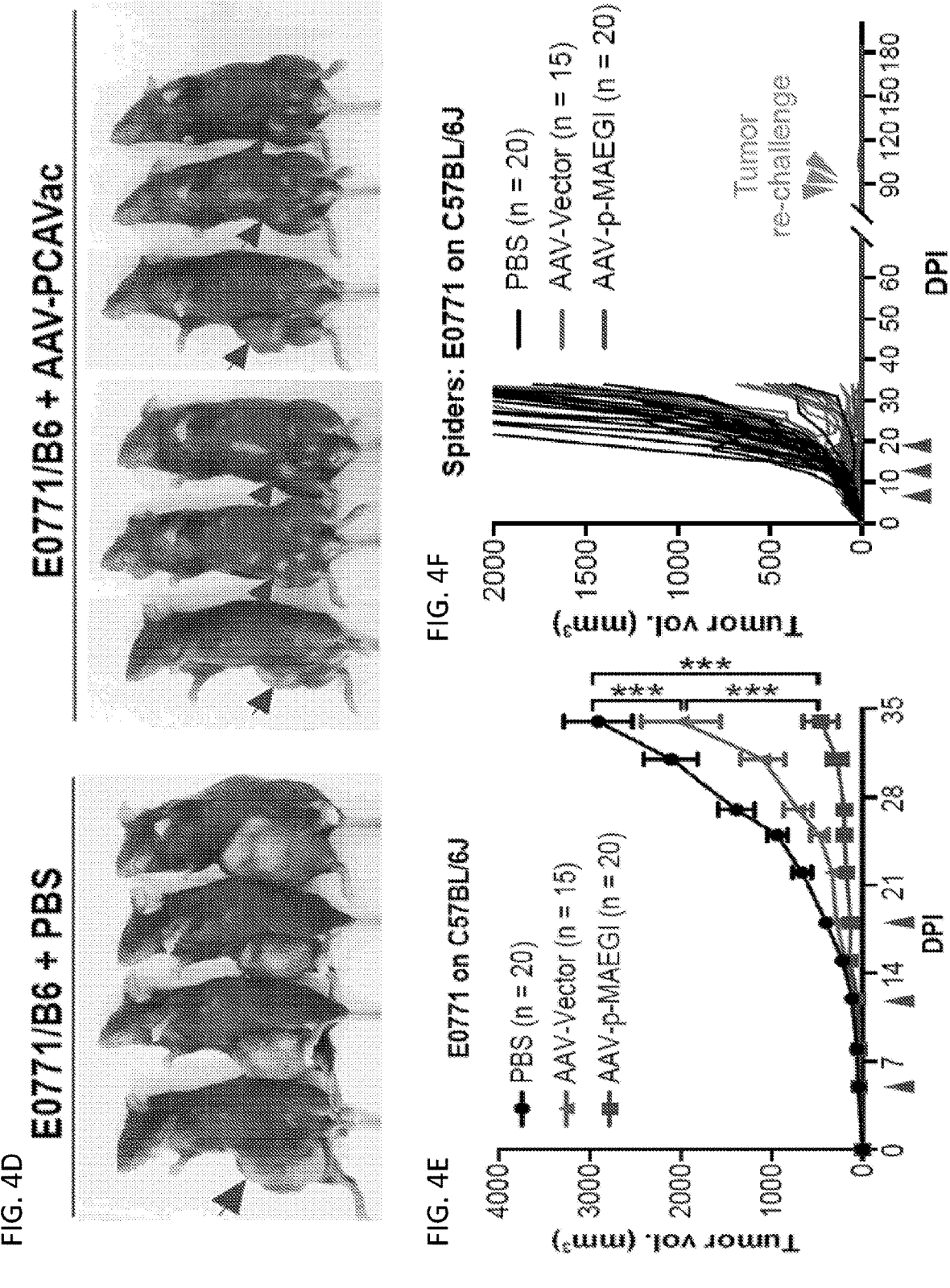
FIG. 4D shows representative images of mice at treatment end-point from PBS and AAV-PCAVac groups in the E0771 syngeneic tumor model.
FIG. 4E illustrates the therapeutic efficacy of AAV-PCAVac against established E0771 syngeneic tumors by intratumoral administration at indicated times (arrows). PBS treated mice, n=20; AAV-Vector treated mice, n=15; AAV-PCAVac (AAV-p-MAEGI) treated mice, n=20. Tumor growth curves of E0771 syngeneic tumors in mice treated by PBS, AAV-Vector, or AAV-PCAVac. Two-way ANOVA: AAV-Vector vs. PBS, p<0.0001; AAV-p-MAEGI vs. PBS, p<0.0001; AAV-PCAVac (AAV-p-MAEGI) vs. AAV-Vector, p<0.0001.
FIG. 4F is a spider plot of tumor growth curves of E0771 syngeneic tumors treated by PBS, AAV-Vector, or AAV-PCAVac (AAV-p-MAEGI). Mice whose tumors had undergone complete response by AAV-PCAVac (AAV-p-MAEGI)(n=9) were subjected to tumor re-challenges (arrows). No tumors grew with re-challenge, indicating that AAV-p-MAEGI induced long-term anti-tumor effects in mice. Treatment days are indicated by arrows.
Figure 41:
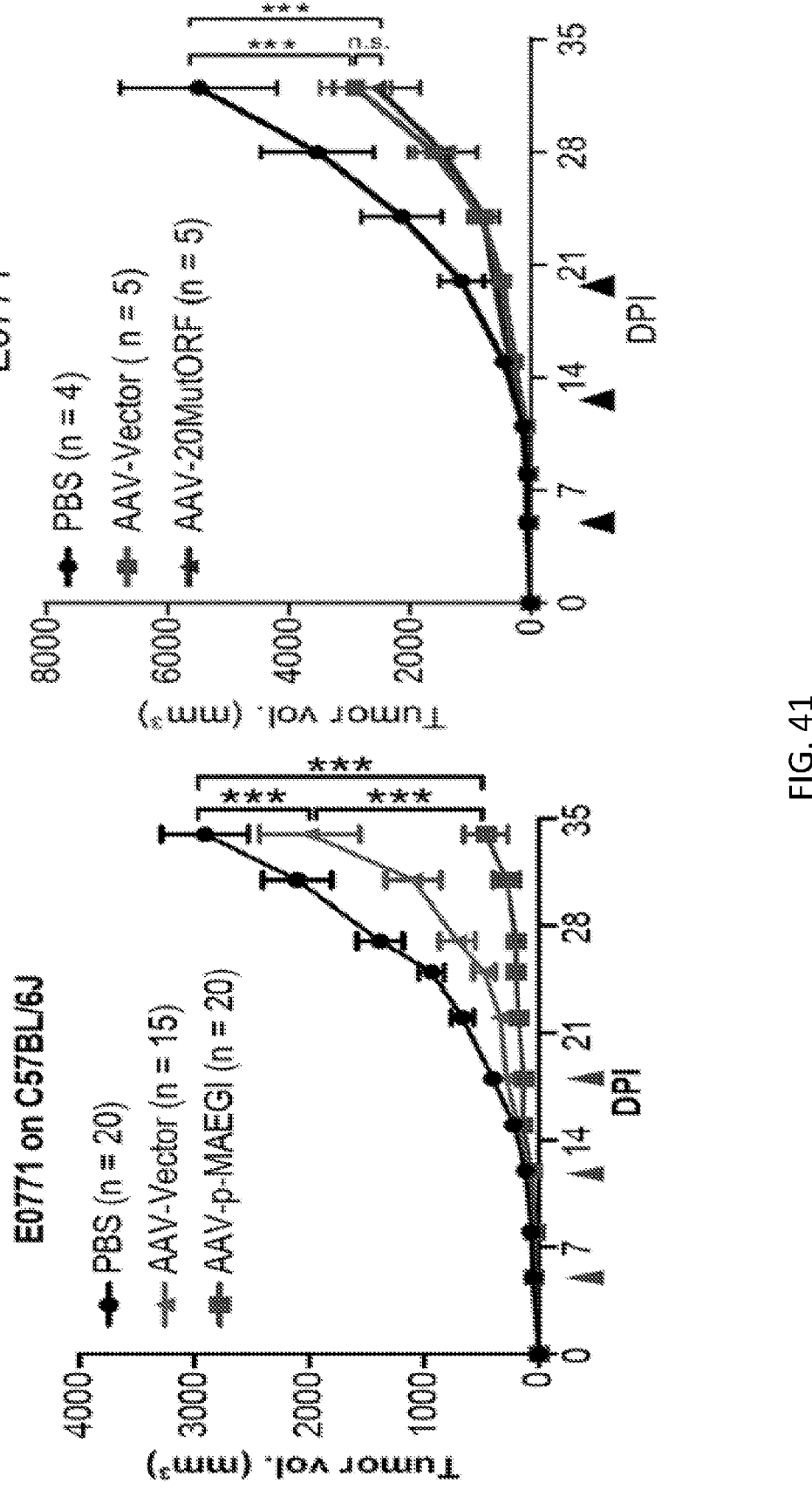

FIG. 41 illustrates that while AAV-MAEGI is highly efficacious (left panel), intratumoral delivery of the predicted top 20 mutant mini-ORFs by AAV (AAV-20MutORF) is not more effective than AAV-Vector alone (left, same as FIG. 4E). Right panel: treatment of E0771 tumor on C57BL/6 mice with PBS, AAV-Vector, or AAV-20MutORF, where the top 20 predicted most antigenic neoantigens were selected based on their mutational profile in E0771 cells and concatenated as an ORF to be expressed in AAV as a transgene.

Figure 42:
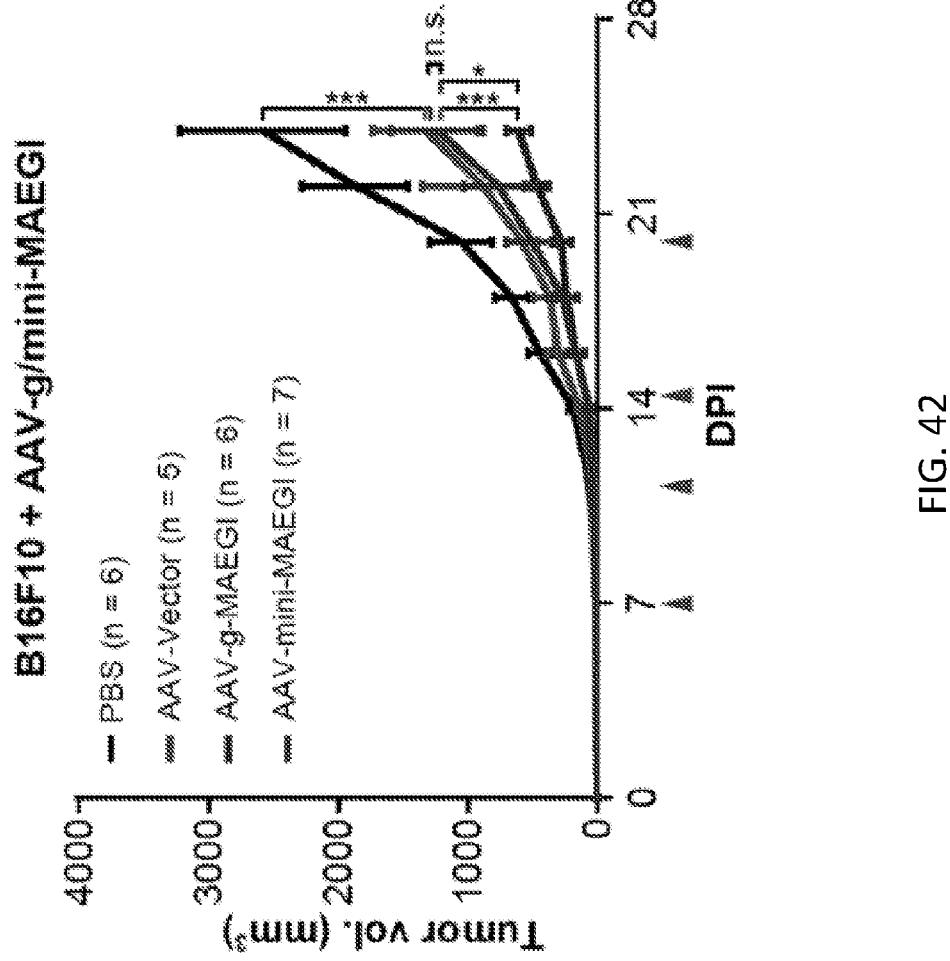

FIG. 42 illustrates data from treatment of B16F10 tumors on C57BL/6 mice with PBS, AAV-Vector, AAV-g-MAEGI (genome-wide library) or AAV-mini-MAEGI, where the 15 genes were selected based on their ranking of the mutational profile in B16F10 cells.

Figure 43:
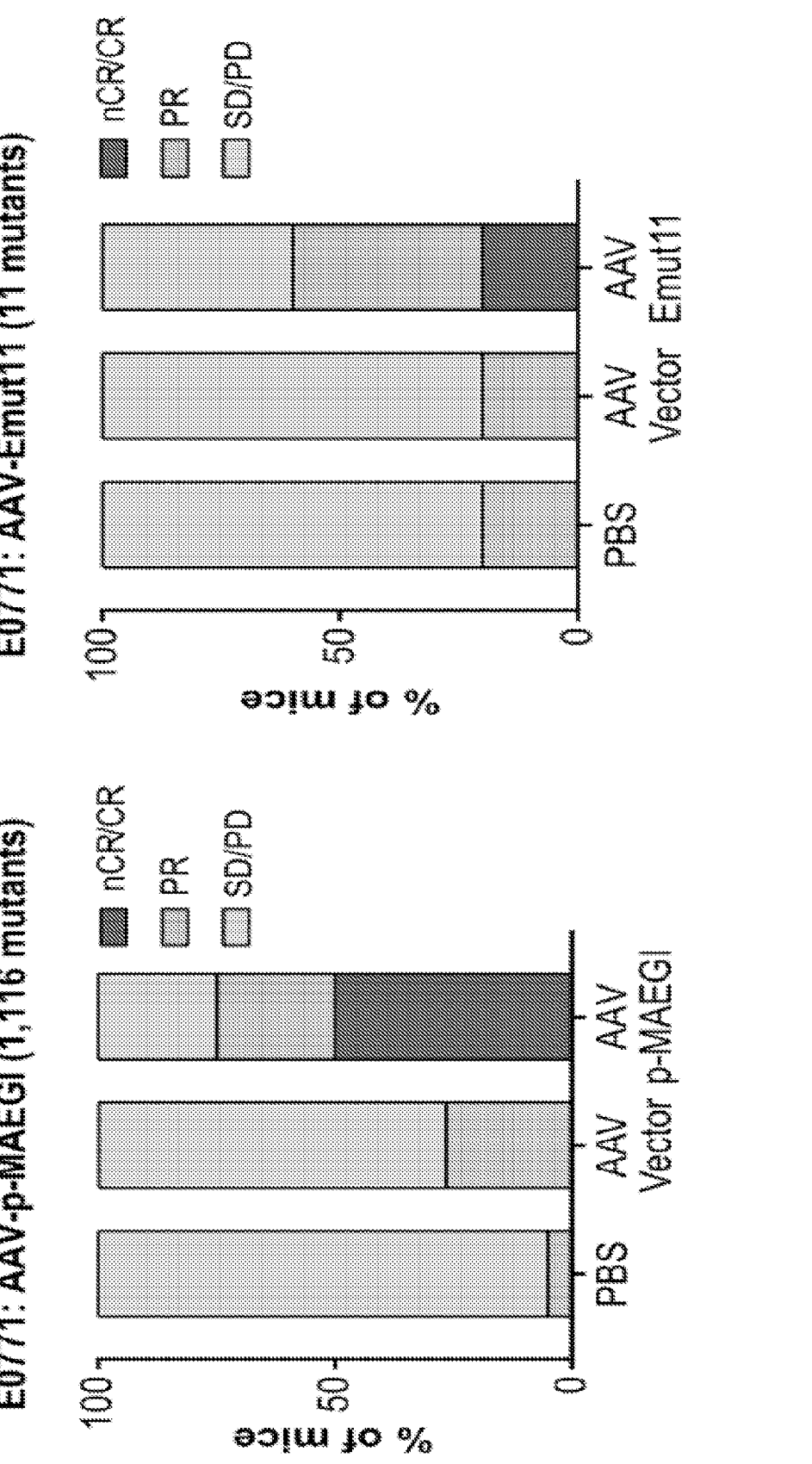

FIG. 43 illustrates reduced efficacy with Emut11, as compared to strong efficacy with E0771-p-MAEGI carrying an sgRNA library targeting 1,116 mutant genes. Left panel: same as FIG. 4M). Right panel: treatment of E0771 tumor on C57BL/6 mice with PBS, AAV-Vector, or AAV-Emut11, where the top 11 genes were selected based on their ranking of the mutational profile in E0771 cells, and their activation was driven by a small sgRNA library targeting the promoter of these genes.

Figures 44A, 44B, 45:
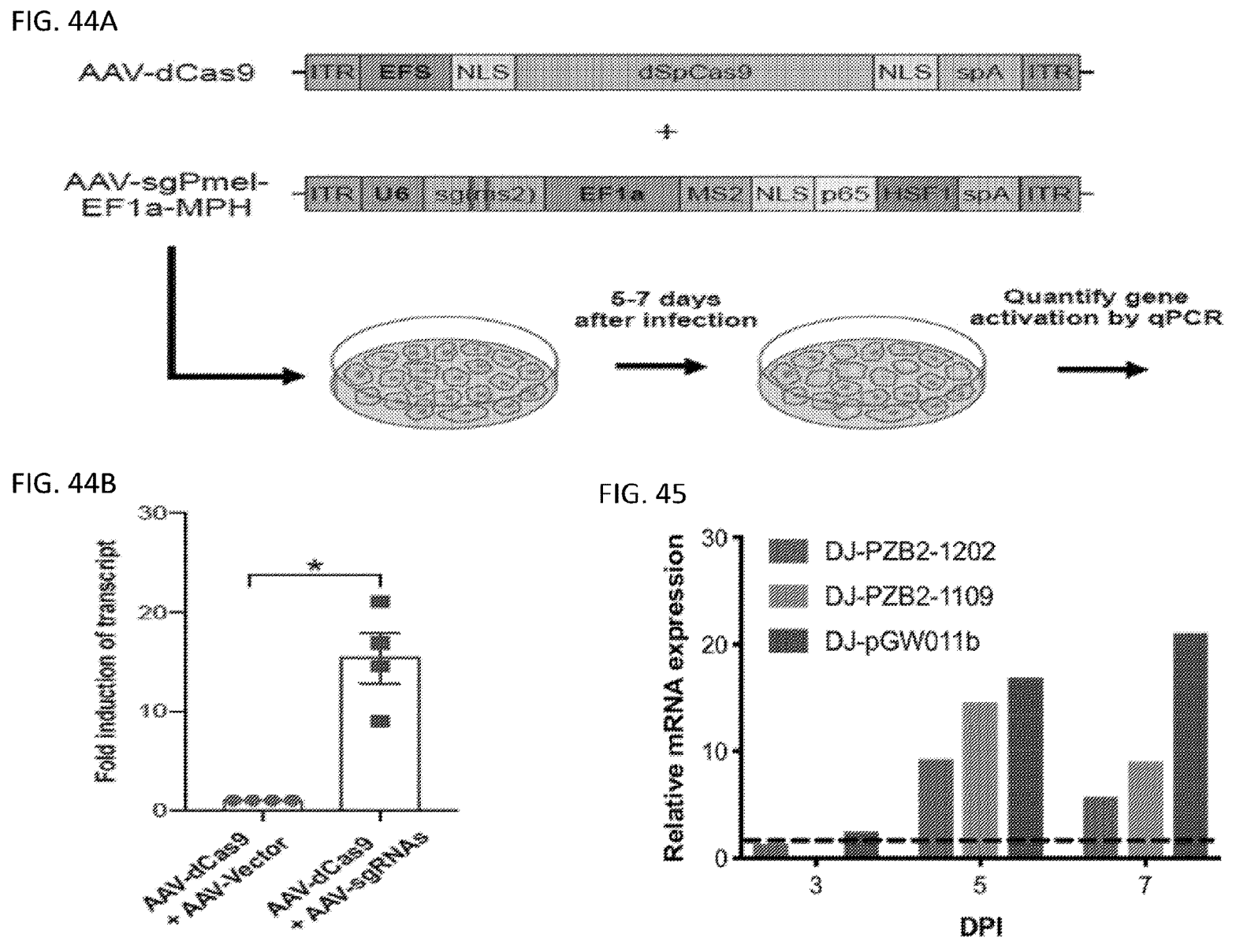

FIGS. 44A-44B illustrate dual AAV delivery for activation of an endogenous gene in E0771 cells using AAV-dCas9 and AAV-sgRNA, both packaged in AAV9. FIG. 44A is a schematic of dual AAV delivery. FIG. 44B shows dual AAV activation of PmeI.

FIG. 45 illustrates Dual AAV delivery for activation of an endogenous gene in E0771 cells using AAV-dCas9 (either PZB2 (SEQ ID NO: X) or pGW011b vector) and AAV-sgRNA, both packaged in AAV-DJ.

FIG. 46 illustrates dual-AAV delivery of a personalized library (AAV-PCAVac, i.e. AAV-p-MAEGI) into fully un-modified parental E0771 cells can mediate anti-tumor activity in vivo in C57BL/6 mice. Top panel: schematic of dual-AAV delivery of personalized library (AAV-PCAVac, i.e. AAV-p-MAEGI) into fully un-modified parental E0771 cells. Bottom panel: tumor growth curves showing Vector or MAEGI mediated anti-tumor activity in vivo on C57BL/6 mice. , $p<0.01$, *, $p<0.001$ by two-way ANOVA.

Figures 47, 48:
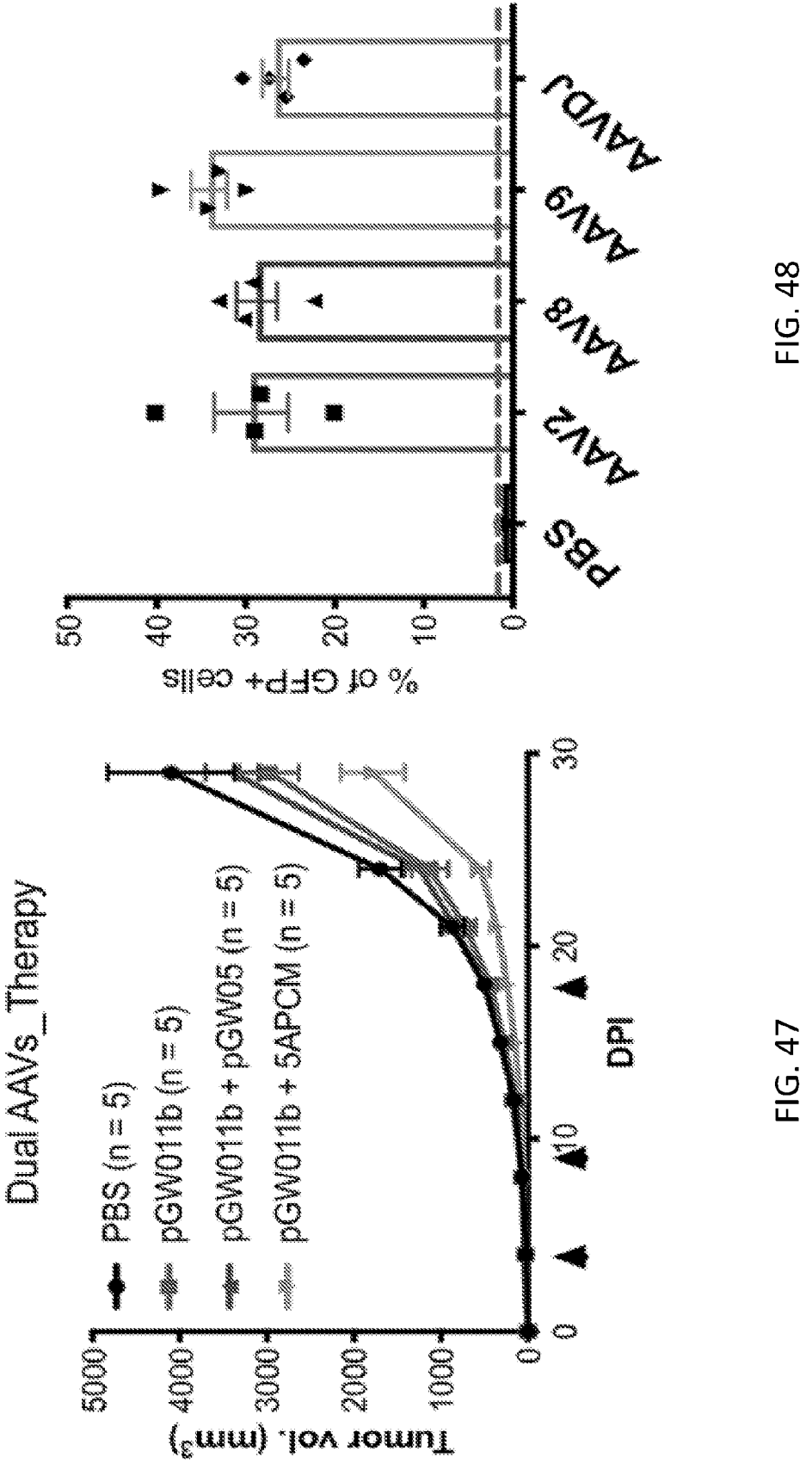

FIG. 47 illustrates tumor growth curves showing dual AAV delivery of an APCM library into fully un-modified parental E0771 cells mediates anti-tumor activity in vivo in C57BL/6 mice. pGW011b+5APCM group (APCM treated mice) vs pGW011b+pGW05 group (vector treated mice), two-way ANOVA $p=0.003$.

FIG. 48 illustrates AAV infection efficiency across serotypes assessed by intratumoral delivery of GFP-expressing AAVs and flow cytometry analysis. Percentage of GFP$^+$ cells within tumors from mice 4 days after intratumoral injection of PBS (n=3) or AAV-GFP (n=12) grouped by CD45$^+$ and CD45$^-$ cells. The background GFP fluorescence was set as the maximum % GFP positivity in PBS samples, denoted by a dashed line. Fractions above AAV conditions denote the number of samples with % GFP positivity above background in the indicated cell population.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the As used herein, the term "autologous" is meant to refer to any material derived from the same individual to which it is later to be re-introduced into the individual.

"Allogeneic" refers to any material derived from a different animal of the same species.

As used herein, the term "bp" refers to base pair.

The term "complementary" refers to the degree of anti-parallel alignment between two nucleic acid strands. Complete complementarity requires that each nucleotide be across from its opposite. No complementarity requires that each nucleotide is not across from its opposite. The degree of complementarity determines the stability of the sequences to be together or anneal/hybridize. Furthermore various DNA repair functions as well as regulatory functions are based on base pair complementarity.

The term "CRISPR/Cas" or "clustered regularly inter-spaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via RNA-guided DNA cleavage.

The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA (sgRNA). The sgRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be changed by changing the targeting sequence present in the sgRNA.

"CRISPRa" system refers to a modification of the CRISPR-Cas9 system that functions to activate or increase gene expression. In certain embodiments, the CRISPRa system is comprised of a catalytically dead RNA/DNA guided endonuclease, such as dCas9, dCas12a/dCpf1, dCas12b/dC2c1, dCas12c/dC2c3, dCas12d/dCasY, dCas12e/dCasX, dCas13a/dC2c2, dCas13b, dCas13c, dead Cascade complex, or others; at least one transcriptional activator; and at least one sgRNA that functions to increase expression of at least one gene of interest. The term "activation" as used herein refers to an increase in gene expression of one or more genes.

"dCas9" as used herein refers to a catalytically dead Cas9 protein that lacks endonuclease activity. A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90%/c identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient vectors for gene delivery. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A "mutation" as used herein is a change in a DNA sequence resulting in an alteration from a given reference sequence (which may be, for example, an earlier collected DNA sample from the same subject). The mutation can comprise deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism (subject).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Parenteral" administration of an immunogenic composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

A "sample" or "biological sample" as used herein means a biological material from a subject, including but is not limited to organ, tissue, exosome, blood, plasma, saliva, urine and other body fluid. A sample can be any source of material obtained from a subject.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

As used herein, "vaccinating" means administering a substance to a subject that induces an immune response against a disease.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention includes compositions and methods for treating or preventing cancer. In certain embodiments, the invention includes methods for treating or preventing cancer using a cell-based or an AAV-based composition that utilizes the CRISPR activation (CRISPRa) system to activate endogenous genes.

It was discovered herein that direct activation of endogenous genes is an effective means to amplify tumor-associated antigens to enhance anti-tumor immune responses. Highly multiplexed and customizable endogenous neoantigen activation has not yet been demonstrated prior to this disclosure. The present invention demonstrates the feasibility of using CRISPR technologies with RNA-guided precise genetic manipulations. The CRISPR activation (CRISPRa) system, based on dead Cas9 without nuclease activity (dCas9) (Qi et al. (20131) Cell 152, 1173-1183), enables simple and flexible regulation of gene expression with dCas9—transcriptional activation domain fusion (Gilbert et al. (2013) Cell 154, 442-451), which is further augmented by the recruitment of synergistic activation mediators (SAM) (Konermann, et al. (2015)Nature 517, 583-588; Chavez, et al. (2015) Nat Methods 12, 326-328; Tanenbaum, et al. (2014) Cell 159, 635-646). Herein, the CRISPRa system was harnessed to manipulate endogenous gene expression to magnify anti-tumor immune responses. The approach was developed into multiplexed tumor vaccination strategies.

Another aspect of the invention includes compositions and methods of both off-the-shelf and customizable endogenous gene vaccination cancer vaccines. The off-the-shelf versions have fixed components, which can have multiple forms, including single component or multi-component vaccines. The customizable versions have variable forms, which are generally multi-component vaccines in which the components are based on mutated genes in a cancer, particularly a patients' mutated genes. The compositions of these forms of cancer vaccines and their pre-clinical efficacy showed that they can be an effective means of prophylactic and therapeutic agents.

CRISPR Activation (CRISPRa) System

The CRISPR activation (CRISPRa) system is comprised of a catalytically inactive RNA-guided endonuclease or other endonucleases, such as but not limited to dCas9, dCas12a/dCpf1, dCas12b/dC2c1, dCas12c/dC2c3, dCas12d/dCasY, dCas12e/dCasX, dCas13a/dC2c2, dCas13b, dCas13c, dead Cascade complex, or others, The CRISPRa system also comprises at least one transcriptional activator, and at least one sgRNA that functions to increase expression of at least one gene of interest. Like a standard CRISPR-Cas9 system, CRISPRa systems rely on sgRNAs to guide Cas9 to intended targets. However, while a standard CRISPR-Cas9 system creates breaks in DNA through the endonuclease activity of Cas9 and then manipulates DNA repair mechanisms for gene editing, CRISPRa systems are modified and employ transcriptional activators to increase expression of genes of interest.

"dCas9" refers to a catalytically dead Cas9 protein that lacks endonuclease activity. This can be accomplished by introducing point mutations in the two catalytic residues (D10A and H840A) of the gene encoding Cas9. In doing so, dCas9 is unable to cleave dsDNA but retains the ability to target and bind DNA. This alone is often enough to attenuate if not outright block transcription of the targeted gene if the gRNA positions dCas9 in a way that prevents transcriptional factors and RNA polymerase from accessing the DNA. However, this ability to bind DNA can also be exploited for activation since dCas9 has modifiable regions, typically the N and C terminus of the protein, that can be used to attach transcriptional activators.

Targeting specificity is determined by complementary base-pairing of a small guide RNA (sgRNA) to the genomic loci. sgRNA is a chimeric noncoding RNA that can be subdivided into three regions: a base-pairing sequence, a dCas9-binding hairpin and a terminator. When designing a synthetic sgRNA, only the base-pairing sequence is modified. Secondary variables must also be considered: off-target effects (for which a simple BLAST run of the base-pairing sequence is required), maintenance of the dCas9-binding hairpin structure, and ensuring that no restriction sites are present in the modified sgRNA, as this may pose a problem in downstream cloning steps. Due to the simplicity of sgRNA design, this technology is amenable to genome-wide scaling. dCas9 can be derived, for example, from *S. pyogenes, S. aureus, N. meningiditis, S. thermopilus, F. novicida C. jejuni, B. laterosporus*, or from other species.

Transcriptional activators are protein domains or whole proteins that can be linked to dCas9 or sgRNAs and assist in the recruitment of important co-factors as well as RNA Polymerase for transcription of the gene(s) targeted by the system. Transcriptional activators have a DNA binding domain and a domain for activation of transcription. The activation domain can recruit general transcription factors or RNA polymerase to the gene sequence. Activation domains can also function by facilitating transcription by stalled RNA polymerases, and in eukaryotes can act to move nucleosomes on the DNA or modify histones to increase gene expression. These activators can be introduced into the system through attachment to dCas9 or to the sgRNA. Transcriptional activators can be either mammalian cellular endogenous proteins that have activator function, activators from other species such as viruses, microbials or plants, their partial or mutant variants, engineered activators, or other forms of activators that can increase gene expression. A list of applicable viral activators include but are not limited to: VP16, VP32, VP64, VP160, HBx, NS proteins, and VMW65. A list of applicable microbial activators include but are not limited to: Lac operons and GAL4. A list of applicable mammalian cellular transcriptional activators include but are not limited to: CAP, ACTN1, ACTN2, ACTN2, ACTN4, ACTN4, ANKRD1, APEX1, ARID5B, ARL2BP, ASCC1, ASXL1, ATN1, ATXN7L3, ATXN7L3, ATXN7L3, BCL9, BCL9L, BCL10, BCL10, BICRA, BIRC2, BRCA1, BRD7, CALCOCO1, CALCOCO1, CAL-COCO1, CALCOCO1, CARM1, CARM1, CARM1, CBFB, CCAR1, CCAR1, CCAR1, CCAR1, CCAR2, CCDC62, CEBPA, CENPJ, CITED1, CITED1, CITED2, CITED2, CITED2, CITED2, CITED2, CITED4, CITED4, CITED4, COPS5, CREBBP, CREBBP, CREBBP, CTBP2, CTNNB1, CTNNB1, CTNNB1, CTNNB1, CTNNB1, DAXX, DAXX, DCAF6, DCC, DDX17, DHX9, DR1, DYRK1B, EDF1, ELF3, ELOB, ENY2, ENY2, ENY2, EP300, EP300, EP300, FAM129B, FGF2, FHL5, FOXC1, GATA3, GATA3, GATA3, GATA4, GM20517, GMEB1, GMEB2, GPS2, GPS2, GTF2A2, GTF2A2, HAND1, HCFC1, HCFC1, HELZ2, HIF3A, HINFP, HIPK2, HMGA1, HMGA1, HMGA1B, HMGB2, HYAL2, ING4, ISL1, JADE1, JMJD6, JMY, JMY, JUN, JUN, JUNB, JUND, JUP, JUP, KAT2A, KAT2B, KAT2B, KAT5, KAT5, KAT6A, KDM1A, KDM5A, KMT2C, KMT2D, LPIN1, LPIN1, LPIN2, LPIN2, LPIN3, MAGED1, MAK, MAML1, MAML1, MAML1, MAML1, MAML2, MAML2, MAML3, MAML3, MAML3, MCIDAS, MED1, MED1, MED1, MED1, MED1, MED1, MED6, MED12, MED12, MED12, MED12L, MED13, MED14, MED16, MED17, MED17, MED20, MED21, MED24, MED27, MED31, MEF2A, MMS19, MRTFA, MRTFB, MRTFB, MTA1, MTA1, MTA1, MTA1, MTA2, MTA3, MTDH, MYCBP, MYOCD, MYOD1, MYSM1, MYT1L, NACA, NCOA1, NCOA1, NCOA1, NCOA1, NCOA1, NCOA2, NCOA2, NCOA2, NCOA2, NCOA2, NCOA2, NCOA3, NCOA3, NCOA3, NCOA3, NCOA3, NCOA6, NCOA6, NCOA7, NEUROD1, NEUROG3, NFE2L1, NKX2-2, NME2, NPAT, NPM1, NR1D1, NR1D2, NR1H2, NR1H3, NR1H3, NR1H4, NR1H5, NR1I2, NR1I3, NR3C1, NRBF2, NRIP1, NRIP1, NRIP1, NRL, NSD3, NUP98, NUPR1, PARK7, PCBD1, PDLIM1, PER2, PHF2, PKN1, PMF1, PMF1, PML, PML, PML, POU2AF1, POU3F, POU3F2, POU3F2, POU4F1, POU4F2, POU5F1, PPARA, PPARD, PPARD, PPARG, PPARG, PPARG, PPARGC1A, PPARGC1A, PPARGC1A, PPARGC1A, PPARGC1A, PPARGC1A, PPARGC1B, PPARGC1B, PPRC1, PRDM16, PRKCB, PRMT2, PRPF6, PRRX1, PSIP1, PSMC3IP, PSMC3IP, PSMD9, PSMD9, PUS1, RAP2C, RARA, RARA, RARB, RARG, RBM14, RBM14, RBM39, RBPMS, RERE, REXO4, RNF20, RRP1B, RUVBL1, RXRB, SCAND1, SERTAD2, SETD3, SFR1, SFR1, SIX3, SLC30A9, SLC30A9, SMARCA2, SMARCA4, SMARCB1, SMARCB1, SMARCD3, SNW1, SNW1, SOX4, SOX11, SOX11, SOX12, SOX17, SP4, SRA1, SRA1, SRA1, SRA1, SRA1, SRA1, SS18, SS18, SS18L1, SS18L2, SUB1, SUB1, SUPT3, SUPT7L, TADA1, TADA1, TADA2A, TADA2B, TADA3, TADA3, TADA3, TAF1, TAF5L, TAF6L, TAF6L, TAF7, TAF7, TAF7L, TAF9, TAF11, TAF11, TAF12, TCF3, TDRD3, TFAP2A, TFAP2A, TFAP2A, TFAP2B, TFAP2B, TFAP2B, TGFB1I1, THRA, THRAP3, THRAP3, THRAP3, THRB, TRIM24, TRIM24, TRIM28, TRIP4, TRIP4, TRRAP, TSG101, UBE2L3, UBE3A, USP16, USP21, USP22, USP22, UTF1, UTF1, VDR, VGLL2, WBP2, WBP2, WBP2NL, WDR77, WNT3A, WWC1, WWOX, WWTR1, WWTR1, YAF2, YAP1, YAP1, ZBTB18, ZCCHC12, ZCCHC2, ZCCHC18, ZMIZ2.

Applicable CRISPRa systems demonstrated to be capable of activating transcription in mammalian species include but are not limited to: VP64-p65-Rta (VPR), Synergistic Activation Mediator (SAM), Suntag, p300, and VP160.

One example of a transcriptional activator (or transactivator domain) is VP64. VP64 is made up of four copies of VP16, a viral protein sequence of 16 amino acids that is used for transcriptional activation. Embodiments of the invention include various forms of VP64, for example a nucleic acid comprising dCas9 and/or VP64, or plasmids or vectors that encode the dCas9 and/or VP64 genes. One non-limiting example includes pcDNA-dCas9-VP64 (Plasmid #47107, from Addgene). Additional elements can be present in the nucleic acid encoding dCas9 and/or VP64, as in for example lenti vector EF1a-NLS-dCas9(N863)-VP64-2A-Blast-WPRE (Plasmid #61425 from Addgene), which additionally encodes a 2A Blast resistance marker. Another non-limiting example includes plasmid pLV hUbC-VP64 dCas9 VP64-T2A-GFP (Plasmid #59791 from Addgene) that co-expresses human optimized *S. pyogenes* dCas9 fused to two copies of VP64 and GFP.

Certain embodiments of the invention utilize the VP64-p65-Rta, or VPR, in which a VP64 transcriptional activator is joined to the C terminus of dCas9. In the dCas9-VPR protein, the transcription factors p65 and Rta are added to the C terminus of dCas9-VP64. Therefore, all three transcription factors are targeted to the same gene. The use of three transcription factors, as opposed to solely VP64, results in increased expression of targeted genes. dCas9-VPR can be used to increase expression of multiple genes within the same cell by putting multiple sgRNAs into the same cell.

In certain embodiments, the invention utilizes the Synergistic Activation Mediator (SAM) system. SAM makes use of not only VP64 but also sgRNA 2.0, which contains a sequence to recruit a viral protein fused to even more effectors (p65-hsf1). In one embodiment the SAM complex comprises dCas9-VP64, sgRNA, MS2-p65HSF-1. In one embodiment, the CRISPRa system comprises a nucleic acid encoding dCas9-VP64, a nucleic acid encoding MS2-p65-HSF1, and a genome-scale lentiviral SAM CRISPRa sgRNA library. Administering this type of CRISPRa system to a plurality of cells results in a highly diverse population of cells encompassing the entire sgRNA library.

The invention should be construed to work with any alternative activator, such as VP16, VP160, p65AD, p300 or any other transcriptional activator.

The invention should also be construed to work with any dCas9/CRISPRa system or any other adaptor system known in the art, including but not limited to: 1) RNA Scaffolds, which also utilizes sgRNA 2.0 and recruits 3 viral proteins fused to VP64.2) Suntag, which sports a protruding chain of 10 peptide epitopes that are recognized by an entourage of antibodies fused to VP64.3) The epigenetic editor p300, which deposits activating H3K27ac. 4) VP160, which is also known as CRISPR-on and has ten times the VPs of VP16. 5) VP64-dCas9-BFP-VP64, which makes use of that much neglected N-terminus.

Methods of Treatment

A. Cell-Based:

The present invention includes methods for treating or preventing cancer in a subject comprising administering to the subject a cell that has been modified by the CRISPR activation (CRISPRa) system to induce expression of endogenous genes. This type of cell-based vaccine/composition can be utilized as a prophylactic treatment, a therapeutic treatment, a personalized, subject-specific treatment, and/or a method of turning 'cold' tumor into a 'hot' tumor, thus making it more susceptible to immunotherapy.

In one aspect, the invention includes a method of preventing cancer in a subject comprising contacting a cell with a composition comprising a CRISPR activation (CRISPRa) system, wherein the CRISPRa system increases expression of a plurality of endogenous genes. A therapeutically effective amount of a composition comprising the cell is administered to the subject, thus preventing cancer in the subject. This method is considered a type of prophylactic cancer treatment, or a method of protecting a subject from developing cancer, or a method of preventing the development of cancer in a subject, or a method of generating an anti-tumor response in a subject.

In another aspect, the invention includes a method of treating cancer in a subject in need thereof. The method comprises contacting a cell with a composition comprising a CRISPRa system, wherein the CRISPRa system increases expression of a plurality of endogenous genes, and administering a therapeutically effective amount of a composition comprising the cell to the subject, thus treating the cancer in the subject.

Another aspect of the invention includes a method of treating cancer in a subject in need thereof. The method comprises obtaining a first cancer cell from the subject and determining at least one mutated endogenous gene, then designing a CRISPRa system comprising an sgRNA library specific for the mutated endogenous gene. A second cancer cell from the subject is then contacted with a composition comprising the CRISPRa system, wherein the CRISPRa system increases expression of the mutated endogenous gene. A therapeutically effective amount of a composition comprising the cell is administered to the subject, thus treating the cancer in the subject. In certain embodiments, the cell comprises a plurality of mutated endogenous genes, and the activation system comprises an sgRNA library specific for the plurality of mutated endogenous genes, and increases expression of the plurality of mutated endogenous genes. In certain embodiments, the sgRNA library comprises at least one sequence selected from the group consisting of SEQ ID NOs. 1-37. In certain embodiments, the sgRNA library comprises at least one sequence selected from the group consisting of SEQ ID NOs. 51-259. In certain embodiments, the sgRNA library comprises at least one sequence selected from the group consisting of SEQ ID NOs. 260-348. In certain embodiments, the sgRNA library comprises at least one sequence selected from the group consisting of SEQ ID NOs. 349-4,187. In certain embodiments, the sgRNA library comprises at least one sequence selected from the group consisting of SEQ ID NOs. 4,188-7,980. In certain embodiments, the sgRNA library comprises at least one sequence selected from the group consisting of SEQ ID NOs. 7,981-11,808. In certain embodiments, the sgRNA library comprises at least one sequence selected from the group consisting of SEQ ID NOs. 11,809-23,776. In certain embodiments, the sgRNA library comprises at least one sequence selected from the group consisting of SEQ ID NOs. 23,779-23,885. In certain embodiments, the sgRNA library comprises at least one sequence selected from the group consisting of SEQ ID NOs. 23,886-24,104.

With regard to any and all sgRNA libraries disclosed herein, it should be understood by one of ordinary skill in the art that when it is stated that the library comprises at least one sgRNA, it should be construed that the library can comprise one or more sgRNAs, all sgRNAs in the library, and and all integer values and numerical ranges of sgRNAs there between. For example, an sgRNA library comprising a total of 219 sgRNAs (e.g. SEQ ID NOs. 23,886-24,104) can comprise one sgRNA, all 219 sgRNAs, or and any and all integer values between 1 and 219. In other words, the library could include 1, 10, 20, 50, 100, 150, 200, or 219 sgRNAs and any and all values in between.

B. Vector-Based:

The invention also includes a vector-based vaccine/composition useful for treating or preventing cancer. The vector comprises the CRISPR activation (CRISPRa) system used to induce expression of endogenous genes and the vector provides a delivery vehicle for administration to a subject. This type of vector-based vaccine/composition can be utilized as a prophylactic treatment, a therapeutic treatment, a personalized, subject-specific treatment, and a method of turning 'cold' tumor into a 'hot' tumor, thus making it more susceptible to immunotherapy.

One aspect of the invention includes a method of treating cancer in a subject in need thereof comprising administering to the subject a therapeutically effective amount of a composition comprising a vector comprising a CRISPRa system, wherein the CRISPRa system increases expression of at least one endogenous gene, thus treating the cancer in the subject.

The vector can be any vector that can carry the gene, including but not limited to, standard viral vectors, chimeric viral vectors, other viral vectors, bacterial vectors, yeast vectors, DNA vectors, mRNA, protein carriers, nanomaterials, or other delivery vehicles. Applicable standard viral vectors for delivery include the vectors from the following types of viruses: dsDNA viruses (e.g. Adenoviruses, Herpesviruses, Poxviruses), ssDNA viruses (+ strand or "sense") DNA (e.g. Parvoviruses), dsRNA viruses (e.g. Reoviruses), (+)ssRNA viruses (+ strand or sense) RNA (e.g. Picornaviruses, Togaviruses), (–)ssRNA viruses (– strand or antisense) RNA (e.g. Orthomyxoviruses, Rhabdoviruses), ssRNA-RT viruses (+ strand or sense) RNA with DNA intermediate in life-cycle (e.g. Retroviruses), and dsDNA-RT viruses DNA with RNA intermediate in life-cycle (e.g. Hepadnaviruses).

In certain embodiments of the invention, the cells are packaged into an AAV vector. Applicable AAV serotypes include, but are not limited to, AAV1, AAV2, AAV3, AAV4, AAV5, AAV6, AAV7, AAV8, AAV9, AAV10, AAV11, AAV12, artificial variants such as AAV.rhlO, AAV.rh32/33, AAV.rh43, AAV.rh64R1, rAAV2-retro, AAV-DJ, AAV-PHP.B, AAV-PHP.S, AAV-PHP.eB, or other engineered versions of AAV. In one embodiment, the AAV vector is AAV9. In one embodiment, the CRISPRa system is cloned into an AAV vector.

In certain embodiments of the invention, the CRISPRa system comprises an sgRNA library, wherein the sgRNA library comprises a plurality of sgRNAs that target endogenous genes in the cell. In certain embodiments, the CRISPRa system comprises a nucleic acid encoding dCas9-VP64, a nucleic acid encoding MS2-p65-HSF1, and a genome-scale lentiviral SAM CRISPRa sgRNA library. In certain embodiments, the sgRNA library comprises at least one sequence selected from the group consisting of SEQ ID NOs. 1-37. In certain embodiments, the sgRNA library comprises at least one sequence selected from the group consisting of SEQ ID NOs. 51-259. In certain embodiments, the sgRNA library comprises at least one sequence selected from the group consisting of SEQ ID NOs. 260-348. In certain embodiments, the sgRNA library comprises at least one sequence selected from the group consisting of SEQ ID NOs. 349-4,187. In certain embodiments, the sgRNA library comprises at least one sequence selected from the group consisting of SEQ ID NOs. 4,188-7,980. In certain embodiments, the sgRNA library comprises at least one sequence selected from the group consisting of SEQ ID NOs. 7,981-11,808. In certain embodiments, the sgRNA library comprises at least one sequence selected from the group consisting of SEQ ID NOs. 11,809-23,776. In certain embodiments, the sgRNA library comprises at least one sequence selected from the group consisting of SEQ ID NOs. 23,779-23,885. In certain embodiments, the sgRNA library comprises at least one sequence selected from the group consisting of SEQ ID NOs. 23,886-24,104.

The cell or cells utilized in the invention can be from any source known to one of ordinary skill in the art. The cells of the invention may be autologous, allogeneic or xenogeneic with respect to the subject undergoing treatment. In some embodiments, the cell is from a cancer cell line. In some embodiments, the cell is from the subject. In some embodiments, the cell from the subject is a cancer cell. In further embodiments, the cancer cell is from a tumor. In some embodiments, the subject is a mammal. In further embodiments, the subject is a human.

The cells or vectors of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials. Cells or vectors of the invention can be administered in dosages and routes and at times to be determined in appropriate pre-clinical and clinical experimentation and trials. Cell and vector compositions may be administered multiple times at various dosages. Administration of the cells or vectors of the invention may be combined with other methods useful to treat the desired disease or condition as determined by those of skill in the art. In one embodiment, administering the therapeutically effective amount of the composition comprises a one dose, a two dose, a three dose, a four dose, or a multi-dose treatment. The administration of the modified cells or vectors of the invention may be carried out in any convenient manner known to those of skill in the art. In one embodiment, the cells are administered intratumorally.

Certain embodiments of the invention further comprise contacting the cell with a substance that induces senescence in the cell prior to administering to the subject. In one embodiment, the substance that induces senescence in the cell is mitomycin.

The invention includes compositions and methods for treating cancer. Types of cancer that can be treated include, but are not limited to, Acute Lymphoblastic Leukemia (ALL), Acute Myeloid Leukemia (AML), Adrenocortical Carcinoma, AIDS-Related Cancers, Kaposi Sarcoma, AIDS-Related Lymphoma, Primary CNS Lymphoma, Anal Cancer, Appendix Cancer (Gastrointestinal Carcinoid Tumors), Astrocytomas, Atypical Teratoid/Rhabdoid Tumor, Brain Cancer, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Non-Hodgkin Lymphoma, Carcinoid Tumors, Carcinoma of Unknown Primary, Cardiac (Heart) Tumors, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma (Mycosis Fungoides and Sézary Syndrome), Ductal Carcinoma In Situ (DCIS), Endometrial Cancer, Ependymoma, Esophageal Cancer, Esthesioneuroblastoma, Ewing Sarcoma, Extracranial Germ Cell Tumor, Eye Cancer, Intraocular Melanoma, Fallopian Tube Cancer, Fibrous Histiocytoma of Bone, Osteosarcoma, Gallbladder Cancer, Gastric Cancer, Stomach Cancer, Gastrointestinal Carcinoid Tumor, Gastrointestinal Stromal Tumors (GIST), Central Nervous System Germ Cell Tumors, Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis (Langerhans Cell), Hodgkin Lymphoma, Hypopharyngeal Cancer, Intraocular Melanoma, Islet Cell Tumors, Pancreatic Neuroendocrine Tumors, Kidney Cancer, Renal Cell Cancer, Langerhans Cell Histiocytosis, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Intraocular (Eye) Melanoma, Merkel Cell Carcinoma (Skin Cancer), Malignant Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, and Oropharyngeal Cancer, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer Recurrent Cancer, Retinoblastoma, Rhabdomyosarcoma, Salivary Gland Cancer, Sarcoma, Vascular Tumors, Uterine Sarcoma, Sézary Syndrome (Lymphoma), Small Cell Lung Cancer, Small Intestine Cancer, Soft Tissue Sarcoma, Squamous Cell Carcinoma, Stomach (Gastric) Cancer, Throat Cancer, Thymoma, Thymic Carcinoma, Thyroid Cancer, Transitional Cell Cancer of the Renal Pelvis and Ureter, Carcinoma of Unknown Primary, Ureter and Renal Pelvis, Transitional Cell Cancer, Urethral Cancer, Uterine Cancer, Vaginal Cancer, Vulvar Cancer, Wilms Tumor, and combinations thereof.

Certain embodiments of the invention further comprise administering an additional treatment to the subject. Certain embodiments of the invention include treating the subject with a combination of a composition of the present invention and an additional treatment. Examples of additional treatments include but are not limited to, chemotherapy, radiation, surgery, medication, immune checkpoint inhibitors, immune checkpoint blockade (ICB) antibodies, immune checkpoint inhibitors that block CTLA-4 or PD1, anti-CTLA4 monoclonal antibody, anti-PD1 monoclonal antibody, anti-PD-L1 monoclonal antibody, adoptive cell transfer, human recombinant cytokines, cancer vaccines, immunotherapy, targeted therapy, hormone therapy, stem cell transplant, precision medicine, non-specific immunotherapy (e.g. cytokines and chemokines, such as IL-2, IFNa, IFNb, IFNg), oncolytic virus therapy, T-cell therapy (e.g. adoptive transfer of TILs, TCR-T, CAR-T), cancer vaccines (e.g. conventional DC vaccine), Ipilimumab (Yervoy), Nivolumab (Opdivo), Pembrolizumab (Keytruda), Atezolizumab (Tecentriq), Avelumab (Bavencio), Durvalumab (Imfinzi), Anti-LAG-3, anti-TIM1, Anti-TIM3, Anti-CSF-R, IDO inhibitor, OX-40 agonist, GITR agonist, CD80 agonist, CD86 agonist, ICOS agonist, ICOSLG agonist, CD276 agonist, VTCN1 agonist, TNFSF14 agonist, TNFSF9 agonist, TNFSF4 agonist, CD70 agonist, CD40 agonist, LGALS9 agonist, CD80 inhibitor, CD86 inhibitor, ICOS inhibitor, ICOSLG inhibitor, CD276 inhibitor, VTCN1 inhibitor, TNFSF14 inhibitor, TNFSF9 inhibitor, TNFSF4 inhibitor, CD70 inhibitor, CD40 inhibitor, LGALS9 inhibitor, TLR9 agonist, CD20 antibody, CD80 antibody, TIGIT antibody, B7-H1 antibody, B7-H2 antibody, B7-H3 antibody, B7-H4 antibody, CD28 antibody, CD47 antibody, anti-BTLA, anti-Galetin9, anti-IL15R, anti-GD2. In some embodiments the monoclonal antibody is fully human, humanized or chimeric.

In certain embodiments, administering a composition of the present invention alters the tumor microenvironment. In certain embodiments, administering the composition augments host immune responses against established tumors.

Certain aspects of the invention include determining subject-specific, or individualized mutations in a gene or genes of the subject. This determination can be carried out by any means known to one of ordinary skill in the art. For example, whole-genome-sequencing (WGS) and/or molecular inversion probe sequencing (MIPS)(Chow et al. 2018) provide other non-limiting ways of determining the subject-specific mutated endogenous gene or genes. In one embodiment, determining the subject-specific mutated endogenous gene or genes comprises whole-exome sequencing of a cancer cell and whole-exome sequencing of a non-cancer cell from the subject. The sequencing data from the cancer cell and the non-cancer cell are compared, determining at least one mutation. By this, the subject-specific mutated endogenous gene or genes are determined. Any type of mutation can be determined, including but not limited to single nucleotide polymorphisms (SNP), insertions, deletions, frameshifts, and rearrangements.

Certain aspects of the invention include activating or increasing expression of a subset of endogenous genes, for example, but not limited to those enhancing immune cell functions such as antigen-presentation. In certain embodiments sgRNAs are designed against the aforementioned endogenous genes or a subset of these genes. In certain embodiments the sgRNAs are selected from a minipool of 6 selected human antigen presentation genes, with multiple sgRNAs per gene. In one embodiment the sgRNAs are selected from the group consisting of SEQ ID NOs: 1-37. In one embodiment the sgRNAs are selected from the group consisting of SEQ ID NOs: 51-259. In certain embodiments the sgRNAs are selected from a minipool of 29 selected immune function genes related to antigen presentation. In certain embodiments the sgRNAs are selected from the group consisting of SEQ ID NOs: 260-348. In certain embodiments the sgRNAs are selected from the group consisting of 23,779-23,885. In certain embodiments the sgRNAs are selected from the group consisting of 23,886-24,104. In certain embodiments, the sgRNAs are designed to target endogeneous mutant genes present in a variety of cancers (e.g. melanoma, glioma, hepatoma, colon cancer, and pancreatic cancer). In certain embodiments the sgRNAs are selected from the group consisting of SEQ ID NOs. 11,809-23,776. These "off the shelf" sgRNA pools and minipools can be administered to a subject in conjunction with compositions and methods of the present invention, without the need for sequencing individualized tumors.

Alternatively, personalized sgRNA minipools can be designed wherein a subject's tumor is sequenced, and sgRNAs are designed specific to that subject's cancer type/ mutations. Examples of personalized sgRNA minipools described herein include: E0771 (TNBC) exome based PCAVac sgRNAs (SEQ ID NOs: 349-4,187), GL261 (GBM)

exome based PCAVac sgRNAs (SEQ ID NOs: 7,981-11, 808), and Lewis (Lung) exome based PCAVac sgRNAs (SEQ ID NOs: 4,188-7,980).

TABLE 1

| sgRNAs selected from a minipool of human antigen presentation genes | | | | | |
|---|---|---|---|---|---|
| Gene Name | Transcript ID | TSS Distance | Guide Sequence | Top/ Bottom | SEQ ID NO: |
| CD70 | NM_001252 | 145 | GGCGGGGAGGGGTTGGGGGC | b | 1 |
| CD70 | NM_001252 | 166 | ATGTCTCCTGCCTGAAGGTC | b | 2 |
| CD70 | NM_001252 | 103 | CAGGATGCAGGCAGTGGCCC | t | 3 |
| CD70 | NM_001252 | 82 | CAACTGCCTCCACCCACTTT | b | 4 |
| CD70 | NM_001252 | 2 | ATGTCCGGCCGGTCGAGGGG | t | 5 |
| CD70 | NM_001252 | 55 | TCAGACTGGCAGCGGTTGGA | b | 6 |
| CD70 | NM_001252 | 124 | GGCAACTCTGAGGCTCACCC | b | 7 |
| CD70 | NM_001252 | 23 | GGGACTTGAGCAATTGGCGA | t | 8 |
| CD80 | NM_005191 | 153 | TTCTCCTCCCCTAGGCCGCC | b | 9 |
| CD80 | NM_005191 | 100 | GCCTCCCTCACCACCGTGCA | t | 10 |
| CD80 | NM_005191 | 61 | GCTTTTGTAGAGGCTGTGGC | t | 11 |
| CD80 | NM_005191 | 7 | CAAACACCCTGTCCAACTCC | b | 12 |
| CD80 | NM_005191 | 38 | TAGAAGAAGACGGCAGCAGA | b | 13 |
| CD80 | NM_005191 | 174 | AATGGTGCCCGAGAAGAGTG | t | 14 |
| CD80 | NM_005191 | 132 | CATGAAACACCACGAGCACC | t | 15 |
| CD86 | NM_001206924 | 7 | TTAAAGAAAGTTAGCTGGGT | t | 16 |
| CD86 | NM_001206924 | 87 | GAGTTTAAACTGCAAGGAAA | t | 17 |
| CD86 | NM_001206924 | 41 | TCAAAATCTGTAGAGAAAAG | t | 18 |
| CD86 | NM_001206924 | 64 | TTAAATTTCTTCCTCAAGTG | t | 19 |
| CD86 | NM_001206924 | 162 | GCTCATCTTAACGTCATGTC | t | 20 |
| CD86 | NM_006889 | 134 | CTCCCTTTGGGGGTTTCCCA | t | 21 |
| CD86 | NM_006889 | 8 | AGAGAAACAACACCACAGCC | b | 22 |
| CD86 | NM_006889 | 157 | CTTTGTCATGTTTGTGGATG | t | 23 |
| CD86 | NM_006889 | 29 | CCAAGCAAGAGCACTGTCCC | t | 24 |
| CD86 | NM_006889 | 50 | TCCAAATAACTTCTGCCGGC | b | 25 |
| CD86 | NM_006889 | 85 | TTTGTAGTCATTCTCATCAG | t | 26 |
| CD86 | NM_006889 | 112 | GCTTTACACTCATGCTCCGA | t | 27 |
| IFNA4 | NM_021068 | 0 | GAAGACTTTGCTCTGTGCAT | t | 28 |
| IFNA4 | NM_021068 | 152 | TATTTTTCACCTGCACTCAA | t | 29 |
| IFNA4 | NM_021068 | 51 | CAACTAGGGAATTTAGAAAA | b | 30 |
| IFNB1 | NM_002176 | 64 | TGAAAGGGAGAAGTGAAAGT | b | 31 |
| IFNB1 | NM_002176 | 33 | ATGGTCCTCTCTCTATTCAG | t | 32 |
| IFNG | NM_000619 | 155 | AGAGTTTCCTTTAGACTCCT | t | 33 |
| IFNG | NM_000619 | 8 | TAAATACCAGCAGCCAGAGG | b | 34 |
| IFNG | NM_000619 | 33 | ATCCTCAGGAGACTTCAATT | b | 35 |
| IFNG | NM_000619 | 121 | AACTAAGGTTTTGTGGCATT | t | 36 |
| IFNG | NM_000619 | 75 | AAGATGAGATGGTGACAGAT | t | 37 |

Additional sequences for cloning synthesized libraries into:
Subpool amplification (SPA) primers:

SPA_1F      CGGGTTCCGTGGAAAGG (SEQ ID NO: 38)

SPA_1Rms2 ttctattctaagcCTCATGTTggcc (SEQ ID NO: 39)

SPA_2F      GTTTATCGGGCGGAAAGG (SEQ ID NO: 40)

SPA_2Rms2 GGTACAGTAAGTCTCATGTTggcc (SEQ ID NO: 41)

SPA_3F      aCCGATGTTGACGGAAAGG (SEQ ID NO: 42)

SPAv3Rms2 GCTATTACGAGCTCATGTTggcc (SEQ ID NO: 43)

SPAv4F      GAGGTCTTTCATGCGGAAAGG (SEQ ID NO: 44)

SPA_Rms2  TATGTTGTGCTCATGTTggcc (SEQ ID NO: 45)

AF          taacttgaaagtatttcgatttcttggctttatatatc
            ttGTGGAAAGGACGAAACACCg (SEQ ID NO: 46)

AR          actattcaagttgataacggactagccttatttt
            aacttgctaTTTCtagctctaaaac (SEQ ID NO: 47)

ARms2     attttaacttgctaggccCTGCAGACATGGGTGATCC
            TCATGTTggcctagctctaaaac (SEQ ID NO: 48)

TABLE 2

| sgRNAs selected from a minipool of immune function genes | | |
| --- | --- | --- |
| Gene | sgRNA Sequence | SEQ ID NO |
| CD70 | CAGTCTGAAGATCCTAAAGT | 51 |
| CD70 | TCTGAAGATCCTAAAGTGGG | 52 |
| CD70 | AATCCCTAATAAATGTGCAG | 53 |
| CD70 | TACTTGCTTCAACCTGTCAG | 54 |
| CD70 | GGACTTGAGCAATTGGCGAG | 55 |
| CD70 | CCACTTTAGGATCTTCAGAC | 56 |
| CD70 | GAAGATCCTAAAGTGGGTGG | 57 |
| CD70 | TCCCCGCCCGACCTTCAGGC | 58 |
| CD70 | TCAGACTGGCAGCGGTTGGA | 59 |
| CD70 | ATCTTCAGACTGGCAGCGGT | 60 |
| CD70 | TGGGCCCCAGAAGAATGAGG | 61 |
| CD70 | GCAACTCTGAGGCTCACCCG | 62 |
| CD70 | CTCTCCACCTCATTCTTCTG | 63 |
| CD70 | CGGGGCCACTGCCTGCATCC | 64 |
| CD70 | TCTCCTGCCTGAAGGTCGGG | 65 |
| CD70 | GGCCGGACATCCCCAGAGAG | 66 |
| CD70 | GGGACTTGAGCAATTGGCGA | 67 |
| CD70 | ATTGAATGTCTCCTGCCTGA | 68 |
| CD70 | CCCTAATAAATGTGCAGTGG | 69 |
| CD70 | GAATGGGCCCCAGAAGAATG | 70 |
| CD70 | AGGGACTTGAGCAATTGGCG | 71 |
| CD70 | GGGCAGGCTGGTCCCCTGAC | 72 |
| CD70 | GGGGATGTCCGGCCGGTCGA | 73 |
| CD70 | TTCAGACTGGCAGCGGTTGG | 74 |
| CD70 | CCAGTCTGAAGATCCTAAAG | 75 |
| CD70 | CCGGCCGGACATCCCCAGAG | 76 |
| CD70 | AGGCAACTCTGAGGCTCACC | 77 |
| CD70 | CCTCTCTGGGGATGTCCGGC | 78 |
| CD70 | CTCAAGTCCCTCCCCTCGAC | 79 |
| CD70 | TCCTGCCTGAAGGTCGGGCG | 80 |
| CD70 | AGTCCCTCCCCTCGACCGGC | 81 |
| CD70 | CGGCCGGACATCCCCAGAGA | 82 |
| CD70 | GGGATGTCCGGCCGGTCGAG | 83 |
| CD70 | CCCAGAAGAATGAGGTGGAG | 84 |
| CD70 | GACCAGCCTGCCCCTCTCTG | 85 |
| CD70 | AGTGGGTGGAGGCAGTTGCC | 86 |
| CD70 | ATGTCTCCTGCCTGAAGGTC | 87 |

TABLE 2-continued

| sgRNAs selected from a minipool of immune function genes | | |
| --- | --- | --- |
| Gene | sgRNA Sequence | SEQ ID NO |
| CD70 | TCTACTTGCTTCAACCTGTC | 88 |
| CD70 | CAGAAGAATGAGGTGGAGAG | 89 |
| CD70 | TGCCCCTCTCTGGGGATGTC | 90 |
| CD70 | CTACTTGCTTCAACCTGTCA | 91 |
| CD70 | CCCCTCCCCGCCCGACCTTC | 92 |
| CD70 | AATGTCTCCTGCCTGAAGGT | 93 |
| CD70 | GGAGGCAGTTGCCAGGATGC | 94 |
| CD70 | AGGATGCAGGCAGTGGCCCC | 95 |
| CD70 | TAGGATCTTCAGACTGGCAG | 96 |
| CD70 | CTCCTGCCTGAAGGTCGGGC | 97 |
| CD70 | CCCTCTCCACCTCATTCTTC | 98 |
| CD70 | CCAGAAGAATGAGGTGGAGA | 99 |
| CD70 | TGTCCGGCCGGTCGAGGGGA | 100 |
| CD70 | CCTCTCCACCTCATTCTTCT | 101 |
| CD70 | AGTTGCCAGGATGCAGGCAG | 102 |
| CD70 | TGGGGATGTCCGGCCGGTCG | 103 |
| CD70 | GGGACCAGCCTGCCCCTCTC | 104 |
| CD70 | AGGTTTGTTGAATAAATGAA | 105 |
| CD70 | GGACATCCCCAGAGAGGGGC | 106 |
| CD70 | GTTGGGGGCAGGCAACTCTG | 107 |
| CD70 | GGTTTGTTGAATAAATGAAT | 108 |
| CD70 | ATGTCCGGCCGGTCGAGGGG | 109 |
| CD70 | GGCAACTCTGAGGCTCACCC | 110 |
| CD70 | CCTGAAGGTCGGGCGGGGAG | 111 |
| CD70 | GCCTGAAGGTCGGGCGGGGA | 112 |
| CD70 | AGGGGAGGGACTTGAGCAAT | 113 |
| CD70 | ATCCCCAGAGAGGGGCAGGC | 114 |
| CD70 | TGCCTGAAGGTCGGGCGGGG | 115 |
| CD70 | GGTCGGGCGGGGAGGGGTTG | 116 |
| CD70 | CAACTGCCTCCACCCACTTT | 117 |
| CD70 | GTCGGGCGGGGAGGGGTTGG | 118 |
| CD70 | CAGGATGCAGGCAGTGGCCC | 119 |
| CD70 | GGCGGGGAGGGGTTGGGGGC | 120 |
| CD70 | AATGAGGTGGAGAGGGGAAT | 121 |
| CD70 | GGACCAGCCTGCCCCTCTCT | 122 |
| CD70 | AGGTCGGGCGGGGAGGGGTT | 123 |
| CD70 | AAGGTCGGGCGGGGAGGGGT | 124 |

TABLE 2-continued

TABLE 2-continued

| | sgRNAs selected from a minipool of immune function genes | | | | sgRNAs selected from a minipool of immune function genes | |
|---|---|---|---|---|---|---|
| Gene | sgRNA Sequence | SEQ ID NO | | Gene | sgRNA Sequence | SEQ ID NO |
| CD80 | GTTTGTTAGTCCATGCACGG | 125 | | CD80 | GCTTTTGTAGAGGCTGTGGC | 162 |
| CD80 | TCAGTGCCAGGAGTTGGACA | 126 | | CD80 | GGGAGGCCAGCTTCATGGGC | 163 |
| CD80 | TGGTGCCCGAGAAGAGTGAG | 127 | | CD80 | TGGGCTGGCTGTTTCTGTGC | 164 |
| CD80 | TAGAAGAAGACGGCAGCAGA | 128 | | CD80 | AGTTGCTTTTGTAGAGGCTG | 165 |
| CD80 | TAGTCCATGCACGGTGGTGA | 129 | | CD80 | TTCTCCTCCCCTAGGCCGCC | 166 |
| CD80 | ATGGTGCCCGAGAAGAGTGA | 130 | | CD80 | AGATGCCCCTCACTCTTCTC | 167 |
| CD80 | ACGAGCACCAGGCGGCCTAG | 131 | | CD80 | GTGATGGGAGGCCAGCTTCA | 168 |
| CD80 | CATGAAACACCACGAGCACC | 132 | | CD86 | CAGTTTAAACTCATTGACGT | 169 |
| CD80 | GAAACACCACGAGCACCAGG | 133 | | CD86 | ACAGATTTTGACCACACTTG | 170 |
| CD80 | CAAACACCCTGTCCAACTCC | 134 | | CD86 | TTTTTTGAGGGAATTTCAAG | 171 |
| CD80 | CATGTTTGTTAGTCCATGCA | 135 | | CD86 | TCAAAATCTGTAGAGAAAAG | 172 |
| CD80 | TAGCCTTGCTGTGTGATGGG | 136 | | CD86 | TTAAATTTCTTCCTCAAGTG | 173 |
| CD80 | ACTCAGTACTTGTCAGTGCC | 137 | | CD86 | GCTCATCTTAACGTCATGTC | 174 |
| CD80 | TCTTCTAGTTGCTTTTGTAG | 138 | | CD86 | ATTCTATTTTGTTGCTGCGG | 175 |
| CD80 | TGGCCTCCCATCACACAGCA | 139 | | CD86 | TTTTTGAGGGAATTTCAAGA | 176 |
| CD80 | TTAGTCCATGCACGGTGGTG | 140 | | CD86 | TTTATTCTATTTTGTTGCTG | 177 |
| CD80 | AATGGTGCCCGAGAAGAGTG | 141 | | CD86 | TTTTGAGGGAATTTCAAGAG | 178 |
| CD80 | GGCTAGCCTTGCTGTGTGAT | 142 | | CD86 | AGCAACAAAATAGAATAAAG | 179 |
| CD80 | TCCATGCACGGTGGTGAGGG | 143 | | CD86 | TGAGTTTAAACTGCAAGGAA | 180 |
| CD80 | TGATGGGAGGCCAGCTTCAT | 144 | | CD86 | TTCTCTTAAAGAAAGTTAGC | 181 |
| CD80 | TGGCTAGCCTTGCTGTGTGA | 145 | | CD86 | AGAGGGGAGATTTTTTATTC | 182 |
| CD80 | CCTAGGCCGCCTGGTGCTCG | 146 | | CD86 | TCTCTTAAAGAAAGTTAGCT | 183 |
| CD80 | CTAGAAGAAGACGGCAGCAG | 147 | | CD86 | GTCAATGAGTTTAAACTGCA | 184 |
| CD80 | CACCATTCTTCTCCTCCCCT | 148 | | CD86 | GAGTTTAAACTGCAAGGAAA | 185 |
| CD80 | AAACAGCCAGCCCATGAAGC | 149 | | CD86 | TTATTTTCTAGGTTTTTTGA | 186 |
| CD80 | CAAAAGCAACTAGAAGAAGA | 150 | | CD86 | TTAAAGAAAGTTAGCTGGGT | 187 |
| CD80 | CTTTTGTAGAGGCTGTGGCT | 151 | | CD86 | TTTATTTTCTAGGTTTTTTG | 188 |
| CD80 | AGCACCAGGCGGCCTAGGGG | 152 | | CD86 | TTCTAATTATTTTATTTTCT | 189 |
| CD80 | CACGAGCACCAGGCGGCCTA | 153 | | IFNA4 | AGAGATAGAAAGTACAACTA | 190 |
| CD80 | CCACGAGCACCAGGCGGCCT | 154 | | IFNA4 | CAGAGATAGAAAGTACAACT | 191 |
| CD80 | GTCAGTGCCAGGAGTTGGAC | 155 | | IFNA4 | TATTTTTCACCTGCACTCAA | 192 |
| CD80 | TACTTGTCAGTGCCAGGAGT | 156 | | IFNA4 | CCATAAAAGCCTTTGAGTGC | 193 |
| CD80 | TTTTGTAGAGGCTGTGGCTG | 157 | | IFNA4 | CAACTAGGGAATTTAGAAAA | 194 |
| CD80 | CAGATGCCCCTCACTCTTCT | 158 | | IFNA4 | CCTGCACTCAAAGGCTTTTA | 195 |
| CD80 | CGAGAAGAGTGAGGGGCATC | 159 | | IFNA4 | GAAGACTTTGCTCTGTGCAT | 196 |
| CD80 | GCCTCCCTCACCACCGTGCA | 160 | | IFNA4 | TTTGAGTGCAGGTGAAAAAT | 197 |
| CD80 | GGCCTAGGGGAGGAGAAGAA | 161 | | IFNA4 | AGTTTTTATCTGTGAAGTAG | 198 |

TABLE 2-continued

| | sgRNAs selected from a minipool of immune function genes | |
|---|---|---|
| Gene | sgRNA Sequence | SEQ ID NO |
| IFNA4 | AAATTTTAATAACACAGATT | 199 |
| IFNB1 | ATATAAATAGGCCATACCCA | 200 |
| IFNB1 | AAATTCCTCTGAATAGAGAG | 201 |
| IFNB1 | TAGGCCATACCCATGGAGAA | 202 |
| IFNB1 | CAAGACTTGGGAGAAAGCAA | 203 |
| IFNB1 | AAAAAGATTTACAAACTGTG | 204 |
| IFNB1 | GTTAGAATGTCCTTTCTCCA | 205 |
| IFNB1 | ATGGTCCTCTCTCTATTCAG | 206 |
| IFNB1 | TATTATATATATCATAAGAT | 207 |
| IFNB1 | TACTAAAATGTAAATGACAT | 208 |
| IFNB1 | ATGACATAGGAAAACTGAAA | 209 |
| IFNB1 | CAAATTGTAAAACAAGACTT | 210 |
| IFNB1 | TTAGAATGTCCTTTCTCCAT | 211 |
| IFNB1 | GAGGACCATCTCATATAAAT | 212 |
| IFNB1 | TATGGCCTATTTATATGAGA | 213 |
| IFNB1 | AATGACATAGGAAAACTGAA | 214 |
| IFNB1 | ATGTCCTTTCTCCATGGGTA | 215 |
| IFNB1 | TGAAAGGGAGAAGTGAAAGT | 216 |
| IFNB1 | TTTGAGGTTCTTGAATTCTC | 217 |
| IFNB1 | CTGAAAGGGAGAAGTGAAAG | 218 |
| IFNB1 | CTGTATCTTTTAGTGTTTTG | 219 |
| IFNB1 | ATCTTATGATATATATAATA | 220 |
| IFNB1 | TATCTTATGATATATATAAT | 221 |
| IFNB1 | GCAAATTGTAAAACAAGACT | 222 |
| IFNG | CATTTTACCAGGGCGAAGTG | 223 |
| IFNG | TGGGTCTGTCTCATCGTCAA | 224 |
| IFNG | TTCAAAGAATCCCACCAGAA | 225 |
| IFNG | TACCTAATTGAAGTCTCCTG | 226 |
| IFNG | AACATTTTACCAGGGCGAAG | 227 |
| IFNG | TGTGAAAATACGTAATCCTC | 228 |
| IFNG | GAATCCCACCAGAATGGCAC | 229 |
| IFNG | ACATTTTACCAGGGCGAAGT | 230 |
| IFNG | TCTCATCGTCAAAGGACCCA | 231 |
| IFNG | CCCACCAGAATGGCACAGGT | 232 |
| IFNG | GAGATGGTGACAGATAGGCA | 233 |
| IFNG | AAAGGACCCAAGGAGTCTAA | 234 |
| IFNG | ATCCTCAGGAGACTTCAATT | 235 |

TABLE 2-continued

| | sgRNAs selected from a minipool of immune function genes | |
|---|---|---|
| Gene | sgRNA Sequence | SEQ ID NO |
| IFNG | GTATAAATACCAGCAGCCAG | 236 |
| IFNG | AAGATGAGATGGTGACAGAT | 237 |
| IFNG | ATAGTTTGTATTAATAACTA | 238 |
| IFNG | ATGGCACAGGTGGGCATAAT | 239 |
| IFNG | TAAATACCAGCAGCCAGAGG | 240 |
| IFNG | TGAGATGGTGACAGATAGGC | 241 |
| IFNG | GAGTTTCCTTTAGACTCCTT | 242 |
| IFNG | TCCCACCAGAATGGCACAGG | 243 |
| IFNG | AAAAATTTCCAGTCCTTGAA | 244 |
| IFNG | ACTTCACACCATTCAAGGAC | 245 |
| IFNG | TTTACCAGGGCGAAGTGGGG | 246 |
| IFNG | GCCCACCTGTGCCATTCTGG | 247 |
| IFNG | TATTAATAACTAAGGTTTTG | 248 |
| IFNG | AACTAAGGTTTTGTGGCATT | 249 |
| IFNG | ACTAAGGTTTTGTGGCATTT | 250 |
| IFNG | CCCACCTGTGCCATTCTGGT | 251 |
| IFNG | ACAAGTTTTTTAAGATGAGA | 252 |
| IFNG | ACAATGTGCTGCACCTCCTC | 253 |
| IFNG | TATGCCCACCTGTGCCATTC | 254 |
| IFNG | CTTTTACTTCACACCATTCA | 255 |
| IFNG | AATGGCACAGGTGGGCATAA | 256 |
| IFNG | GCTGCACCTCCTCTGGCTGC | 257 |
| IFNG | AGAGTTTCCTTTAGACTCCT | 258 |
| IFNG | ATTCTGGTGGGATTCTTTGA | 259 |

TABLE 3

| | sgRNAs selected from a minipool of 29 selected immune function genes related to antigen presentation | |
|---|---|---|
| Gene Name | Guide Sequence | SEQ ID NO: |
| CD70F1 | GCTTCAGTTTGTCTGTGGGA | 260 |
| CD70F2 | ATTCACTGAGCATCTATTAG | 261 |
| CD70F3 | ATCAGGAAGCATCCGCATCC | 262 |
| CD80F1 | GAGAGTTCTGAATCAGGGTG | 263 |
| CD80F2 | TCCAGGCCTGTTCTGAGCAC | 264 |
| CD80F3 | GGACCTTTGAGTTGCCCTCA | 265 |
| CD83F1 | CCAAGTCCGCGTTGCTGCTG | 266 |

TABLE 3-continued

| | sgRNAs selected from a minipool of 29 selected immune function genes related to antigen presentation | |
|---|---|---|
| Gene Name | Guide Sequence | SEQ ID NO: |
| CD83F2 | ATCTGCATGACCCACTCGAT | 267 |
| CD83F3 | GTTTGAGGGTCATCTAGCTG | 268 |
| CD86F1 | GCAGGCAGGAGTGGGTGGGT | 269 |
| CD86F2 | CTTTGTAGATTATTCGAGTT | 270 |
| CD86F3 | GAGTTCGGTTTCAGTCTTGA | 271 |
| IFNa4F1 | AAAGAGAATTGGAAAGCAAG | 272 |
| IFNa4F2 | TGTGTACATCTCTCTTAAAT | 273 |
| IFNa4F3 | CAGGCTCTCAGAGAACCTGT | 274 |
| IFNb1F1 | GAAATTCCTCTGAGGCAGAA | 275 |
| IFNb1F2 | CCTGTGCTATTTATAAGGGA | 276 |
| IFNb1F3 | GTGAGAATGATCTTCCTTCA | 277 |
| IFNgF1 | AGAGTTTCCTTTCGACTCCT | 278 |
| IFNgF2 | TTAAGATGGTGACAGATAGG | 279 |
| IFNgF3 | ATACCTGATCGAAGGCTCCT | 280 |
| OX40LF1 | AAGTCACTCAATTCATAACT | 281 |
| OX40LF2 | CAACTCCCTGTTAGCCCGGA | 282 |
| GITRLF1 | AGTGCTTAGCAGTGTTCCAA | 283 |
| GITRLF2 | GCACCAGGCCAAACATACAA | 284 |
| GITRLF3 | CACTACAAGGGAAGTTCAGA | 285 |
| Flt3LF1 | CGCCACCTAGTGGTAACAAG | 286 |
| Flt3LF2 | GGGCCCTGAAAGGATAGCGA | 287 |
| Flt3LF3 | TTCTACATACACTTCGAAGC | 288 |
| LIGHT-F1 | TGTGACTCAGGTGGGATGGA | 289 |
| LIGHT-F2 | GAGGAGGTACGTGAGGAAAG | 290 |
| LIGHT-F3 | CAGTGAGAGTGATCGACCGG | 291 |
| ICOSL-F1 | GAGACTTGGGCATGAGTTAC | 292 |
| ICOSL-F2 | AACCCAATCGGCTGCTGAGC | 293 |
| ICOSL-F3 | CCGCCTGTGCCCAATTAGCC | 294 |
| 4-1BBL-F1 | CCCTCCCTCCCTTCCCTCCC | 295 |
| 4-1BBL-F2 | ACAGGGCCTGGACAGGGAAG | 296 |
| 4-1BBL-F3 | AGAAAGTTCCGGGAGTCGAG | 297 |
| TL1A-F1 | CAGAGGGCTGTCAGAGGGAG | 298 |
| TL1A-F2 | AACTTGGTTTCTGTTGTAGG | 299 |
| TL1A-F3 | ATTCCCTAGCCGGGCAGGGC | 300 |
| CD30L-F1 | AATTGTAGCGAGATAGACGA | 301 |
| CD30L-F2 | GTGGTTGGTGTACACTCACG | 302 |

TABLE 3-continued

| | sgRNAs selected from a minipool of 29 selected immune function genes related to antigen presentation | |
|---|---|---|
| Gene Name | Guide Sequence | SEQ ID NO: |
| CD30L-F3 | CGTTCTGTGGCTGAGCCTAA | 303 |
| TAP1F1 | TGCAGGCAACTTGCAGACTG | 304 |
| TAP1F2 | TTCACGCAAGCAAGTTAAGG | 305 |
| TAP1F3 | CGTGCCGTTCTACCAGCATT | 306 |
| B2M-F1 | ACGACCTCCGGATCTGAGTC | 307 |
| B2M-F2 | CCGTGATATTTCAAACAGCC | 308 |
| B2M-F3 | AGCATCAACAGCTAGGAGAC | 309 |
| CXCL9-F1 | AAACCCTACTCTCAGATCCC | 310 |
| CXCL9-F2 | TAGTTCTTCTAGGTCAGCTG | 311 |
| CXCL9-F3 | TAACCACAAATTGATCGTCC | 312 |
| CXCL10-F1 | ACTTTGGAGATGACTCAGCA | 313 |
| CXCL10-F2 | TTTATTGTGACCCATGAACT | 314 |
| CXCL10-F3 | GCAATGCCCTCGGTTTACAG | 315 |
| Tsn-F1 | GCGGAGTCTAGGCTGATAAA | 316 |
| Tsn-F2 | GGTCTGGGAACGCGGGAGTG | 317 |
| Tsn-F3 | TATTTATTGGTCACTTCACT | 318 |
| TAPBPR F1 | CTCCAGCCCTCTCATAGTTG | 319 |
| TAPBPR F2 | AGGATTTAACATGGACTGAA | 320 |
| TAPBPR F3 | CTGTGATCGAACAGACGAGA | 321 |
| PDIA3-F1 | GCAGTGTGGCAGCCGCCGAT | 322 |
| PDIA3-F2 | AACAGCTGGTAACTGCCGAT | 323 |
| PDIA3-F3 | CTGCGTCACGCAGCGTCGGG | 324 |
| CalR-F1 | GGTCGCACTATGGGCCAATG | 325 |
| CalR-F2 | GTAGGTCTAAACCAGTCAAA | 326 |
| CalR-F3 | GGGTCGACCACGCGTTGTGG | 327 |
| ERAP1-F1 | TGATAGGGAATGCATTCTCC | 328 |
| ERAP1-F2 | ACTTTGAGTTCCCGAAGCCC | 329 |
| ERAP1-F3 | CAAGCCTAAGGGATCTAGCC | 330 |
| NLRC5-F1 | AGCTGGCCGTGCAGAGAGGA | 331 |
| NLRC5-F2 | TCATCTGGGAGATGAGCCTC | 332 |
| NLRC5-F3 | TTCGGTTGGCATTCGGCTAA | 333 |
| TAP2F1 | GGGTCTGAGATGCTTTGAAA | 334 |
| TAP2F2 | GGCGCCTGTCAATTTGCGGG | 335 |
| TAP2F3 | TTGCTAGTAGCGGCCTTGGA | 336 |
| Hmmr-F1 | CCTTCCGATTGGGCGGCGGT | 337 |
| Hmmr-F2 | AGCTGTTTGCGGCGACGATC | 338 |

TABLE 3-continued sgRNAs selected from a minipool of
29 selected immune function genes
related to antigen presentation

| Gene Name | Guide Sequence | SEQ ID NO: |
|---|---|---|
| Hmmr-F3 | AATCTAGTGCGCATGCTCTT | 339 |
| Trp53-F1 | GTCTAAGATATAGAGCTGTG | 340 |
| Trp53-F2 | GATAGTCGCCATAACAAGTA | 341 |
| Trp53-F3 | TTGTGCCAGGAGTCTCGCGG | 342 |
| Tlr9-F1 | TTGTGGGGTGGGGAGGAGAG | 343 |
| Tlr9-F2 | GAAAGAGGAAGGGGTTGAGG | 344 |
| Tlr9-F3 | CCACAGCTCTTTGGGGGGTG | 345 |
| Tlr9-F4 | TGTCCCTACCCTGAAAGAGC | 346 |
| Tlr9-F5 | ACATCATTTGCATAGTCAGA | 347 |
| Tlr9-F6 | GGGGCATATGTGATACCCTT | 348 |

Compositions

Certain aspects of the invention include compositions comprising the cells or vectors of the present invention. One aspect of the invention includes a composition comprising a cancer vaccine, comprising a modified cell comprising a CRISPRa system capable of increasing expression of a plurality of endogenous genes. In certain embodiments, the cell is packaged in an AAV vector. In certain embodiments, the CRISPRa system comprises an sgRNA library.

In certain embodiments, the composition comprises an sgRNA library. In one embodiment, the sgRNA library comprises sequences selected from the group consisting of SEQ ID NOs: 1-37. In one embodiment the sgRNA library comprises sequences selected from the group consisting of SEQ ID NOs: 51-259. In one embodiment the sgRNA library comprises sequences selected from the group consisting of SEQ ID NOs: 260-348. In one embodiment the sgRNA library comprises sequences selected from the group consisting of SEQ ID NOs: 349-4,187. In one embodiment the sgRNA library comprises sequences selected from the group consisting of SEQ ID NOs: 4,188-7,980. In one embodiment the sgRNA library comprises sequences selected from the group consisting of SEQ ID NOs: 7,981-11,808. In one embodiment the sgRNA library comprises sequences selected from the group consisting of SEQ ID NOs: 11,809-23,776. In one embodiment the sgRNA library comprises sequences selected from the group consisting of SEQ ID NOs: 23,779-23,885. In one embodiment the sgRNA library comprises sequences selected from the group consisting of SEQ ID NOs: 23,886-24,104.

In one embodiment, the invention comprises a vector comprising a U6-sgRNA and a EFS-MPH (activator). In one embodiment, the invention comprises a vector comprising two sgRNA cassettes in a CRISPRa system, wherein the first sgRNA cassette is used for activation of antigen presentation machinery, and the second sgRNA cassette is used for activation of patient-specific mutated endogenous genes, either in single gene or pooled format. In one embodiment, the vector comprises SEQ ID NO: 49. In one embodiment, the vector comprises SEQ ID NO: 50.

In one embodiment, the invention comprises a vector comprising SEQ ID NO: 24,105. In one embodiment, the invention comprises a vector comprising SEQ ID NO: 24,106.

Tolerable variations of the any one of the vectors will be known to those of skill in the art. For example, in some embodiments the vector comprises a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO: 49, SEQ ID NO: 50, SEQ ID NO: 49, SEQ ID NO: 24,105, or SEQ ID NO: 24,106.

```
CRISPRa AAV vector:
pGW005_pAAV-U6sgbbBsmBI(MS2)-EF1a-MPH-sPA2
                                                          (SEQ ID NO: 49)
     1 cctgcaggca gctgcgcgct cgctcgctca ctgaggccgc ccgggcaaag cccgggcgtc 61 gggcgacctt tggtcgcccg gcctcagtga gcgagcgagc gcgcagagag ggagtggcca 121 actccatcac taggggttcc tgcggccgca gggacccaga gagggcctat ttcccatgat 181 tccttcatat ttgcatatac gatacaaggc tgttagagag ataattagaa ttaatttgac 241 tgtaaacaca aagatattag tacaaaatac gtgacgtaga aagtaataat ttcttgggta 301 gtttgcagtt ttaaaattat gttttaaaat ggactatcat atgcttaccg taacttgaaa 361 gtatttcgat ttcttggctt tatatatctt gtggaaagga cgaaacaccg gaagagcgag 421 ctcttctgtt ttagagctag gccaacatga ggatcaccca tgtctgcagg gcctagcaag 481 ttaaaataag gctagtccgt tatcaacttg gccaacatga ggatcaccca tgtctgcagg 541 gccaagtggc accgagtcgg tgcttttttg gatccaagct tggcgtaact agatcttgag 601 acaaatggga cagcagagat ccagtttggt taattagcta gctgcaaaga tggataaagt 661 tttaaacaga gaggaatctt tgcagctaat ggaccttcta ggtcttgaaa ggagtgggaa 721 ttggctccgg tgcccgtcag tgggcagagc gcacatcgcc cacagtcccc gagaagttgg
```

-continued

```
 781 ggggaggggt cggcaattga accggtgcct agagaaggtg gcgcggggta aactgggaaa 841 gtgatgtcgt gtactggctc cgcctttttc ccgagggtgg gggagaaccg tatataagtg 901 cagtagtcgc cgtgaacgtt ctttttcgca acgggtttgc cgccagaaca caggtaagtg 961 ccgtgtgtgg ttcccgcggg cctggcctct ttacgggtta tggcccttgc gtgccttgaa 1021 ttacttccac ctggctgcag tacgtgattc ttgatcccga gcttcgggtt ggaagtgggt 1081 gggagagttc gaggccttgc gcttaaggag ccccttcgcc tcgtgcttga gttgaggcct 1141 ggcctgggcg ctggggccgc cgcgtgcgaa tctggtggca ccttcgcgcc tgtctcgctg 1201 ctttcgataa gtctctagcc atttaaaatt tttgatgacc tgctgcgacg cttttttttct 1261 ggcaagatag tcttgtaaat gcgggccaag atctgcacac tggtatttcg gtttttgggg 1321 ccgcgggcgg cgacggggcc cgtgcgtccc agcgcacatg ttcggcgagg cggggcctgc 1381 gagcgcggcc accgagaatc ggacgggggt agtctcaagc tggccggcct gctctggtgc 1441 ctggcctcgc gccgccgtgt atcgccccgc cctgggcggc aaggctggcc cggtcggcac 1501 cagttgcgtg agcggaaaga tggccgcttc ccggccctgc tgcagggagc tcaaaatgaa 1561 ggacgcggcg ctcgggagag cgggcgggtg agtcacccac acaaaggaaa agggcctttc 1621 cgtcctcagc cgtcgcttca tgtgactcca cggagtaccg ggcgccgtcc aggcacctcg 1681 attagttctc gagctttngg agtacgtcgt ctttaggttg gggggagggg ttttatgcga 1741 tggagtttcc ccacactgag tgggtggaga ctgaagttag gccagcttgg cacttgatgt 1801 aattctcctt ggaatttgcc cttttttgagt ttggatcttg gttcattctc aagcctcaga 1861 cagtggttca aagttttttt cttccatttc aggtgtcgtg acgtacggcc accatggctt 1921 caaactttac tcagttcgtg ctcgtggaca atggtgggac aggggatgtg acagtggctc 1981 cttctaattt cgctaatggg gtggcagagt ggatcagctc caactcacgg agccaggcct 2041 acaaggtgac atgcagcgtc aggcagtcta gtgcccagaa gagaaagtat accatcaagg 2101 tggaggtccc caaagtggct acccagacag tgggcggagt cgaactgcct gtcgccgctt 2161 ggaggtccta cctgaacatg gagctcacta tcccaatttt cgctaccaat tctgactgtg 2221 aactcatcgt gaaggcaatg cagggggctcc tcaaagacgg taatcctatc ccttccgcca 2281 tcgccgctaa ctcaggtatc tacagcgctg gaggaggtgg aagcggagga ggaggaagcg 2341 gaggaggagg tagcggacct aagaaaaaga ggaaggtggc ggccgctgga tccccttcag 2401 ggcagatcag caaccaggcc ctggctctgg cccctagctc cgctccagtg ctggcccaga 2461 ctatggtgcc ctctagtgct atggtgcctc tggcccagcc acctgctcca gcccctgtgc 2521 tgaccccagg accaccccag tcactgagcg ctccagtgcc caagtctaca caggccggcg 2581 aggggactct gagtgaagct ctgctgcacc tgcagttcga cgctgatgag gacctgggag 2641 ctctgctggg gaacagcacc gatcccggag tgttcacaga tctggcctcc gtggacaact 2701 ctgagtttca gcagctgctg aatcagggcg tgtccatgtc tcatagtaca gccgaaccaa 2761 tgctgatgga gtaccccgaa gccattaccc ggctggtgac cggcagccag cggccccccg 2821 accccgctcc aactcccctg ggaaccagcg cctgcctaa tgggctgtcc ggagatgaag 2881 acttctcaag catcgctgat atggactttta gtgccctgct gtcacagatt tcctctagtg 2941 ggcaggagg aggtggaagc ggcttcagcg tggacaccag tgccctgctg gacctgttca 3001 gcccctcggt gaccgtgccc gacatgagcc tgcctgacct tgcagcagc ctggccagta 3061 tccaagagct cctgtctccc caggagcccc caggcctcc cgaggcagag aacagcagcc 3121 cggattcagg gaagcagctg gtgcactaca gcgcgcagcc gctgttcctg ctggaccccg 3181 gctccgtgga caccgggagc aacgacctgc cggtgctgtt tgagctggga gagggctcct
```

-continued

```
3241 acttctccga aggggacggc ttcgccgagg accccaccat ctccctgctg acaggctcgg 3301 agcctcccaa agccaaggac cccactgtct cctaagaatt cgatatcaag cttaataaaa 3361 gatctttatt ttcattagat ctgtgtgttg gttttttgtg tggtaaccac gtgcggaccg 3421 agcggccgca ggaacccta gtgatggagt tggccactcc ctctctgcgc gctcgctcgc 3481 tcactgaggc cgggcgacca aaggtcgccc gacgcccggg ctttgcccgg cggcctcag 3541 tgagcgagcg agcgcgcagc tgcctgcagg ggcgcctgat gcggtatttt ctccttacgc 3601 atctgtgcgg tatttcacac cgcatacgtc aaagcaacca tagtacgcgc cctgtagcgg 3661 cgcattaagc gcggcgggtg tggtggttac gcgcagcgtg accgctacac ttgccagcgc 3721 cctagcgccc gctcctttcg ctttcttccc ttcctttctc gccacgttcg ccggctttcc 3781 ccgtcaagct ctaaatcggg ggctcccttt agggttccga tttagtgctt tacggcacct 3841 cgaccccaaa aaacttgatt tgggtgatgg ttcacgtagt gggccatcgc cctgatagac 3901 ggtttttcgc cctttgacgt tggagtccac gttctttaat agtggactct tgttccaaac 3961 tggaacaaca ctcaacccta tctcgggcta ttctttgat ttataaggga ttttgccgat 4021 ttcggcctat tggttaaaaa atgagctgat ttaacaaaaa tttaacgcga attttaacaa 4081 aatattaacg tttacaattt tatggtgcac tctcagtaca atctgctctg atgccgcata 4141 gttaagccag ccccgacacc cgccaacacc cgctgacgcg ccctgacggg cttgtctgct 4201 cccggcatcc gcttacagac aagctgtgac cgtctccggg agctgcatgt gtcagaggtt 4261 ttcaccgtca tcaccgaaac gcgcgagacg aaagggcctc gtgatacgcc tatttttata 4321 ggttaatgtc atgataataa tggtttctta gacgtcaggt ggcactttc ggggaaatgt 4381 gcgcggaacc cctatttgtt tatttttcta aatacattca aatatgtatc cgctcatgag 4441 acaataaccc tgataaatgc ttcaataata ttgaaaaagg aagagtatga gtattcaaca 4501 tttccgtgtc gcccttattc ccttttttgc ggcattttgc cttcctgttt ttgctcaccc 4561 agaaacgctg gtgaaagtaa aagatgctga agatcagttg ggtgcacgag tgggttacat 4621 cgaactggat ctcaacagcg gtaagatcct tgagagtttt cgccccgaag aacgttttcc 4681 aatgatgagc acttttaaag ttctgctatg tggcgcggta ttatcccgta ttgacgccgg 4741 gcaagagcaa ctcggtcgcc gcatacacta ttctcagaat gacttggttg agtactcacc 4801 agtcacagaa aagcatctta cggatggcat gacagtaaga gaattatgca gtgctgccat 4861 aaccatgagt gataacactg cggccaactt acttctgaca acgatcggag gaccgaagga 4921 gctaaccgct tttttgcaca acatggggga tcatgtaact cgccttgatc gttgggaacc 4981 ggagctgaat gaagccatac caaacgacga gcgtgacacc acgatgcctg tagcaatggc 5041 aacaacgttg cgcaaactat taactggcga actacttact ctagatccc ggcaacaatt 5101 aatagactgg atggaggcgg ataaagttgc aggaccactt ctgcgctcgg cccttccggc 5161 tggctggttt attgctgata aatctggagc cggtgagcgt gggtctcgcg gtatcattgc 5221 agcactgggg ccagatggta agccctcccg tatcgtagtt atctacacga cggggagtca 5281 ggcaactatg gatgaargaa atagacagat cgctgagata ggtgcctcac tgattaagca 5341 ttggtaactg tcagaccaag tttactcata tatactttag attgatttaa aacttcattt 5401 ttaatttaaa aggatctagg tgaagatcct ttttgataat ctcatgacca aaatccctta 5461 acgtgagttt tcgttccact gagcgtcaga ccccgtagaa aagatcaaag gatcttcttg 5521 agatcctttt tttctgcgcg taatctgctg cttgcaaaca aaaaaaccac cgctaccagc 5581 ggtggtttgt ttgccggatc aagagctacc aactctttttt ccgaaggtaa ctggcttcag
```

-continued

```
5641 cagagcgcag ataccaaata ctgtccttct agtgtagccg tagttaggcc accacttcaa 5701 gaactctgta gcaccgccta catacctcgc tctgctaatc ctgttaccag tggctgctgc 5761 cagtggcgat aagtcgtgtc ttaccgggtt ggactcaaga cgatagttac cggataaggc 5821 gcagcggtcg ggctgaacgg ggggttcgtg cacacagccc agcttggagc gaacgaccta 5881 caccgaactg agatacctac agcgtgagct atgagaaagc gccacgcttc ccgaagggag 5941 aaaggcggac aggtatccgg taagcggcag ggtcggaaca ggagagcgca cgagggagct 6001 tccaggggga aacgcctggt atctttatag tcctgtcggg tttcgccacc tctgacttga 6061 gcgtcgattt ttgtgatgct cgtcaggggg cggagcctta tggaaaaacg ccagcaacgc 6121 ggccttttta cggttcctgg cctttttgctg gcctttttgct cacatgt
``` pAAV-U6sgbbBsmBI(MS2)-U6CD80MS2-EF1a-MPH-sPA (SEQ ID NO: 50)

```
   1 cctgcaggca gctgcgcgct cgctcgctca ctgaggccgc ccgggcaaag cccgggcgtc 61 gggcgacctt tggtcgcccg gcctcagtga gcgagcgagc gcgcagagag ggagtggcca 121 actccatcac tagggggttcc tgcggccgca cgcgttctag aagagggcct atttcccatg 181 attccttcat atttgcatat acgatacaag gctgttagag agataattgg aattaatttg 241 actgtaaaca caaagatatt agtacaaaat acgtgacgta gaaagtaata atttcttggg 301 tagtttgcag ttttaaaatt atgttttaaa atggactatc atatgcttac cgtaacttga 361 aagtatttcg atttcttggc tttatatatc ttgtggaaag gacgaaacac cggaagagcg 421 agctcttctg ttttagagct aggccaacat gaggatcacc catgtctgca gggcctagca 481 agttaaaata aggctagtcc gttatcaact tggccaacat gaggatcacc catgtctgca 541 gggccaagtg gcaccgagtc ggtgcttttt tggatccaag cttggcgtaa ctagatcttg 601 agacaaatgg gacagcagag atccagtttg gttaattagg acccagaga gggcctattt 661 cccatgattc cttcatattt gcatatacga tacaaggctg ttagagagat aattagaatt 721 aatttgactg taaacacaaa gatattagta caaaatacgt gacgtagaaa gtaataattt 781 cttgggtagt ttgcagtttt aaaattatgt tttaaaatgg actatcatat gcttaccgta 841 acttgaaagt atttcgattt cttggcttta tatatcttgt ggaaaggacg aaacaccgag 901 agttctgaat cagggtggtt ttagagctag gccaacatga ggatcaccca tgtctgcagg 961 gcctagcaag ttaaaataag gctagtccgt tatcaacttg gccaacatga ggatcaccca 1021 tgtctgcagg gccaagtggc accgagtcgg tgcttttttg gatccaagct tggcgtaact 1081 agatcttgag acaaatggct agctgcaaag atggataaag ttttaaacag agaggaatct 1141 ttgcagctaa tggaccttct aggtcttgaa aggagtggga attggctccg gtgcccgtca 1201 gtgggcagag cgcacatcgc ccacagtccc cgagaagttg gggggagggg tcggcaattg 1261 aarcggtgcc tagagaaggt ggcgcggggt aaactgggaa agtgatgtcg tgtactggct 1321 ccgcctttttt cccgagggtg ggggagaacc gtatataagt gcagtagtcg ccgtgaacgt 1381 tctttttcgc aacgggtttg ccgccagaac acaggtaagt gccgtgtgtg gttcccgcgg 1441 gcctggcctc tttacgggtt atggcccttg cgtgccttga attacttcca cctggctgca 1501 gtacgtgatt cttgatcccg agcttcgggt tggaagtggg tgggagagtt cgaggccttg 1561 cgcttaagga gccccttcgc ctcgtgcttg agttgaggcc tggcctgggc gctggggccg 1621 ccgcgtgcga atctggtggc accttcgcgc ctgtctcgct gctttcgata agtctctagc 1681 catttaaaat ttttgatgac ctgctgcgac gctttttttc tggcaagata gtcttgtaaa 1741 tgcgggccaa gatctgcaca ctggtatttc ggttttttggg gccgcgggcg gcgacggggc 1801 ccgtgcgtcc cagcgcacat gttcggcgag gcggggcctg cgagcgcggc caccgagaat
```

-continued

```
1861 cggacggggg tagtctcaag ctggccggcc tgctctggtg cctggcctcg cgccgccgtg 1921 tatcgccccg ccctgggcgg caaggctggc ccggtcggca ccagttgcgt gagcggaaag 1981 atggccgctt cccggccctg ctgcaggggag ctcaaaatga aggacgcggc gctcgggaga 2041 gcggcgggt gagtcaccca cacaaaggaa aagggccttt ccgtcctcag ccgtcgcttc 2101 atgtgactcc acggagtacc gggcgccgtc caggcacctc gattagttct cgagcttttg 2161 gagtacgtcg tctttaggtt gggggggaggg gttttatgcg atggagtttc cccacactga 2221 gtgggtggag actgaagtta ggccagcttg gcacttgatg taattctcct tggaatttgc 2281 ccttttttgag tttggatctt ggttcattct caagcctcag acagtggttc aaagtttttt 2341 tcttccattt caggtgtcgt gacgtacggc caccatggct tcaaacttta ctcagttcgt 2401 gctcgtggac aatggtggga caggggatgt gacagtggct ccttctaatt cgctaatgg 2461 ggtggcagag tggatcagct ccaactcacg gagccaggcc tacaaggtga catgcagcgt 2521 caggcagtct agtgcccaga agagaaagta taccatcaag gtggaggtcc ccaaagtggc 2581 tacccagaca gtgggcggag tcgaactgcc tgtcgccgct tggaggtcct acctgaacat 2641 ggagctcact atcccaattt cgctaccaa ttctgactgt gaactcatcg tgaaggcaat 2701 gcaggggctc ctcaaagacg gtaatcctat cccttccgcc atcgccgcta actcaggtat 2761 ctacagcgct ggaggaggtg gaagcggagg aggaggaagc ggaggaggag gtagcggacc 2821 taagaaaaag aggaaggtgg cggccgctgg atccccttta gggcagatca gcaaccaggc 2881 cctggctctg gcccctagct ccgctccagt gctggcccag actatggtgc cctctagtgc 2941 tatggtgcct ctggcccagc cacctgctcc agccctgtg ctgaccccag gaccacccca 3001 gtcactgagc gctccagtgc ccaagtctac acaggccggc gaggggactc tgagtgaagc 3061 tctgctgcac ctgcagttcg acgctgatga ggacctggga gctctgctgg ggaacagcac 3121 cgatcccgga gtgttcacag atctggcctc cgtggacaac tctgagtttc agcagctgct 3181 gaatcagggc gtgtccatgt ctcatagtac agccgaacca atgctgatgg agtacccga 3241 agccattacc cggctggtga ccggcagcca gcggccoccc gaccccgctc caactcccct 3301 gggaaccagc ggcctgccta atgggctgtc cggagatgaa gacttctcaa gcatcgctga 3361 tatggacttt agtgccctgc tgtcacagat ttcctctagt gggcagggag gaggtggaag 3421 cggcttcagc gtggacacca gtgccctgct ggacctgttc agcccctcgg tgaccgtgcc 3481 cgacatgagc ctgcctgacc ttgacagcag cctggccagt atccaagagc tcctgtctcc 3541 ccaggagccc cccaggcctc ccgaggcaga gaacagcagc ccggattcag ggaagcagct 3601 ggtgcactac acagcgcagc cgctgttcct gctggacccc ggctccgtgg acaccgggag 3661 caacgacctg ccggtgctgt ttgagctggg agagggctcc tacttctccg aaggggacgg 3721 cttcgccgag gaccccacca tctccctgct gacaggctcg gagcctccca aagccaagga 3781 ccccactgtc tcctaagaat tcgatatcaa gcttaataaa agatctttat tttcattaga 3841 tctgtgtgtt ggttttttgt gtggtaacca cgtgcggacc gagcggccgc aggaacccct 3901 agtgatggag ttggccactc cctctctgcg cgctcgctcg ctcactgagg ccgggcgacc 3961 aaaggtcgcc cgacgcccgg gctttgcccg ggcggcctca gtgagcgagc gagcgcgcag 4021 ctgcctgcag gggcgcctga tgcggtattt tctccttacg catctgtgcg gtatttcaca 4081 ccgcatacgt caaagcaacc atagtacgcg ccctgtagcg gcgcattaag cgcggcgggt 4141 gtggtggtta cgcgcagcgt gaccgctaca cttgccagcg ccctagcgcc cgctcctttc 4201 gctttcttcc cttcctttct cgccacgttc gccggctttc cccgtcaagc tctaaatcgg
```

-continued

```
4261 gggctccctt tagggttccg atttagtgct ttacggcacc tcgaccccaa aaaacttgat 4321 ttgggtgatg gttcacgtag tgggccatcg ccctgataga cggttttttcg ccctttgacg 4381 ttggagtcca cgttctttaa tagtggactc ttgttccaaa ctggaacaac actcaacccct 4441 atctcgggct attcttttga tttataaggg attttgccga tttcggccta ttggttaaaa 4501 aatgagctga tttaacaaaa atttaacgcg aattttaaca aaatattaac gtttacaatt 4561 ttatggtgca ctctcagtac aatctgctct gatgccgcat agttaagcca gccccgacac 4621 ccgccaacac ccgctgacgc gccctgacgg gcttgtctgc tcccggcatc cgcttacaga 4681 caagctgtga ccgtctccgg gagctgcatg tgtcagaggt tttcaccgtc atcaccgaaa 4741 cgcgcgagac gaaagggcct cgtgatacgc ctattttttat aggttaatgt catgataata 4801 atggtttctt agacgtcagg tggcactttt cggggaaatg tgcgcggaac ccctatttgt 4861 ttatttttct aaatacattc aaatatgtat ccgctcatga caataaacc ctgataaatg 4921 cttcaataat attgaaaaag gaagagtatg agtattcaac atttccgtgt cgcccttatt 4981 ccctttttttg cggcatttttg ccttcctgtt tttgctcacc cagaaacgct ggtgaaagta 5041 aaagatgctg aagatcagtt gggtgcacga gtgggttaca tcgaactgga tctcaacagc 5101 ggtaagatcc ttgagagttt tcgccccgaa gaacgttttc caatgatgag cacttttaaa 5161 gttctgctat gtggcgcggt attatcccgt attgacgccg ggcaagagca actcggtcgc 5221 cgcatacact attctcagaa tgacttggtt gagtactcac cagtcacaga aaagcatctt 5281 acggatggca tgacagtaag agaattatgc agtgctgcca taaccatgag tgataacact 5341 gcggccaact tacttctgac aacgatcgga ggaccgaagg agctaaccgc ttttttgcac 5401 aacatggggg atcatgtaac tcgccttgat cgttgggaac cggagctgaa tgaagccata 5461 ccaaacgacg agcgtgacac cacgatgcct gtagcaatgg caacaacgtt gcgcaaacta 5521 ttaactggcg aactacttac tctagcttcc cggcaacaat taatagactg gatggaggcg 5581 gataaagttg caggaccact tctgcgctcg gcccttccgg ctggctggtt tattgctgat 5641 anatctggag ccggtgagcg tgggtctcgc ggtatcattg cagcactggg gccagatggt 5701 aagccctccc gtatcgtagt tatctacacg acggggagtc aggcaactat ggatgaacga 5761 aatagacaga tcgctgagat aggtgcctca ctgattaagc attggtaact gtcagaccaa 5821 gtttactcat atatacttta gattgattta aaacttcatt tttaatttaa aaggatctag 5881 gtgaagatcc ttttttgataa tctcatgacc aaaatccctt aacgtgagtt ttcgttccac 5941 tgagcgtcag accccgtaga aaagatcaaa ggatcttctt gagatccttt ttttctgcgc 6001 gtaatctgct gcttgcaaac aaaaaaacca ccgctaccag cggtggtttg tttgccggat 6061 caagagctac caactctttt tccgaaggta actggcttca gcagagcgca gataccaaat 6121 actgtccttc tagtgtagcc gtagttaggc caccacttca agaactctgt agcaccgcct 6181 acatacctcg ctctgctaat cctgttacca gtggctgctg ccagtggcga taagtcgtgt 6241 cttaccgggt tggactcaag acgatagtta ccggataagg cgcagcggtc gggctgaacg 6301 gggggttcgt gcacacagcc cagcttggag cgaacgacct acaccgaact gagatacccta 6361 cagcgtgagc tatgagaaag cgccacgctt cccgaaggga gaaaggcgga caggtatccg 6421 gtaagcggca gggtcggaac aggagagcgc acgagggagc ttccaggggg aaacgcctgg 6481 tatctttata gtcctgtcgg gtttcgccac ctctgacttg agcgtcgatt tttgtgatgc 6541 tcgtcagggg ggcggagcct atggaaaaac gccagcaacg cggccttttt acggttcctg 6601 gccttttgct ggccttttgc tcacatgt
``` pZB2_EFS-LTR-dCas9_addgene-plasmid-106430

-continued (SEQ ID NO: 24, 105)

```
cctgcaggcagctgcgcgctcgctcgctcactgaggccgcccgggcgtcgggcgacctttggtcgcccggcctcagtgag cgagcgagcgcgcagagagggagtggccaactccatcactaggggttcctgcggcctctagaaaggatctgcgatcgctc cggtgcccgtcagtgggcagagcgcacatcgcccacagtccccgagaagttgggggagggtcggcaattgaacgggtg cctagagaaggtggcgcggggtaaactgggaaagtgatgtcgtgtactggctccgccttttcccgagggtgggggagaa ccgtatataagtgcagtagtcgccgtgaacgttcttttcgcaacgggtttgccgccagaacacagctgaagcttcgagg ggctcgcatctctccttcacgcgcccgccgccctacctgaggccgccatccacgccggttgagtcgcgttctgccgcctc ccgcctgtggtgcctcctgaactgcgtccgccgtctaggtaagtttaaagctcaggtcgagaccgggcattgtccggcg ctccatggagcctacctagactcagccggctctccacgctttgcctgaccctgcttgctcaactctacgtctttgtttc gttttctgttctgcgccgttacagatccaagctgtgaccggcgcctacaccggtgccaccatgtacccatacgatgttcc agattacgcttcgccgaagaaaaagcgcaaggtcgaagcgtccgacaagaagtactccattgggctcgctatcggcacaa acagcgtcggctgggccgtcattacggacgagtacaaggtgccgagcaaaaaattcaaagttctgggcaataccgatcgc cacagcataaagaagaacctcattggcgccctcctgttcgactccggggagacggccgaagccacgcggctcaaaagaac agcacggcgcagatatacccgcagaaagaatcggatctgctacctgcaggagatctttagtaatgagatggctaaggtgg atgactattcttccataggctggaggagtcctttttggtggaggaggataaaaagcacgagcgccacccaatctttggc aatatcgtggacgaggtggcgtaccatgaaaagtacccaaccatatatcatctgaggaagaagcttgtagacagtactga taaggctgacttgcggttgatctatctcgcgctggcgcatatgatcaaatttcggggacacttcctcatcgaggggggacc tgaacccagacaacagcgatgtcgacaaactctttatccaactggttcagacttacaatcagatttcgaagagaacccg atcaacgcatccggagttgacgccaaagcaatcctgagcgctaggctgtccaaatcccggcggctcgaaaacctcatcgc acagctccctggggagaagaagaacggcctgtttggtaatcttatcgccctgtcactcgggctgacccccaactttaaat ctaacttcgacctggccgaagatgccaagcttcaactgagcaaagacacctacgatgatgatctcgacaatctgctggcc cagatcggcgaccagtacgcagacctttttttggcggcaaagaacctgtcagacgccattctgctgagtgatattctgcg agtgaacacggagatcaccaaagctccgctgagcgctagtatgatcaagcgctatgatgagcaccaccaagacttgactt tgctgaaggccatgtcagacagcaactgcctgagaagtacaaggaaattttcttcgatcagtctaaaaatggctacgcc ggatacattgacggcggagcaagccaggaggaattttacaaatttattaagcccatcttggaaaaaatggacggcaccga ggagctgctggtaaagcttaacagagaagatctgttgcgcaaacagcgcactttcgacaatggaagcatcccccaccaga ttcacctgggcgaactgcacgctatcctcaggcggcaagaggatttctaccccUtttgaaagataacagggaaaagatt gagaaaatcctcacatttcggataccctactatgtaggcccctcgcccgggaaattccagattcgcgtggatgactcg caaatcagaagagaccatcactccctggaacttcgaggaagtcgtggataaggggggcctctgcccagtccttcatcgaaa ggatgactaactttgataaaaatctgcctaacgaaaggtgatcctaaacactctctgctgtacgagtacttcacagtt tataacgagctcaccaaggtcaaatacgtcacagaagggatgagaaagccagcattcctgtctggagagcagaagaaagc tatcgtggacctcctcttcaagacgaaccggaaagttaccgtgaaacagctcaaagaagactatttcaaaaagattgaat gtttcgactctgttgaaatcagcggagtggaggatcgcttcaacgcatccctgggaacgtatcacgatctcctgaaaatc attaaagacaaggacttcctggacaatgaggagaacgaggacattcttgaggacattgtcctcacccttacgttgtttga agatagggagatgattgaagaacgcttgaaaacttacgctcatctcttcgacgacaaagtcatgaaacagctcaagaggc gccgatatacaggatggggcggctgtcaagaaaactgatcaatgggatccgagacaagcagagtggaaagacaatcctg gattttcttaagtccgatggatttgccaaccggaacttcatgcagttgatccatgatgactctctcacctttaaggagga catccagaaagcacaagtttctggccaggggacagtcttcacgagcacatcgctaatcttgcaggtagcccagctatca aaaagggaatactgcagaccgttaaggtcgtggatgaactcgtcaaagtaatgggaaggcataagcccgagaatatcgtt atcgagatggcccgagagaaccaaactacccagaagggacagaagaacagtagggaaaggatgaagaggattgaagaggg tataaaagaactggggtcccaaatccttaaggaacacccagttgaaaacacccagcttcagaatgagaagctctacctgt
```

-continued

```
actacctgcagaacggcagggacatgtacgtggatcaggaactggacatcaatcggctctccgactacgacgtggctgct atcgtgccccagtcttttctcaaagatgattctattgataataaagtgttgacaagatccgataaagctagagggaagag tgataacgtcccctcagaagaagttgtcaagaaaatgaaaaattattggcggcagctgctgaacgccaaactgatcacac aacggaagttcgataatctgactaaggctgaacgaggtggcctgtctgagttggataaagccggatcatcaaaaggcag cttgttgagacacgccagatcaccaagcacgtggcccaaattctcgattcacgcatgaacaccaagtacgatgaaaatga caaactgattcgagaggtgaaagttattactctgaagtctaagctggtctcagatttcagaaaggactttcagtttttata aggtgagagagatcaacaattaccaccatgcgcatgatgcctacctgaatgcagtggtaggcactgcacttatcaaaaaa tatcccaagcttgaatctgaatttgtttacggagactataaagtgtacgatgttaggaaaatgatcgcaaagtctgagca ggaaataggcaaggccaccgctaagtacttcttttacagcaatattatgaatttttttcaagaccgagattacactggcca atggagagattcggaagcgaccacttatcgaaacaaacggagaaacaggagaaatcgtgtgggacaagggtagggatttc gcgacagtccggaaggtcctgtccatgccgcaggtgaacatcgttaaaaagaccgaagtacagaccggaggcttctccaa ggaaagtatcctcccgaaaaggaacagcgacaagctgatcgcacgcaaaaaagattgggaccccaagaaatacggcggat tcgattctcctacagtcgcttacagtgtactggttgtggccaaagtggagaaagggaagtctaaaaaactcaaaagcgtc aaggaactgctgggcatcacaatcatggagcgatcaagcttcgaaaaaaaccccatcgactttctcgaggcgaaaggata taaagaggtcaaaaaagacctcatcattaagcttcccaagtactctctctttgagcttgaaaacggccggaaacgaatgc tcgctagtgcgggcgagctgcagaaaggtaacgagctggcactgccctctaaatacgttaatttcttgtatctggccagc cactatgaaaagctcaaagggtctcccgaagataatgagcagaagcagctgttcgtggaacaacacaaacactaccttga tgagatcatcgagcaaataagcgaattctccaaaagagtgatcctcgccgacgctaacctcgataaggtgctttctgctt acaataagcacagggataagcccatcagggagcaggcagaaaacattatccacttgtttactctgaccaacttgggcgcg cctgcagccttcaagtacttcgacaccaccatagacagaaagcggtacacctctacaaaggaggtcctggacgccacact gattcatcagtcaattacggggctctatgaaacaagaatcgacctctctcagctcggtggagacagccccaagaagaaga gaaaggtggaggccagctaagaattcaataaaaagatctttatttttcattagatctgtgtgttggtttttttgtgtgcggcc gcaggaacccctagtgatggagttggccactccctctctgcgcgctcgctcgctcactgaggccgggcgaccaaaggtcg cccgacgcccgggctttgcccgggcggcctcagtgagcgagcgagcgcgcagctgcctgcaggggcgcctgatgcggtat tttctccttacgcatctgtgcggtatttcacaccgcatacgtcaaagcaaccatagtacgcgccctstagcggcgcatta agcgcggcgggtgtggtggttacgcgcagcgtgaccgctacacttgccagcgccttagcgcccgctcctttcgctttctt cccttcctttctcgccacgttcgccggctttccccgtcaagctctaaatcggggctcccctttagggttccgatttagtg ctttacggcacctcgaccccaaaaaacttgatttgggtgatggttcacgtagtgggccatcgccctgatagacggttttt cgccctttgacgttggagtccacgttctttaatagtggactcttgttccaaactggaacaacactcaactctatctcggg ctattctatgatttataagggattttgccgatttcggtctattggttaaaaaatgagctgatttaacaaaaatttaacg cgaattttaacaaaatattaacgtttacaattttatggtgcactctcagtacaatctgctctgatgccgcatagttaagc cagccccgacacccgccaacacccgctgacgcgccctgacgggcttgtctgctccoggcatccgcttacagacaagctgt gaccgtctccgggagctgcatgtgtcagaggttttcaccgtcatcaccgaaacgcgcgagacgaaagggcctcgtgatac gcctatttttataggttaatgtcatgataataatggtttcttagacgtcaggtggcacttttcggggaaatgtgcgcgga acccctatttgtttatttttctaaatacattcaaatatgtatccgctcatgagacaataaccctgataaatgcttcaata atattgaaaaaggaagagtatgagtattcaacatttccgtgtcgccatattcccttttttgcggcattttgccttcctg ttttttgctcacccagaaacgctggtgaaagtaaaagatgctgaagatcagttgggtgcacgagtgggttacatcgaactg gatctcaacagcggtaagatccttgagagttttcgccccgaagaacgttttccaatgatgagcacttttaaagttctgct atgtggcgcggtattatcccgtattgacgccgggcaagagcaactcggtcgccgcatacactattctcagaatgacttgg ttgagtactcaccagtcacagaaaagcatatacggatggcatgacagtaagagaattatgcagtgctgccataaccatg agtgataacactgcggccaacttacttctgacaacgatcggaggaccgaaggagctaaccgcttttttgcacaacatggg
```

-continued ggatcatgtaactcgccttgatcgttgggaaccggagctgaatgaagccataccaaacgacgagcgtgacaccacgatgc ctgtagcaatggcaacaacgttgcgcaaactattaactggcgaactacttactctagcttcccggcaacaattaatagac tggatggaggcggataaagttgcaggaccacttctgcgctcggcccttccggctggctggtttattgctgataaatctgg agccggtgagcgtggaagccgcgggtatcattgcagcactggggccagatggtaagccctcccgtatcgtagttatctaca cgacggggagtcaggcaactatggatgaacgaaatagacagatcgctgagataggtgcctcactgattaagcattggtaa ctgtcagaccaagtttactcatatatactttagattgatttaaaacttcatttttaatttaaaaggatctaggtgaagat cctttttgataatctcatgaccaaaatcccttaacgtgagttttcgttccactgagcgtcagacccccgtagaaaagatca aaggatcttcttgagatcctatatctgcgcgtaatctgctgcttgcaaacaaaaaaaccaccgctaccagcggtggtt tgtttgccggatcaagagctaccaactcttttttccgaaggtaactggcttcagcagagcgcagataccaaatactgttct tctagtgtagccgtagttaggccaccacttcaagaactctgtagcaccgcctacatacctcgctctgctaatcctgttac cagtggctgctgccagtggcgataagtcgtgtcttaccgggttggactcaagacgatagttaccggataaggcgcagcgg tcgggctgaacggggggttcgtgcacacagcccagcttggagcgaacgacctacaccgaactgagatacctacagcgtga gctatgagaaagcgccacgcttcccgaagggagaaaggcggacaggtatccggtaagcggcagggtcggaacaggagagc gcacgagggagcttccaggggaaacgcctggtatctttatagtcctgtcgggtttcgccacctctgacttgagcgtcga tttttgtgatgctcgtcaggggggcggagcctatggaaaaacgccagcaacgcggcctttttacggttcctggccttttg ctggcctttgctcacatgt pGW011b_pAAV-EFS-dCAS9-spA (SEQ ID NO: 24, 106)

cctgcaggcagctgcgcgctcgctcgctcactgaggccgcccgggcaaagcccgggcgtcgggcgacctttggtcgcccg gcctcagtgagcgagcgagcgcgcagagagggagtggccaactccatcactaggggttcctgcggccgcacgcgttctag gtcttgaaaggagtgggaattggctccggtgcccgtcagtgggcagagcgcacatcgcccacagtccccgagaagttggg gggaggggtcggcaattgatccggtgcctagagaaggtggcgcggggtaaactgggaaagtgatgtcgtgtactggctcc gcctattcccgaggtggggggagaaccgtatataagtgcagtagtcgcgcgtgaacgttattttcgcaacgggtttgccgc cagaacacaggTGTCGTGACGCGcGTACGtaatacgactcactatagggccgccaccATGAAAAGGCCG

GCGGCCACGAAAAAGGCCGGCCAGGCAAAAAAGAAAAAGGACAAGAAGTAC

AGCATCGGCCTGGCCATCGGCACCAACTCTGTGGGCTGGGCCGTGATCACCG

ACGAGTACAAGGTGCCCAGCAAGAAATTCAAGGTGCTGGGCAACACCGACCG

GCACAGCATCAAGAAGAACCTGATCGGAGCCCTGCTGTTCGACAGCGGCGAA

ACAGCCGAGGCCACCCGGCTGAAGAGAACCGCCAGAAGAAGATACACCAGA

CGGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGA

GGATAAGAAGCACGAGCGGCACCCCATCTTCGGCAACATCGTGGACGAGGTG

GCCTACCACGAGAAGTACCCCACCATCTACCACCTGAGAAAGAAACTGGTGG

ACAGCACCGACAAGGCCGACCTGCGGCTGATCTATCTGGCCCTGGCCCACAT

GATCAAGTTCCGGGGCCACTTCCTGATCGAGGGCGACCTGAACCCCGACAAC

AGCGACGTGGACAAGCTGTTCATCCAGCTGGTGCAGACCTACAACCAGCTGT

TCGAGGAAAACCCCATCAACGCCAGCGGCGTGGACGCCAAGGCCATCCTGTC

TGCCAGACTGAGCAAGAGCAGACGGCTGGAAAATCTGATCGCCCAGCTGCCC

GGCGAGAAGAAGAATGGCCTGTTCGGCAACCTGATTGCCCTGAGCCTGGGCC

TGACCCCCAACTTCAAGAGCAACTTCGACCTGGCCGAGGATGCCAAACTGCA

GCTGAGCAAGGACACCTACGACGACGACCTGGACAACCTGCTGGCCCAGATC

-continued

```
GGCGACCAGTACGCCGACCTGTTTCTGGCCGCCAAGAACCTGTCCGACGCCA

TCCTGCTGAGCGACATCCTGAGAGTGAACACCGAGATCACCAAGGCCCCCCT

GAGCGCCTCTATGATCAAGAGATACGACGAGCACCACCAGGACCTGACCCTG

CTGAAAGCTCTCGTGCGGCAGCAGCTGCCTGAGAAGTACAAAGAGATTTTCT

TCGACCAGAGCAAGAACGGCTACGCCGGCTACATTGACGGCGGAGCCAGCCA

GGAAGAGTTCTACAAGTTCATCAAGCCCATCCTGGAAAAGATGGACGGCACC

GAGGAACTGCTCGTGAAGCTGAACAGAGAGGACCTGCTGCGGAAGCAGCGG

ACCTTCGACAACGGCAGCATCCCCCACCAGATCCACCTGGGAGAGCTGCACG

CCATTCTGCGGCGGCAGGAAGATTTTTACCCATTCCTGAAGGACAACCGGGA

AAAGATCGAGAAGATCCTGACCTTCCGCATCCCCTACTACGTGGGCCCTCTG

GCCAGGGGAAACAGCAGATTCGCCTGGATGACCAGAAAGAGCGAGGAAACCA

TCACCCCCTGGAACTTCGAGGAAGTGGTGGACAAGGGCGCTTCCGCCCAGAG

CTTCATCGAGCGGATGACCAACTTCGATAAGAACCTGCCCAACGAGAAGGTG

CTGCCCAAGCACAGCCTGCTGTACGAGTACTTCACCGTGTATAACGAGCTGA

CCAAAGTGAAATACGTGACCGAGGGAATGAGAAAGCCCGCCTTCCTGAGCGG

CGAGCAGAAAAAGGCCATCGTGGACCTGCTGTTCAAGACCAACCGGAAAGTG

ACCGTGAAGCAGCTGAAAGAGGACTACTTCAAGAAAATCGAGTGCTTCGACT

CCGTGGAAATCTCCGGCGTGGAAGATCGGTTCAACGCCTCCCTGGGCACATA

CCACGATCTGCTGAAAATTATCAAGGACAAGGACTTCCTGGACAATGAGGAA

AACGAGGACATTCTGGAAGATATCGTGCTGACCCTGACACTGTTTGAGGACA

GAGAGATGATCGAGGAACGGCTGAAAACCTATGCCCACCTGTTCGACGACAA

AGTGATGAAGCAGCTGAAGCGGCGGAGATACACCGGCTGGGGCAGGCTGAG

CCGGAAGCTGATCAACGGCATCCGGGACAAGCAGTCCGGCAAGACAATCCTG

GATTTCCTGAAGTCCGACGGCTTCGCCAACAGAAACTTCATGCAGCTGATCC

ACGACGACAGCCTGACCTTTAAAGAGGACATCCAGAAAGCCCAGGTGTCCGG

CCAGGGCGATAGCCTGCACGAGCACATTGCCAATCTGGCCGGCAGCCCCGCC

ATTAAGAAGGGCATCCTGCAGACAGTGAAGGTGGTGGACGAGCTCGTGAAAG

TGATGGGCCGGCACAAGCCCGAGAACATCGTGATCGAAATGGCCAGAGAGAA

CCAGACCACCCAGAAGGGACAGAAGAACAGCCGCGAGAGAATGAAGCGGAT

CGAAGAGGGCATCAAAGAGCTGGGCAGCCAGATCCTGAAAGAACACCCCGT

GGAAAACACCCAGCTGCAGAACGAGAGCTGTACCTGTACTACCTGCAGAA

TGGGCGGGATATGTACGTGGACCAGGAACTGGACATCAACCGGCTGTCCGAC

TACGATGTGGACCACATCGTGCCTCAGAGCTTTCTGAAGGACGACTCCATCG

ACAACAAGGTGCTGACCAGAAGCGACAAGGCCCGGGGCAAGAGCGACAACGT

GCCCTCCGAAGAGGTCGTGAAGAAGATGAAGAACTACTGGCGGCAGCTGCTG

AACGCCAAGCTGATTACCCAGAGAAAGTTCGACAATCTGACCAAGGCCGAGA

GAGGCGGCCTGAGCGAACTGGATAAGGCCGGCTTCATCAAGAGACAGCTGGT

GGAAACCCGGCAGATCACAAAGCACGTGGCACAGATCCTGGACTCCCGGATG

AACACTAAGTACGACGAGAATGACAAGCTGATCCGGGAAGTGAAAGTGATCA

CCCTGAAGTCCAAGCTGGTGTCCGATTTCCGGAAGGATTTCCAGTTTTACAA

AGTGCGCGAGATCAACAACTACCACCACGCCCACGACGCCTACCTGAACGCC
```

-continued

```
GTCGTGGGAACCGCCCTGATCAAAAAGTACCCTAAGCTGGAAAGCGAGTTCG

TGTACGGCGACTACAAGGTGTACGACGTGCGGAAGATGATCGCCAAGAGCGA

GCAGGAAATCGGCAAGGCTACCGCCAAGTACTTCTTCTACAGCAACATCATG

AACTTTTTCAAGACCGAGATTACCCTGGCCAACGGCGAGATCCGGAAGCGGC

CTCTGATCGAGACAAACGGCGAAACCGGGGAGATCGTGTGGGATAAGGGCC

GGGATTTTGCCACCGTGCGGAAAGTGCTGAGCATGCCCCAAGTGAATATCGT

GAAAAAGACCGAGGTGCAGACAGGCGGCTTCAGCAAAGAGTCTATCCTGCCC

AAGAGGAACAGCGATAAGCTGATCGCCAGAAAGAAGGACTGGGACCCTAAG

AAGTACGGCGGCTTCGACAGCCCCACCGTGGCCTATTCTGTGCTGGTGGTGG

CCAAAGTGGAAAAGGGCAAGTCCAAGAAACTGAAGAGTGTGAAAGAGCTGCT

GGGGATCACCATCATGGAAAGAAGCAGCTTCGAGAAGAATCCCATCGACTTT

CTGGAAGCCAAGGGCTACAAAGAAGTGAAAAAGGACCTGATCATCAAGCTG

CCTAAGTACTCCCTGTTCGAGCTGGAAAACGGCCGGAAGAGAATGCTGGCCT

CTGCCGGCGAACTGCAGAAGGGAAACGAACTGGCCCTGCCCTCCAAATATGT

GAACTTCCTGTACCTGGCCAGCCACTATGAGAAGCTGAAGGGCTCCCCCGAG

GATAATGAGCAGAAACAGCTGTTTGTGGAACAGCACAAGCACTACCTGGACG

AGATCATCGAGCAGATCAGCGAGTTCTCCAAGAGAGTGATCCTGGCCGACGC

TAATCTGGACAAAGTGCTGTCCGCCTACAACAAGCACCGGGATAAGCCCATC

AGAGAGCAGGCCGAGAATATCATCCACCTGTTTACCCTGACCAATCTGGGAG

CCCCTGCCGCCTTCAAGTACTTTGACACCACCATCGACCGGAAGAGGTACAC

CAGCACCAAAGAGGTGCTGGACGCCACCCTGATCCACCAGAGCATCACCGGC

CTGTACGAGACACGGATCGACCTGTCTCAGCTGGGAGGCGACAgcgctGGAG

GAGGTGGAAGCGGAGGAGGAGGAAGCGGAGGAGGAGGTAGCggacctaagaa aaagaggaaggtggcggccgctggatccGGACGGGCTGACGCATTGGACGAT

TTTGATCTGGATATGCTGGGAAGTGACGCCCTCGATGATTTTGACCTTGACA

TGCTTGGTTCGGATGCCCTTGATGACTTTGACCTCGACATGCTCGGCAGTGA

CGCCCTTGATGATTTCGACCTGGACATGCTGATTTAACtgtacgaattcAAT

AAATAAAGATCTTTATTTTCATTAGATCTGTGTGTTGGTTTTTTGTGTG cggaccgagcggccgcaggaacccctagtgatggagttggc cactccctctctgcgcgctcgctcgctcactgaggccgggcgaccaaaggtcgcccgacgcccgggctttgcccgggcggc ctcagtgagcgagcgagcgcgcagctgcctgcaggggcgcctgatgcggtattttctccttacgcatctgtgcggtatttc acaccgcatacgtcaaagcaaccatagtacgcgccctgtagcggcgcattaagcgcggcgggtgtggtggttacgcgcagc gtgaccgctacacttgccagcgccctagcgcccgctcctttcgctttcttcccttcctttctcgccacgttcgccggcttt ccccgtcaagctctaaatcggggggctcccctttagggttccgatttagtgctttacggcacctcgaccccaaaaaacttgat ttgggtgatggttcacgtagtgggccatcgccctgatagacggttttttcgccctttgacgttggagtccacgttctttaat agtggactcttgttccaaactggaacaacactcaaccctatctcgggctattcttttgatttataagggattttgccgatt tcggcctattggttaaaaaatgagctgatttaacaaaaatttaacgcgaattttaacaaaatattaacgtttacaatttta tggtgcactctcagtacaatctgctctgatgccgcatagttaagccagccccgacacccgccaacacccgctgacgcgccc tgacgggcttgtctgctcccggcatccgcttacagacaagctgtgaccgtctccgggagctgcatgtgtcagaggttttca ccgtcatcaccgaaacgcgcgagacgaaagggcctcgtgatacgcctatttttataggttaatgtcatgataataatggtt
```

-continued

```
tcttagacgtcaggtggcacttttcggggaaatgtgcgcggaacccctatttgtttattttttctaaatacattcaaatatg tatccgctcatgagacaataaccctgataaatgcttcaataatattgaaaaaggaagagtatgagtattcaacatttccgt gtcgcccttattcccttttttgcggcattttgccttcctgttttttgctcacccagaaacgctggtgaaagtaaaagatgct gaagatcagttgggtgcacgagtgggttacatcgaactggatctcaacagcggtaagatccttgagagttttcgccccgaa gaacgttttccaatgatgagcacttttaaagttctgctatgtggcgcggtattatcccgtattgacgccgggcaagagcaa ctcggtcgccgcatacactattctcagaatgacttggttgagtactcaccagtcacagaaaagcatcttacggatggcatg acagtaagagaattatgcagtgctgccataaccatgagtgataacactgcggccaacttacttctgacaacgatcggagga ccgaaggagctaaccgcttttttgcacaacatgggggatcatgtaactcgccttgatcgttgggaaccggagctgaatgaa gccataccaaacgacgagcgtgacaccacgatgcctgtagcaatggcaacaacgttgcgcaaactattaactggcgaacta cttactctagcttcccggcaacaattaatagactggatggaggcggataaagttgcaggaccacttctgcgctcggccctt ccggctggctggtttattgctgataaatctggagccggtgagcgtgggtctcgcggtatcattgcagcactggggccagat ggtaagccctcccgtatcgtagttatctacacgacggggagtcaggcaactatggatgaacgaaatagacagatcgctgag ataggtgcctcactgattaagcattggtaactgtcagaccaagtttactcatatatactttagattgatttaaaacttcat ttttaatttaaaaggatctaggtgaagatcctttttgataatctcatgaccaaaatcccttaacgtgagttttcgttccac tgagcgtcagacccctagaaaagatcaaaggatcttcttgagatcctttttttctgcgcgtaatctgctgcttgcaaaca aaaaaaccaccgctaccagcggtggtttgtttgccggatcaagagctaccaactctttttccgaaggtaactggcttcagc agagcgcagataccaaatactgtccttctagtgtagccgtagttaggccaccacttcaagaactctgtagcaccgcctaca tacctcgctctgctaatcctgttaccagtggcrgctgccagtggcgataagtcgtgtcttaccgggttggactcaagacga tagttaccggataaggcgcagcggtcgggctgaacggggggttcgtgcacacagcccagcttggagcgaacgacctacacc gaactgagatacctacagcgtgagctatgagaaagcgccacgcttcccgaagggagaaaggcggacaggtatccggtaagc ggcagggtcggaacaggagagcgcacgagggagcttccaggggaaacgcctggtatctttatagtcctgtcgggtttcgc cacctctgacttgagcgtcgatttttgtgatgctcgtcaggggggcggagcctatggaaaaacgccagcaacgcggccttt ttacggttcctggcctttgctggccttttgctca catgt
```

In one aspect, the invention provides a precision CAVac. Precision CAVac, or personalized CAVac, is a derivative of CAVac that is customized based on the genetic composition of an individual's tumor, such as those identified from genomic profiling of a patient's resected tumor or biopsy.

In one aspect, the invention provides an off-the-shelf APCM, which is an approach of endogenous gene activation that targets a small set of genes regardless of patient's tumor's genetic identity.

In one aspect, the invention provides methods of dual-AAV delivery comprising delivery of any one of the vectors described herein with sgRNAs or sgRNA pools cloned into them, together with the delivery of a second vector (e.g. an AAV-dCas9 vector such as pZB2_EFS-LTR-dCas9_addgene-plasmid-106430 or pGW011b_pAAV-EFS-dCAS9-spA). Compositions comprising said dual-AAV delivery systems and methods of using said dual-delivery systems for treating cancer are also provided with the invention.

Generation of AAV-PCAVac:

I. Patient Tumor Sequencing

For a personalized vaccine, genomic DNA is extracted from each patient's tumor biopsy, along with matched normal sample such as peripheral blood. The gDNA is subjected to whole-exome sequencing (WES) and/or whole-genome sequencing (WGS). Mutations are identified from WES of tumor sample, and subtracted from matched normal to exclude background and germline variants, and associated to annotated genes. This will produce a personalized tumor mutation panel of genes (Patient-mutation-geneset).

II. Geneset Choice

This gene set can be further filtered by one or more of the filtering metrics:

1. Select for Immunogenicity, by prediction of immunogenic scores including but not limited to tools such as PVACseq 2. Select against Oncogenecity, by excluding known oncogenes and/or genes amplified in any types of cancer in cancer genomics datasets/databases including but not limited to TCGA, COSMIC, TARGET, cBio-Portal.

3. Consider Coding capacity, by choosing coding genes only, or coding and non-coding genes The filtered (Patient-mutation-geneset-filt) or unfiltered gene set (Patient-mutation-geneset) will be subjected to library design. The gene set can be ranging from 1 to 20,000.

III. SgRNA Design and Library Generation

1. SgRNAs are chosen from a pre-defined sequence list for these genes, or designed ab initio using existing or customized codes.

2. An sgRNA library for each patient is synthesized using pooled oligo synthesis, using individual or commercial vendors including but not limited to Yale/Keck ISP, IDT, Thermofisher, Customarray, Agilent.

3. A synthesized sgRNA library is pool cloned into the AAV-CRISPRa vector, or derivatives, or similar vectors using other effectors, adaptors, Cas enzymes for the same purpose.

4. A cloned library is sequence verified using Sanger and/or Illumina sequencing using custom methods and primers as described herein.

5. Plasmid library is subjected to amplification for viral packaging

IV. Generation of AAV-PCAVac

1. An AAV library is generated by packaging the plasmid library into viral particles using various viral packaging systems including the one described herein 2. An AAV library is purified using methods including the one described herein 3. An AAV library is titered using methods including the one described herein such as qPCR 4. Additional GIP, GMP and/or cGMP methods of AAV production may be adopted Carriers of the vaccine or personalized vaccine can be AAVs of different serotypes for different tissue-specificity/tropism, including but not limited to natural variants AAV1, AAV2, AAV3, AAV4, AAV5, AAV6, AAV7, AAV8, AAV9, AAV10, AAV11, AAV12, artificial variants such as AAV.rhlO, AAV.rh32/33, AAV.rh43, AAV.rh64R1, rAAV2-retro, AAV-DJ, AAV-PHP.B, AAV-PHP.S, AAV-PHP.eB, or other engineered versions of AAV, other novel AAV variants, or any combinations thereof.

The invention should be construed to encompass any type of viral vector known to one of ordinary skill in the art. For example, the carrier of the vaccine or personalized vaccine can be AAV (described herein), but can also be other viral vectors including but not limited to adenovirus, retrovirus, lentivirus, hybrid viral vectors, or any combinations thereof.

Introduction of Nucleic Acids

In certain embodiments an expression system is used for the introduction of gRNAs and (d) Cas9 proteins into the cells of interest. Typically employed options include but are not limited to plasmids and viral vectors such as adeno-associated virus (AAV) vector, adenoviral vector or lentivirus vector.

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors have become the most widely used method for introducing genes into mammalian, e.g., human cells. Other viral vectors can include as listed above. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about –20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the cells, transfecting the cells, and electroporating the cells. One nucleic acid may be introduced by one method and another nucleic acid may be introduced into the cell by a different method.

RNA

In one embodiment, the nucleic acids introduced into the cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA. To enable synthesis of RNA from a DNA template, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has a cap on the 5' end and a 3' poly(A) tail which determine ribosome binding, initiation of translation and stability mRNA in the cell. On a circular DNA template, for instance, plasmid DNA, RNA polymerase produces a long concatameric product which may not be suitable for expression in eukaryotic cells. The transcription of plasmid DNA linearized at the end of the 3' UTR results in normal sized mRNA which may not be effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is by molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of Cells

In one embodiment, cells are obtained from a subject. Non-limiting examples of subjects include humans, dogs, cats, mice, rats, pigs and transgenic species thereof. Preferably, the subject is a human. Cells can be obtained from a number of sources, including peripheral blood mononuclear cells, bone marrow, lymph node tissue, spleen tissue, umbilical cord, cancer cells and tumors. In certain embodiments, any number of cell lines available in the art, may be used. In certain embodiments, cells can be obtained from a unit of blood collected from a subject using any number of techniques known to the skilled artisan, such as Ficoll separation. In one embodiment, cells from the circulating blood of an individual are obtained by apheresis or leukopheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, cells are isolated from peripheral blood. Alternatively, cells can be isolated from umbilical cord. In any event, a specific subpopulation of cells can be further isolated by positive or negative selection techniques.

Cells can also be frozen. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1 per minute and stored in the vapor phase of a liquid nitrogen storage tank. Other methods of controlled freezing may be used as well as uncontrolled freezing immediately at −20° C. or in liquid nitrogen.

Pharmaceutical Compositions

Pharmaceutical compositions of the present invention may comprise the modified cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the modified cells described herein may be administered at a dosage of $10^4$ to $10^9$ cells/kg body weight, in some instances $10^5$ to $10^6$ cells/kg body weight, including all integer values within those ranges. Compositions of the invention may also be administered multiple times at these dosages. The cells or vectors can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified cells or vectors of the invention may be carried out in any convenient manner known to those of skill in the art. The cells or vectors of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullarly, intracystically intramuscularly, by intravenous (i.v.) injection, parenterally or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002).

These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Lentiviral SAM library production: Mouse CRISPR activation plasmid libraries (lenti-U6-mSAM-EFS-Puro) were expanded by electroporation (Konermann et al. (2015) *Nature* 517, 583-588). An estimated library coverage of >100× (>100 colonies per sgRNA) was achieved in electroporation, and the coverage of sgRNAs was subsequently sequence-verified by Illumina sequencing. For lentivirus production, 20 µg of plasmids of lenti-EF1a-NLS-dCas9-VP64-P2A-Blast, lenti-EF1a-MS2-p65-HSF1-P2A-Hygro or lenti-U6-SAM-EFS-Puro library, together with 10 µg of pMD2.G and 15 µg of psPAX2 were co-transfected into HEK293FT cells in 150 mm-dish at 80-90% confluency using 130 µg polyethyleneimine (PEI) as the transfection reagent. 6-12 hours later, the media was replaced by fresh DMEM+10% FBS. Virus supernatant was collected 48 h and 72 h post-transfection, centrifuged at 1500 g for 10 min and passed through 0.45-µm filter to remove the cell debris; aliquoted and stored at −80° C. Virus was titrated by infecting E0771 cells followed by the selection under 5 µg/ml puromycin.

Generation of cell-based CAVac: E0771 cells stably expressing dCas9-VP64 and MS2-P65-HSF1 (E0771-dCas9-MPH) were generated by transducing lentiviruses containing lenti-EF1a-NLS-dCas9-VP64-2A-Blast and lenti-EF1a-MS2-p65-HSF1-2A-Hygro into E0771 cells, followed by 7 days of selection under the pressure of 10 µg/ml blasticidin and 500 µg/ml hygromycin. Then, the E0771-dCas9-MPH cells were transduced with mSAM-library-containing lentiviruses at an MOI of 0.2-0.3, with a minimal representation of 200× transduced cells per sgRNA as described previously (Konermann et al. (2015) *Nature* 517, 583-588). Briefly, $1×10^8$ cells were infected by lib-containing viruses at a calculated MOI of 0.2 and cultured at 37° C. more than 1 day before replacing with 5 µg/ml puromycin containing media, and the transduced cells were drug-selected for 7 days before using.

Sequencing confirmation of SAM sgRNA library representation: Library transduced cells were subjected to genomic DNA (gDNA) extraction using standard molecular biology protocols. The sgRNA library readout was performed using a two-step PCR strategy, where the first PCR includes enough genomic DNA to preserve full library complexity and the second PCR adds appropriate sequencing adapters to the products from the first PCR.

```
PCR1 primers:
Forward:
                              (SEQ ID NO: 23, 777)
AATGGACTATCATATGCTTACCGTAACTTGAAAGTATTTCG
```

-continued

```
Reverse:
                                   (SEQ ID NO: 23, 778)
CTTTAGTTTGTATGTCTGTTGCTATTATGTCTACTATTCTTTCCC
```

PCR was performed using Phusion Flash High Fidelity Master Mix (PF) or DreamTaq Green PCR Master Mix (DT) (ThermoFisher). For reactions using PF, in PCR #1, the thermocycling parameters were: 98° C. for 1 min, 16-20 cycles of (98° C. for Is, 62° C. for 5 s, 72° C. for 30 s), and 72° C. for 2 min. For reactions using DT, the thermocycling parameters were adjusted according to manufacturer's protocol. In each PCR #1 reaction, 3 μg of total gDNA was used. A total of 8 to 12 of PCR #1 reactions was used to capture the full representation of the library in the cells. PCR #1 products for each biological sample were pooled and used for amplification with barcoded second PCR primers.

```
Barcoding second PCR primers used:
SF5:
                                   (SEQ ID NO: 24, 107)
AATGATACGGCGACCACCGAGATCTACACTCTTTCCCTACACGACGCT

CTTCCGATCTTCGATCGTTACCATCTTGTGGAAAGGACGAAACACCG (SEQ ID NO: 24, 108)
SF6:
AATGATACGGCGACCACCGAGATCTACACTCTTTCCCTACACGACGCT

CTTCCGATCTATCGATTCCTTGGTTCTTGTGGAAAGGACGAAACACCG

SR1:
                                   (SEQ ID NO: 24, 109)
CAAGCAGAAGACGGCATACGAGATAAGTAGAGGTGACTGGAGTTCAGA

CGTGTGCTCTTCCGATCTTTCTACTATTCTTTCCCCTGCACTGT

SR2:
                                   (SEQ ID NO: 24, 110)
CAAGCAGAAGACGGCATACGAGATACACGATCGTGACTGGAGTTCAGA

CGTGTGCTCTTCCGATCTATTCTACTATTCTTTCCCCTGCACTGT

SR3:
                                   (SEQ ID NO: 24, 1111)
CAAGCAGAAGACGGCATACGAGATCGCGCGGTGTGACTGGAGTTCAGA

CGTGTGCTCTTCCGATCTGATTCTACTATTCTTTCCCCTGCACTGT

SR4:
                                   (SEQ ID NO: 24, 112)
CAAGCAGAAGACGGCATACGAGATCATGATCGGTGACTGGAGTTCAGA

CGTGTGCTCTTCCGATCTCGATTCTACTATTCTTTCCCCTGCACTGT

SR5:
                                   (SEQ ID NO: 24, 113)
CAAGCAGAAGACGGCATACGAGATCGTTACCAGTGACTGGAGTTCAGA

CGTGTGCTCTTCCGATCTCGATCTCTACTATTCTTTCCCCTGCACTGT

SR6:
                                   (SEQ ID NO: 24, 114)
CAAGCAGAAGACGGCATACGAGATTCCTTGGTGTGACTGGAGTTCAGA

CGTGTGCTCTTCCGATCTTTCTACTATTCTTTCCCCTGCACTGT
```

For reactions using PF, in PCR #2, the thermocycling parameters were: 98° C. for 1 min, 18-24 cycles of (98° C. for is, 60° C. for 5 s, 72° C. for 30 s), and 72° C. for 2 min. Second PCR products were pooled and then normalized for each biological sample before combining uniquely barcoded separate biological samples. The pooled product was then gel purified from a 2% E-gel EX (Life Technologies) using the QiaQuick kit (Qiagen). The purified pooled library was then quantified with a gel-based method using the Low- Range Quantitative Ladder Life Technologies, dsDNA High-Sensitivity Qubit (Life Technologies), BioAnalyzer (Agilent) and/or qPCR. Diluted libraries with 5-20/PhiX were sequenced with MiSeq, HiSeq 2500 or HiSeq 4000 systems (Illumina).

Raw single-end fastq read files were filtered and demultiplexed using Cutadapt (Martin et al. (2011) *EMBnet.journal* 17, 10-12). To remove extra sequences downstream (i.e. 3' end) of the sgRNA spacer sequences, the following settings were used: cutadapt—discard-untrimmed–a GTTTTAGAGCTAGGCCAAC (SEQ ID NO: 24,115). As the forward PCR primers used to readout sgRNA representation were designed to have a variety of barcodes to facilitate multiplexed sequencing, these filtered reads were then demultiplexed with the following settings: cutadapt -g file: fbc.fasta --no-trim, where fbc.fasta contained the 12 possible barcode sequences within the forward primers. Finally, to remove extra sequences upstream (i.e. 5' end) of the sgRNA spacers, the following settings were used: cutadapt --discard-untrimmed -g GTGGAAAGGACGAAACACCG (SEQ ID NO: 24,116). Through this procedure, the raw fastq read files could be pared down to the 20 bp sgRNA spacer sequences. These 20 bp sgRNA spacer sequences from each demultiplexed sample were mapped the sgRNA spacers to the mSAM library using Bowtie 1.1.2 (Langmead et al. (2009) *Genome Biol* 10, R25): bowtie -v1 --suppress 4,5,6, 7—chunkmbs 2000—best. Using the resultant mapping output, the number of reads that had mapped to each sgRNA within the library were quantitated. To count sgRNA representation, a detection threshold of $\log_2$ rpm≥1 was set and the number of unique sgRNAs present in each sample was counted.

Mice: All animal work was approved by IACUC and performed with approved protocols. Mice of both sexes, between 5-12 weeks of age were used for the study. Various animals were used in this study. 5-10 week old C57BL/6J mice were used for experiments. Female mice were used for breast cancer models. Male mice were used for pancreatic adenocarcinoma (Pan2) models. A mix of both male and female mice were used for melanoma (B16F10) models. All animals were housed in standard individually ventilated, pathogen-free conditions, with 12 h:12 h or 13 h:11 h light cycle, room temperature (21-23° C.) and 40-60% relative humidity. Sample size was determined based on number of animals used. Prior estimation of number of mice used was estimated based on similar tumor models in the field. When a cohort of animals receive multiple treatments, animals were randomized by 1) randomly assign animals to different groups using littermates, 2) random mixing of females prior to treatment, maximizing the evenness or representation of mice from different cages in each group, and/or 3) random assignment of mice to each group, in order to minimize the effect of litter, small difference in age, cage, housing position, where applicable.

Tumorigenesis of E0771-SAM in C57BL/6J, Nu/Nu, or $Rag1^{-/-}$ mice: $5 \times 10^6$ of E0771-SAM or E0771-Vector tumor cells were injected into the orthotopic mammary fat pad of syngeneic 5-8 weeks old female C57BL/6J mice, Nu/Nu, or $Rag1^{-/-}$ mice. Tumor sizes were measured every 3-4 days by caliper on the three diameters, and sizes were calculated as approximate spheroids with the formula: Vol=π/6*x*y*z. Statistical significance of all tumor growth curves in the study was assessed by analysis of variance (2-way ANOVA), jointly considering the effect of treatment and the passage of time on tumor growth. For CD4 and CD8 T cell depletion, 200 ug α-CD4 (GK1.5, BioXcell) and 200 ug α-CD8 (YTS 169.4) were intraperitoneally injected into tumor-transplanted C57BL/6J mice at dpi 7 and dpi 14 to block the effect of T cells at an early stage of tumorigenesis. The successful depletion of CD8 T cells was confirmed by isolating PBMCs from mice at dpi 14 and 21 and analyzing the CDC T cell population with flow cytometry.

Generation of cell-based MAEGI: Cell-based MAEGI (c-MAEGI) was produced by treating E0771-SAM cells (described above) with 10 ug/ml mitomycin for more than 2 hrs to restrain their proliferation ability while maintaining cellular integrity. In parallel, mitomycin-treated E0771-Vector (referred to as mock Cell-Vector) was used as control. The therapeutic effects of heat-inactivated lysates of the same numbers of E0771-mSAM and E0771-Vector cells were also used for comparison. Heat induced cell lysis of E0771 and c-MAEGI was performed by incubation at 65° C. for 30 minutes followed by 3 freezing-thaw cycles, lysing the cells and disrupting the integrity of peptide-MHC complexes on the cell surface.

Prophylactic application of CAVac (c-MAEGI) in syngeneic tumor models: $5 \times 10^6$ mSAM-transduced E0771 tumor cells were injected orthotopically into mammary fatpad of syngeneic 5-8 weeks old female C57BL/6J mice. 3, 7, or 14 days after CAVac inoculation, $5 \times 10^6$ E0771 tumor cells were transplanted into the mammary fatpad in C57BL/6J mice. For the challenges with tumors derived from different cells of origin, $5 \times 10^6$ LCC cells were injected subcutaneously into flank of E0771-CAVac vaccinated C57BJ6J mice. The growth of tumors was continuously monitored and measured by caliper, twice per week. Statistical significance was assessed by paired f-test and/or analysis of variance (ANOVA) where applicable.

Therapeutic effects of CAVac (c-MAEGI) in syngeneic tumor models: Syngeneic orthotopic breast tumors were established by transplanting $2 \times 10^6$ or $5 \times 10^6$ E0771 cells into the mammary fatpad of 5-8 weeks old female C57BL/6J mice. 4, 8 and 14 days after transplantation, therapeutic CAVac made using $5 \times 10^6$-$1 \times 10^7$ mSAM-transduced E0771 cells was s.c. injected into left flank of tumor-bearing mice. Tumors were measured every 3-4 days using caliper and sizes were calculated with the formula: Vol=$\pi/6 \times x \times y \times z$.

Generation of AAV-CAVac (AAV-based MAEGI): An AAV version of the CRISPR activation vector (AAV-CRIS-PRa vector, i.e. U6p-sgSapI-EF1a-MS2-p65-HSF1-WPRE), and an AAV version of dCas9 vector (AAV-dCas9, i.e. EFS-dCas9-VP64-spA), were generated by restriction cloning and Gibson assembly. The sgRNA libraries of mSAM were cloned into the above CRISPRa plasmid by linearization with SapI digestion and Gibson assembly. The purification and electroporation of Gibson products into Endura electrocompetent cells were performed as previously described (Joung, et al. (2017) *Nat Protoc* 12, 828-863), with at least 100× coverage of colonies represented per sgRNA. AAV9 was produced by co-transfecting HEK293FT cells with above AAV plasmids of CRISPR activation vector or library (AAV-mSAM), AAV9 serotype plasmid and helper plasmid PDF6. Briefly, 5.2 μg of AAV-vector or AAV-mSAM, 8.7 μg of AAV9 serotype plasmid and 10.4 μg of pDF6 were mixed with PEI, room temperature 10 min before drop-wisely adding them into HEK293FT cells in 150 mm-dish at 80-90% confluency. Replicates collected from multiple dishes were pooled to enhance production yield. Cells were collected 72 h post transfection. For AAV9 purification, ¹⁄₁₀ volume of chloroform was added and the mixture was vigorously shaken for 1 h at 37° C. NaCl was added to a final concentration of 1 M and the mixture was shaken until dissolved and then pelleted at 20,000 g at 4° C. for 15 min. The aqueous layer was discarded while the chloroform layer was transferred to another tube. PEG8000 was added to 10% (w/v) and shaken until dissolved. The mixture was incubated at 4° C. for 1 h and then spun at 20,000 g at 4° C. for 15 min. The supernatant was discarded and the pellet was resuspended in DPBS plus $MgCl_2$ and treated with Benzonase (Sigma) and incubated at 37° C. for 30 min. Chloroform (1.1 volume) was then added, shaken, and spun down at 12,000 g at 4° C. for 15 min. The aqueous layer was isolated and passed through a 100 kDa MWCO (Millipore). The concentrated solution was washed with PBS and the filtration process was repeated. Genomic copy number (GC) of AAV was determined by real-time quantitative PCR using custom Taqman assays (ThermoFisher) targeted to the engineered U6 promoter.

Combinatorial therapy using CAVac (c-MAEGI) and monoclonal antibodies: To check the synergistic effect between therapeutic CAVac (c-MAEGI) and immune checkpoint blockade or CD4 depletion, 5 mg/kg anti-CTLA4 monoclonal antibody (9D9, BioXcell), 8 mg/kg anti-PD1 monoclonal antibody (RMP1-14, BioXcell) or 200 μg per mouse anti-CD4 antibody (GK1.5, BioXcell) were administrated by i.p. injection at day 7 and day 14 with or without CAVac vaccination as described elsewhere herein. Two-way ANOVA was used to compare growth curves between treatment groups. Tumor re-challenge was done by injecting $5 \times 10^6$ E0771 cells into the contralateral fatpad of mice underwent complete response.

ELISPOT assay: IFN-γ ELISPOT mouse kits (BD Biosciences) were used according to the manufacturer's instructions. Briefly, 96-well filtration plates were coated overnight at 4° C. with capturing monoclonal antibody; the plates were then washed and blocked with RPMI-1640 medium containing 10% FBS for 2 h at room temperature. Splenocytes in RPMI-1640 ($1 \times 10^6$ cells/well) were then added, and $5 \times 10^4$ mitomycin-treated E0771 cells was subsequently added as the stimulation antigen; the plates were cultured for approximately 45 hours at 37° C. and 5% $CO_2$. After washing once with DI water and three times with PBST, the plates were incubated with biotinylated detection antibody at room temperature for 2 h. Then, plates were incubated with HRP-conjugated streptavidin at room temperature for 1 h after washing three times with PBST. Spots were revealed using an AEC substrate reagent kit (BD Bioscience) at room temperature and counted using an Immunospot Reader (Cellular Technology).

Therapeutic testing of AAV-CAVac (g-MAEGI) in syngeneic tumor models: Syngeneic orthotopic breast tumors were established by transplanting $2 \times 10^6$ E0771-dCas9-VP64 cells into the mammary fatpad of 5-8 weeks old female C57BL/6J mice. 4, 10, 14, and 21 days after transplantation, $2$-$5 \times 10^{10}$ GCs of AAV-CAVac or PBS were injected intratumorally to tumor-bearing mice. For the B16F10 melanoma model, $5 \times 10^5$ dCas9-VP64 expressing cancer cells were injected subcutaneously into the flank of C57BL/6J mice. 7, 10, 14, and 20 days after transplantation, $5$-$10 \times 10^{10}$ GCs of AAV-CAVac (AAV-g-MAEGI), AAV-Vector, or PBS were intratumorally administrated into tumor-bearing mice. For the pancreatic tumor model, $2 \times 10^6$ Pan02 cancer cells were injected subcutaneously into the flank of C57BL/6J mice. 5, 13, 21, and 35 days after transplantation, $5$-$10 \times 10^{10}$ GCs of AAV-CAVac or PBS were intratumorally administrated into tumor-bearing mice. Tumors were measured every 3-4 days using caliper and sizes were calculated with the formula: Vol=$\pi/6 \times x \times y \times z$.

Splenocytes and tumor infiltrating lymphocyte isolation: Syngeneic breast tumors were established by transplanting $2 \times 10^6$ E0771 cells into the mammary fatpad of 5-8 weeks old female C57BL/6J mice. Tumor-bearing mice were randomly assembled into different treatment group and treated with PBS, CAVac, ICB monoclonal antibodies, CAVac+ICB antibodies accordingly. Mice were euthanized 35 days' post-transplantation, tumors and spleens were collected and kept in ice-cold 2% FBS. For spleens, they were placed in ice-cold 2% FBS and mashed through a 100 μm filter. Splenocytes were washed once with 2% FBS. RBCs were lysed with 1 ml of ACK Lysis Buffer (Lonza) per spleen by incubating 2 mins at room temperature, which was followed by the dilution with 10 ml 2% FBS and pass through a 40 μm filter. Splenocytes were resuspended in 2% FBS buffer, counted for flow cytometry staining or RNA isolation. Tumors were minced into 1-3 mm size pieces using scalper and then digested using 100 U/mL Collagenase IV for 30-60 min while stirred at 37° C. Tumor suspensions were filtered twice through 100 μm cell strainer, and once through 40 μm cell strainer to remove large bulk. Subsequently, single cell suspensions can be directly used for FACS staining, or further Ficoll purification to obtain tumor-infiltrating lymphocytes. For Ficoll-Paque purification, single cell suspensions at density of ($\sim 10^7$ cells/ml) were carefully layered onto Ficoll-Paque media (GE Healthcare) and centrifuge at 400 g for 30 min. Cells at the interface were carefully collected, and washed twice with 2% FBS, counted, and used for RNA isolation or flow cytometry staining.

Flow cytometry: All antibodies were purchased from Biolegend. Single cell suspensions from tumors or spleens were prepared as previous described. For surface staining, cells were blocked with anti-Fc receptor anti-CD16/CD32 and surface stained with anti-CD45.2-APC/Cy7, anti-CD3-PE, anti-CD4-FITC, anti-CD8a-APC, in PBS+2% FBS on ice for 30 min. Samples were washed twice with PBS+2% FBS before analyzed or sorted on a BD FACSAria. The data was analyzed using FlowJo software on a MAC® workstation.

Fluorescence-activated cell soring (FACS) isolation of CD45$^+$ cells from tumors: Single tumor cell suspensions were prepared using the gentleMACS system with the method described in "Splenocytes and tumor infiltrating lymphocyte isolation". Tumor cells were blocked using anti-Fc receptor anti-CD16/CD32. Live cells were distinguished from dead cells in flow cytometry by staining with LIVE/DEAD™ Fixable Near-IR Dead Cell Stain Kit following manufacturer's instructions. Cells at a density of 10/ml were stained with DMSO dissolved live/dead staining dye and PerCP/Cy5.5 or APC conjugated CD45 antibody in PBS+2% FBS, and incubated on ice for 30 min. Stained cells were washed three times before being analyzed and FACS isolated on a BD FACSAria. Tumor-infiltrating CD45+ pan-immune cells (TIICs) were isolated by gating on PerCP/Cy7$^+$APC/Cy7$^-$ or APC$^+$APC/Cy7$^-$ populations. Sorted TIICs were counted, and used for scRNAseq and ELISpot analysis.

Immune cell profiling by single-cell RNA-seq: Single cell suspensions from tumors were prepared as previously described. For CD45$^+$ cell isolation, cells were blocked with anti-Fc receptor anti-CD16/CD32 and surface stained with anti-CD45.2 in PBS+2% FBS on ice for 30 min. Samples were washed twice with PBS+2% FBS, and CD45$^+$ cell populations in tumors were FACS sorted using a BD FACSAria. Sorted cells were collected in PBS+2% FBS, cell numbers and viabilities were assessed by trypan blue staining and counting in Countess II FL Automated Cell Counter (Thermo). 10,000 CD45$^+$ cells isolated from tumors were used for single-cell RNAseq by following the protocol from 10× Genomics.

Single cell RNA-seq data processing: Pan-immune cell scRNA-seq data was pre-processed using established and custom pipelines. Briefly, raw Illumina data files were processed by Cell Ranger 1.3 (10× Genomics)(Zheng, et al. (2017) Nat Commun 8, 14049), using cellranger mkfastq to wrap Illumina's bcl2fastq to correctly demultiplex sequencing samples and to convert barcode and read data to FASTQ files. Then, cellranger count was used to take FASTQ files and perform alignments to the mouse genome (mm10) (Dobin, et al. (2013) Bioinformatics 29, 15-21), filtering, and UMI counting. Using Seurat (Butler & Satija (2017) bioRxiv), cells passing the initial quality control metrics imposed by the Cell Ranger pipeline were further filtered by excluding all cells in which mitochondrial genes disproportionately comprised the total % of the library (empirically determined cutoff of 5% mitochondrial reads). With this filter, a final set of 7,458 cells was retained for further analysis (from initial of 7,492 cells). After log normalization, the 27,998 genes/features were filtered using a flat cutoff metric such that genes with low variance were excluded, leaving 1267 genes. The data were then scaled based on UMI total counts and the % of mitochondrial reads. Using the final normalized and processed dataset above, t-SNE dimension reduction was performed (Maaten & Hinton (2008) J. Mach. Learn. Res. 9, 2579-2605; Maaten (2014) J. Mach. Learn. Res. 15, 3221-3245). Individual data points were colored based on the treatment condition for each cell, or based on unbiased k-means clustering performed in Seurat. Differential expression analyses between clusters and/or treatment conditions was performed by nonparametric Wilcoxon rank sum test. Multiple hypothesis correction was performed by the Benjamini-Hochberg method. Significantly differentially expressed genes were defined as having a Benjamini-Hochberg adjusted $p<0.05$.

RNA extraction, reverse transcription, and quantitative PCR: RNA in cells, splenocytes, and tumor infiltrating lymphocytes were extracted using TRIzol Reagent (Invitrogen) by following standard RNA extraction protocols. The first-strand cDNA of RNA was synthesized using Super-Script™ IV Reverse Transcriptase (Invitrogen). After normalizing the concentrations of cDNA with nuclease-free water, quantitative PCR (qPCR) was performed by adding designated Taqman probe of interested genes, and GAPDH was used as an internal positive control.

Western Blot: E0771, E0771-dCas9-VP64, and E0771-dCas9-VP64-MPH cells in 6-well plate were washed twice with ice cold PBS before lysis with 1×RIPA buffer which was kept on ice for 15 min. Cell lysates were centrifuged at 12,000 g for 15 min at 4° C. and protein-containing supernatant was collected. Protein concentration was measured using a standard Bradford assay (BioRad) and 20 μg of protein in each sample were loaded into SDS-PAGE gel. After electrophoresis, proteins separated in gel were transferred into nitrocellulose membranes. Membranes were blocked at room temperature for 1 h using 5% skim-milk in TBST, followed by the incubation with primary antibody in 4° C. overnight. After washing three times with TBST, horseradish peroxidase (HRP)-conjugated secondary antibody was added and incubated at room temperature for 30-60 min. The chemiluminescent substrate (Clarity Western ECL Substrate, Bio-Rad) was added on top of blot membrane according to the manufacturer's instructions. The signals were captured using a CCD camera-based imager (GE Healthcare).

Histology and immunohistochemistry: At matched time points, tumors from different treatment group were collected and fixed in 10% neutral formalin for 2-5 days. Tissues were transferred into 70% ethanol for long-term storage. Haematoxylin and eosin (H&E) staining or antibody staining were performed on 3-5 μm tissue sections using standard procedures.

T cell receptor sequencing (TCR-seq): Mice in different treatment groups were euthanized at 30-40 days' post-transplantation. Tumors and spleens were collected and kept in ice-cold 2% FBS before use. Single cell suspensions from tumors or spleens were prepared as previous described. The RNA from collected splenocytes and TILs were extracted using Trizol according to manufacturer's instructions.

TCR-seq data analysis: Raw fastq files from TCR-seq were processed to clonotypes using MiXCR following the author recommendations for 5' RACE-based library protocols (Bolotin, et al. (2015) Nat Methods 12, 380-381). Specifically, the mixer align function was first used to align to the V segment transcript, followed by collotype assembly using mixer assemble and mixcr exportClones. Subsequently, TCR-seq data were analyzed using the tcR package (Nazarov, et al. (2015) BMC Bioinformatics 16, 175) to determine clonal proportions and occupied clonal homeostasis in each sample. Metrics of diversity were calculated using ecological diversity, Gini-Simpson, and Chao indices.

Exome sequencing of E0771 and identification of all genic mutational spectrum: E0771 cells and freshly-dissected mammary fatpad from healthy, untreated 6-8 wk old female C57BL/6J mice were subjected to gDNA extraction following standard protocol. A total of 2 μg of gDNA per sample were subjected to exome capture using mouse exome probes (Roche) and then Illumina library preparation following manufacturer's protocols. Exome capture paired-end fastq files were mapped to the mm10 genome using Bowtie v2.2.9 (Langmead et al. (2009) Genome Biol 10, R25), and sorted by Samtools (Li et al. (2009) Bioinformatics 25, 2078-2079). VarScan v2.3.9 (Koboldt, D. C. et al. (2012) Genome Res 22, 568-576) was then used in somatic mode to call indels and SNPs that were specific to E0771 cells and not found in wildtype C57BL/6J mammary fatpad tissue. Germline calls were subsequently filtered out. The remaining variants were collapsed to the gene level, and the number of indels or SNPs for each gene was tabulated.

Generation of mutational spectrum guided precision AAV-CAVac (AAV-PCAVac/AAV-p-MAEGI): Genes were ranked by their number of somatic variants present in E0771 cells but not in healthy mammary fatpad. A set of 1,116 top mutated genes were chosen as differentially mutated genes in E0771 and 3 sgRNAs per gene (for the majority of genes) targeting promoter regions were chosen. A CRISPRa library consisting of 3,839 sgRNAs (SEQ ID NOs: 349-4,187) were designed for the E0771 top mutated gene set, pool-synthesized (Customarray), and cloned into the AAV-CRISPRa vector above. AAV library packaging was done as above to generate AAV-PCAVac for E0771.

Therapeutic testing of AAV-PCAVac (p-MAEGI): Syngeneic TNBC were established by orthotopic transplantation of $2\times10^6$ E0771 cells into the mammary fat pad of 5-8 weeks old female C57BL/6J mice. 5, 12 and 18 days after tumor induction, $5\times10^{10}$-$1\times10^{11}$ GCs of AAV-CAVac, AAV-Vector, or PBS were intratumorally administrated into tumor-bearing mice. For testing of the abscopal effect, syngeneic TNBC were established by orthotopic transplantation of $2\times10^6$ E0771 cells into an ipsilateral mammary fat pad, and 2.5× $10^5$ E0771 cells into the contralateral mammary fat pad. 4, 11, 18 and 24 days after tumor induction, $5\times10^{10}$-$1\times10^{11}$ GCs of AAV-p-MAEGI or AAV-Vector were intratumorally administrated into the ipsilateral tumor. Tumors were measured every 3-4 days using caliper and sizes were calculated with the formula: $Vol=\pi/6*x*y*z$. Two-way ANOVA was used to compare growth curves between treatment groups. Response to therapy was defined by a method similar to RECIST 1.1 criteria (CR, complete response, where endpoint tumor size=0; Near-CR, near complete response, where tumor size<50 $mm^3$ for the last 2 measurements; PR, partial response, where tumor sizes decreased for at least 2 consecutive measurements; SD, stable disease, where tumor size is between 70~100% of initial tumor size at the first treatment; PD, progressive disease, where tumor size>initial tumor size at the first treatment).

The results of the experiments are now described.

Figure 1A:
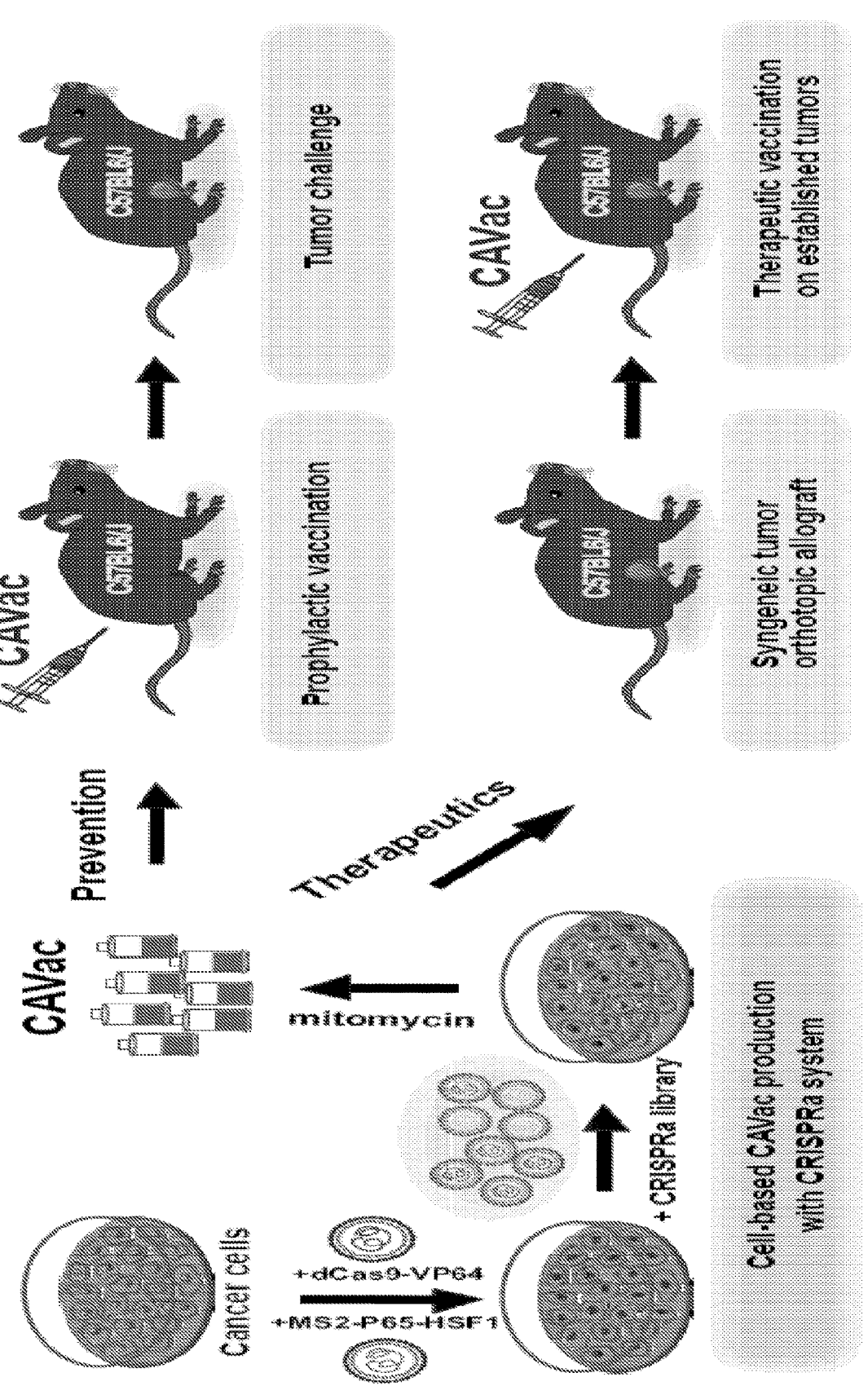
FIGS. 1A-K illustrate CRISPRa based endogenous gene activation as prophylactic and therapeutic vaccines.
Figure 5A:
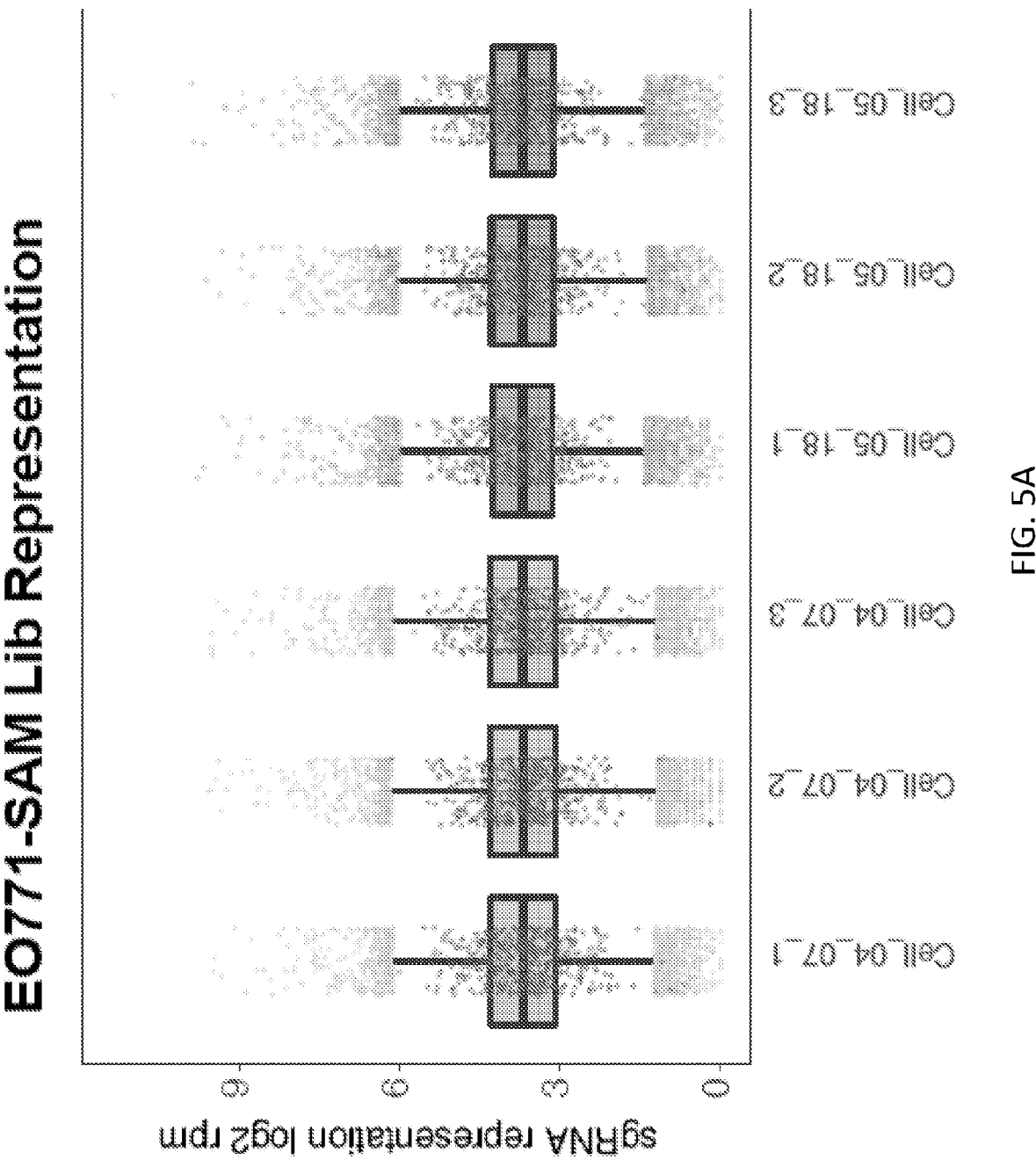
FIGS. 5A-5D illustrate library representation of mouse CRISPRa library transduced E0771 cells.
Figure 5B:
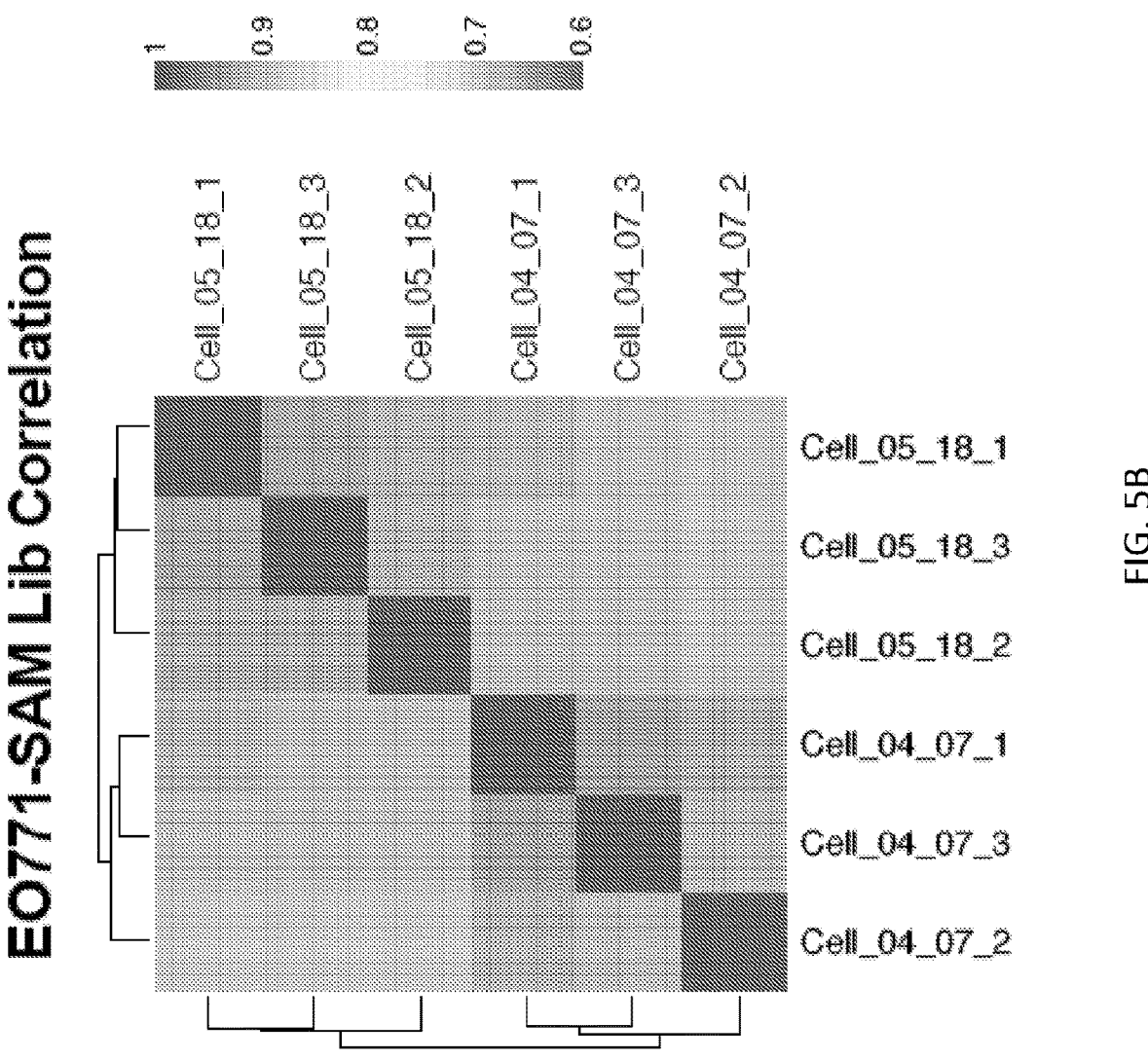

Example 1: Endogenous Gene Activation Induces Protective Anti-Tumor Responses Mutation profiles can vary dramatically between patients. Thus, to investigate a generalized multiplexed tumor vaccination concept, experiments first tested whether an unbiased activation of all endogenous coding genes can lead to an enhanced anti-tumor response in vivo. A syngeneic mouse model of triple-negative breast cancer (TNBC) was used wherein E0771 cells were transplanted in the mammary fatpad of fully immunocompetent hosts. E0771 cells were transduced with lentiviral vectors expressing dCas9-VP64 and MS2-p65-HSF1 (E0771-dCas9-MPH) (FIG. 1A). After confirming robust endogenous gene activation with the CRISPRa system (FIG. 5B), a mouse genome-scale lentiviral SAM CRISPRa sgRNA library (mSAM, or SAM for short) (Konermann et al. (2015) Nature 517, 583-588) was transduced into E0771-dCas9-MPH cells, generating a highly diverse population of cells encompassing the entire library (E0771-SAM). This was confirmed by Illumina sequencing readout of library representation for all 6 independent replicates used in the in vivo experiments (FIGS. 5A-5B). The E0771-SAM cell pool was transplanted into C57BL/6J mice to test their ability to form syngeneic tumors. In sharp contrast to vector transduced E0771 cells (0/8 rejection, i.e. 8/8 engrafted, all with large tumors), the E0771-SAM cell pool was rejected in most (42/50, 84%) of the mice, and the remaining 8/50 (16%) grew small tumors (p<2.2e-16, FIGS. 6A-6B). Of note, the E0771-SAM outgrown tumors were sensitive to checkpoint blockade immunotherapy (CBI), with rapid complete regression under the treatment of monoclonal immune checkpoint blockade (ICB) antibodies against programmed death-1 (PD-1) or cytotoxic T-lymphocyte associated antigen-4 (CTLA-4) (p<1e-5, FIGS. 7A-7D). To test the roles of innate and adaptive immune responses in tumor rejection responses, E0771-SAM cells were transplanted into the mammary fatpad of immune-deficient Nu/Nu and Rag1$^{-/-}$ mice. In sharp contrast to immunocompetent C57BL/6J hosts (2/5 with small modules, 3/5 tumor-free), all Nu/Nu (4/4) and Rag1$^{-/-}$ (5/5) mice grew large breast tumors from E0771-SAM (p<1e-5, FIGS. 6C-6F). Notably, E0771-SAM formed significantly larger tumors in Rag1$^{-/-}$ mice compared to that in Nu/Nu mice (p<0.0001, FIG. 6C). Furthermore, when both CD4$^+$ and CD8$^+$ T cells were pharmacologically depleted in C57BL/6J mice by treatment with both anti-CD4+anti-CD8 monoclonal antibodies, all mice receiving E0771-SAM transplantation formed large tumors (4/4), again in sharp contrast to non-treated (0/11) (p<1e-9, FIGS. 6G-6H). Together, these results indicated that activation of endogenous genes using the CRISPRa system in a genome-scale manner induced potent protective anti-tumor immune responses in vivo, leading to robust tumor rejection of syngeneic cancer cells by immunocompetent hosts.

Figures 1B, 1C:
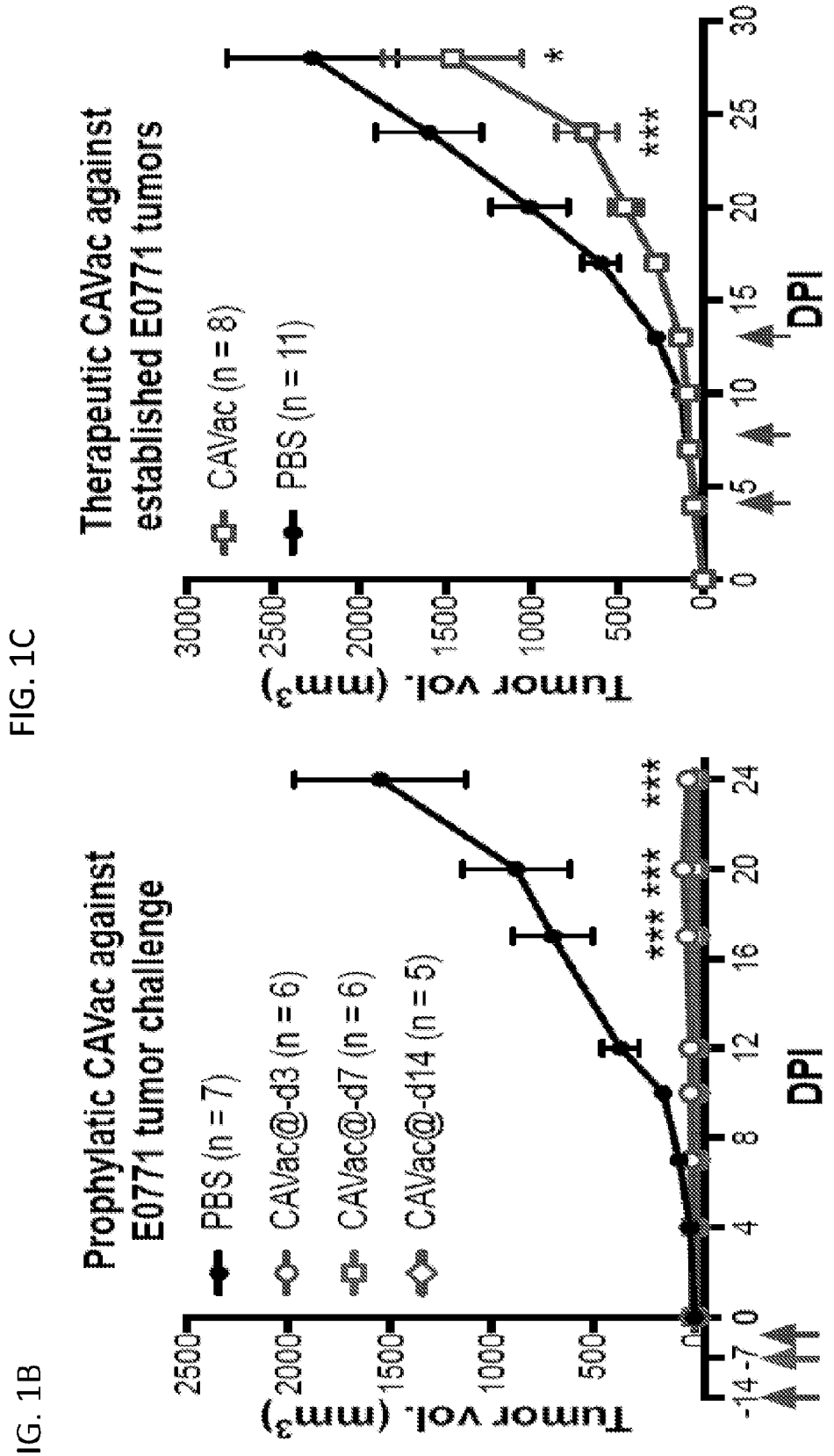

Example 2: Massively Parallel Gene Activation as Prophylactic and Therapeutic Cancer Vaccines The observations that E0771-SAM library cells were consistently rejected by the hosts led to the postulation that multiplexed activation of endogenous genes can stimulate broad anti-tumor immune responses to protect the host from the same type of tumor, thereby serving as prophylactic or therapeutic vaccines (FIG. 1A). To test the application of CRISPRa mediated endogenous gene Activation as a vaccine (CAVac), E0771-CAVac was generated by transducing genome-scale CRISPRa sgRNA libraries into E0771-dCas9-MPH cells followed by mitomycin treatment to induce senescence, and then tested as a cell-based vaccine (E0771-CAVac, or CAVac for short). To test the concept of a prophylactic vaccine, E0771-CAVac was inoculated into C57BL/6J mice prior to tumor induction (FIG. 1A). In sharp contrast to unvaccinated mice (0% tumor free), vaccination with E0771-CAVac granted the host complete protection (100% tumor free) against a subsequent tumor challenge with the unmodified parental cancer cell line (E0771), across two vaccination regiments (7 or 14 days prior to tumor challenge) (p<2.2e-16, 2.2e-16, respectively). Vaccination 3 days prior to tumor challenge also granted the host a close-to-complete protection (1/6 mouse with a small module, 5/6 tumor-free) (p<1e-10) (FIG. 1B). The results demonstrated that genome-scale activation of endogenous genes using CRISPRa is an effective approach to generate prophylactic vaccination against tumors with otherwise identical genetic backgrounds.

Figures 1D, 1E:
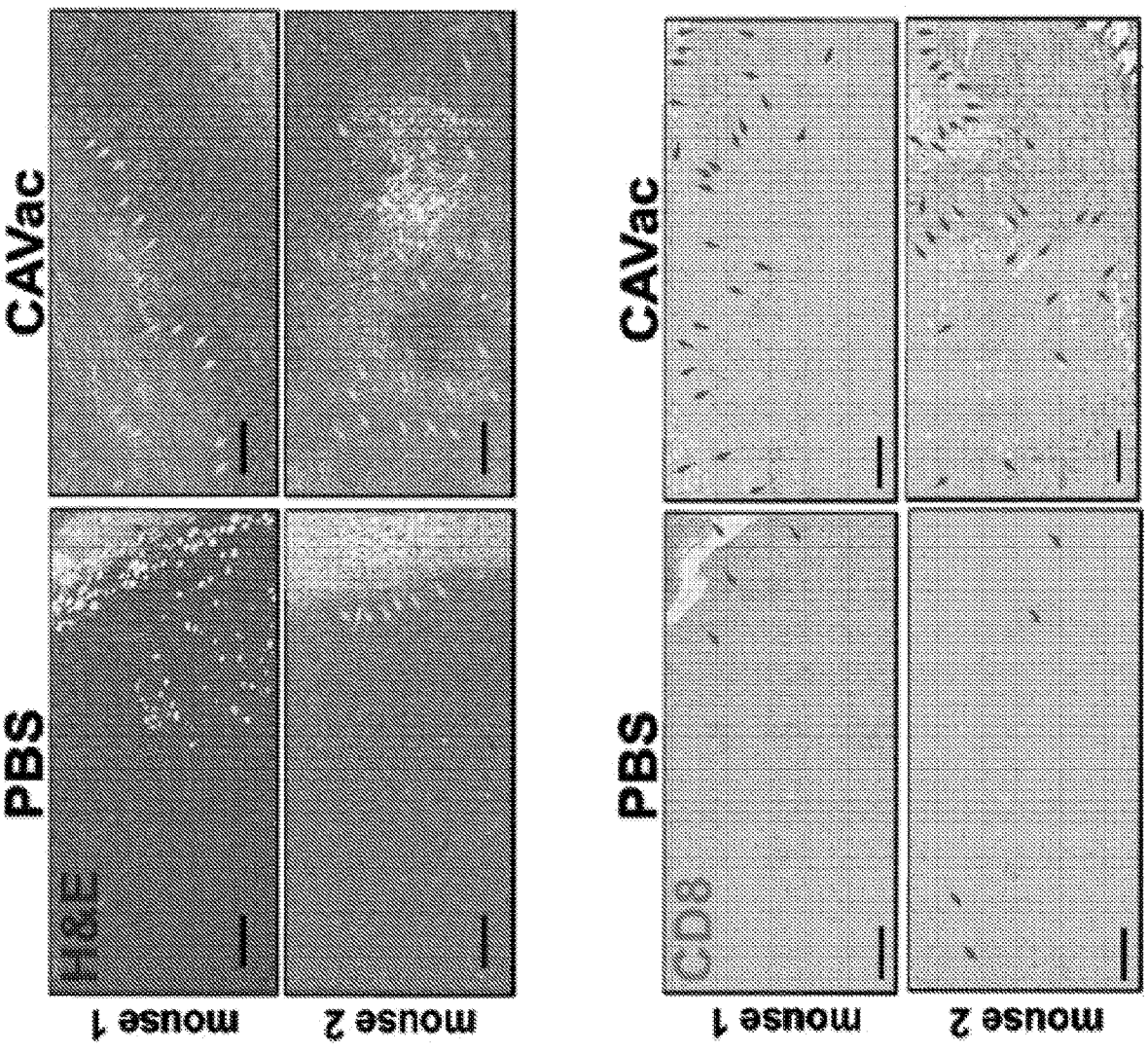
Figure 1F:
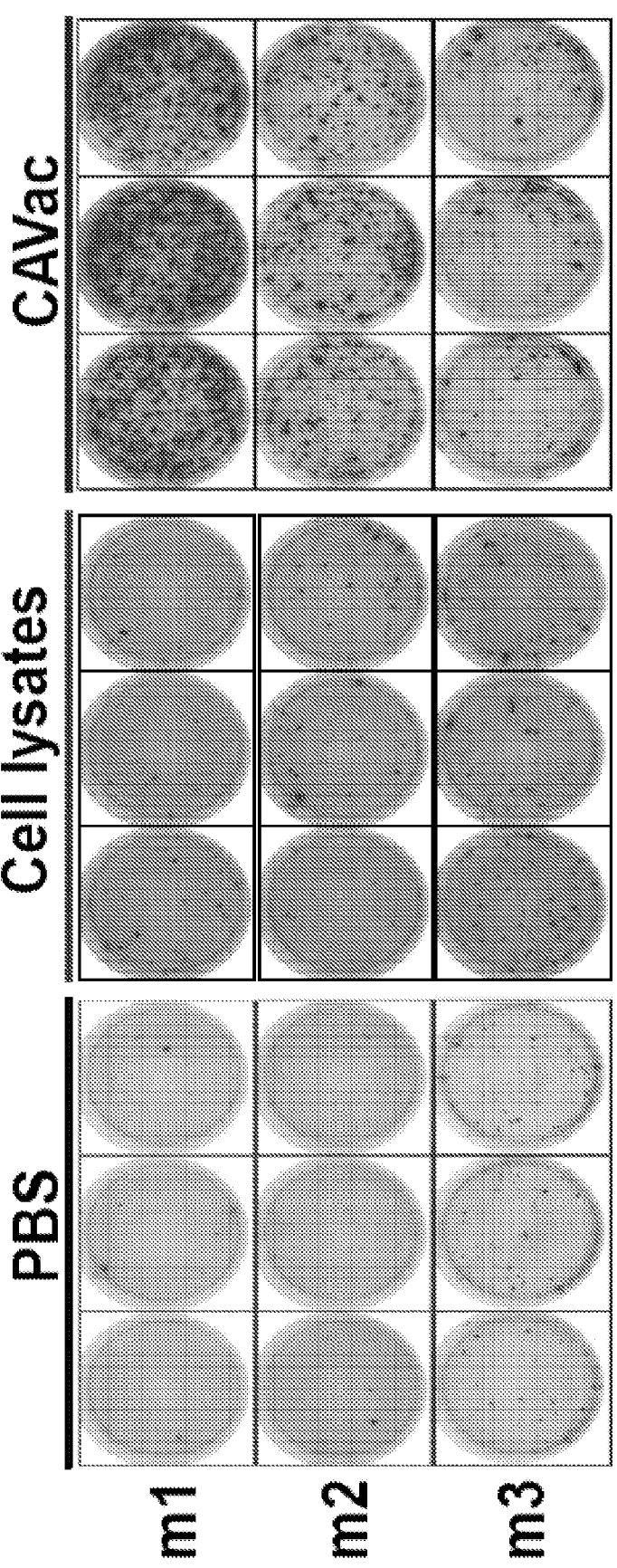

To test CAVac as a therapeutic intervention, orthotopic syngeneic E0771 tumors were induced before treating the mice with CAVac (FIG. 1A). Following a three-dose treatment scheme, CAVac treated mice tumors were significantly smaller than those of PBS treated (p<0.05, FIG. 1C, FIG. 8A-8B). The efficacy was not observed using the parental cell line without gene activation (p=0.77, FIG. 9A). Moreover, the therapeutic effect was abolished if CAVac was heat-inactivated (p=0.775, FIG. 9B). Of note, even a single dose CAVac treatment achieved comparable efficacy as the three dose treatment (p<0.05, FIG. 9C). At the experimental endpoint, the histopathology of the tumors were analyzed and large inflamed areas with CD8[+] lymphocytes and cancer cell death was observed in CAVac treated tumors, as compared to the rapidly proliferating PBS treated tumors with little inflammation and few CD8[+] cells (FIG. 1D-1E). To examine whether the anti-tumor effect was mediated by cancer-specific T cell response (at least in part), enzyme-linked immunospot (ELISPOT) assays were performed. CAVac significantly augmented the tumor-specific interferon γ (Ifnγ) production of vaccinated mice (p<0.05, FIG. 1F-1G). Furthermore, depletion of CD8[+] T lymphocytes alone (but not CD4[+] T lymphocytes) with anti-CD8 antibody abolished the therapeutic efficacy of CAVac (FIG. 9D), indicating that CD8[+] T cells are essential for anti-tumor response elicited by CAVac.

Figures 1G, 1H:
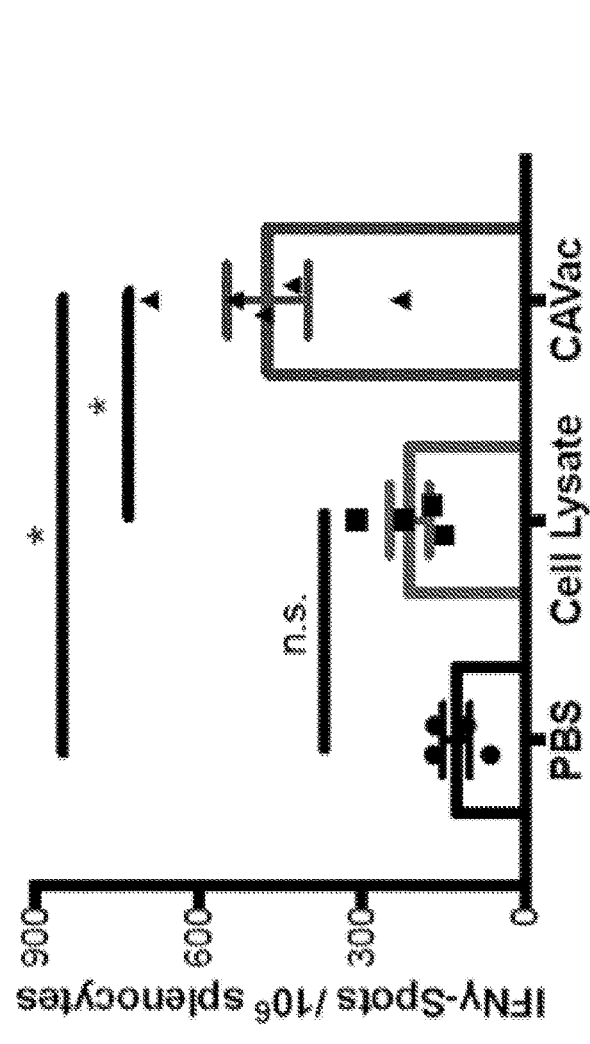
Figures 8A, 8B, 8C, 8D:
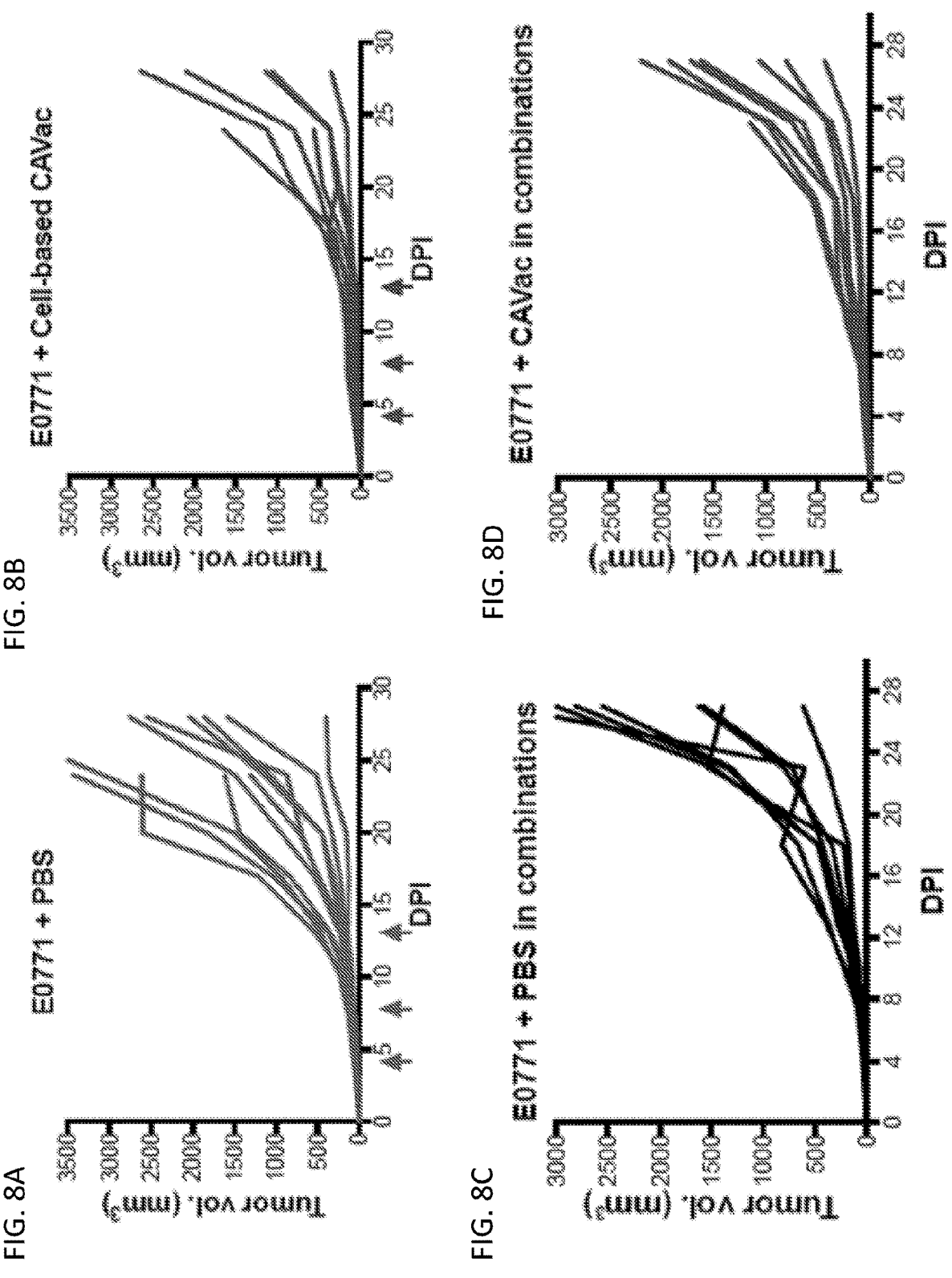
FIGS. 8A-8G illustrate additional spider plots of growth curves of cell-based CAVac and combinatorial treatments.
Figures 8E, 8F, 8G:
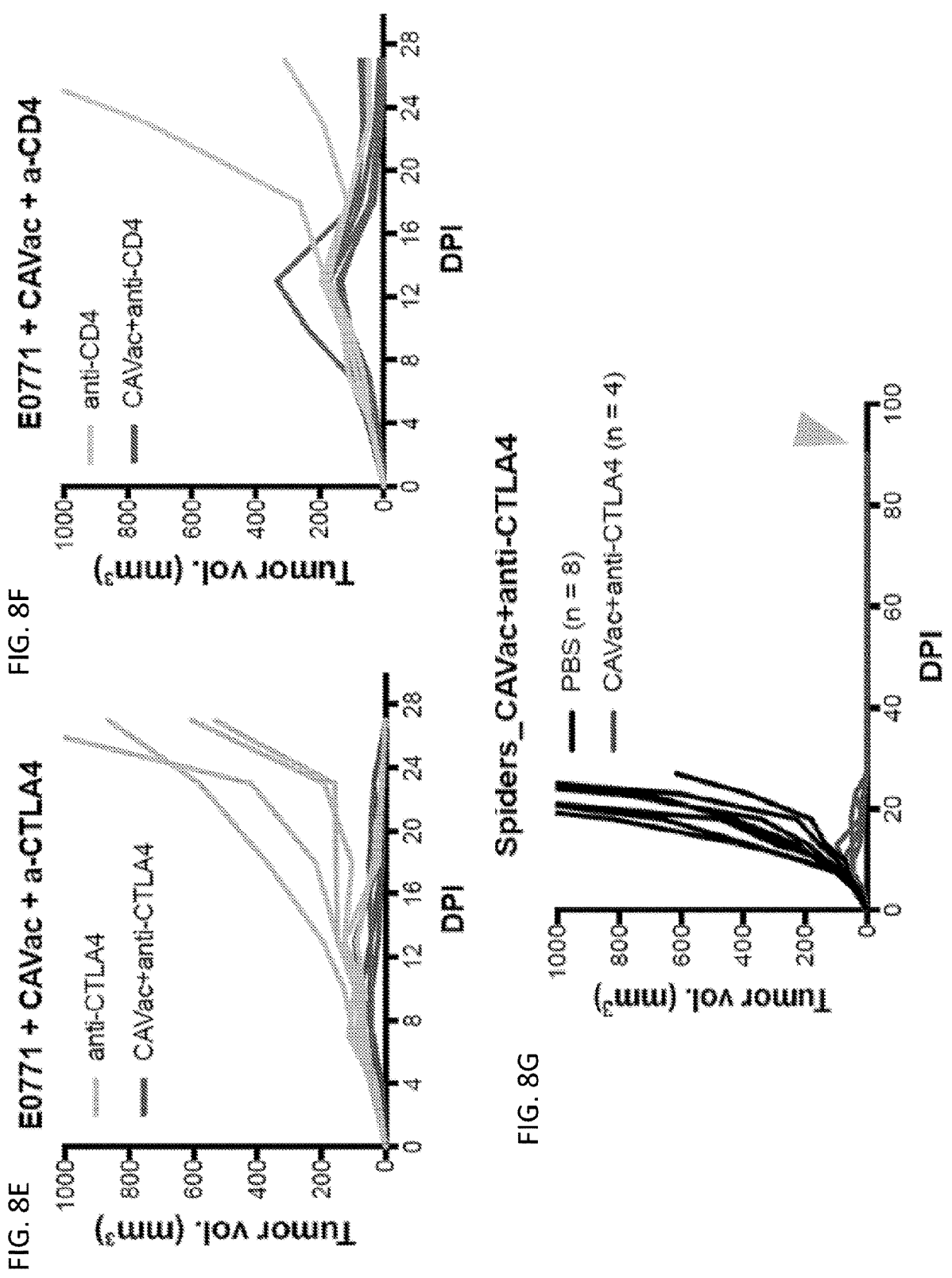
Figures 9A, 9B, 9C, 9D:
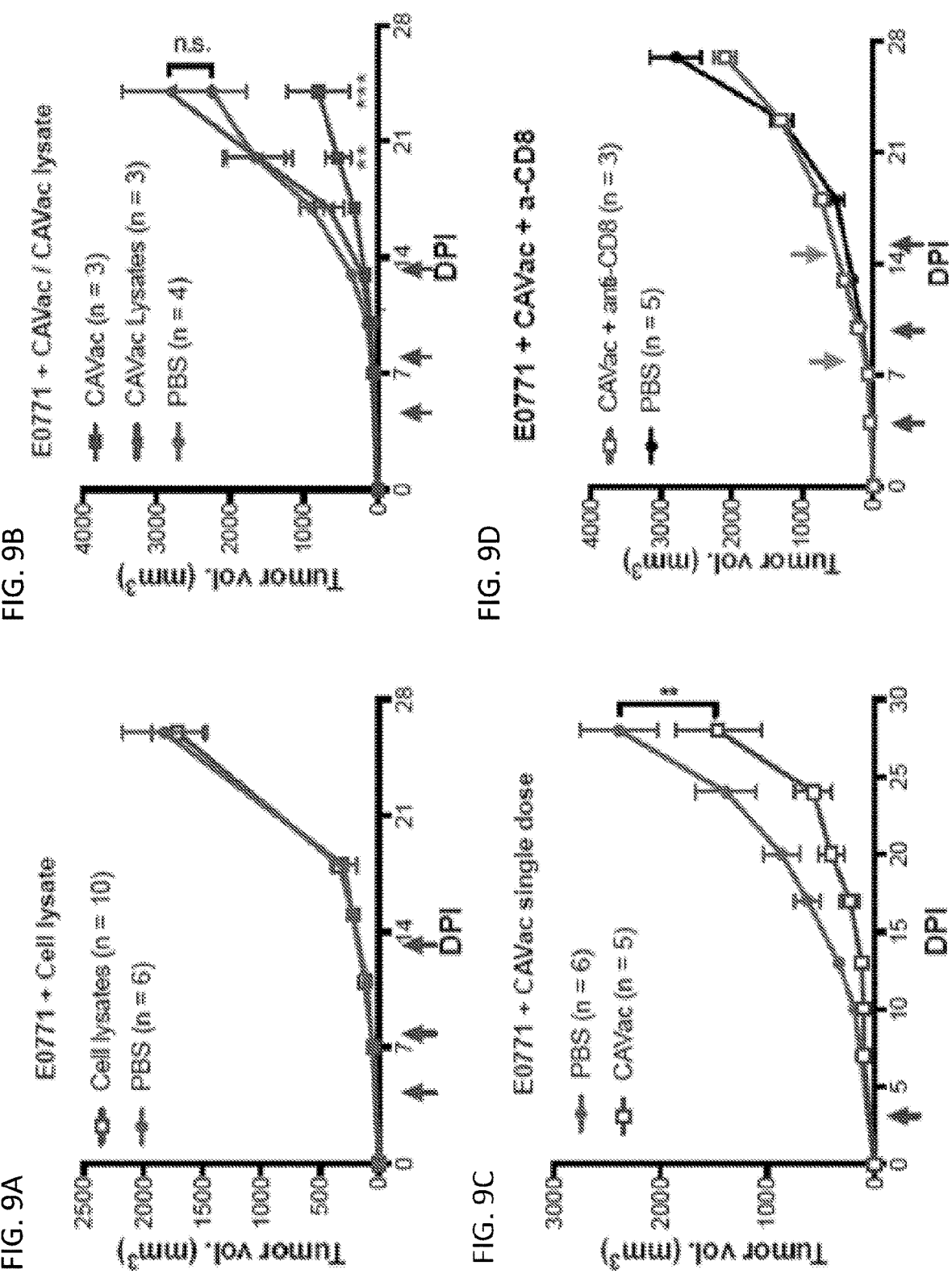
FIGS. 9A-9D illustrate results from additional testing of cell-based CAVac.

To test whether CAVac can be used in conjunction with other immunotherapy or immune modulation, CAVac treatment was tested in combination anti-CTLA4 (FIG. 1H). The combination of CAVac+anti-CTLA4 boosted the efficacy of both CAVac alone (p<1e-7) and anti-CTLA4 alone (p<1e-4) in the same E0771 TNBC syngeneic model, leading to complete regression of established tumors (FIGS. 1I-1J; FIGS. 8C-8E), without any relapse observed until day 90 as the experiment ended (FIG. 8G), suggesting long-term protective memory in these mice. The immunosuppressive microenvironment is known to be a major contributing factor for dampened anti-tumor immune responses and checkpoint blockade immunotherapies, where CD4[+] regulatory T lymphocytes often negatively regulate the cytotoxic effect of CD8[+] T cells in breast cancer. For this reason, it was tested whether depletion of CD4[+] T cells could influence the efficacy of CAVac. CD4[4] depletion using monoclonal anti-CD4 antibody significantly boosted the efficacy of CAVac (p<1e-4, FIGS. 1I-1K; FIGS. 8C-8D & 8F), where the combination of CAVac+anti-CD4 led to nearly complete regression of established tumors (FIG. 1K; FIG. 8F).

Figure 2A:
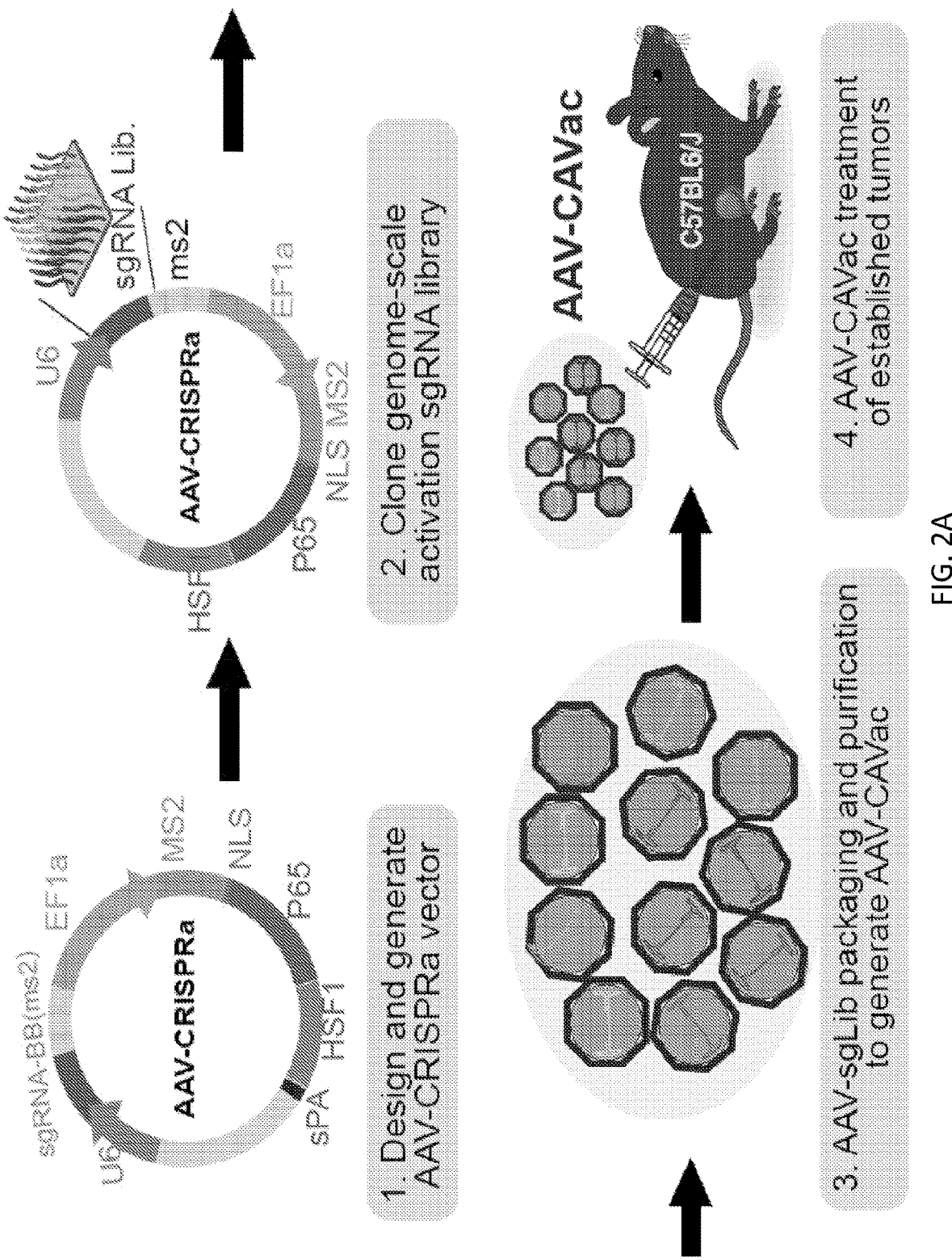
FIGS. 2A-2G illustrate AAV-carried CRISPR activation system (AAV-CAVac) as a therapeutic treatment agent against established tumors.
Figures 2B, 2C:
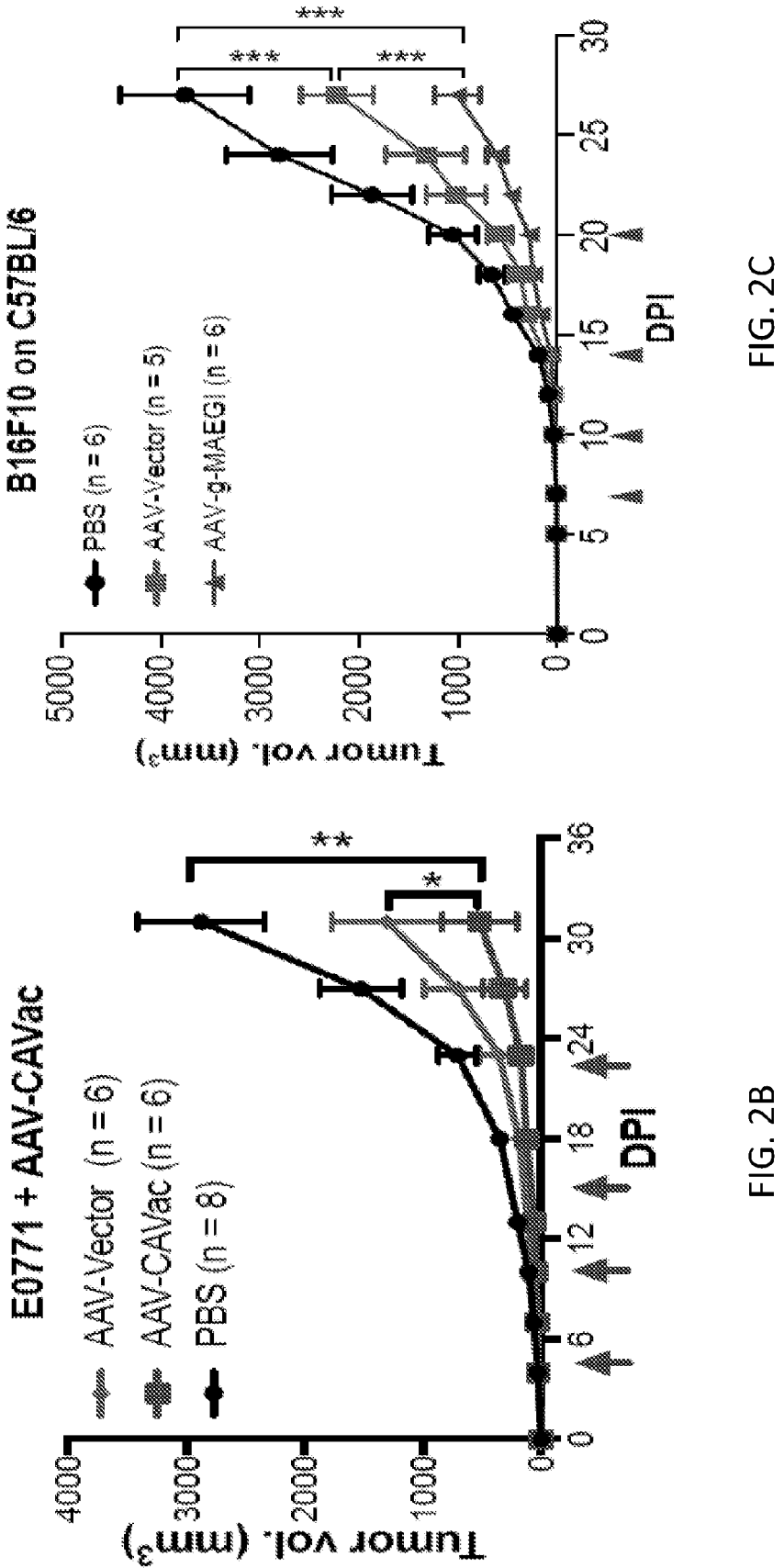
Figure 2D:
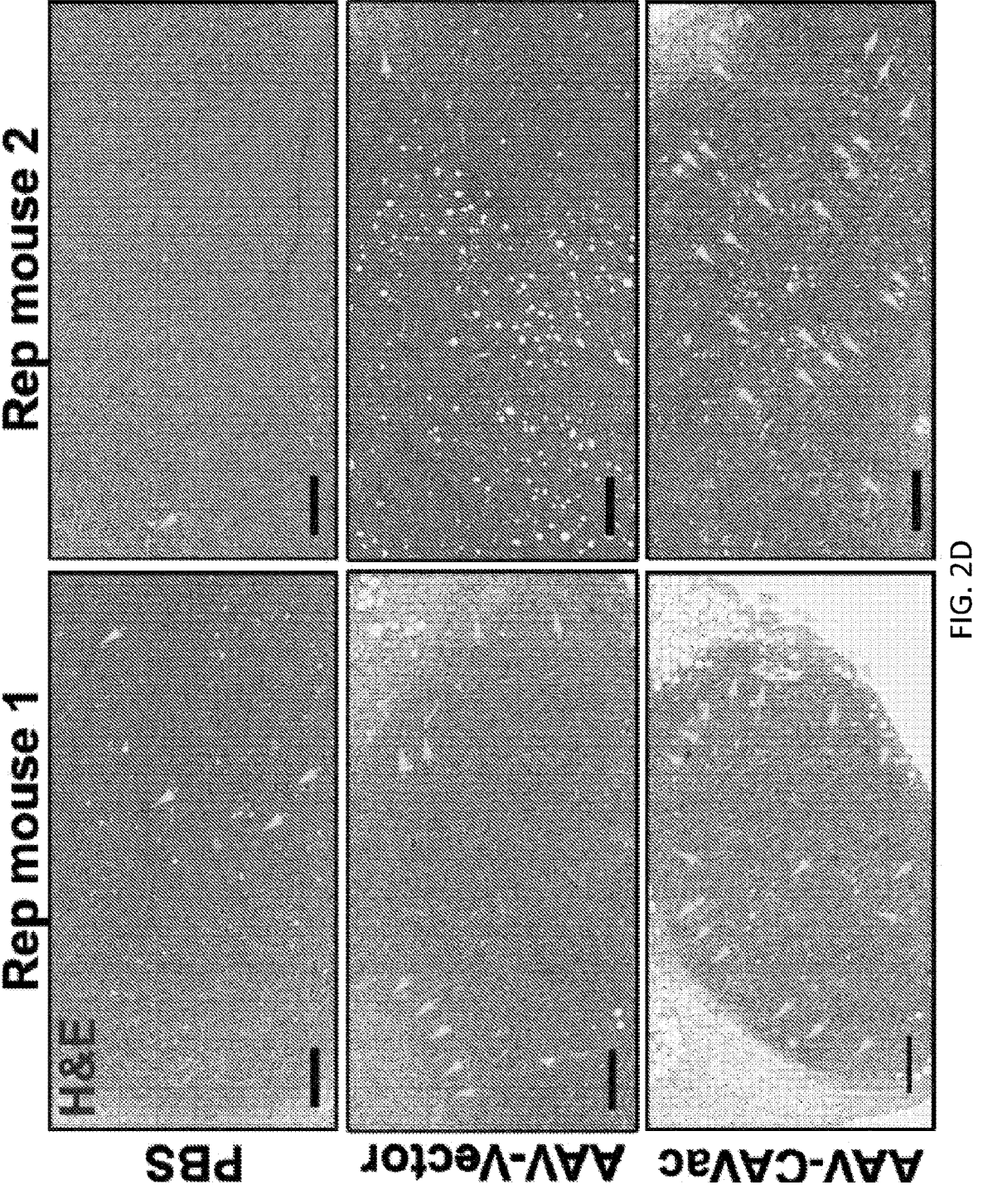
Figure 2E:
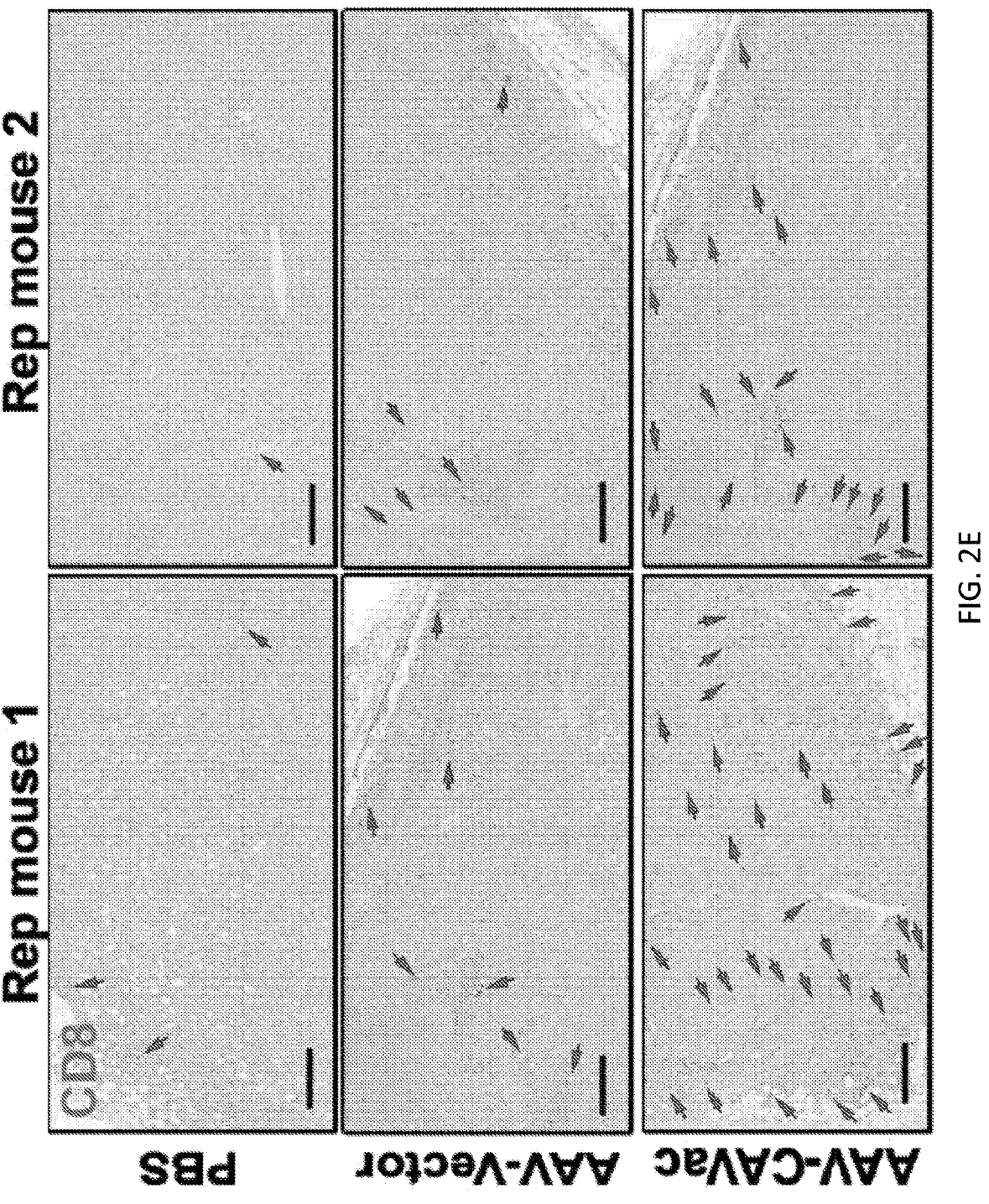
Figures 10B, 10C, 10D:
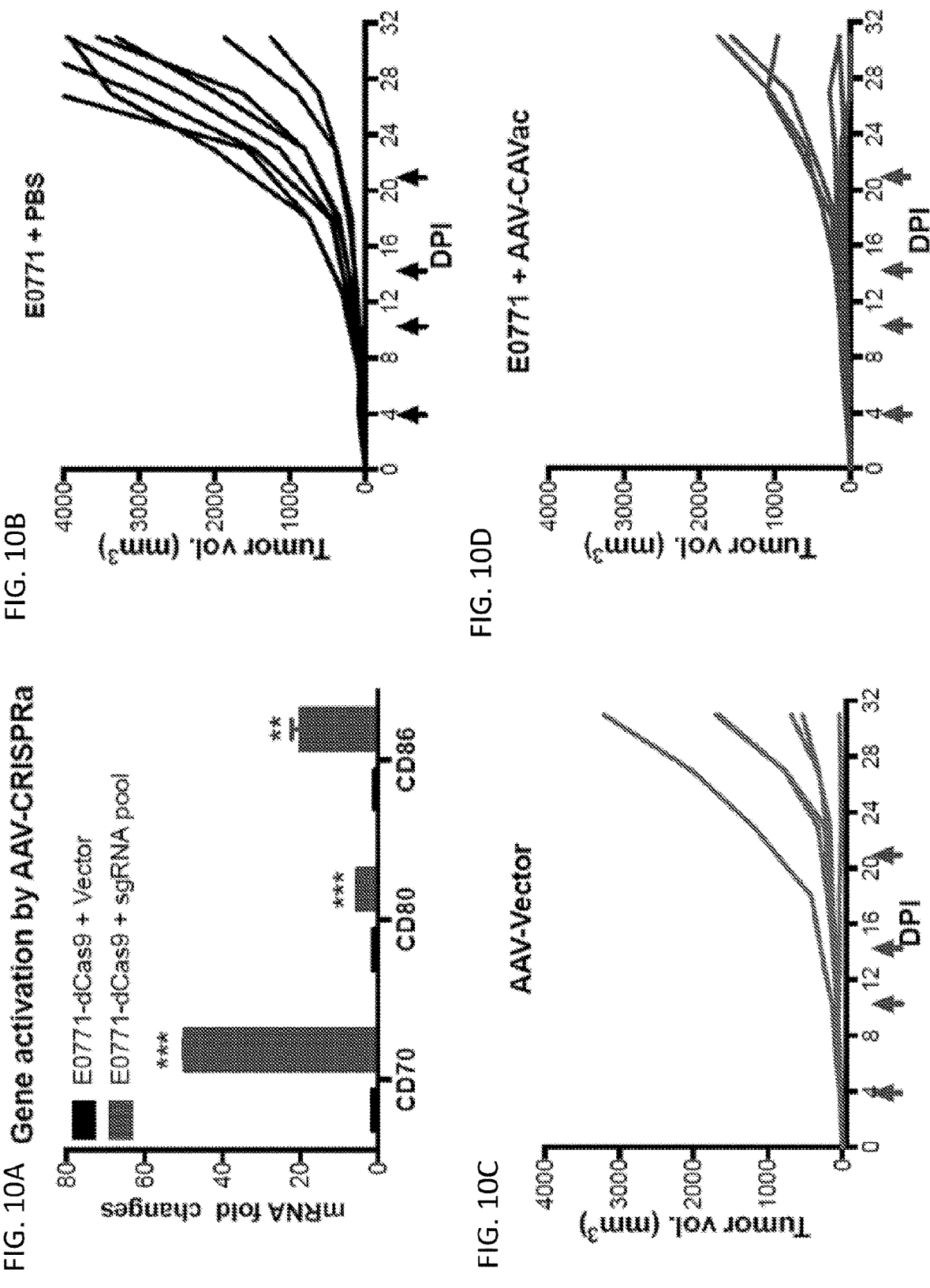

Example 3: Multiplexed In Situ Vaccination Using AAV-CAVac Against Established Tumors Because a live cell-based vaccine has clear limitations for clinical translation, a safer delivery vehicle to carry CAVac for direct in vivo tumor vaccination was investigated. Adeno-associated viruses (AAVs) are potent non-propagating viral vectors shown to mediate efficient transgene delivery into various organs in mouse models and humans. Because of these properties, AAVs have been commonly used in clinical trials for gene therapy, and recently received FDA approvals. To enable direct delivery of CAVac, an AAV version of CAVac (AAV-CAVac) was devised by generating an AAV-CRISPRa vector and cloning SAM modules as well as the genome-scale sgRNA library, then pool-packaging into AAV9 (FIG. 2A). The effectiveness of pool-packaged AAV-CRISPRa in activating endogenous genes was confirmed by infecting tumor cells with AAVs carrying a small pool of sgRNAs targeting genes including Cd70, Cd80, and CD86 (FIG. 10A). C57BL/6J mice bearing syngeneic orthotopic E0771 tumors were treated with this form of vaccine by intratumoral administration (FIG. 2A). A strong effect of AAV-CAVac alone against these tumors was observed, with a fraction of mice (3/9, 33%) exhibiting complete or near complete regression (FIG. 10D) compared to PBS (p=0.00014, FIG. 2B and FIGS. 10B-10D) and AAV-Vector (p=0.0078, FIG. 2B and FIGS. 10B-10D). Of note, AAV-vector treatment showed a moderate, yet statistically insignificant effect against tumor in the E0771 model, but significantly weaker than that of AAV-CAVac (p=0.26, FIG. 2B). To test the broader utility of AAV-CAV, similar treatment was performed on a syngeneic metastatic melanoma mouse model (B16F10), which again demonstrated significant efficacy (FIG. 2C, FIGS. 10C-10D). At the endpoint of the experiment, the histopathology of the tumors were analyzed. Large inflamed areas with CD8[+] lymphocytes and cancer cell death was observed in AAV-CAVac treated tumors, as compared to the rapid proliferation and rare CD8[+] lymphocyte infiltration in PBS or AAV-Vector treated tumors (FIGS. 2D-2E). Using ELISPOT, it was confirmed that AAV-CAVac elicited much stronger anti-tumor T cell response (in terms of IFNγ producing splenocytes) compared to PBS (p=0.0028, FIG. 2F-2G) and to AAV-Vector (p=0.005, FIGS. 2F-2G). No difference was observed in T cell IFNγ response between PBS and AAV-Vector (FIGS. 2F-2G), suggesting the moderate anti-tumor effect from AAV-Vector is unlikely to be mediated by T cells. Retrospective comparison showed that AAV-CAVac has a stronger efficacy as compared to cell-based CAVac (unpaired t test, two sided, p=0.016) in settings where PBS-treated tumors grew at similar dynamics (p=0.3). These data showed that In situ vaccination by AAV-mediated delivery of CAVac can augment specific host immune responses against established tumors.

Example 4: AAV-CAVac Remodels the Host Tumor Microenvironment

Figure 3A:
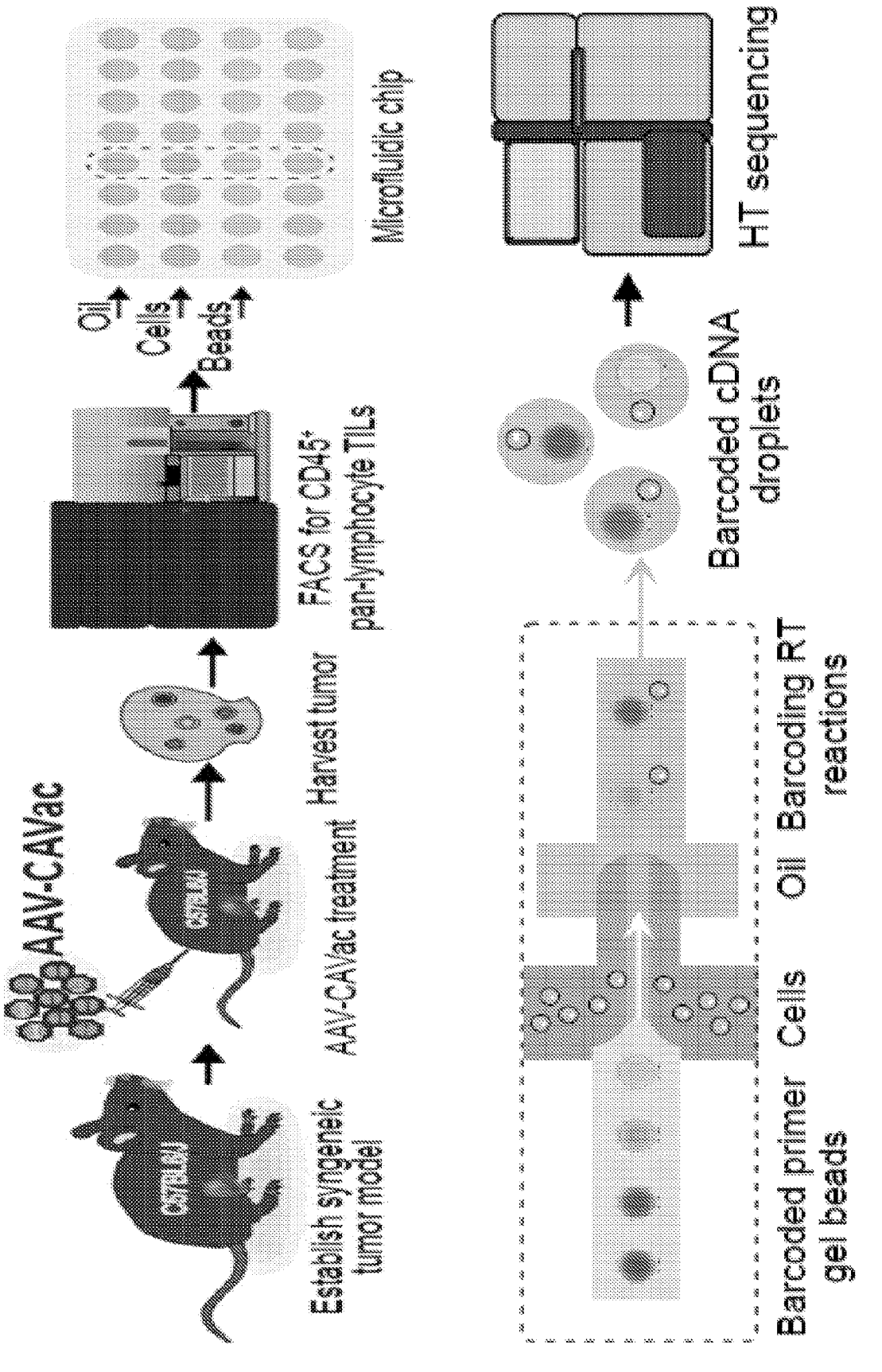
FIGS. 3A-3E illustrate results from interrogation of immune cell population, repertoire shift, and gene expression changes upon therapeutic CAVac treatment using single cell RNA-seq.
Figures 3B, 3C:
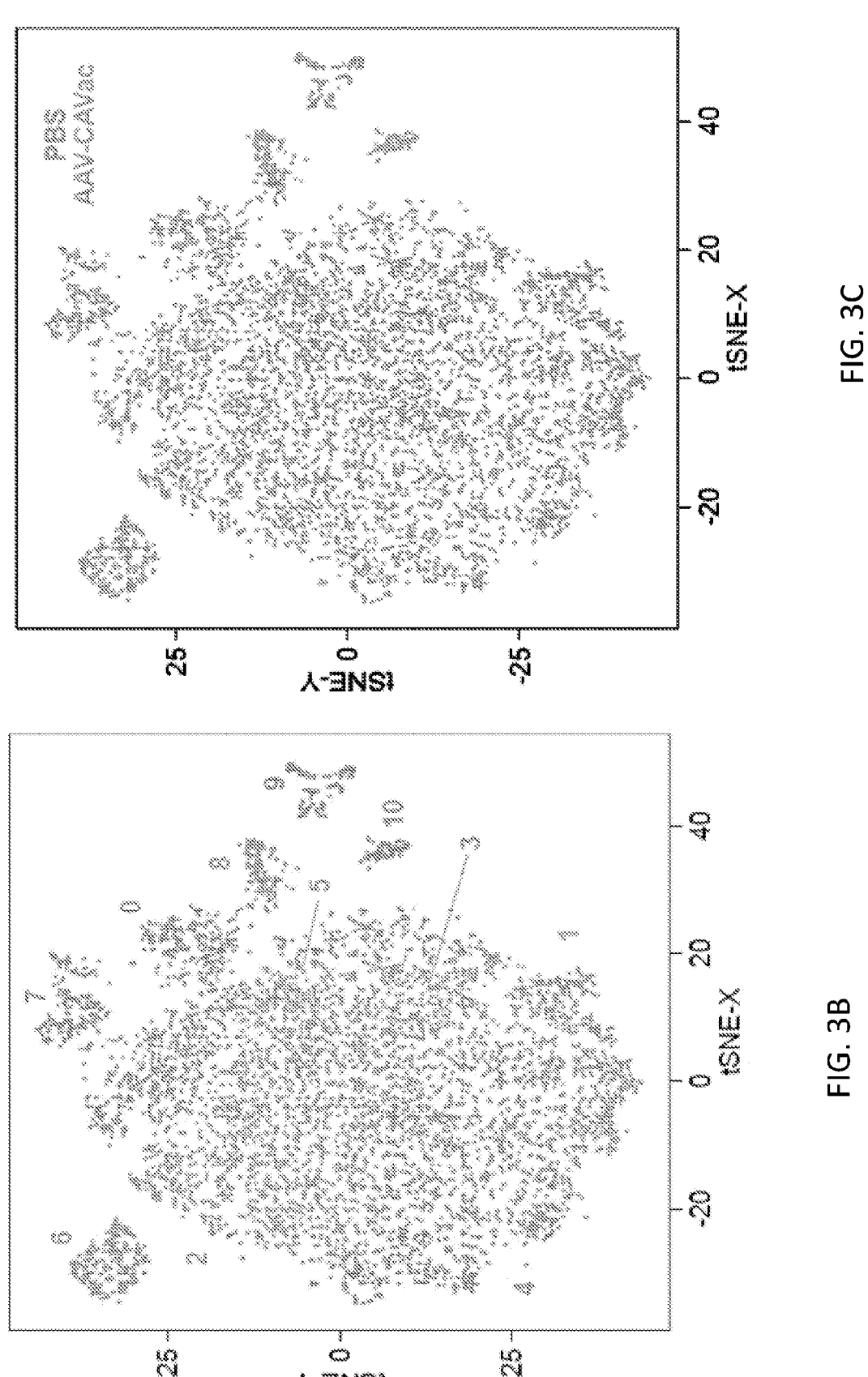
Figure 3D:
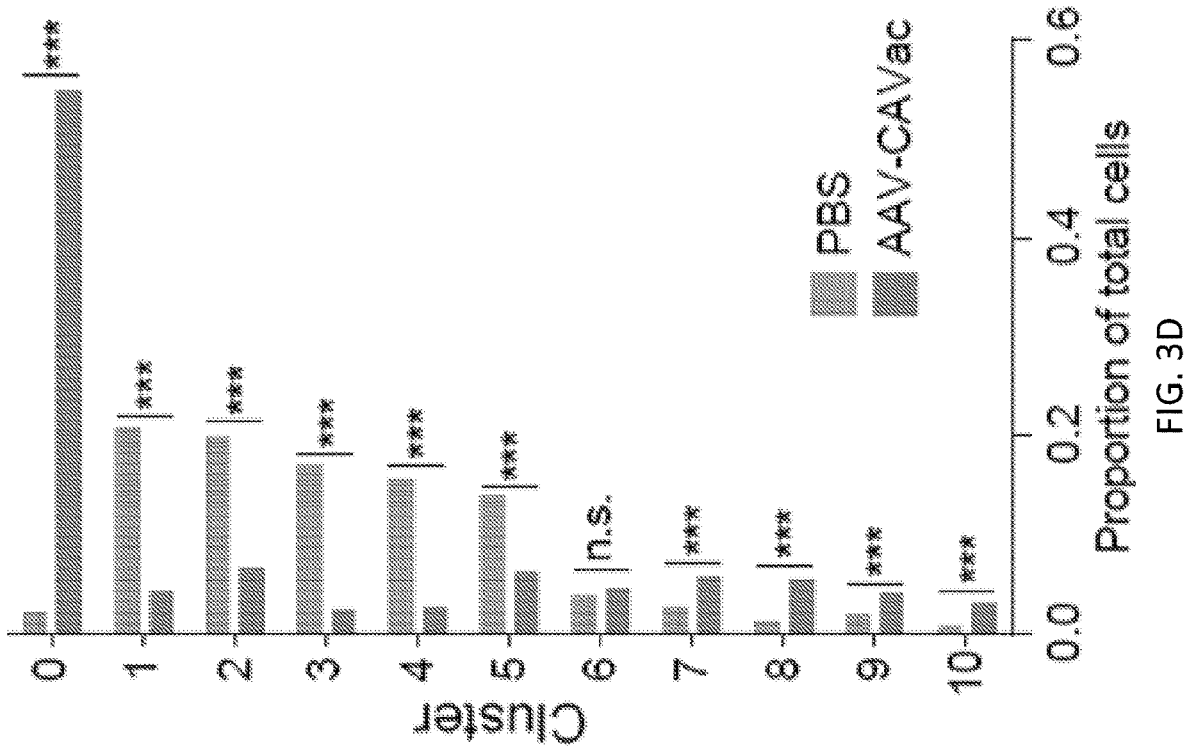
Figure 3E:
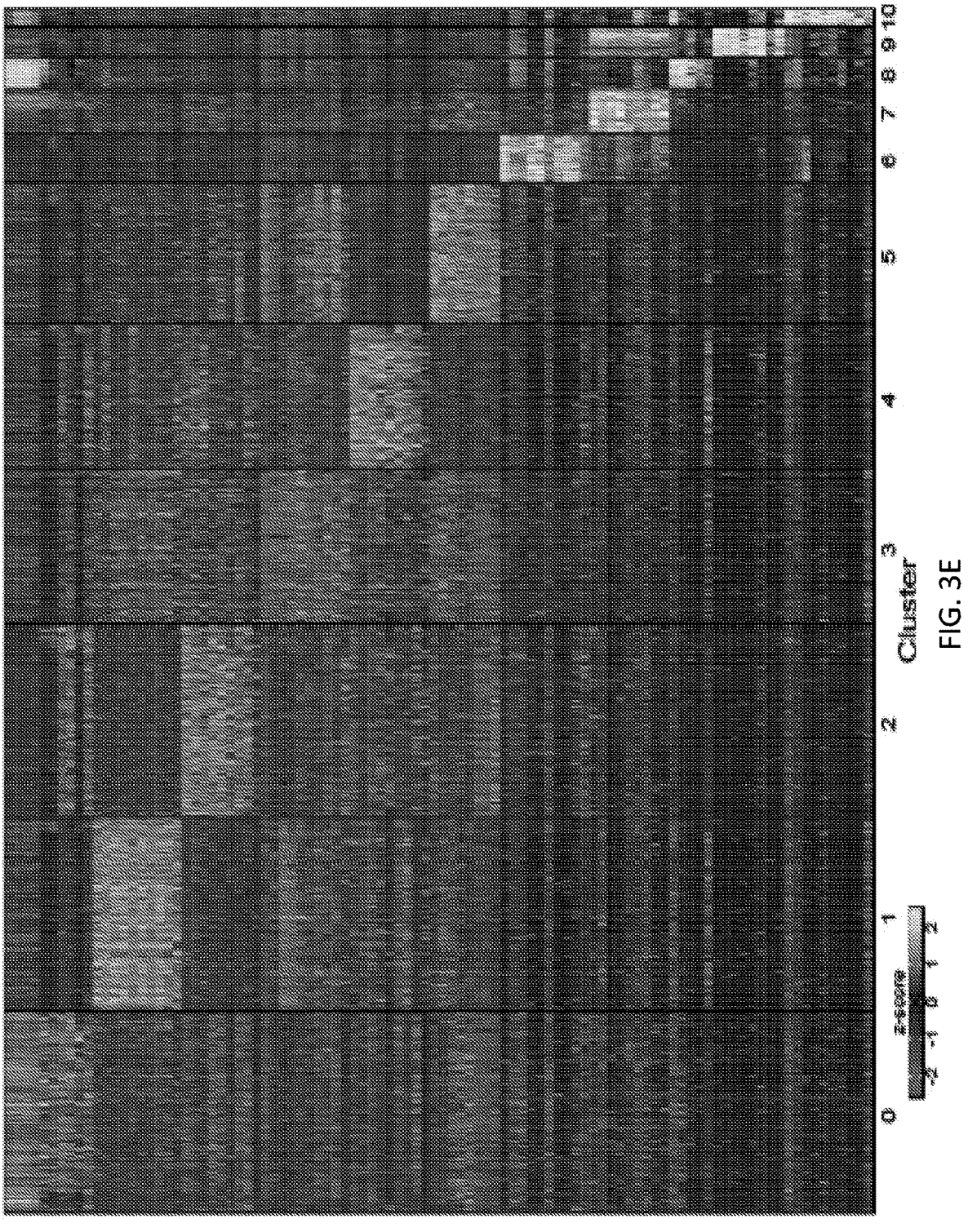

To investigate the effect of AAV-CAVac on the host tumor microenvironment, single cell RNA sequencing (scRNA-seq) was performed to simultaneously profile the whole population of tumor-infiltrating immune cells (THs) and their gene expression signatures (FIG. 3A). From single cell suspension of end-point tumors, total TIIs were isolated by fluorescence activated cell sorting (FACS) of CD45$^+$ immune cells, then a total of 2,075 CD45$^+$ cells from AAV-CAVac-treated mice, as well as 5,383 from PBS-treated mice were sequenced (FIGS. 3B-3C). Using clustering and dimensionality reduction, a total of 11 unique clusters of TIIs were identified from both AAV-CAVac and PBS group (FIGS. 3B-3C). Strikingly, most (10/11) of these clusters exhibit strong shifts in AAV-CAVac as compared to PBS (p<0.001, FIG. 3D). Cluster-specific expression analysis revealed the gene signatures specific to each cluster. Notably, the first cluster (cluster #0) was drastically increased in AAV-CAVac TH population as compared to PBS (54.75% vs. 2.23% of total cells, p<2.2*10$^{-16}$, FIG. 3D). This population possessed high levels of MHC class II transcripts (such as H2-Aa, H2-Ab1 and H2-Eb1), which is characteristic of antigen presenting cells (FIG. 3E). The second most abundant population (cluster #1) was reduced in AAV-CAVac TII population as compared to PBS (FIGS. 3D-3E). This population expressed genes associated innate immune cells such as the Ifit (Interferon induced proteins with tetratricopeptide repeats) gene family.

Figures 11A, 11B, 11C:
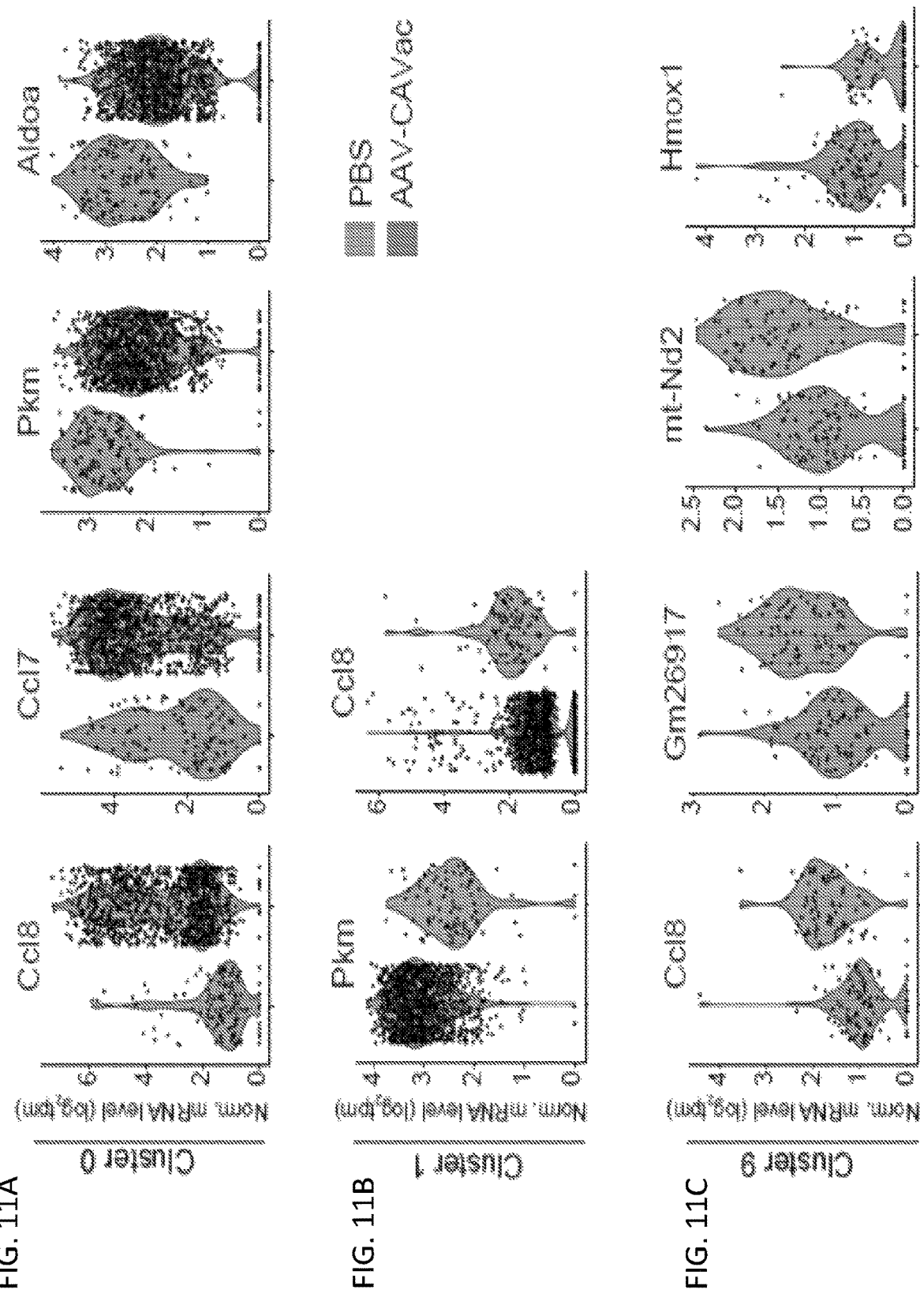
FIGS. 11A-11C are a series of Violin plots of representative cluster-specific differentially expressed genes in the scRNA-seq of TILs between AAV-CAVac and PBS treated mice.

Interestingly, cluster #9, bearing resemblance to T cells due to the highly differentiating expression of Cd3d, Cd3g and Gzmb (Granzyme B) transcripts (FIG. 3E), exhibited a significant proportional increase within the AAV-CAVac TII population (FIG. 3D). Differential expression analysis by cluster revealed significantly altered gene expression in each cell population. For example, Ccl7 and Ccl8 were significantly upregulated in cluster #0 of the AAV-CAVac TII population as compared to that of PBS, whereas Pkm and Aldoa were significantly downregulated (FIG. 11A). Tils in cluster #1 also showed upregulation of Ccl8 and downregulation of Pkm (FIG. 11B). The putative T cell cluster (#9) within the AAV-CAVac TII population showed elevated expression of genes such as Ccl8, mt-Nd2 (Mitochondrially Encoded NADH:Ubiquinone Oxidoreductase Core Subunit 2) and Gm26917 (an uncharacterized gene), and downregulated genes such as Hmox1 (Heme Oxygenase 1) (FIG. 11C).

Figure 12A:
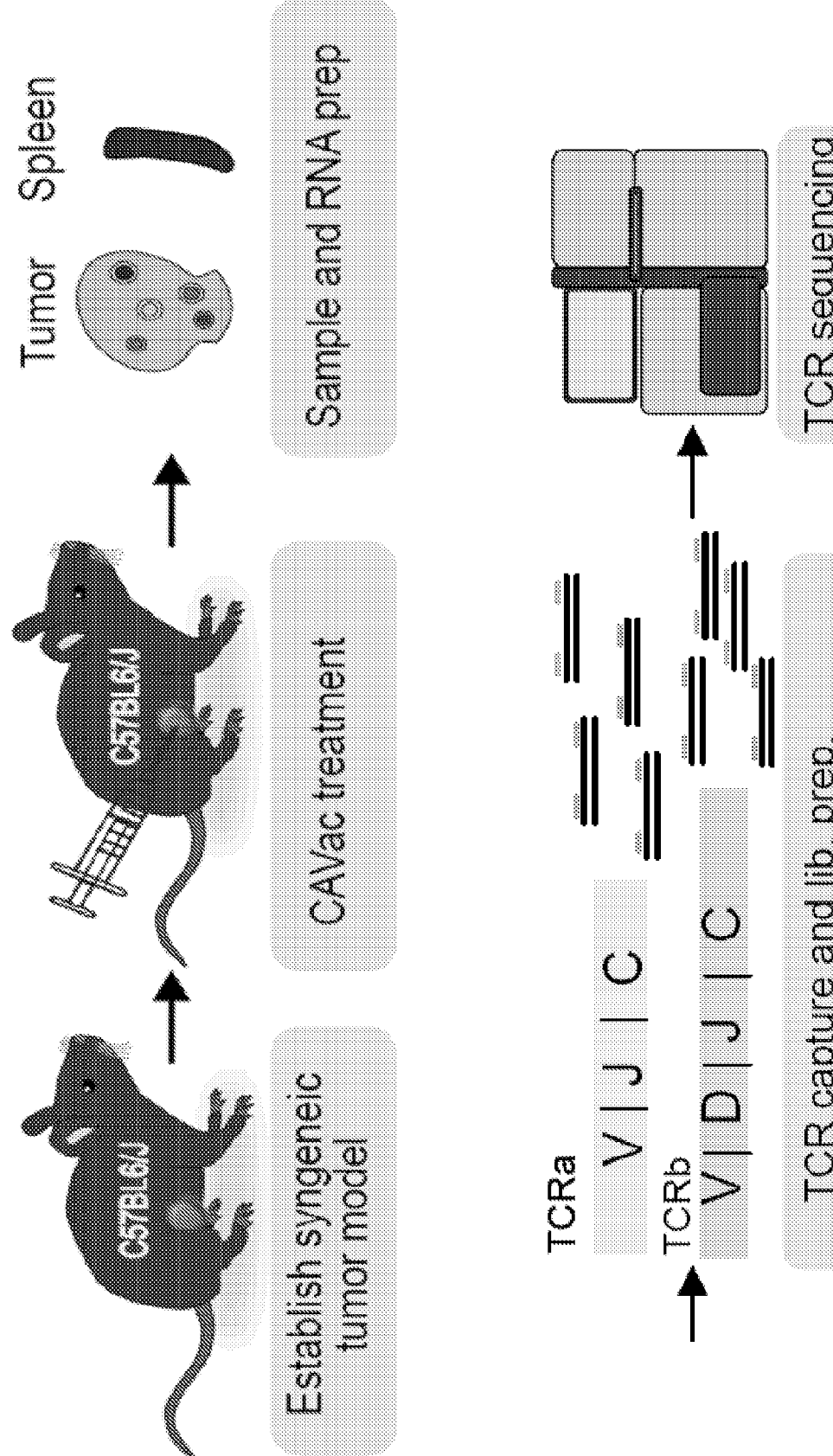
Figure 12B:
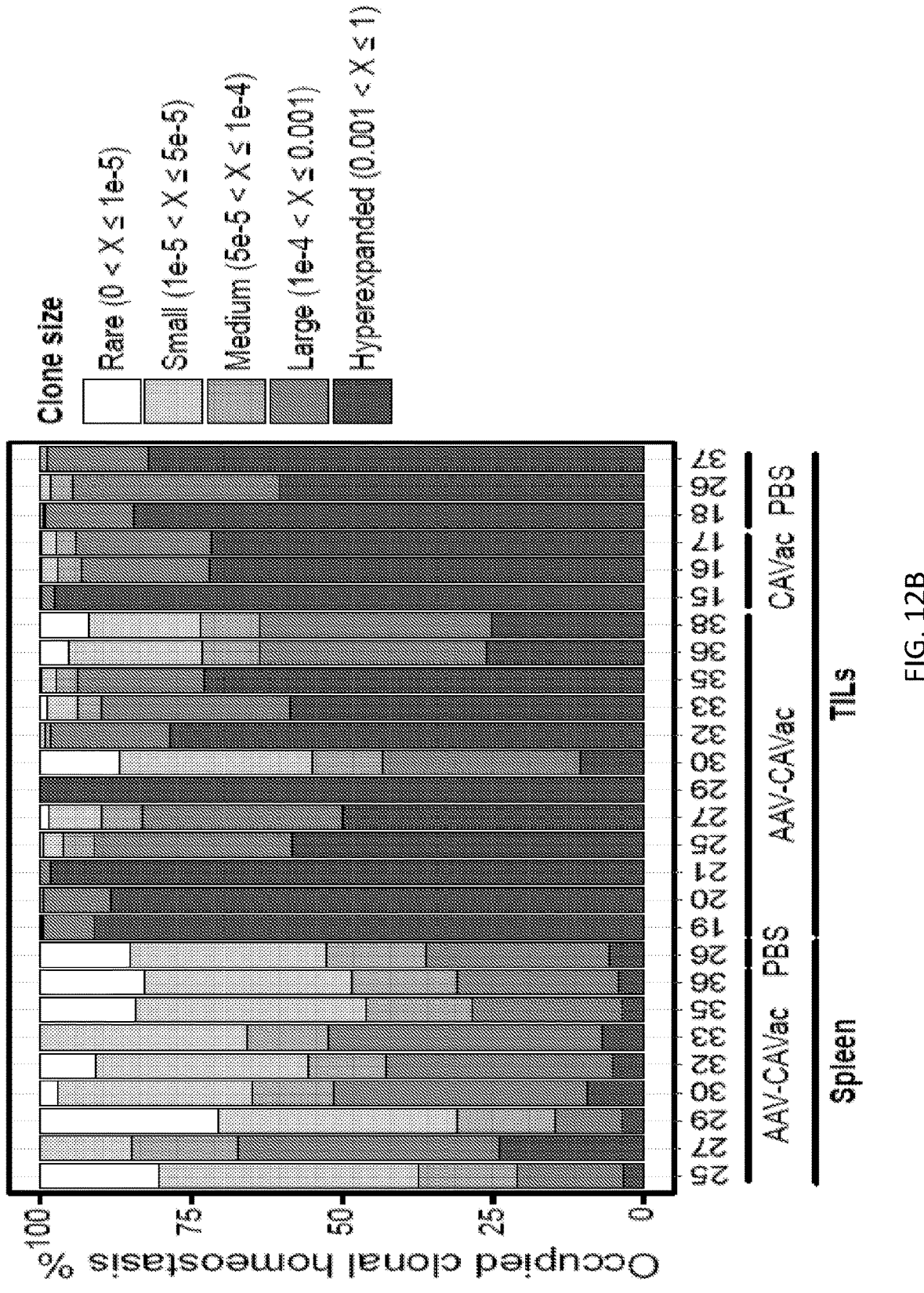
Figure 12C:
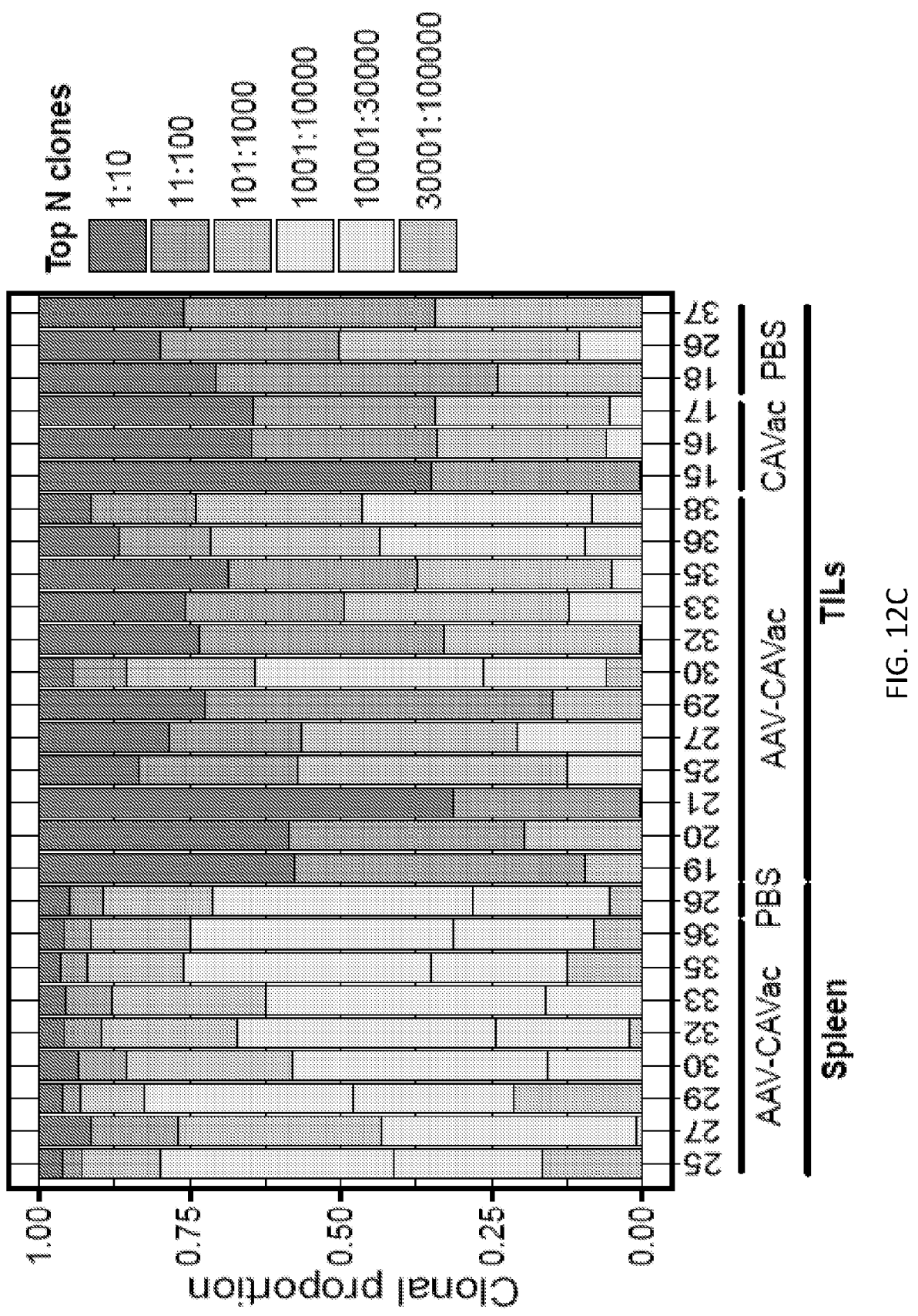
Figure 12D:
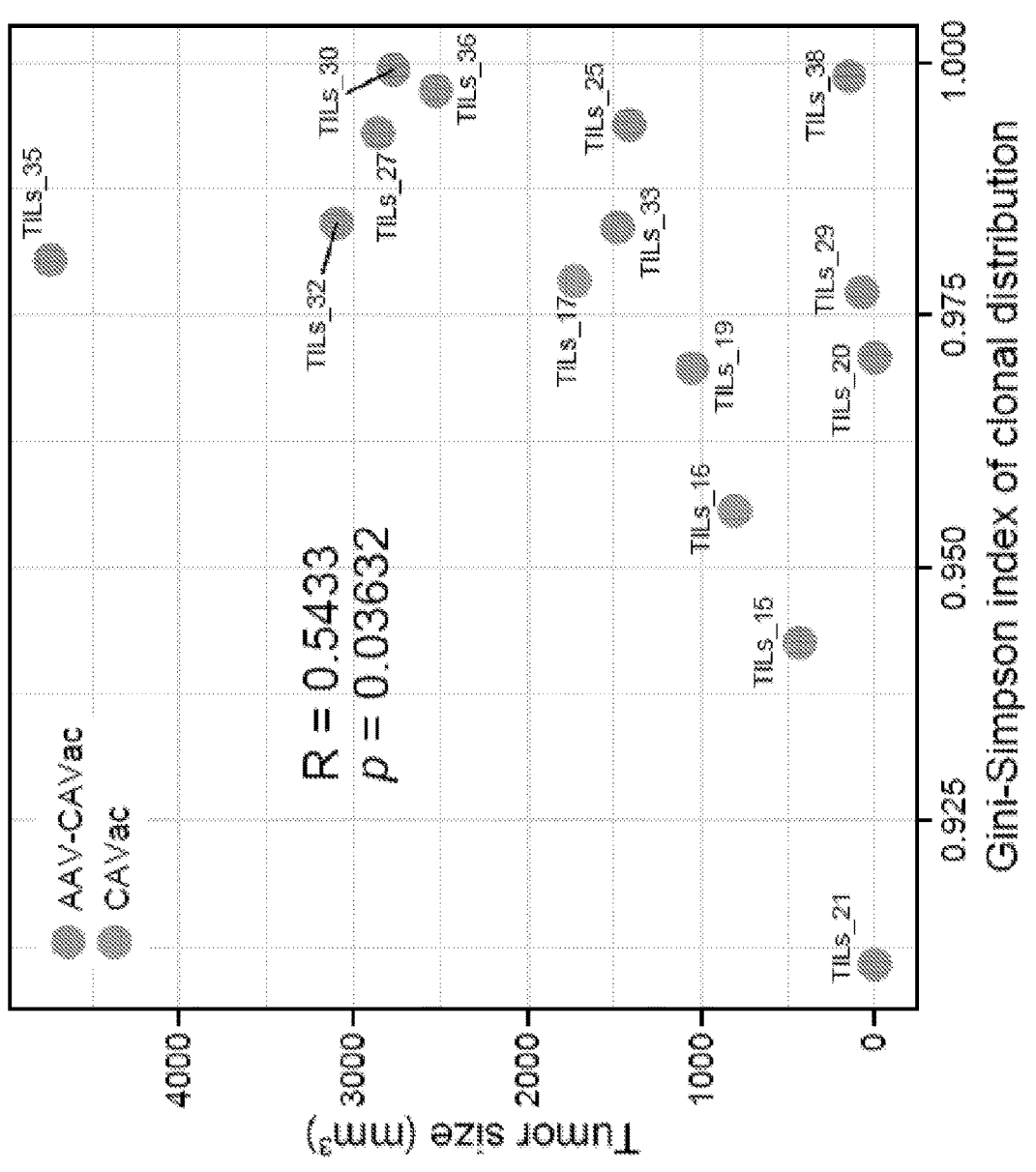

T cell receptor sequencing (TCR-seq) was performed to profile the TCR repertoire in CAVac vaccinated, AAV-CAVac vaccinated and unvaccinated mice (FIG. 12A). While the spleens preserved a highly diverse TCR repertoire, clonal expansion of a subset of clones in tumor infiltrating lymphocytes (TILs) was observed (FIGS. 12B-12C). Interestingly, across all vaccinated animals, the Gini-Simpson index of clonal distribution significantly decreased as the tumor size decreased, where a smaller Gini-Simpson index denotes greater skewness in clone size distribution (R=0.54, p=0.036, FIG. 12D). This finding implied that enhanced anti-tumor activity is associated with more potent selection in vivo. Examination of the complementarity-determination region 3 (CDR3) peptide sequences of the TILs revealed the most dominant clones in CAVac and AAV-CAVac vaccinated tumors, in which some clones can reach ultra-high frequencies of up to 20.7% (FIG. 12E). These observations together revealed that vaccination by AAV-CAVac significantly altered the host tumor microenvironment.

Example 5: Pool-Activation of Mutated Genes as Proof-of-Concept Multiplexed Precision Vaccination As each individual tumor has its unique profile of mutations, the AAV-CAVac system was also capable of activating a customized set of mutated endogenous genes, with the adaptation of a precise targeted library design (Precision AAV-CAVac, or AAV-PCAVac) (FIG. 4A). Customizing the AAV library for endogenous gene activation both enriched for potentially antigenic mutants and selectively excluded genes that potentially caused adverse effects. Whole-exome sequencing of the E0771 cancer cells was performed and all SNPs, insertions and deletions (indels) were called in all annotated genes, by comparison to healthy mammary fat pad from wildtype C57BL/6J mice (FIG. 4A). The whole E0771-specific mutation profile was revealed (FIGS. 4B-4C). These data were fed into CRISPRa sgRNA library design, generating a library of 3,839 activating sgRNAs (SEQ ID NOs: 349-4,187) targeting 1,116 E0771-mutated genes (FIGS. 4A & 4C). The library was synthesized and pool-cloned, generating an E0771-specific precision vaccine (E0771 AAV-PCAVac) (FIG. 4A). C57BL/6J mice bearing E0771 syngeneic orthotopic TNBC were treated with the AAV-PCAVac and strong efficacy was observed (p<1e-7, FIGS. 4D-4G). Of note, there was a moderate yet statistically insignificant effect in AAV-vector treated group (p=0.25, FIG. 4E). In sharp contrast, all AAV-PCAVac treated tumors either fully regressed, decrease in size towards zero, or remained as small nodules within three weeks after treatment, as compared to large and rapidly growing tumors in all mice in the PBS treated group and most mice in the AAV-Vector group (FIGS. 4D-4F). The therapeutic benefit of AAV-PCAVac persists in the mice that underwent complete regression, as no sign of relapse was detected in longer-term observations (FIG. 4F).

Figure 4G:
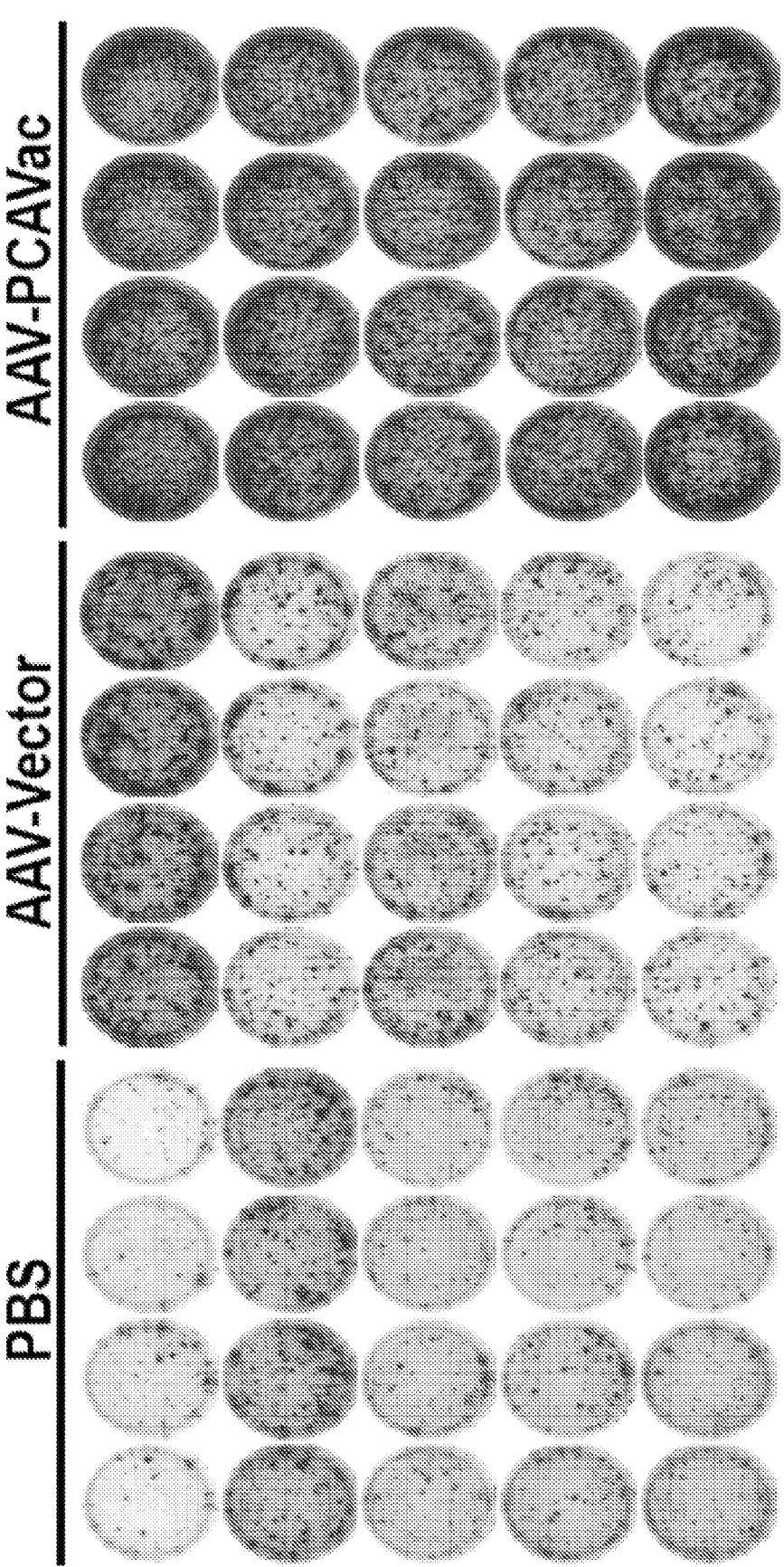
FIG. 4G shows representative pictures of spots obtained from quadruple per mouse with five mice for each treatment group (PBS, AAV-Vector, and AAV-CAVac).
Figure 4H:
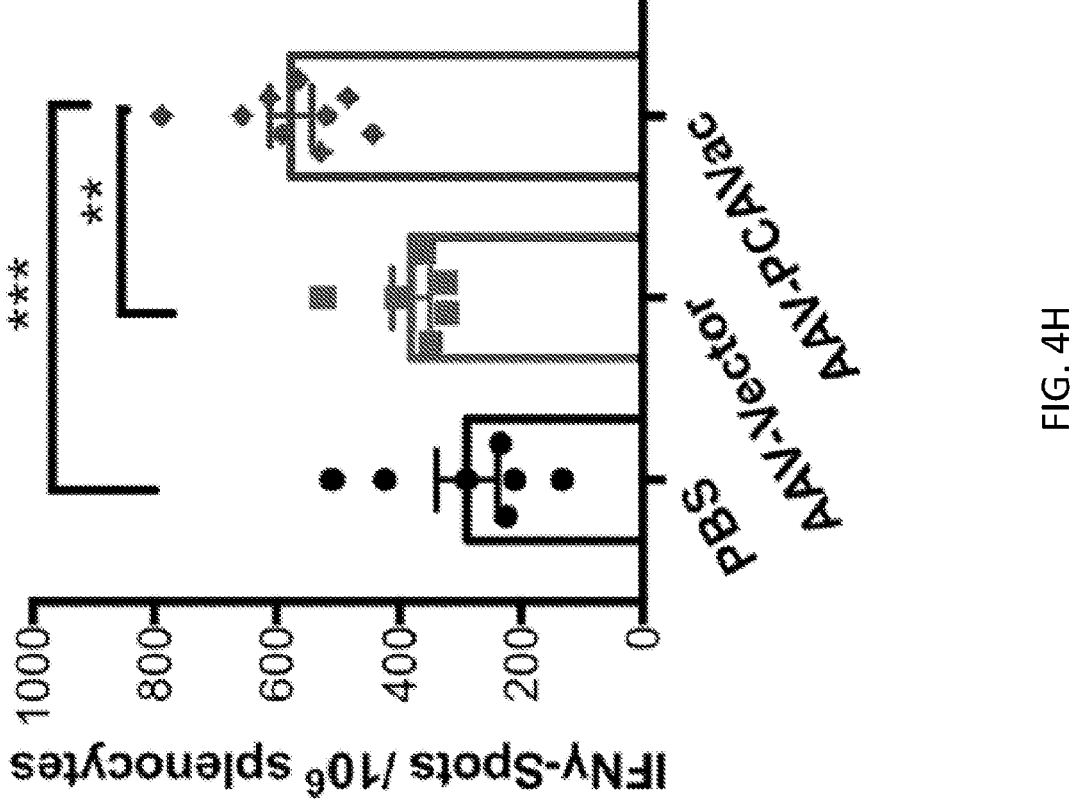
FIG. 4H shows quantification of ELISPOT experiments of PBS (n=7), AAV-Vector (n=6) and AAV-CAVac (n=9). Two sided Mann-Whitney test for AAV-CAVac vs. PBS, p=0.002; AAV-CAVac vs. AAV-Vector, p=0.002. Results were shown from the combination of 2 independent experiments. Error bars: All data points in this figure were presented as mean s.e.m. Asterisks: * p<0.05,  p<0.01, * p<0.001.
Figure 4I:
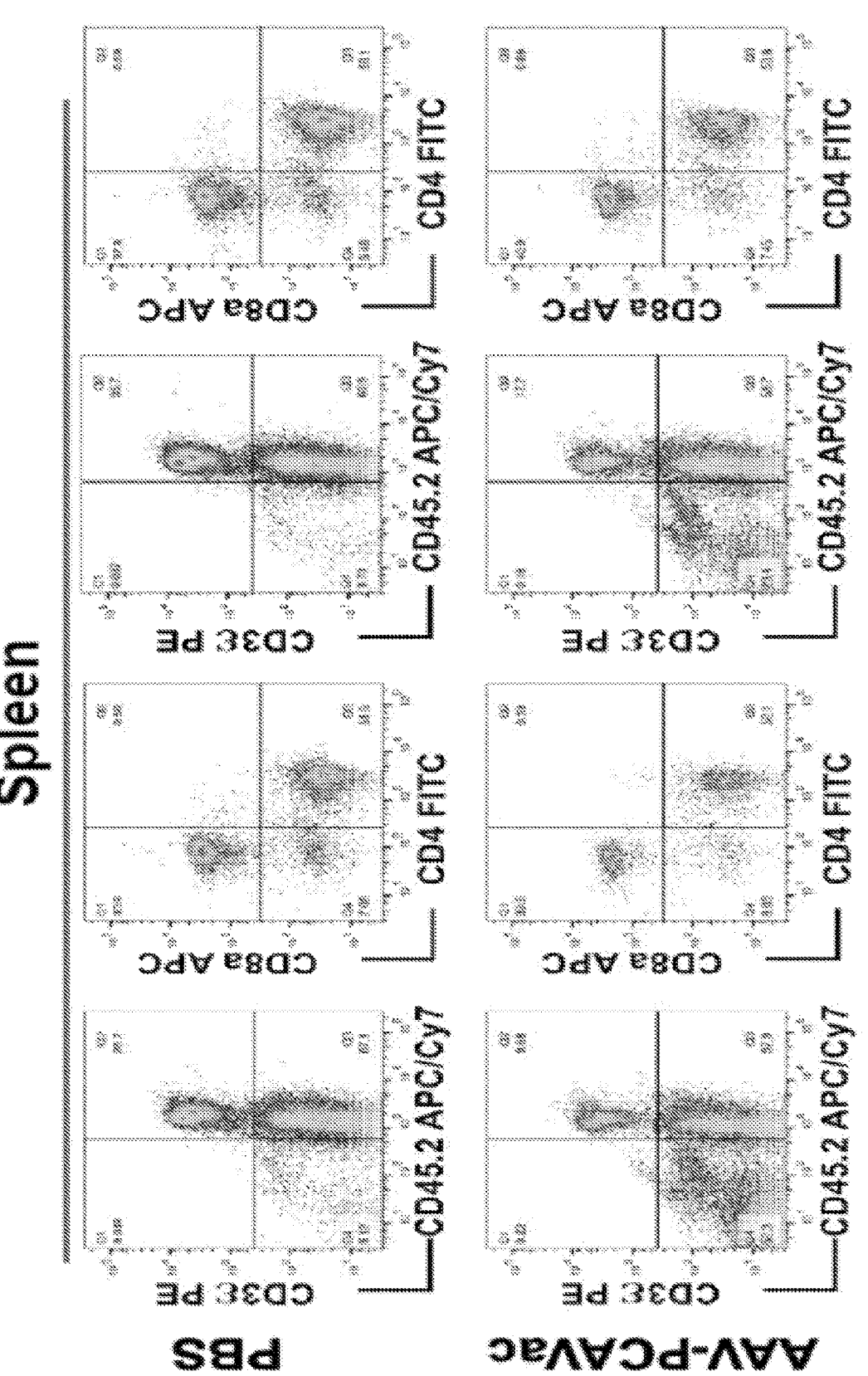
FIG. 4I shows representative flow cytometry plots and gating of $CD45^+$, $CD3^+$, $CD4^+$, and $CD8^+$ T cell populations in the spleens (splenocytes) from tumor-bearing mice treated with PBS or AAV-PCAVac.
Figure 4J:
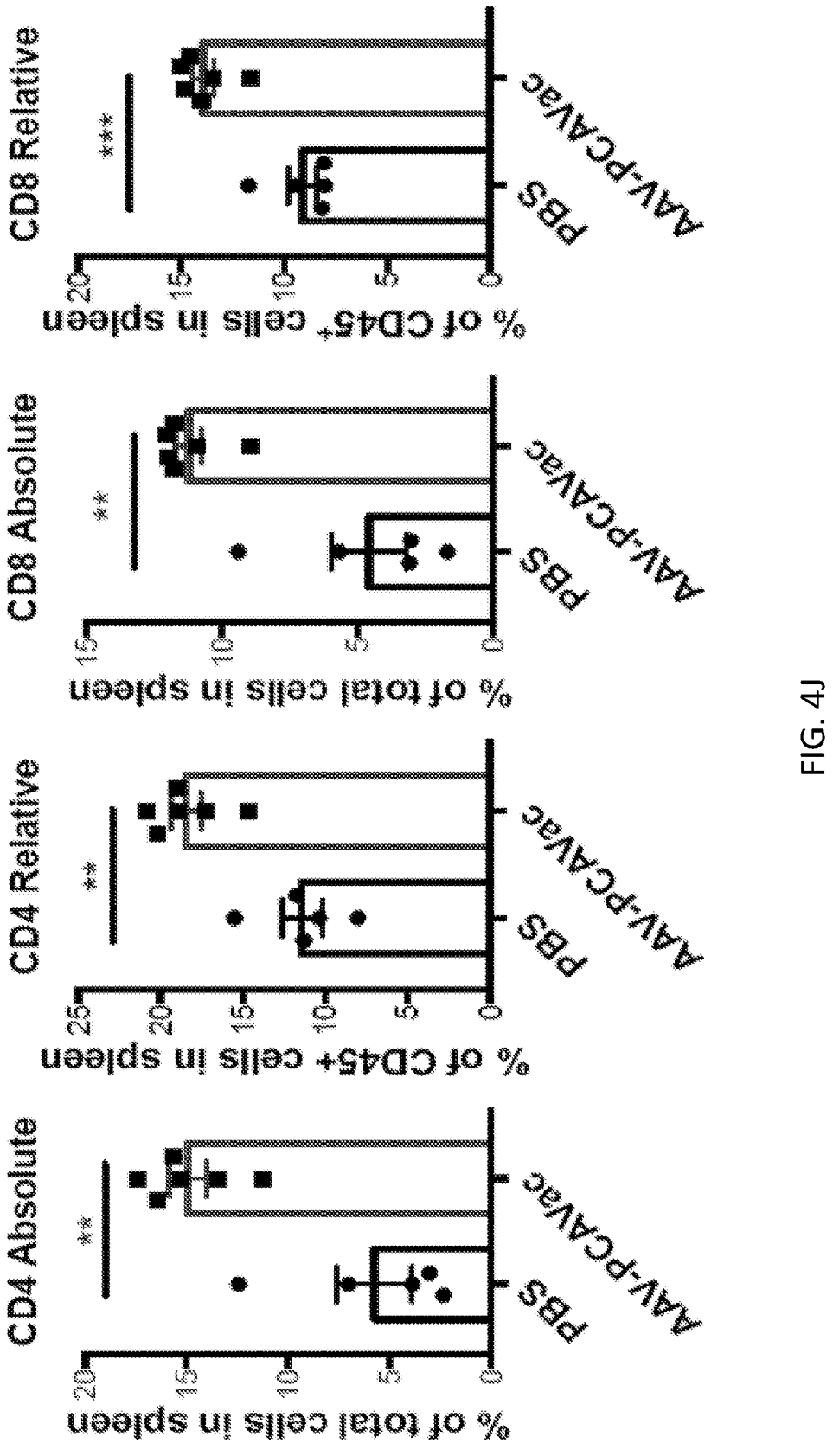
FIG. 4J shows quantification of $CD4^+$ and $CD8^+$ T cell populations from splenocytes of tumor-bearing mice treated with PBS or AAV-PCAVac. From left to right, bar-dot plots with two-sided unpaired t test for the following comparisons: Fraction of $CD4^+$ T cells in all cells in spleen (absolute fraction); AAV-PCAVac vs. PBS, p=0.0046. Fraction of $CD4^+$ T cells in all $CD45^+$ immune cells in spleen (relative fraction); AAV-PCAVac vs. PBS, p=0.0017. Fraction of $CD8^+$ T cells in all cells in spleen (absolute fraction); AAV-PCAVac vs. PBS, p=0.0059. Fraction of $CD8^+$ T cells in all $CD45^+$ immune cells in spleen (relative fraction); AAV-PCAVac vs. PBS, p=0.0007.
Figure 4K:
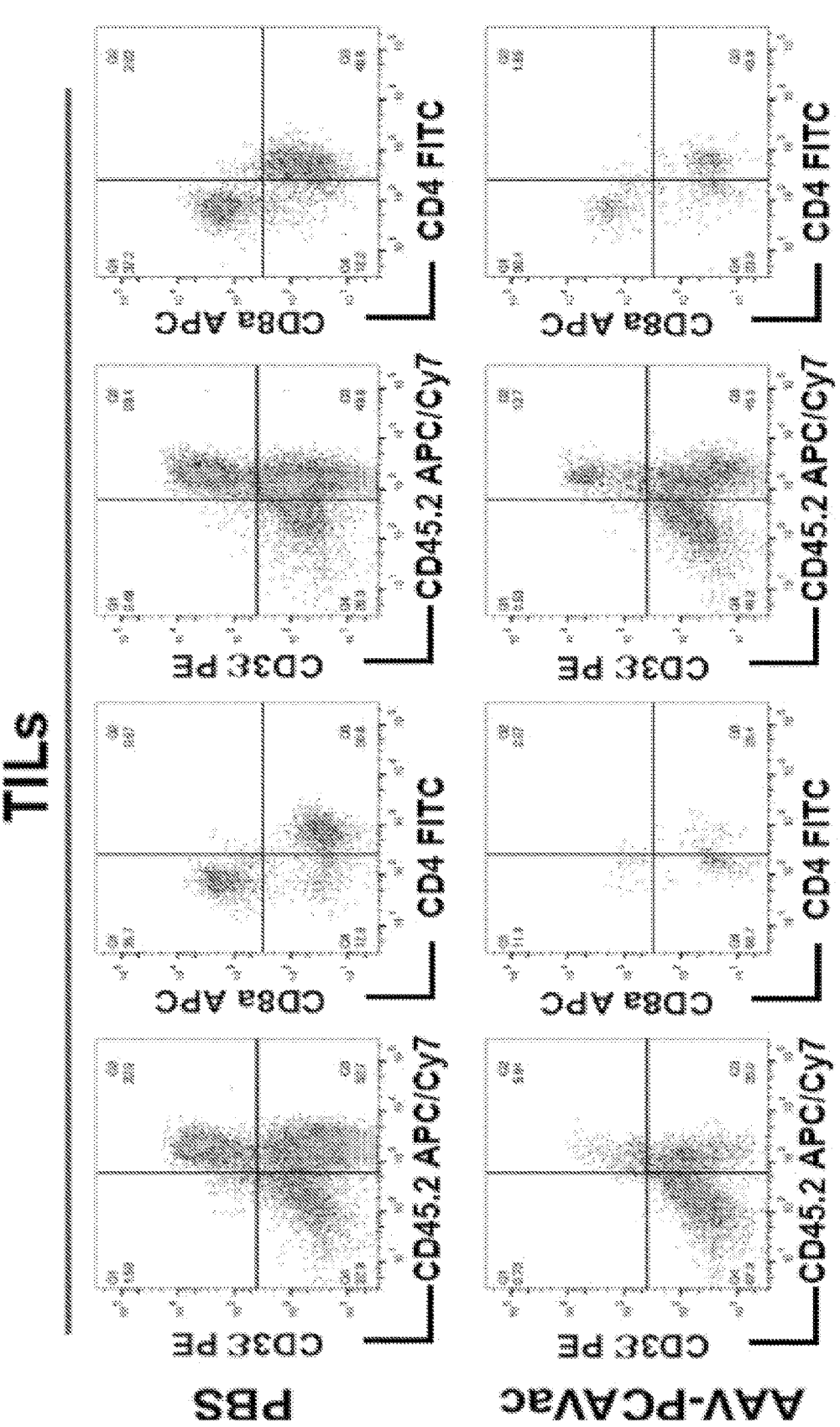
FIG. 4K shows representative flow cytometry plots and gating of $CD45^+$, $CD3^+$, $CD4^+$, and $CD8^+$ T cell populations in the tumor (TILs) from tumor-bearing mice treated with PBS or AAV-PCAVac.
Figure 4L:
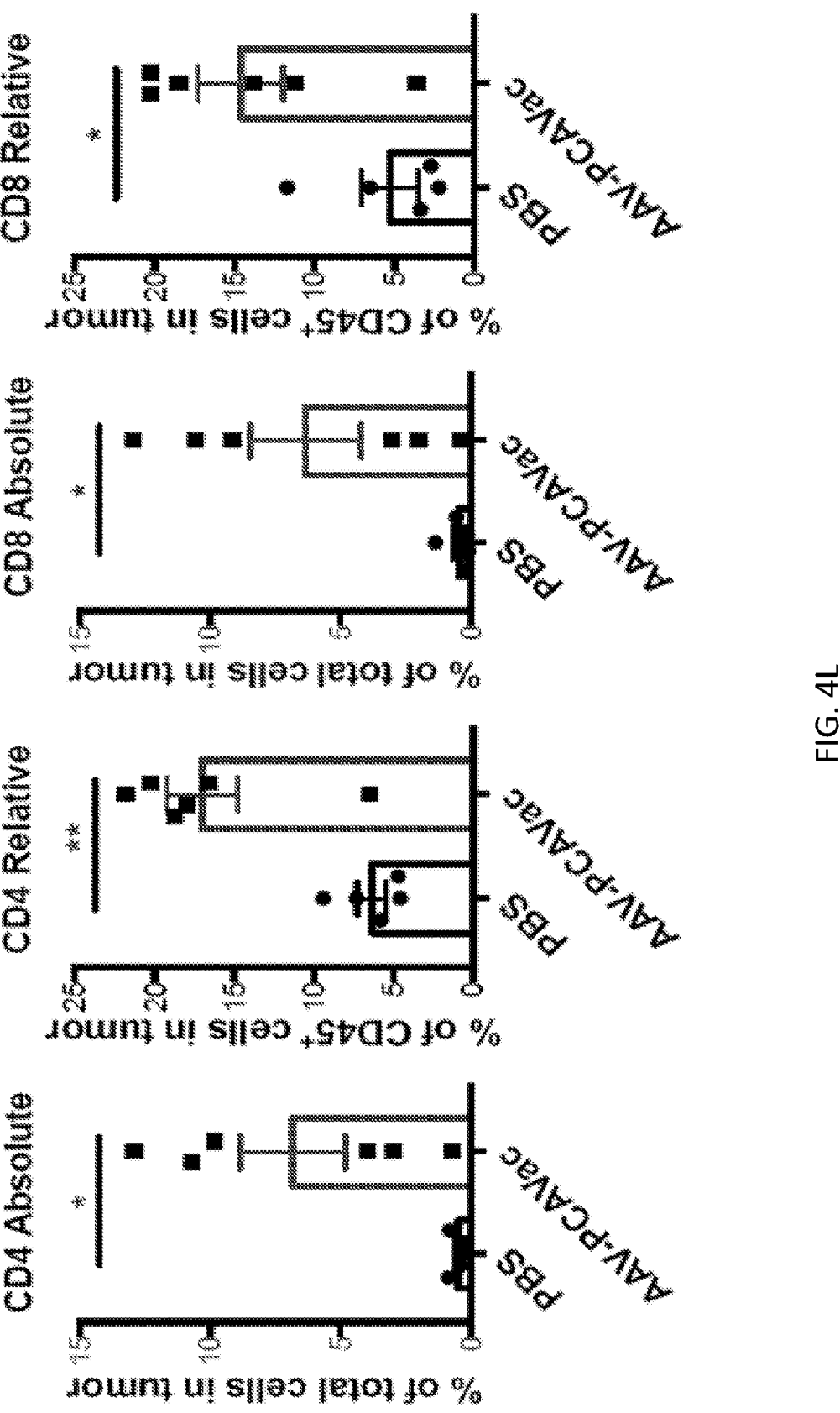
FIG. 4L shows quantification of $CD4^+$ and $CD8^+$ T cell populations from TILs of tumor-bearing mice treated with PBS or AAV-PCAVac. From left to right, bar-dot plots with two-sided unpaired t test for the following comparisons: Fraction of $CD4^+$ T cells in all cells in tumor (absolute fraction); AAV-PCAVac vs. PBS, p=0.025. Fraction of $CD4^+$ T cells in all $CD45^+$ immune cells in tumor (relative fraction); AAV-PCAVac vs. PBS, p=0.0035. Fraction of $CD8^+$ T cells in all cells in tumor (absolute fraction); AAV-PCAVac vs. PBS, p=0.039. Fraction of $CD8^+$ T cells in all $CD45^+$ immune cells in tumor (relative fraction); AAV-PCAVac vs. PBS, p=0.019. Error bars: All data points in this figure were presented as mean±s.e.m. Asterisks: * p<0.05,  p<0.01, * p<0.001.
Figure 13A:
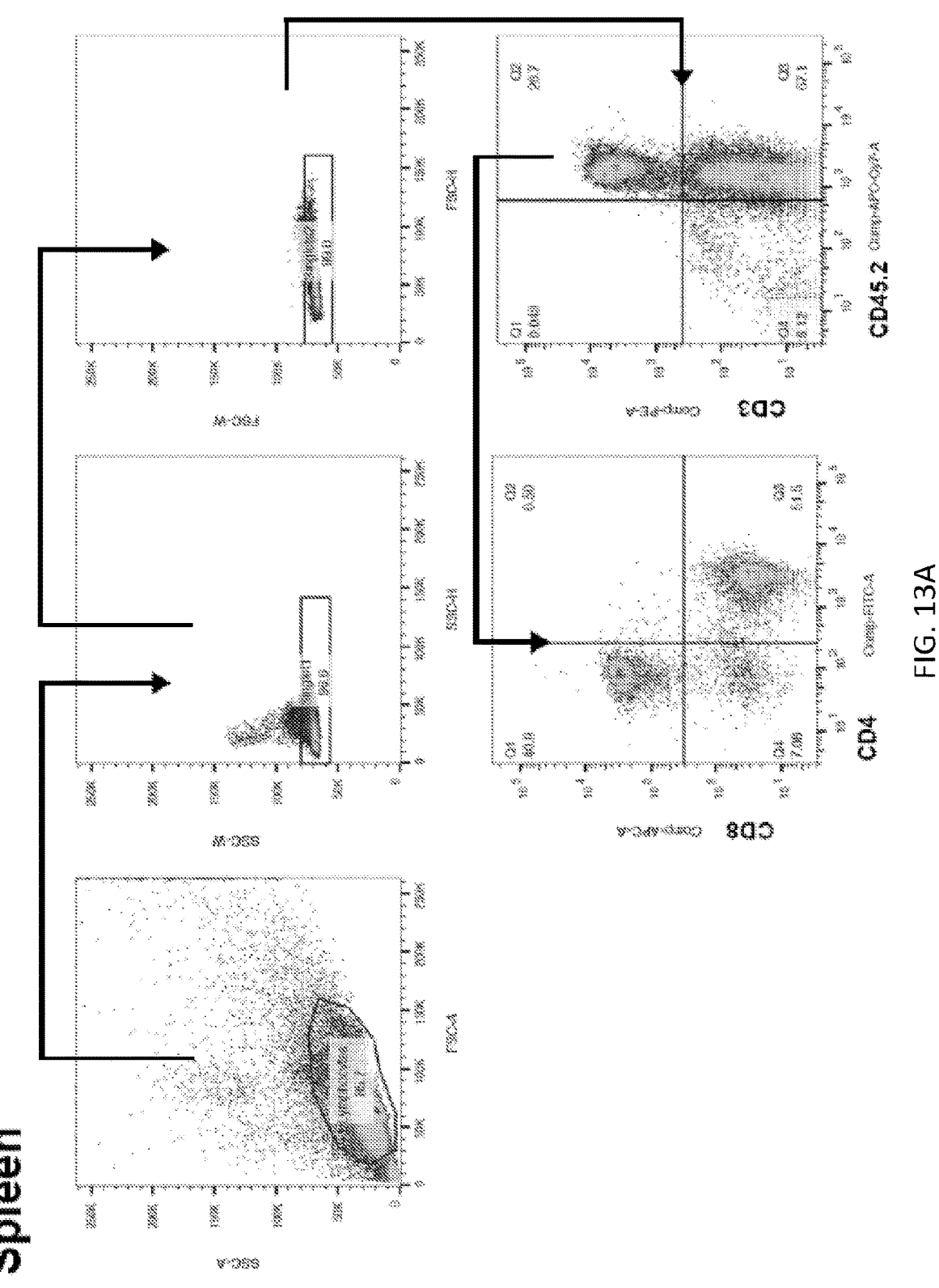
FIGS. 13A-13B illustrate FACS gating of representative spleen and tumor samples. Single cell suspension from samples were gated by FSC, SSC and then CD45$^+$, CD3$^+$, CD4$^+$, and CD8$^+$ T cell populations in the spleen (top) or tumor (bottom).
Figure 13B:
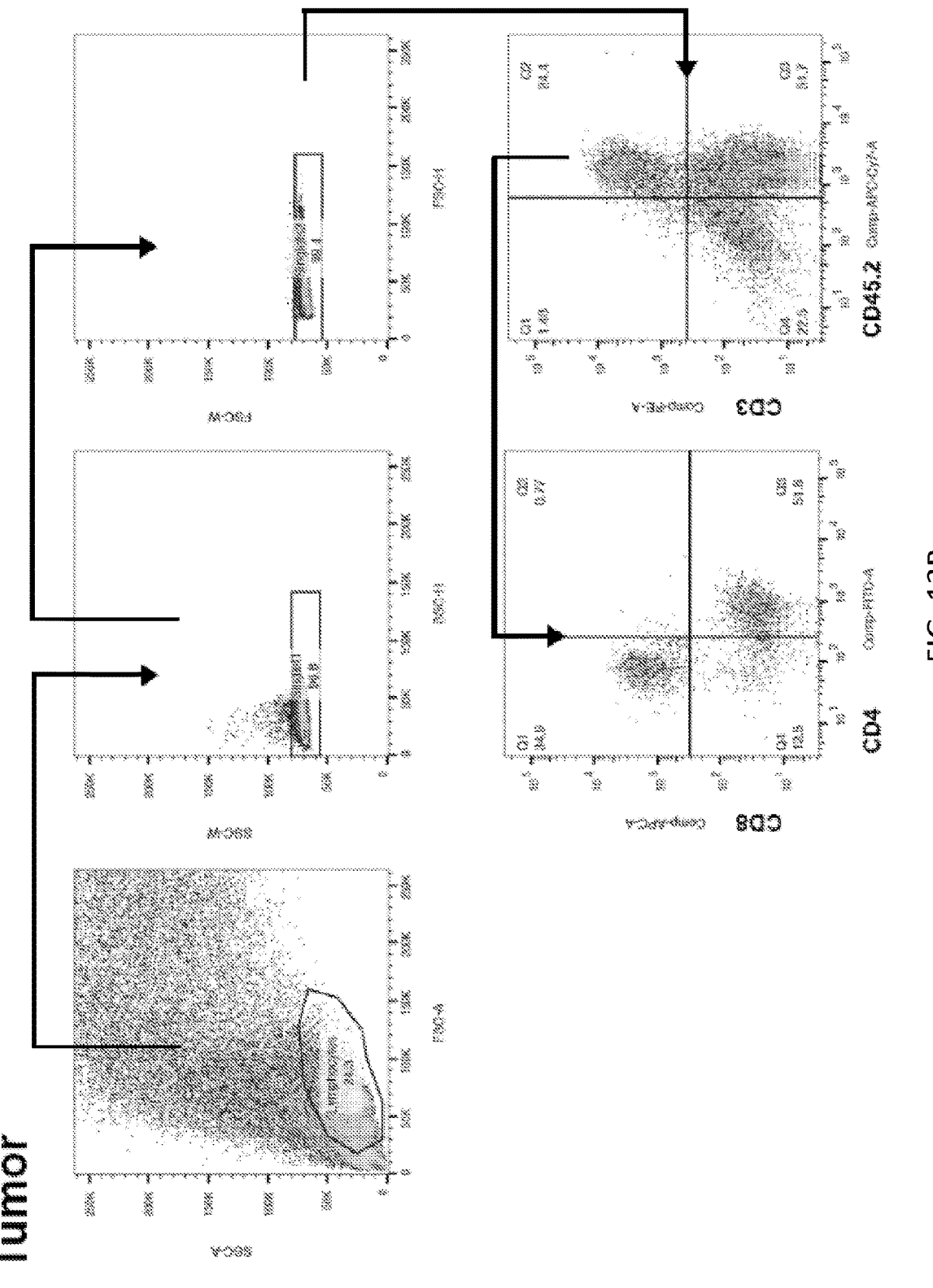
Figure 15A:
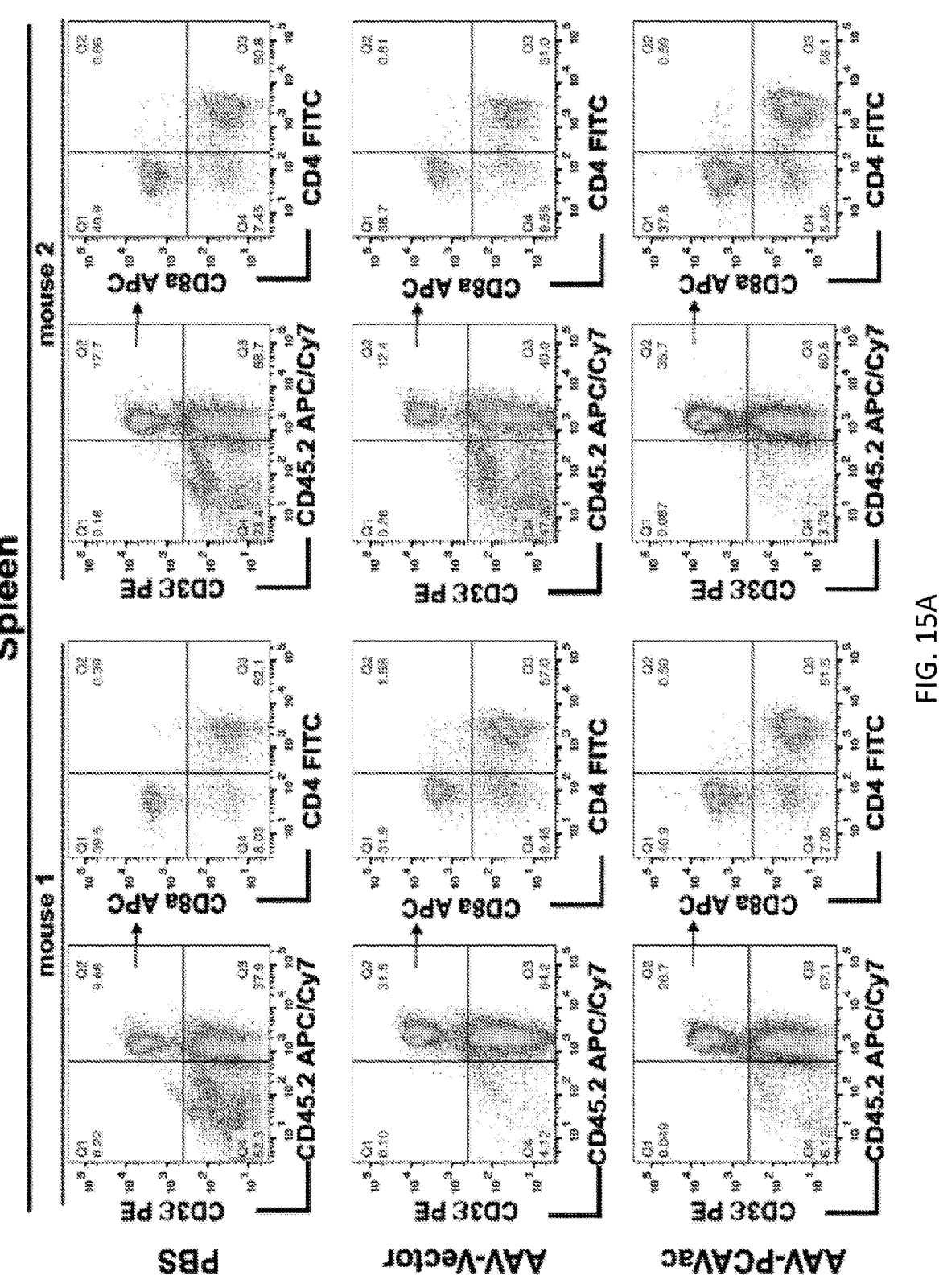
FIGS. 15A-15D illustrates CD4$^+$ and CD8$^+$ T cells in the spleen and tumors of mice treated with PBS, AAV-Vector, or AAV-PCAVac.
Figure 15B:
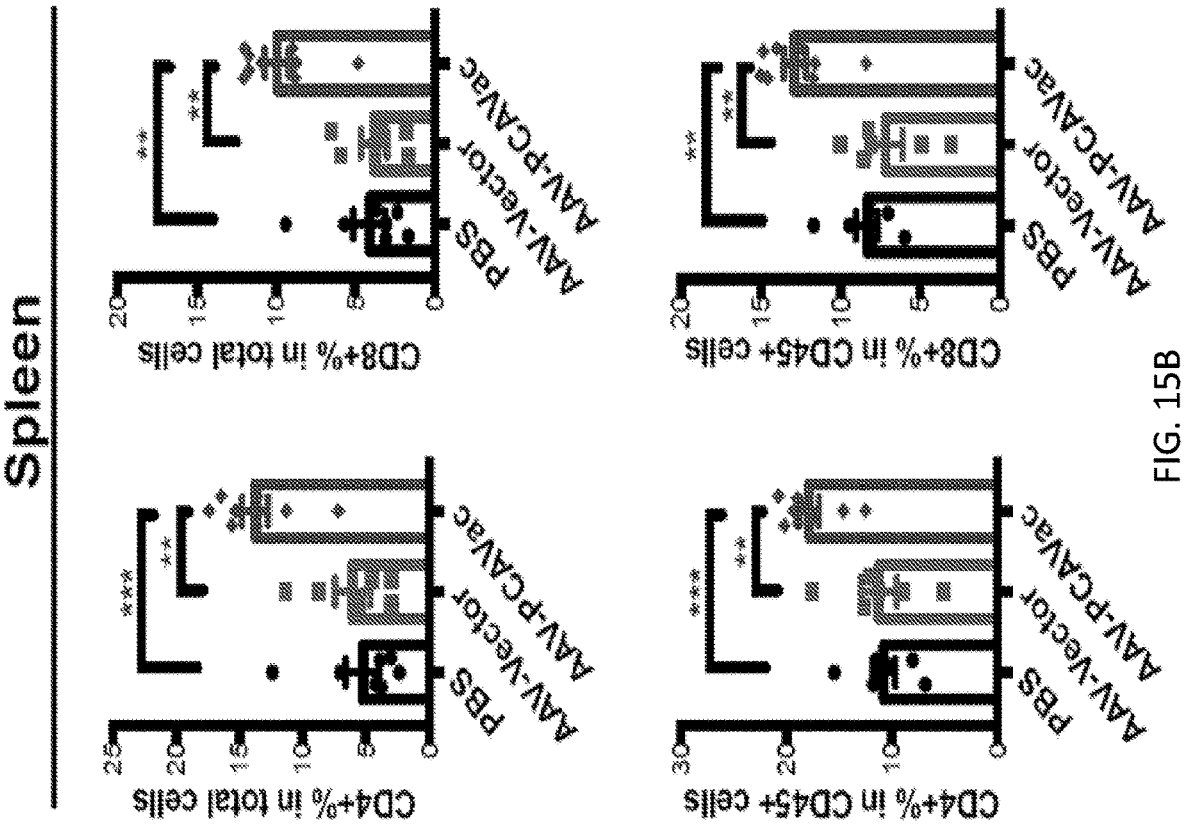
Figure 15C:
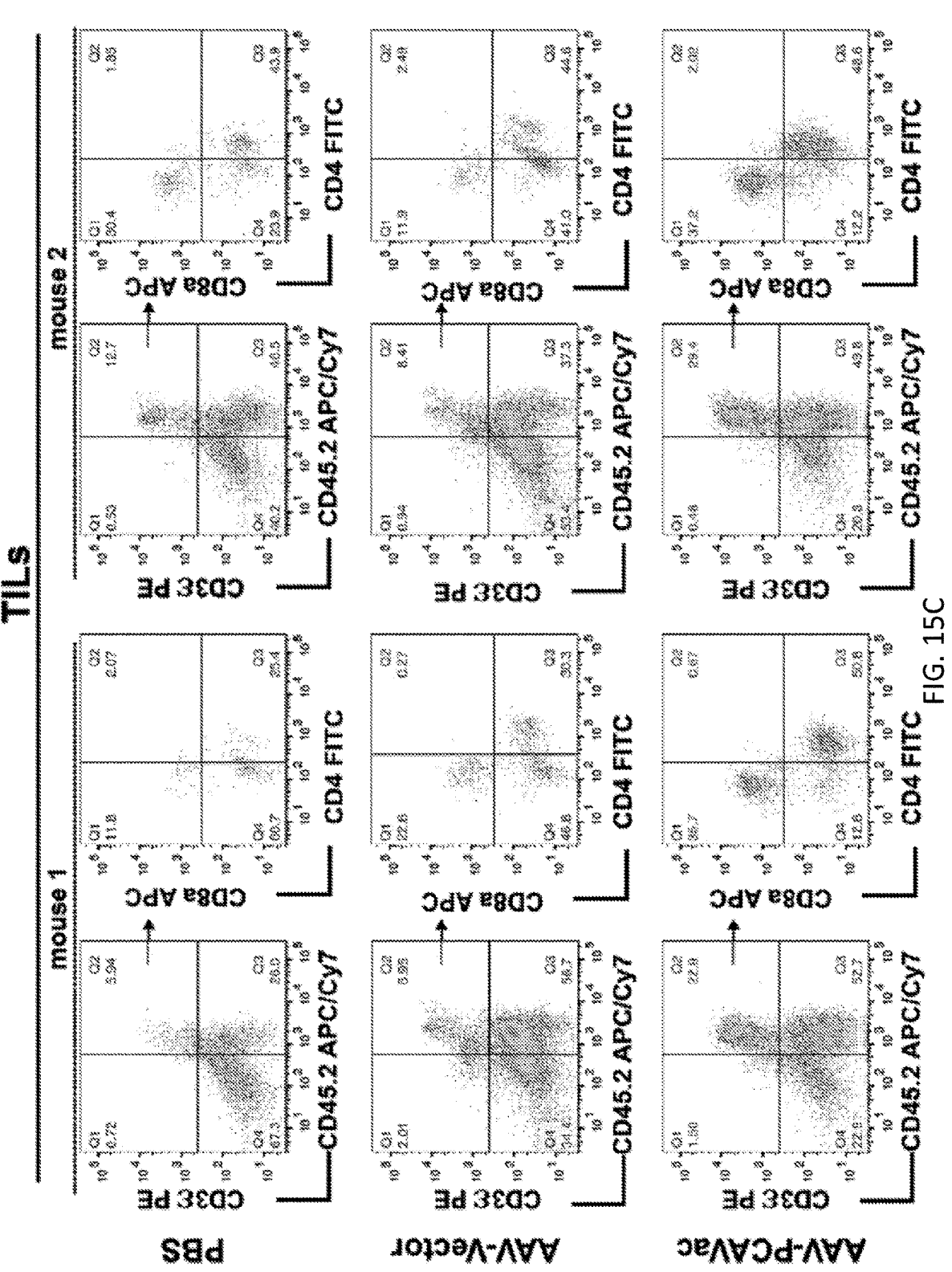
Figure 15D:
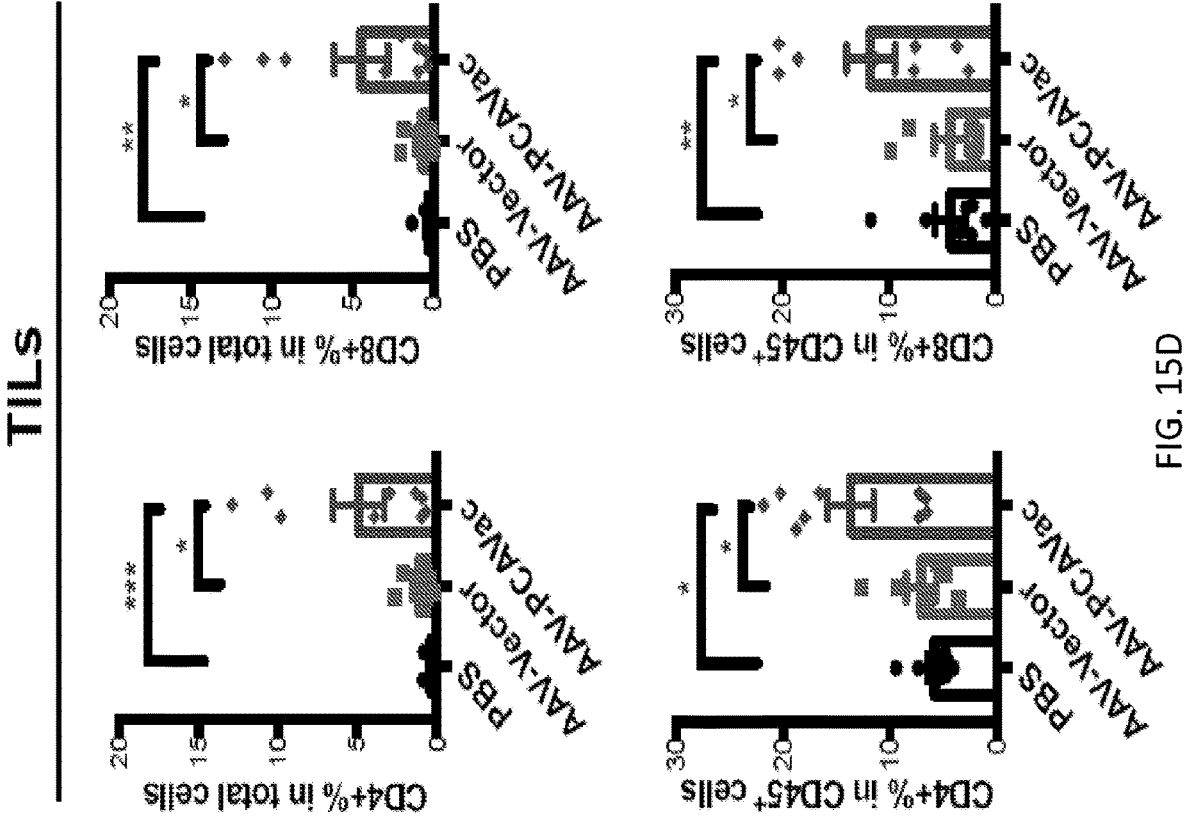
Figures 16A, 16B, 16C, 16D:
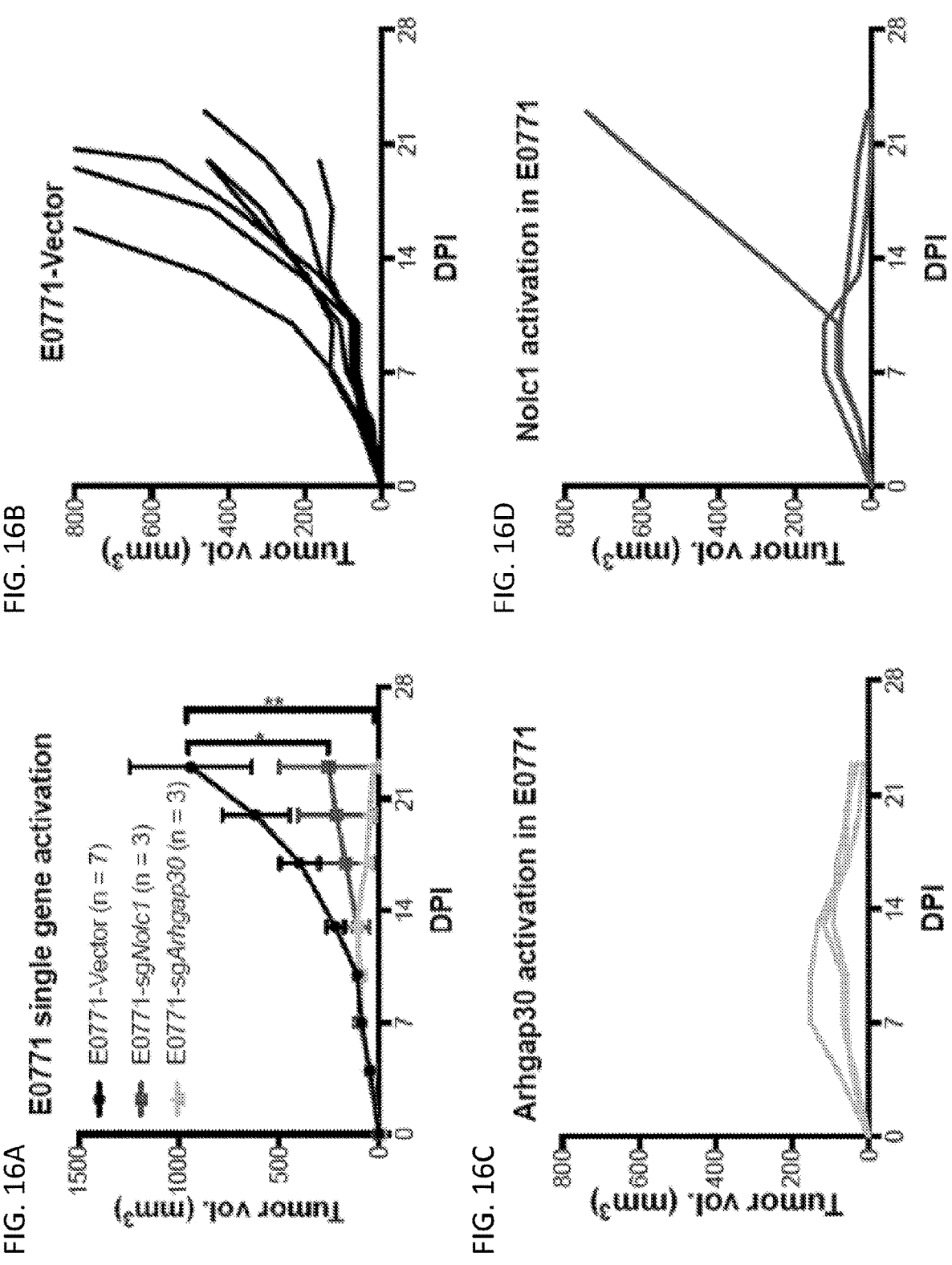

Using ELISPOT, it was observed that AAV-PCAVac significantly augmented tumor-specific Ifnγ producing splenocytes in vaccinated mice compared to PBS (p<0.001) and AAV-vector (p<0.01) (FIG. 4G-4H). To examine the adaptive immune responses, FACS analysis was performed on T cell populations from both the spleen and tumor (FIGS. 13A-13B). In the splenocyte population, AAV-PCAVac treatment significantly increased CD4$^+$ and CD8$^+$ T cells' abundance, in total cells and in CD45$^+$-relative fractions (FIGS. 4H-4I, FIGS. 15A-15B). For example, AAV-PCAVac treated mice have greater than 2.4-fold increase of CD8$^+$ T cells as compared to PBS and AAV-vector treated mice (p<0.01, FIG. 4I, FIG. 5B). These observations hold in the TIL population (FIGS. 4J-4K, FIGS. 15C-15D), for example, AAV-PCAVac treated tumors have an average 15-fold more CD8$^+$ TILs as compared to PBS treated mice (p<0.05, FIG. 4K, FIG. 5D), consistent with the strong anti-tumor immune response induced by AAV-PCAVac treatment (FIGS. 4D-4G). These data together revealed that AAV-PCAVac is a potent means to stimulate specific anti-tumor immune responses resulting in significant regression or elimination of established tumors, which represents a proof-of-concept of a cost-effective precision multiplexed vaccination approach.

Example 6: Discussion

New technologies that have harnessed the immune system to destroy malignant tumor cells have transformed cancer therapeutics. The concept of cancer immunotherapy was first proposed over a century ago, and was subsequently revitalized when it was formally proposed that the immune system could recognize and eliminate tumor cells in the immune surveillance theory. However, it is now known that cancers can rapidly adapt to these immune pressures, acquiring new alterations to escape immune elimination using many different mechanisms. Tumor cells can acquire mutations to reduce immune recognition or increase resistance to cytotoxic killing, and also foster immunosuppressive microenvironments in various different ways. Cytotoxic T lymphocytes (CTLs) play an essential role in anti-tumor immunity, most prominently by the specific killing of tumor cells in response to tumor-associated antigens (TAAs). Adoptive transfer of ex vivo expanded naturally occurring or engineered chimeric antigen T (CAR-T) cells has achieved success in immunotherapy of multiple types of liquid cancers. However, many factors including insufficient infiltration, anergy, exhaustion, and suppressive microenvironments can lead to non-responsiveness of T cell based treatments in solid tumors. Co-stimulatory and co-inhibitory receptors play a pivotal role in the status and fate of T cells. For example, CTLA-4 and PD-1 are two important receptors on T cells designed to rheostat immune responses to avoid autoimmunity, but they can be manipulated by tumors to block anti-tumor immunity. Immune checkpoint blockade therapies by blocking CTLA-4 and PD-1 with antibodies have yielded significant clinical benefits across many tumor types with durable responses even in metastatic and chemo-resistant tumors. Nevertheless, only a portion of patients show sustained clinical responses, demonstrating the need for other therapeutic approaches or combinatorial therapeutics. The present invention provides such an approach.

Vaccination has achieved exceptional success in protecting hosts from infectious agents due to its efficacy in stimulating durable adaptive immune defenses. However, approved cancer therapies based on therapeutic vaccines are scarce. Tumor antigen recognition is key to T cell mediated tumor rejection, and the load of TAAs, especially neoantigens, has been shown to be correlated with cytolytic T cell activities and patients' responsiveness to immune checkpoint blockade. However, spontaneous immune recognition of mutations and self-antigens is usually inefficient for effective tumor rejection, due to the complex in vivo cancer-immune evolution processes such as cancer immunoediting. This was also observed in a clinical setting where neoantigen landscape dynamics in human melanoma was shared by cancer cell—T cell interactions. Vaccination is potentially an effective approach to boost immune recognition of cancer specific mutants. However, many factors may contribute to the lack of efficacy of vaccines in mediating effective anti-tumor responses. Most current vaccines cannot mediate effective anti-tumor responses by T cells, or encounter tumor escape by immunoediting and other mechanisms. In particular, low-affinity of invoked T cell receptors to the peptide-MHC class I (p-MHCI) complex and the shift of antigenic repertoire in advanced cancers are potential reasons underlying the lack of efficacy for many vaccine formulations, especially those with only one or a handful of polypeptides. With high-throughput exome sequencing, the notion of personalized immunotherapy targeting patient-specific mutations has become technologically feasible, and recent studies using peptide- and RNA-based vaccines have shown that targeted delivery of mutated neoantigens can generate strong anti-tumor effects. Large-scale screening and generation of effective peptides or RNAs is expensive and time consuming. Selection of a subset of RNAs or peptides may miss other immunogenic neoantigens in the full spectra of endogenous mutations, thereby leaving the door open for continued immune evasion through tumor evolution. Furthermore, both peptides and RNAs have relatively short half-lives. For longitudinal induction of effective anti-tumor immune responses, continuous expression of antigens may prove beneficial. Direct activation of endogenous genes overcomes these challenges by providing sustained and tunable overexpression of mutated genes to amplify the signal of neoantigens (FIG. 14). Pooled gene activation using CRISPRa libraries can be customized to augment the expression of any selected set of genes, or the whole genome, thereby boosting neoantigen presentation for T cell recognition. Although the mechanism of action underlying the anti-tumor responses observed here are likely more complicated than involving T cells alone, the data demonstrate that endogenous gene activation-based therapies, including CAVac, AAV-CAVac and AAV-PCAVac, offer an orthogonal vaccination approach for cancer immunotherapy that can function in concert with other established immunotherapeutic modalities.

Example 7: Exome-Guided AAV-CRISPRa Based Mutated Gene Set Activation as Precision Multiplexed Tumor Vaccination (AAV-PCAVac) Against Human Tumors Step 1—Patient Tumor Profiling:

Genomic DNA of tumor samples from core biopsi(es) and normal samples (peripheral blood) is extracted, purified, and subjected to whole-exome sequencing. Optional: RNA of tumor samples from core biopsi(es) and normal samples (peripheral blood) is extracted, purified, and subjected to RNA sequencing to detect gene expression, which will is also used for both mutation call and expression of potential antigenic mutants.

Step 2—Mutation Mapping and Mutant Gene Ranking:

Somatic SNPs and indels in cancer cells are identified by comparison to matched normal tissues, and the mutations are mapped to each gene.

Step 3—CRISPRa sgRNA Library Design:

CRISPRa sgRNAs targeting these mutants are designed. The mutated gene set customized sgRNA library is synthesized and pool-cloned into the AAV-CRISRPa vector, which is packaged into AAV9 to generate tumor-mutation matched (precision/personalized) AAV vaccine (AAV-PCAVac).

Step 4—AAV GMP/cGMP:

The AAV-PCAVac is subjected to GMP/cGMP for production and quality check.

Step 5a—AAV-PCAVac Delivery into Unresectable Tumor:

In a clinical trial or clinical treatment setting, clinicians deliver AAV-PCAVac to the primary or metastatic tumor site which is an unresectable disease, as a treatment to elicit immune response against the residue or potentially metastasized cancer cells harboring the particular mutated genes.

Step 5b—AAV-PCAVac Delivery into Tumor as an Adjuvant of Surgery:

In a clinical trial or clinical treatment setting, clinicians deliver AAV-PCAVac to the residue tumor site after surgery as an adjuvant treatment to elicit an immune response against the residue or potentially metastasized cancer cells harboring the particular mutated genes.

Example 8: Comparison with Existing Methods and Discussion of the Uniqueness and Advantages of the Present Invention With high-throughput exome sequencing, the notion of personalized immunotherapy targeting patient-specific mutations has become technologically feasible, and recent studies using peptide- and RNA-based vaccines have shown that targeted delivery of mutated neoantigens can generate strong anti-tumor effects. However, large-scale screening and generation of effective peptides or RNAs is expensive and time consuming. On the other hand, pre-selection of a subset of RNAs or peptides will likely miss other important immunogenic neoantigens within the full landscape of endogenous mutations, thereby leaving the door open for continued immune evasion through tumor evolution. Furthermore, both peptides and RNAs have relatively short half-lives, potentially limiting the durability of such interventions, or requires more frequent re-dosing. For longitudinal induction of effective anti-tumor immune responses, continuous expression of antigens has its advantages.

As demonstrated herein, direct activation of endogenous genes overcomes these challenges by providing sustained and tunable overexpression of mutated genes to amplify the signal of neoantigens that may not be expressed at baseline (FIG. 14). Since CRISPR activation works on the endogenous genes themselves, if a new mutation encoding a potential neoantigen is acquired, the CRISPR activation library will automatically drive the expression of the new mutant gene. Due to the nature of endogenous gene activation, this vaccination approach will continue to evolve alongside the tumor itself, which will naturally lockdown mutated cancer cells and thereby eliminate an avenue of immune escape. Importantly, pooled gene activation using CRISPRa libraries can be customized to augment the expression of any selected set of genes, or the whole genome, thereby boosting neoantigen presentation for T cell recognition. Although the mechanism of action underlying the anti-tumor responses observed here are likely more complicated than involving T cells alone, the data herein demonstrate that endogenous gene activation-based therapies, including CAVac, AAV-CAVac and AAV-PCAVac, offer an orthogonal vaccination approach for cancer immunotherapy that can function in concert with other established immunotherapeutic modalities.

Example 9: Compositions and Methods for Off-the-Shelf and Customizable Endogenous Gene Vaccination Cancer Vaccine Presented herein are two modes of multiplexed vaccination with endogeneous gene activation using the CRISPRa system. In an unvaccinated individual, a tumor cell contains tumor-specific mutated genes that are transcribed, translated, then presented as peptides (neoantigens) on MHC class I molecules (FIG. 17A). Oftentimes these neoantigens are expressed at a low level, and thus elicit a weak response upon binding to a TCR of a CD8+ T cell. In one approach described herein, Multiplexed Vaccination by Mutated Gene CRISPR Activation (MGCA), a plurality of mutant endogenous genes are activated by the CRISPRa system using sgRNAs specific for these mutant endogenous genes (see Examples 4, 5, and 6). This leads to high expression of neoantigens on MHC class I molecules yielding a robust CD8+ T cell response (FIG. 17B). In a second approach utilized herein, Multiplexed Vaccination by Antigen Presentation CRISPR Manipulation (APCM), a plurality of antigen presentation genes are activated by the CRISPRa system using sgRNAs specific for these antigen presentation genes (see Example 10 below). This leads to augmentation of antigen presentation machinery, increased expression of cytokines and/or immunological modulators, increased presentation of neoantigens on MHC class I molecules, and a robust CD8+ T cell response (FIG. 17C).

The precision ("Personalized") AAV-PCAVac system was proven effective as a therapeutic vaccine. The AAV-PCAVac was designed to target a set of the most highly mutated genes in E0771 cells as compared to normal mammary fatpad of C57BL/6J female mice (SEQ ID NOs: 349-4,187; Table 4). The efficacy of the AAV-PCAVac multiplexed endogeneous gene activation was tested using a syngeneic orthotopic model in C57BL/6J hosts. E0771 triple-negative breast cancer (TNBC) cells were engrafted in the mammary fatpad of female C57BL/6J mice. Mice were treated with PBS, AAV-Vector, or the AAV-PCAVac library (SEQ ID NOs. 349-4,187). Survival over time was monitored for all treatment groups (FIG. 18). Efficacy was seen in both AAV-Vector and AAV-PCAVac, however AAV-PCAVac had a stronger anti-tumor effect (FIGS. 18-19).

A two-sided tumor induction was performed, wherein tumors (E0771 TNBC) were induced at two locations, a primary and a distal site, in C57BL/6J mice. Mice were treated at the primary site with either PBS, AAV-Vector, or AAV-PCAV. Regression of both the primary and distant tumors was observed in the AAV-PCAVac treated mice (FIG. 20).

Using the syngenic orthotopic TNBC model, C57BL/6J mice were re-challenged with E0771 tumor cells after complete regression of a first E0771 tumor following AAV-PCAVac treatment. No growth was seen in the AAV-PCAVac treated mice following re-challenge (FIG. 21).

The Precision ("Personalized") AAV-PCAVac system was further validated as a therapeutic vaccine against TNBC. E0771 TNBC were engrafted in the mammary fatpad of C57BL/6J female mice. Mice were treated with PBS, AAV-Vector, AAV-Emut11 library or AAV-PCAVac library. The Emut11 library targets a set of the topmost 11 mutated genes in E0771 cells (Tekt2, RSC1a1, Acer2, Sc36a1, Tmem106b, Gabrg2, Ago4, G3bp1, FAT2, Hmmr, Trp53). Efficacy was seen in both AAV-Vector, AAV-Emut11 and AAV-PCAVac, however AAV-PCAVac had the strongest anti-tumor effect (FIG. 22).

SgRNAs were designed to target a set of the most highly mutated genes in B16F10 (melanoma), GL261 (glioma), Hepa1-6 (hepatoma), MC38 (colon cancer), and Pan02 (pancreatic cancer) cells (SEQ ID NOs. 11,809-23,776). The sgRNAs were cloned into an adeno-associated viral vector and packaged, as described elsewhere herein.

Example 10: Antigen Presentation CRISPR Manipulation (AAV-APCM) System

An off-the-shelf Antigen Presentation CRISPR Manipulation (AAV-APCM) system was designed and tested as a therapeutic vaccine. An AAV-Apcm library was designed by first selecting a small set of genes that elicit immune responses: B2M, B7-H2 (ICOSL), Calnexin, Calreticulin, CCL5, CD30L(TNFSF8), CD40L, CD70, CD80, CD83, CD86, CXCL10, CXCL3, CXCL9, Cystatin B, Cystatin C (x), ERAP1, ERp57(PDIA3), Flt3L, GITRL(TNFSF18), IFNa4, IFNb1, IFNg, IL-2, LIGHT (TNFRSF14), NLRC5/

CITA, OX40L/TNFSF4, Sec61a1, Sec61b, Sec61g, TAP1, TAP2, Tapasin, TAPBPR, TL1A (TNFSF15), and TNFSF9 (4-1BBL). SgRNA sequences were designed to target these genes in mice, yielding a library of 107 sgRNAs (SEQ ID NOs. 23,779-23,885) (FIG. 27). Because the composition is fixed, by definition this APCM library is also an "Off"-the-shelf vaccine, while it can definitively be combined with personalized vaccine. The sgRNAs were cloned into an adeno-associated viral vector and packaged, as described elsewhere herein. Efficacy of the AAV-APCM multiplexed endogenous gene activation was tested in a syngeneic ortho-topic model in C57BL/6J hosts. E0771 TNBC cells were engrafted in the mammary fatpad of C57BL/6J female mice. Mice were treated with PBS, AAV-Vector, or the AAV-Apcm library. Efficacy was seen in both AAV-Vector and AAV-Apcm treatment, however the AAV-Apcm treatment had a stronger anti-tumor effect (FIG. 23).

A second AAV-APCM library (AAV-Apch) was generated that was designed/optimized specifically for human genes. SgRNAs were designed to target the same set of antigen presentation genes as above, yielding a library of 219 sgRNAs (SEQ ID NOs: 23,886-24,104) (FIGS. 28A-28B). The sgRNAs were cloned into an adeno-associated viral vector and packaged, as described elsewhere herein.

Example 11: "Off-the-Shelf" Whole-Genome Libraries

An off-the-shelf whole-genome AAV-CAVac system was designed and tested as a therapeutic vaccine against mela-noma. Therapeutic efficacy of whole-genome gene activa-tion AAV-CAVac (i.e. AAV-SAM) against established ortho-topic syngeneic B16F10 tumors by intratumoral administration was demonstrated. Growth curves of ortho-topic transplanted B16F10 tumors in C57BL/6J mice treated with PBS and AAV-CAVac at indicated times (days post-injection; arrows) are shown in FIG. 24.

The off-the-shelf whole-genome AAV-CAVac system was also established as a therapeutic vaccine against pancreatic cancer. Therapeutic efficacy of whole-genome gene activa-tion AAV-CAVac (i.e. AAV-SAM) against established ortho-topic syngeneic Pan02 tumors by intratumoral administra-tion was demonstrated. Growth curves of subcutaneous transplanted Pan02 tumors in C57BL/6J mice treated with PBS and AAV-CAVac at indicated times (arrows) are shown in FIG. 25.

An off-the-shelf AAV-SingleCAVac system was proven effective as a prophylatic vaccine (FIG. 26). Efficacy of AAV-SingleCAVac endogenous gene activation in a synge-neic orthotopic model in C57BL/6J host was demonstrated. Shown are growth curves of Arhgap30 or Nolc1 activated E0771 cell induced syngeneic orthotopic tumor. As com-pared to vector transduced cells, sg-Arhgap30 or sg-Nolc1 transduced E0771 cells generated tumors that grew slower and often got rejected by the C57B/6J host.

A human version of the AAV-CAVac (i.e. AAV-SAM) system is designed for therapeutic and prophylactic use against different cancer types. SgRNAs are designed against endogeneous human genes expressed in different cancer types. SgRNAs are cloned and packaged into viral vectors as described herein.

Example 12: Multiplexed Endogenous Gene Activation Leads to Tumor Rejection Through an Immune-Mediated Mechanism The CRISPRa system uses a catalytically dead Cas9 without nuclease activity (dCas9), enabling simple and flexible regulation of gene expression through dCas9—transcriptional activation domain fusion. This system can be further enhanced by the recruitment of other effectors such as synergistic activation mediators (SAM). Herein, broad genome-wide CRISPRa libraries were utilized for initial experiments, since activation of all coding genes in the genome includes activation of all mutated genes.

To test the effect of endogenous gene activation on the immunogenicity of cancer cells, it was essential to utilize fully immunocompetent tumor models. The E0771 synge-neic mouse model of triple-negative breast cancer (TNBC), in which E0771 cancer cells are transplanted into the mam-mary fat pad of fully immunocompetent C57BL/6 mice, was used. E0771 cells were transduced with CRISPRa lentiviral vectors expressing dCas9-VP64 and MS2-p65-HSF1 (E0771-dCas9-VP64-MPH) (FIG. 29A and FIG. 30A). Observing that dCas9-VP64 alone has a moderate effect on tumor growth (FIG. 30B), all subsequent experiments were performed using E0771-dCas9-VP64 cells. Next, a mouse genome-scale lentiviral SAM CRISPRa sgRNA library (mSAM, or SAM for short) (Konermann et al. (2015) Nature 517, 583-588) was transduced into E0771-dCas9-VP64-MPH cells, generating a highly diverse population of cells encompassing the entire library (E0771-dCas9-VP64-MPH-SAM cell pool, or E0771-SAM for short). This was con-firmed by Illumina sequencing for 6 independent replicates (FIG. 30C). For controls, E0771-dCas9-VP64-MPH cells transduced with the empty lentiviral vector expressing an inert sgRNA and a MS2-loop-tracrRNA chimeric backbone (E0771-Vector for short) were used.

The E0771-SAM cell pool was transplanted into C57BL/6J mice to test their ability to form syngeneic tumors (FIG. 29A). In sharp contrast to E0771-Vector cells (0/8 rejection, i.e. 8/8 engrafted, all with large tumors), the E0771-SAM cell pool was rejected in most (42/50, 84%) of the mice, with the remaining mice (8/50, 16%) developing small tumors (FIG. 29B). To examine the contribution of innate and adaptive immune responses towards rejection of E0771-SAM cells, E0771-SAM cells were transplanted into the mammary fat pad of immunodeficient Nu/Nu and Rag1$^{-/-}$ mice. Unlike in immunocompetent C57BL/6J hosts (5/5 either completely rejected or only with small modules), all immunodeficient Nu/Nu (4/4) and Rag1$^{-/-}$ (5/5) mice rap-idly grew large tumors from E0771-SAM cells (FIG. 29C). Notably, E0771-SAM cells formed significantly larger tumors in Rag1$^{-/-}$ mice compared to in Nu/Nu mice (FIG. 29C). When both CD4$^+$ and CD8$^+$ T cells were pharmaco-logically depleted in C57BL/6J mice by treatment with α-CD4 and α-CD8 monoclonal antibodies, all mice that received E0771-SAM transplantation formed large tumors (4/4), in contrast to untreated mice (0/11 with tumors) (FIG. 29D). Of note, the E0771-SAM outgrown "escaper" tumors were sensitive to immune checkpoint blockade (ICB), with rapid complete regression upon treatment with antibodies against programmed death-1 (PD-1) or cytotoxic T-lympho-cyte associated antigen-4 (CTLA-4) (FIGS. 30D-30G). Together, these results indicated that pooled activation of endogenous genes using the CRISPRa system in a genome-scale manner induced potent tumor rejection in vivo only in immunocompetent hosts.

Figures 5C, 5D:
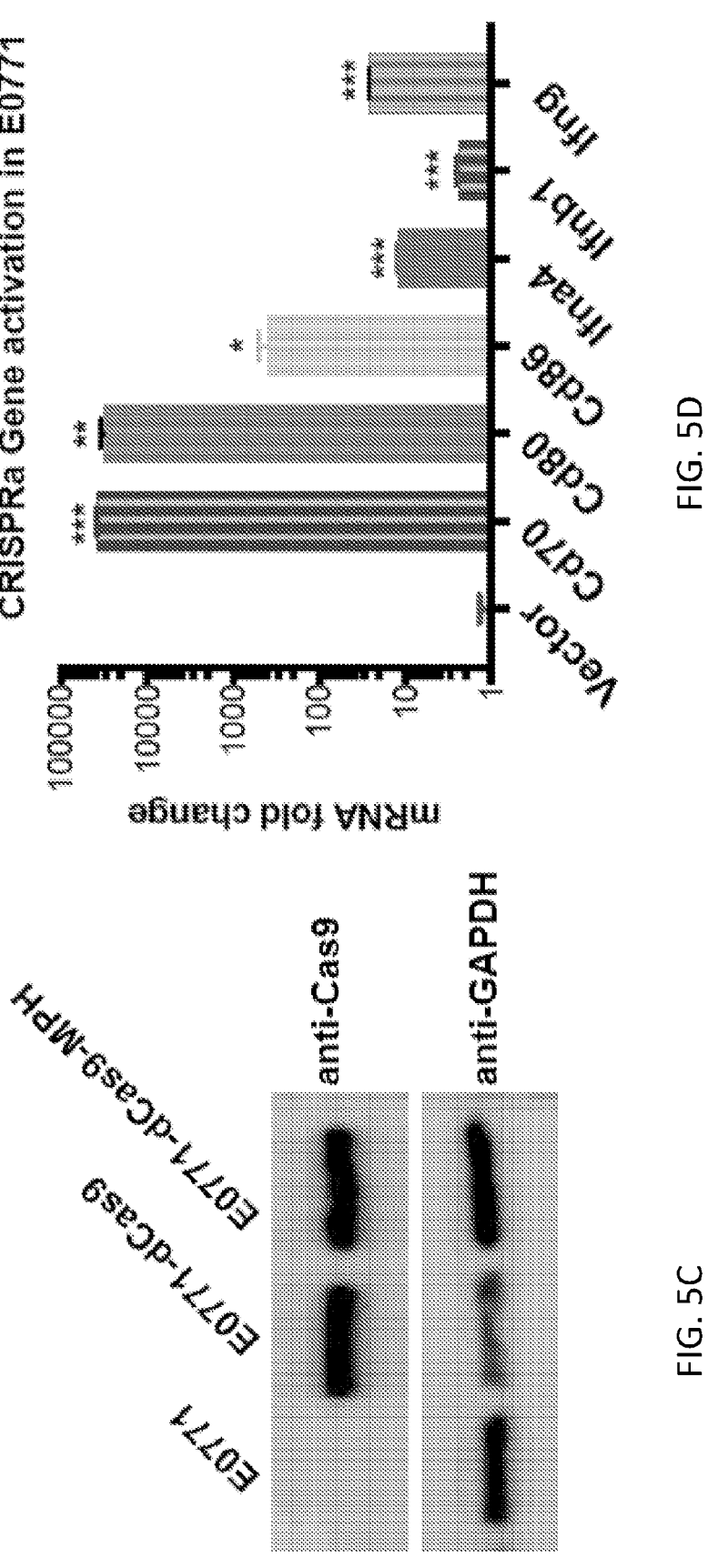
Figures 7A, 7B, 7C, 7D:
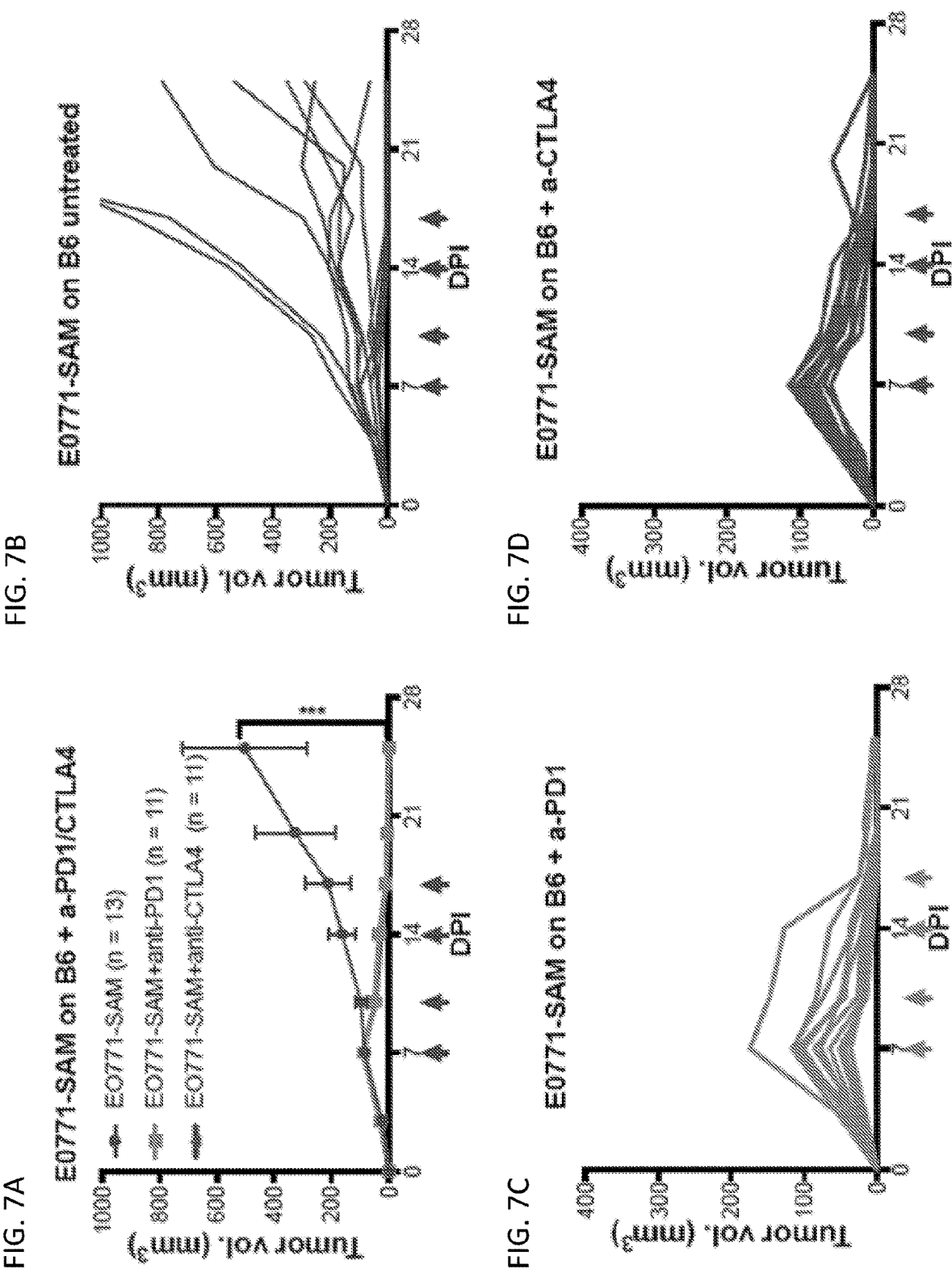
FIGS. 7A-7D illustrate the finding that tumors from E0771 with genome-scale activation of endogenous genes are sensitive to checkpoint blockade.

Example 13: Cell-Based Multiplexed Activation of Endogenous Genes as an Immunotherapy (MAEGI) has Prophylactic and Therapeutic Efficacy in Syngeneic Tumor Models Intrigued that the host immune system consistently rejected the E0771-SAM cells, it was next investigated whether CRISPRa-mediated activation of endogenous genes within tumor cells could stimulate broad anti-tumor immune responses. It was hypothesized that multiplexed activation of endogenous genes can be harnessed as a new approach of immunotherapy (MAEGI or CAVac, used interchangeably herein) distinct from all existing modalities. To test this experimentally, CRISPR-mediated gene activation was confirmed in the system (FIG. 5D). The SAM lentiviral-sgRNA library was then transduced into E0771-dCas9-VP64-MPH cells to generate E0771-SAM cells, followed by mitomycin treatment to induce senescence while maintaining the integrity of peptide-MHC-I complex on cell surface. This procedure generated the cell-based MAEGI (c-MAEGI or cell-based CAVac, which are used interchangeably herein). As a control, E0771-Vector cells that were treated with mitomycin in parallel (Cell-Vector control) were used. c-MAEGI was inoculated into C57BL/6J mice prior to E0771 tumor induction. In sharp contrast to untreated mice or Cell-Vector control treated mice (both 0% tumor free), c-MAEGI treated mice had complete protection (100% tumor free) against a subsequent tumor challenges with the unmodified parental cancer cell line (E0771). This held true across two vaccination regiments, i.e. 7 or 14 days prior to tumor challenge, while vaccination 3 days prior to tumor challenge granted near-complete protection (1/6 mice with a small nodule, 5/6 tumor-free). The results demonstrated that genome-scale activation of endogenous genes using CRISPRa (c-MAEGI) is an effective approach for prophylaxis against tumors with otherwise identical genetic background.

Given its efficacy as a prophylactic agent, it was postulated that c-MAEGI could also be used as a therapeutic intervention in established tumors. To test this, orthotopic syngeneic E0771 tumors were induced before treating the mice with c-MAEGI. Using a three-dose treatment scheme, tumors in c-MAEGI treated mice were significantly smaller than those in mice treated with Cell-Vector control or PBS. No efficacy was observed using heat-inactivated lysates of E0771 parental cells, or heat-inactivated c-MAEGI (FIGS. 31A-31B), suggesting the importance of maintaining the integrity of cellular components for immune stimulation in this setting. To examine the contribution of T cell-mediated immunity in driving the anti-tumor response, CD8 T lymphocytes were specifically depleted in C57BL/6J mice with an α-CD8 antibody. CD8$^+$ T cell depletion abolished the therapeutic efficacy of c-MAEGI (FIGS. 31C-31F), indicating that CD8$^+$ T cells are essential for the c-MAEGI mediated anti-tumor responses.

Figures 1I, 1J, 1K:
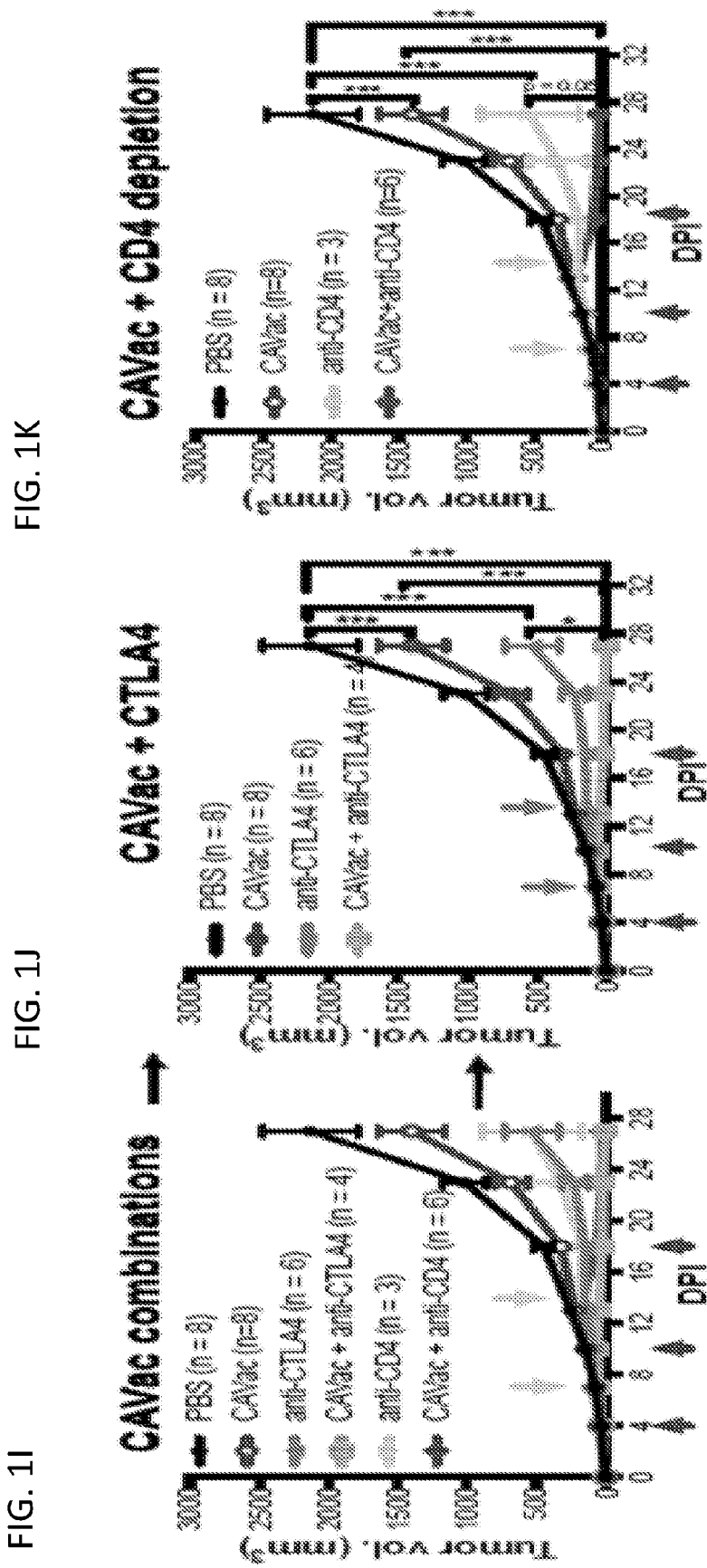

It was then investigated whether c-MAEGI could be used in conjunction with other immunotherapies or immunomodulatory agents. Interestingly, the combination of c-MAEGI+α-CTLA4 was significantly more effective than c-MAEGI alone (p<0.0001) or anti-CTLA4 alone (p=0.0005), leading to complete regression of established tumors (FIG. 1J). Moreover, the mice that underwent complete responses were completely resistant to tumor rechallenges (FIG. 31G), suggesting long-term protective memory in treated mice.

Example 14: AAV-Mediated In Situ Activation of Endogenous Genes as an Immunotherapeutic Agent (AAV-MAEGI)

Although the cell-based MAEGI showed significant anti-tumor efficacy, it was reasoned that direct in vivo delivery of MAEGI with viral vehicles to the target tumors can yield a deliverable therapeutic modality and might also further improve efficacy. Adeno-associated viruses (AAVs) are potent viral vectors capable of mediating efficient transgene delivery into various organs in mice and humans. They are non-replicative without helper adenovirus, have serotype-specified tropism and cause minimal toxicity or undesired immune responses. Because of these properties, AAVs have been commonly used in clinical studies of gene therapy, and an AAV-based treatment recently received FDA approval. To enable direct delivery of MAEGI to tumors, an AAV version of MAEGI was devised by generating an AAV-CRISPRa vector with the CRISPRa modules (EF1α-MPH and U6-sgRNABackbone-MS2) and cloning in the genome-scale SAM sgRNA library (AAV-g-MAEGI or AAV-CAVac, used interchangeably herein). The resultant library was then pool-packaged into AAV (FIG. 2A). The effectiveness of pool-packaged AAV-CRISPRa in activating endogenous genes was confirmed by infecting E0771-dCas9-VP64 cells with CRISPRa AAVs carrying a small pool of sgRNAs targeting genes including Cd70, Cd80, and Cd86 (FIG. 32A). Furthermore, by introducing a model antigen transgene (chicken ovalbumin, OVA) driven by a PGK promoter into E0771-dCas9-VP64 cells, it was confirmed that PGK promoter-targeted sgRNAs delivered by AAV can significantly increase the presentation of processed antigenic peptide on the cell surface, as revealed by flow cytometry staining with antibody specific to the complex of SIINFEKL peptide bound to class I major histocompatibility complex (pMHC-I) (FIG. 32B-32C).

Figure 2F:
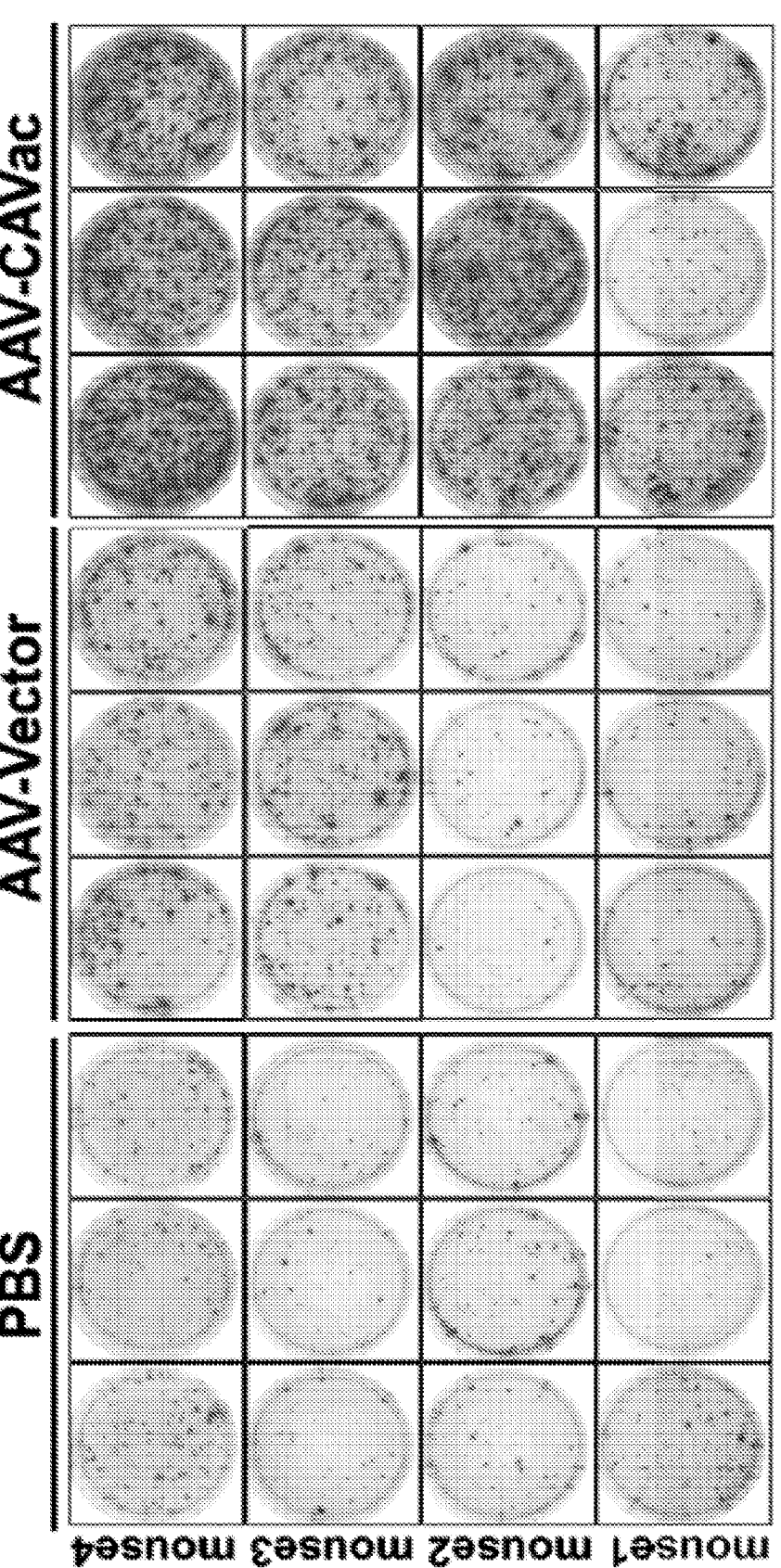
Figure 2G:
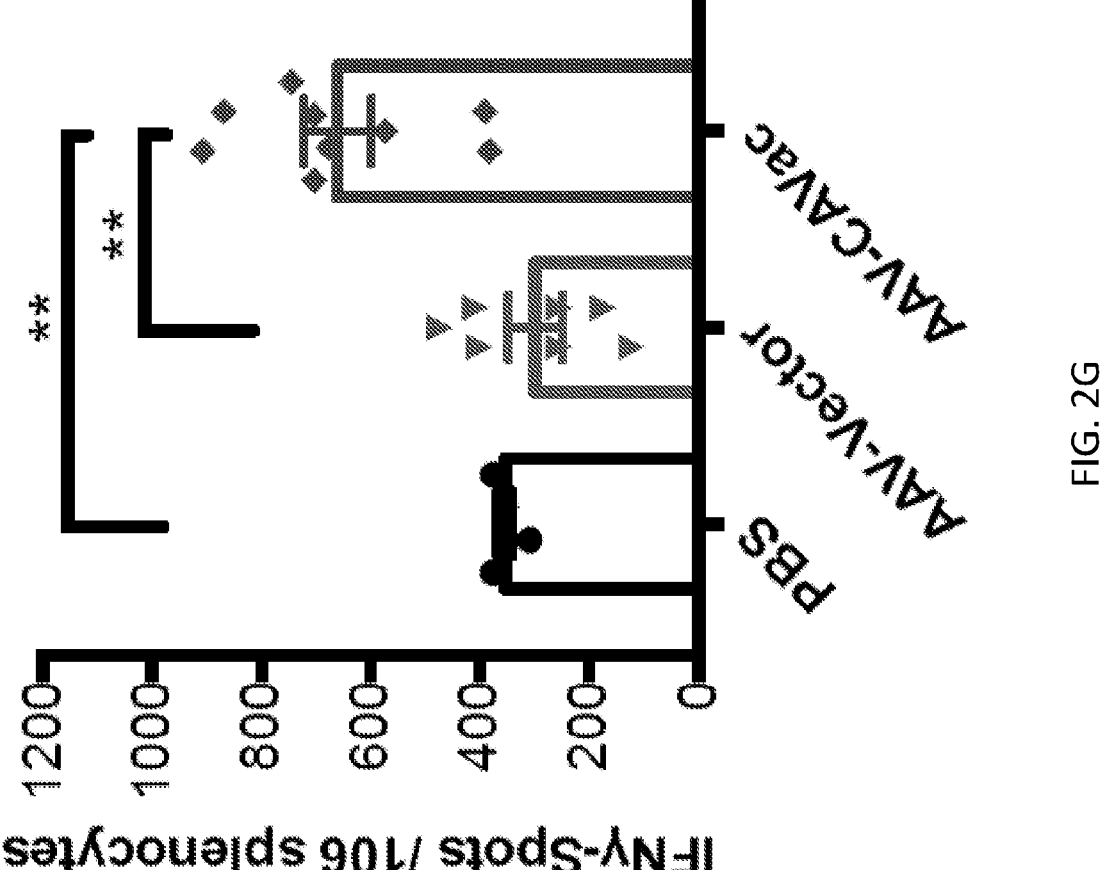

C57BL/6J mice bearing syngeneic orthotopic E0771 tumors were then treated with AAV-g-MAEGI by intratumoral administration (FIG. 2A). AAV-g-MAEGI was significantly more efficacious compared to either AAV-Vector or PBS (FIG. 2B). Of note, the AAV-Vector treatment also showed a significant effect against tumors in the E0771 model (viral vector with EF1α-MPH and U6-sgRNABackbone-MS2), but was nevertheless significantly weaker than AAV-g-MAEGI (FIG. 2A). CD8$^+$ T cell infiltration into the tumors was observed by histology and immunohistochemistry (FIG. 33A-33B). AAV-g-MAEGI elicited higher frequencies of tumor-reactive immune cells in treated mice (in terms of the frequencies of IFNγ producing splenocytes stimulated by tumor antigens) compared to AAV-Vector or PBS (FIGS. 2F-2G). No difference was observed in the frequencies of tumor-reactive IFNγ-secreting splenocytes between PBS and AAV-Vector (FIG. 2G). These data demonstrated that multiplexed in situ activation of endogenous genes by AAV-g-MAEGI can elicit robust and specific anti-tumor immune responses.

To test the broader utility of MAEGI, the same modality for treatment of other highly aggressive tumor types was tested. On a syngeneic melanoma mouse model (B16F10, expressing dCas9-VP64), AAV-g-MAEGI again demonstrated significant efficacy (FIG. 2C). Additionally, the efficacy of AAV-g-MAEGI in a syngeneic model of pancreatic cancer was tested using the Pan02 cell line. Against established Pan2-dCas9-VP64 tumors, AAV-Vector again had an anti-tumor effect compared to PBS, while AAV-g-MAEGI had significantly stronger efficacy against these tumors, both compared to AAV-Vector and to PBS (FIG. 25). To assess the infection rate of intratumoral AAV delivery, the experiments were repeated using titer-matched AAVs containing a GFP reporter. Four days following intratumoral AAV injection, tumor cells, tumor-infiltrating immune cells (TIICs, CD45$^+$), and cells from non-tumor organs were harvested. Analysis of GFP expression by flow cytometry revealed that the cancer cells were transduced by AAV in all tumors injected (12/12, 100%), with an infection rate of 4.2±0.51% (mean±s.e.m.) for tumor cells, reflecting a local injection (FIG. 33C). In contrast, 25% (4/12) of injected tumors showed above-background transduction in pan-immune (CD45$^+$) cells, with an infection rate of 0.74±0.25% (FIG. 33C). The off-target infection rate for the spleen, liver, lung and heart in the same cohort of mice was 0±0%, 0.04±0.04%, 0.18±0.06% and 0.11±0.08%, respectively (FIG. 33D). These data together demonstrated that in situ MAEGI by AAV-mediated delivery of a genome-scale CRISPRa library elicits host immune responses against established tumors across multiple aggressive cancer types, with minimal effect on non-cancer cells and other off-target organs.

Example 15: Multiplexed In Situ Activation of Tumor-Specific Mutated Gene Sets as a Precision Immunotherapy Since individual tumors have their own unique mutation profiles that distinguish them from normal tissues, the MAEGI approach was customized to tumor-specific mutated gene sets. This approach was termed precision MAEGI (p-MAEGI or PCAVac, which are used interchangeably herein) (FIG. 4A). By customizing the AAV library to tumor-specific mutant genes, it was hypothesized that the precision version could both enrich for potentially antigenic mutants as well as exclude genes that could cause adverse effects. Whole-exome sequencing of the E0771 cancer cells was performed and all SNPs, insertions and deletions (indels) in annotated genes were called, by comparison to healthy mammary fat pad cells from wildtype C57BL/6J mice that were sequenced in parallel (FIG. 4A). The exome sequencing data revealed the E0771-specific mutation profile (FIGS. 4B-4C). The differential mutation data was then harnessed for CRISPRa sgRNA library design, generating a library of 3,839 activating sgRNAs (SEQ ID NOs: 349-4, 187) targeting 1,116 E0771-mutated genes. The library was synthesized and pool-cloned. Successful cloning was verified by Illumina sequencing, and the AAV pool was produced as an E0771-specific precision MAEGI (E0771 AAV-p-MAEGI or E0771 AAV-PCAVac, used interchangeably herein).

Figures 4M, 4N, 4O:
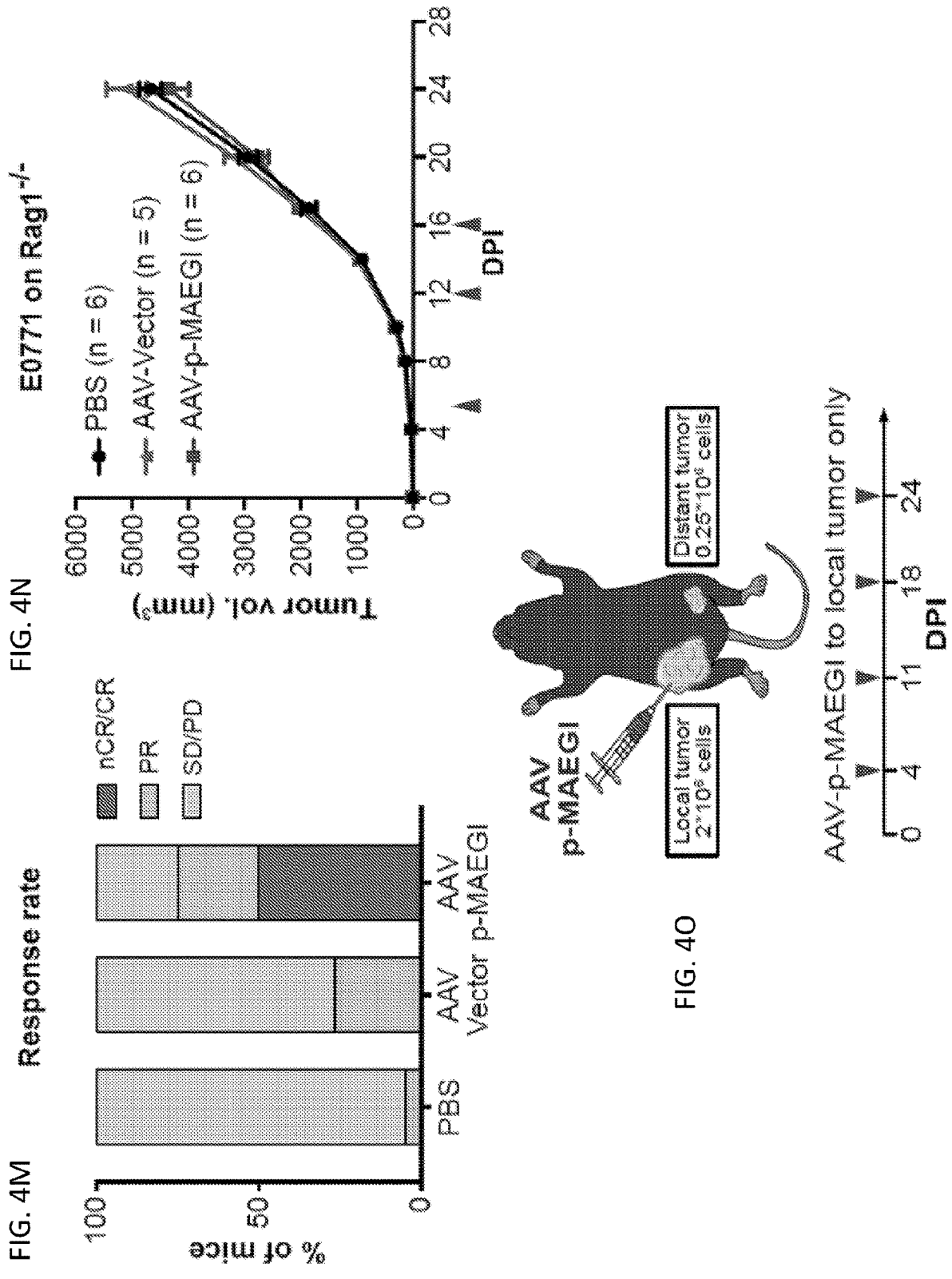
FIG. 4M shows response rates for PBS, AAV-Vector, or AAV-PCAVac (AAV-p-MAEGI) treatments, categorized by near-complete or complete response (nCR/CR), partial response (PR), or stable/progressive disease (SD/PD).
FIG. 4N shows growth curves of E0771 syngeneic tumors in $Rag1^{-/-}$ mice treated by PBS (n=6), AAV-Vector (n=5), or AAV-PCAVac (AAV-p-MAEGI) (n=6). AAV-PCA- Vac (AAV-p-MAEGI) was ineffective against established E0771 tumors in immunodeficient $Rag1^{-/-}$ mice by intratumoral administration at indicated times (arrows). Two-way ANOVA: AAV-Vector vs. PBS, p=0.0653; AAV-PCAVac vs. PBS, p=0.6982; AAV-p-MAEGI vs. AAV-Vector, p=0.0634.
FIG. 4O is a schematic of an experimental design for evaluating the induction of systemic anti-tumor immunity by AAV-p-MAEGI. $2\times10^6$ or $0.25\times10^6$ E0771 tumor cells were respectively transplanted into the left or right flank of C57BL/6J mice to model a local and a distant tumor. AAV-p-MAEGI was administered only into the local tumors at the indicated times (arrows).

C57BL/6J mice bearing E0771 syngeneic orthotopic TNBC were treated with AAV-p-MAEGI, along with AAV-Vector and PBS controls. While the AAV-vector itself showed anti-tumor effects as compared to PBS, AAV-p-MAEGI exhibited dramatic efficacy compared to both AAV-Vector and PBS (FIG. 4E), indicating that the mutant gene-specific CRISPRa sgRNAs generated potent anti-tumor responses. The complete response (CR) and near-complete (nCR) rates were determined for each treatment, which revealed a combined nCR/CR rate of 0% for PBS, 0% for AAV-Vector, and 50% for AAV-p-MAEGI (FIG. 4M). Three months after the initial tumor transplantation, 9 AAV-p-MAEGI treated mice that had undergone complete response were re-challenged. All (9/9) mice completely rejected the E0771 tumor re-challenges (FIG. 4F). The complete response of AAV-p-MAEGI treated mice retained a long-term benefit for over 180 days as the end of experiment (FIG. 4F). These data indicated that AAV-p-MAEGI had induced potent and durable anti-tumor responses.

The efficacy of AAV-p-MAEGI was completely abolished in immunodeficient hosts, as evidenced by near-identical growth curves of all treatment groups in Rag1−/− mice (FIG. 4N), indicating that the adaptive immune system is essential for the anti-tumor effect of AAV-p-MAEGI. Consistent with this, CD8$^+$ T cell infiltration into tumors was observed by histology and immunohistochemistry (FIGS. 34A-34B).

Figures 4P, 4Q:
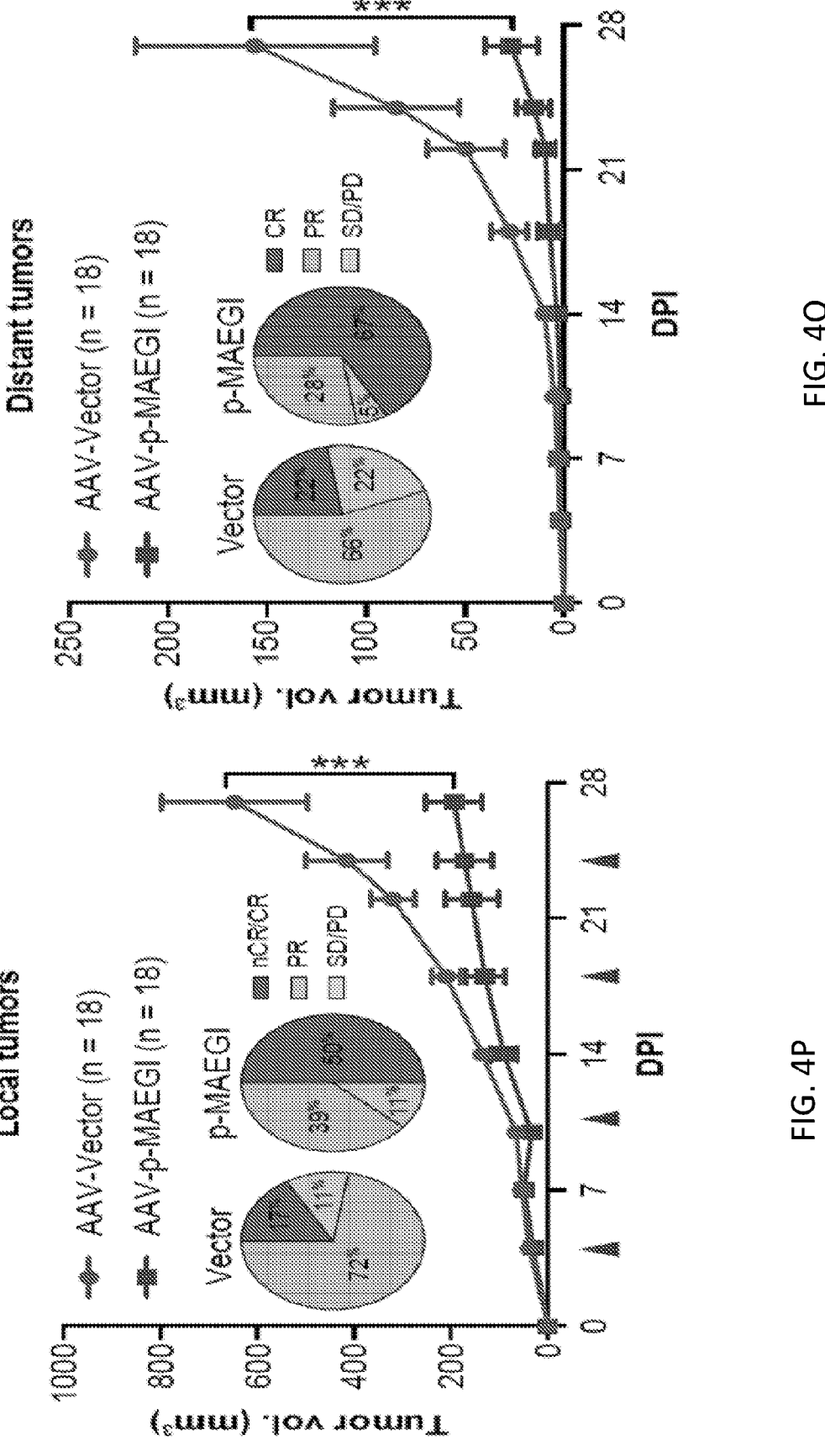

AAV-p-MAEGI treated tumors also showed reduced proliferation (FIGS. 34C-34D). Given the importance of adaptive immunity in driving these anti-tumor responses, it was investigated whether intratumoral delivery of AAV-p-MAEGI could elicit systemic anti-tumor immunity to affect distant sites (FIG. 4O). In a syngeneic model of E0771 TNBC where mice bear both local and distant mammary fat pad tumors, after administration of AAV-p-MAEGI only to local tumors, significant anti-tumor effects against both local tumors and distant tumors were observed, which had not been directly infected by AAV-p-MAEGI (FIGS. 4P-4Q). A 67% complete response rate was observed at distant tumors under AAV-p-MAEGE treatment (FIG. 4Q). These data demonstrated that AAV-p-MAEGI treatment had successfully galvanized systemic anti-tumor immune responses.

Example 16: AAV-p-MAEGI Recruits Active T Effector Cells into Tumors

To examine the T cell adaptive immune responses over a time-course, flow cytometry analysis of tumor-infiltrating T cell populations was performed at several time points (FIG. 35A). AAV-p-MAEGI treatment significantly augmented CD4$^+$ and CD8$^+$ T cell tumor infiltration as compared to AAV-Vector or PBS treatment, with significantly increased CD8$^+$ T cells and CD4$^+$ T cells from day 29 onwards (FIGS. 36A-36B). Other immune cell populations were examined at day 19, as this is the time point with initial observation of striking tumor regression (FIG. 35B). The results showed that AAV-p-MAEGI treatment increased the fraction of MHC-II$^+$ antigen-presenting cells over AAV-Vector treatment (FIG. 36C), with a trend of increased dendritic cells (FIG. 36D), but no significant changes in macrophages, monocytes, or neutrophil abundance (FIGS. 36E-36G). These data together revealed that AAV-p-MAEGI treatment increased T cell infiltration into tumors and changed the composition of certain infiltrating immune cells, ultimately resulting in tumor regression.

Given these findings, it was next investigated whether the adaptive immune responses induced by AAV-p-MAEGI were tumor-specific. By performing ELISPOT on splenocytes taken from E0771 tumor-bearing mice, it was observed that AAV-p-MAEGI significantly augmented the frequencies of tumor-reactive IFNγ producing splenocytes compared to PBS and AAV-vector treated mice (FIG. 36H-36J). To test whether these stimulated immune cells are specific to the endogenous tumor antigens but not healthy normal tissues, E0771 tumor-bearing mice were again treated with AAV-p-MAEGI or AAV-Vector. ELISPOT assays were performed on both splenocytes and fluorescence activated cell sorting (FACS)-isolated tumor-infiltrating immune cells (TIICs), stimulated with either E0771 cancer cells or matched normal tissues (primary C57BL/6J wildtype cells isolated from mammary fat pad)(FIG. 36H). In both AAV-Vector and AAV-p-MAEGI conditions, the ELISPOT assays showed significantly higher IFNγ-producing splenocytes and TIICs after stimulation by E0771 tumor cells, as compared to stimulation with normal primary cells (FIG. 36K-36N). Importantly, within the E0771-stimulated experimental groups, AAV-p-MAEGI treated mice had significantly higher frequencies of IFNγ-secreting immune cells than AAV-Vector treated mice. This effect was particularly pronounced in TIICs, where AAV-p-MAEGI significantly augmented the frequencies of IFNγ-secreting immune cells in response to E0771 stimulation, but not to matched normal cells (FIG. 36M-36N). The anti-tumor specificity of AAV-p-MAEGI was similarly observed in splenocytes (FIG.

36K-36L). These results demonstrated that tumor-antigen specific immune responses were elicited by AAV-p-MAEGI.

Example 17: AAV-p-MAEGI Remodels the Host Tumor Microenvironment

To understand the repertoire of T cells recruited by MAEGI, T cell receptor sequencing (TCR-seq) was performed to profile the TCR repertoire in mice treated with AAV-p-MAEGI, AAV-g-MAEGI, AAV-Vector or PBS (FIG. 37A). TCR clonal proportion was assessed and various metrics were calculated (FIG. 37B-37D). In comparison to PBS or AAV-Vector, AAV-p-MAEGI significantly increased TCR diversity in both spleens and TILs as measured by the Chao1 index (FIG. 37C). In comparison to AAV-g-MAEGI treated mice (genome-wide AAV-MAEGI), splenocytes from AAV-p-MAEGI treated mice (precision AAV-MAEGI) had higher Chao1 indices, with no significant difference among TILs (FIG. 37C). Next, the Gini-Simpson indices were calculated, which quantify the evenness of TCR clonal abundances. While there were no significant differences among spleen samples from differing treatment conditions, TILs from AAV-p-MAEGI treated mice had significantly higher Gini-Simpson indices compared to PBS or AAV-Vector treated mice, but not compared to AAV-g-MAEGI treated mice. Intrigued by the increased TCR diversity and clonal evenness among TILs from AAV-p-MAEGI treated mice, it was investigate whether these changes were due to differences in T cell infiltration. The number of unique CDR3 clonotypes identified in each sample (i.e. TCR richness) were examined (FIG. 35C). AAV-p-MAEGI mice had significantly more unique clonotypes than PBS or AAV-Vector samples in both spleen and TIL samples (FIGS. 37E-37F). Collectively, the TCR-sequencing data affirmed the conclusion from the flow cytometry analysis that AAV-p-MAEGI significantly enhanced T cell infiltration into tumors, while additionally revealing the richness and diversity of these tumor-infiltrating T cells.

To further investigate the effect of AAV-p-MAEGI on the tumor microenvironment, single cell RNA sequencing (scR-NAseq) was performed to profile the composition of TIICs, and simultaneously, their gene expression signatures (FIG. 38A). From single cell suspension of tumors, total TIICs were isolated by FACS of CD45$^+$ cells and scRNAseq was performed, recovering a total of 4,381 cells from AAV-p-MAEGI and 3,482 cells from AAV-Vector treated mice (n=3 mice pooled for each condition). After filtering low-quality cells and lowly-expressed genes, imputation and k-means clustering were performed to identify a total of 9 distinct clusters. Analysis of differentially expressed genes in each cluster revealed the cell type identities of each cluster (FIG. 38B and FIGS. 39A-39F). After excluding a population of cells (k-means cluster 7, or k7) that were negative for Cd45 gene expression (encoded by Ptprc) (FIG. 39A-39B), the final dataset of TIICs comprised the transcriptomes of 4,065 single cells from AAV-p-MAEGI and 2,799 cells from AAV-Vector treated mice (FIG. 38C).

Given that the flow cytometry data and TCR-seq analyses had both identified increased T cell tumor infiltration with AAV-p-MAEGI compared to AAV-Vector, it was investigated whether these findings were recapitulated by scR-NAseq at a global scale. To perform in silico analysis on T cell populations, mRNA transcript expression levels were filtered ("mRNA-gated") on cells in k6 or k9, as these clusters comprise the cells that robustly express Cd3e, Cd4, and Cd8a (FIG. 39C). Examining the Cd3e+ cells within k6 and k9, the cells were mRNA-gated into Cd8a$^+$Cd4$^-$ and Cd4$^+$Cd8a$^-$ populations. Visualization of these cell groups by t-SNE dimensional reduction revealed clear separation of putative CD8$^+$ T cells (defined by Cd8a$^+$Cd3e$^+$Cd4$^-$ mRNA gating) from CD4$^+$ T cells (defined by Cd4$^+$Cd3e$^+$Cd8a$^-$ mRNA gating) (FIG. 38D). The relative abundance of these different T cell populations in k6 and k9 were quantified, revealing that AAV-p-MAEGI mice had significantly more Cd3e$^+$ T cells, putative CD8$^+$ T cells, and putative CD4$^+$ T cells (FIG. 38E). Furthermore, among these putative CD4$^+$ T cells, AAV-p-MAEGI treated mice had increased abundance of Tbx21$^+$, Ifng$^+$, and Tbx21$^+$Ifng$^+$ cells, indicative of anti-tumor Th1 cells (FIG. 38F). Thus, the single cell transcriptomic analyses on the global TIICs reaffirmed the earlier cell type specific observations by FACS and TCR-seq, that AAV-p-MAEGI promotes T cell tumor infiltration.

To investigate whether AAV-p-MAEGI treatment led to transcriptomic changes in tumor-infiltrating T cells, differential expression analyses were performed to compare T cells from AAV-p-MAEGI and AAV-Vector treated mice. Among the putative CD8$^+$ T cells in k6 (characterized by higher Gzmb expression compared to k9) (FIG. 39C), 267 upregulated and 753 downregulated genes were identified in AAV-p-MAEGI treated mice compared to AAV-Vector (FIG. 40A). Gene ontology analysis revealed enrichment of several T cell signatures within the upregulated gene set, including adaptive immunity, T cell activation, and the T cell receptor complex. Interestingly, the strongest enriched gene set was the AIG1 family of GTPases, particularly Gimap genes (GTPases of immunity-associated protein). Gimap proteins are known to play critical roles in T cell activation and survival. As for the putative CD8$^+$ T cells in k9, 665 genes were upregulated and 80 genes downregulated with AAV-p-MAEGI treatment (FIG. 40B). Enriched gene ontologies in the upregulated gene set included mitochondrion, exosome, proteasome, RNA-binding, adaptive immunity, ribonucleoprotein, AIG1/Gimaps, and rRNA processing. The same analysis was performed on putative CD4$^+$ T cells, revealing 335 upregulated and 65 downregulated genes with AAV-p-MAEGI treatment (FIG. 40C). AAV-p-MAEGI upregulated gene ontologies in putative CD4$^+$ T cells included the proteasome, extracellular exosome, poly (A) RNA binding, mitochondrion, splicosome, and ribonucleoprotein. Collectively, the scRNAseq data further refined the mechanism of action that AAV-p-MAEGI increased T cell tumor infiltration, additionally revealing significant transcriptomic changes in TILs following MAEGI treatment.

Example 18: Comparison to RNA or Peptide Neoantigen Vaccines

Current state-of-the-art approaches to target tumor neoantigens are largely focused on delivering mutant RNAs or peptides to lymphatic tissues. The AAV-MAEGI approach is not directly comparable to these neoantigen vaccines, as AAV-MAEGI directly amplifies tumor immunogenicity by intratumoral injection. Nevertheless, under the intratumoral/in situ treatment scheme, experiments were performed to compare AAV-mediated CRISPRa gene activation with AAV-mediated mutant mini-ORF expression (the closest analog to RNA or peptide vaccines while still maintaining the mode of delivery). Notably, the mutant mini-ORF strategy has been adopted by some biotech startups, using viral vectors such as oncolytic viruses.

Interestingly, in the same E0771 syngeneic model (FIG. 41), the data indicates that while AAV-MAEGI is highly efficacious (FIG. 41, left panel), intratumoral delivery of the predicted top 20 mutant mini-ORFs by AAV (AAV-20Mu-tORF) is not more effective than AAV-Vector alone. One may wonder if >1,000 mutant ORFs could be used for a closer comparison to AAV-p-MAEGI, but doing so is currently impractical because ~50 different AAV-ORF constructs each with 20 peptide-encoding CDSs would have to be created. Similar issues regarding scalability would apply to mRNA ORFs (also needs ~50 mRNA constructs) or synthetic peptides (>1000 constructs)—both well beyond the realm of clinical feasibility. However, the AAV-MAEGI approach is highly scalable, because sgRNAs can be synthesized as a pool and generated as one mixed product, as demonstrated herein. This supports the promise of AAV-MAEGI as a new approach, with multiple advantages over existing neoantigen-based approaches.

Example 19: Comparison to Other Intratumoral Approaches to Amplify Tumor Cell Immunogenicity Several other approaches for directly amplifying tumor cell immunogenicity have been described in the literature. However, none can match the flexibility and scalability of the CRISPR-based MAEGI approach. To evaluate the importance of library size (and hence scalability) in the anti-tumor efficacy of AAV-MAEGI, AAV-g-MAEGI (exome-wide library) was directly compared with a mini-pool MAEGI (AAV-mini-MAEGI) in the B16F10 syngeneic model. AAV-g-MAEGI outperformed AAV-mini-MAEGI (targeting the same 15 genes chosen based on predicted antigenicity for prior B16F10 melanoma vaccines) (FIG. 42). Indeed, the antigen/expression-based mini-pool showed some initial efficacy, but the effect rapidly disappeared as the tumors grew (with similar growth curves as AAV-Vector), possibly due to immune escape of the 15 selected antigens. In contrast, the broader AAV-g-MAEGI library showed stronger and more sustained efficacy.

Moreover, experiments targeting a small set of mutated genes for the E0771 model (Emut11, carrying an sgRNA library targeting the top 11 mutant genes in E0771) were also performed. As the data in FIG. 43 illustrates, reduced efficacy was observed with Emut11 (right panel, only 20% nCR/CR rate), as compared to strong efficacy with E0771-p-MAEGI carrying an sgRNA library targeting 1,116 mutant genes (left panel, 50% nCR/CR rate).

Therefore, the ability to target a larger number of mutant genes is key for optimally accessing the maximal efficacy space. While this quickly becomes impractical for traditional mRNA/peptide/CDS approaches, it is readily feasible with the CRISPRa approaches disclosed herein by scaling the desired number of sgRNAs in the library, up to the entire genome.

Example 20: Dual-AAV Delivery

It was demonstrated herein that dual-AAV delivery into fully un-modified parental E0771 cells can mediate activation of endogenous genes (FIGS. 44A-44B). This was achieved using two different AAV serotypes: both AAV9 and AAV-DJ (FIGS. 44A-45).

A dual AAV system for in vitro and in vivo delivery of MAEGI was developed herein. The dual AAV vector system of CRISPR activation (AAV-dCas9, i.e. EFs-dSpCas9-spA; and AAV-CRISPRa vector, i.e. U6p-sgSapI-EF1a-MS2-p65-HSF1-WPRE), was generated by restriction cloning and Gibson assembly. Individual sgRNA or sgRNA libraries were cloned into the AAV-CRISPRa plasmid. dCas9 or U6-sgRNA-EF1a-MS2-p65-HSF1 expressing AAVs produced using the methods as described in detail elsewhere herein. For in vitro and in vivo delivery, AAV-dCas9 and AAV-CRISPRa were simultaneously added into cultured cells or co-injected into tumors at a ratio of 1:1.

Syngeneic TNBC were established by orthotopic transplantation of $2 \times 10^6$ E0771 cells into the mammary fat pad of 5-8 weeks old female C57BL/6J mice. 4, 9 (or 11) and 18 days after tumor induction, $1-5 \times 10^{10}$ GCs of AAV-dCas9, together with same titers of AAV-p-MAEGI or AAV-Vector, or PBS were intratumorally administrated into tumor-bearing mice. Tumors were measured every 3-4 days using caliper and sizes were calculated with the formula: $Vol = \pi / 6 * x * y * z$. Two-way ANOVA was used to compare growth curves between treatment groups.

Dual-AAV delivery of a personalized library (AAV-PCA-Vac, i.e. AAV-p-MAEGI) into fully un-modified parental E0771 cells mediated anti-tumor activity in vivo in C57B/6 mice (FIG. 46).

It was also demonstrated that dual-AAV delivery of an APCM library into fully un-modified parental E0771 cells can mediate anti-tumor activity in vivo in C57BL/6 mice (FIG. 47).

Example 21: AAV Infectivity In Vivo by Serotypes

AAV infection efficiency across serotypes was assessed by intratumoral delivery of GFP-expressing AAVs and flow cytometry analysis (FIG. 48). Percentage of GFP$^+$ cells within tumors from mice 4 days after intratumoral injection of PBS (n=3) or AAV-GFP (n=12), was grouped by CD45+ and CD45$^-$ cells. The background GFP fluorescence was set as the maximum % GFP positivity in PBS samples, denoted by a dashed line. Fractions above AAV conditions denote the number of samples with % GFP positivity above background in the indicated cell population. The data demonstrated that in vivo infectivity across different AAV serotypes was similar (FIG. 48).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Lengthy table referenced here

US12678493-20260714-T00001

Please refer to the end of the specification for access instructions.

Lengthy table referenced here

US12678493-20260714-T00002

Please refer to the end of the specification for access instructions.

LENGTHY TABLES

The patent contains a lengthy table section. A copy of the table is available in electronic form from the USPTO web site (https://seqdata.uspto.gov/docdetail?docId=US12678493B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/docdetail?docId=US12678493B2). An electronic copy of the sequence listing will also be available from the USPTO upon request and payment of the fee set forth in 37 CFR 1.19(b)(3).

What is claimed is:

1. A composition comprising a cancer vaccine, comprising a modified cell comprising a CRISPRa system capable of increasing expression of a plurality of endogenous human antigen presentation genes resulting in the modified cell expressing at least one tumor associated antigen (TAA),
   wherein the CRISPRa system comprises an sgRNA library,
   wherein the plurality of endogenous human antigen presentation genes are selected from the group consisting of CD70, CD80, CD86, IFNA4, IFNB1, and IFNG; and
   wherein the sgRNA library comprises every nucleic acid sequence of SEQ ID NOs: 1, 2, 5, 6, 9, 11-13, 16, 18, 21, 22, 24, 25, 28, 30, 31, and 33-35.

2. A method of vaccinating against cancer in a subject in need thereof, the method comprising
   administering to the subject a therapeutically effective amount of the composition of claim 1.

3. The method of claim 2, wherein the CRISPRa system is in an AAV vector, a lentiviral vector, or an adenoviral vector, wherein the AAV vector is selected from the group consisting of AAV2, AAV8, AAV9, or AAV-DJ.

4. The method of claim 2, wherein the CRISPRa system comprises:
   (a) a nucleic acid encoding dCas9-VP64, a nucleic acid encoding MS2-p65-HSF 1, and a genome-scale lentiviral synergistic activation mediator (SAM) CRISPRa sgRNA library; or
   (b) a nucleic acid encoding MS2-p65-HSF 1, and a nucleic acid encoding a genome-scale lentiviral SAM CRISPRa sgRNA library.

5. The method of claim 2, wherein the subject is a human.

6. The method of claim 2, wherein administering the therapeutically effective amount of the composition comprises a one dose, a two dose, a three dose, a four dose, or a multi-dose treatment.

7. The method of claim 2, further comprising contacting the cell with a substance that induces senescence in the cell prior to administering to the subject, wherein the substance that induces senescence in the cell is mitomycin.

* * * * *